(12) United States Patent
Ashwell et al.

(10) Patent No.: US 7,902,354 B2
(45) Date of Patent: Mar. 8, 2011

(54) LAPACHONE COMPOUNDS AND METHODS OF USE THEREOF

(75) Inventors: Mark A. Ashwell, Carlisle, MA (US); Manish Tandon, Framingham, MA (US); Jean-Marc Lapierre, Pelham, NH (US); Syed Ali, North Andover, MA (US); David Vensel, Somerville, MA (US); Chiang J. Li, Cambridge, MA (US)

(73) Assignee: ArQule, Inc., Woburn, MA (US)

( * ) Notice: Subject to any disclaimer, the term of this patent is extended or adjusted under 35 U.S.C. 154(b) by 743 days.

(21) Appl. No.: 11/894,900

(22) Filed: Aug. 21, 2007

(65) Prior Publication Data

US 2009/0105166 A1    Apr. 23, 2009

Related U.S. Application Data

(60) Provisional application No. 60/839,361, filed on Aug. 21, 2006.

(51) Int. Cl.
*C07D 225/04* (2006.01)

(52) U.S. Cl. ...................................... 540/466

(58) Field of Classification Search .................. 540/466
See application file for complete search history.

(56) References Cited

U.S. PATENT DOCUMENTS

| | | | |
|---|---|---|---|
| 5,763,625 A | 6/1998 | Boothman et al. | 549/390 |
| 5,824,700 A | 10/1998 | Frydman et al. | 514/454 |
| 5,969,163 A | 10/1999 | Frydman et al. | 549/389 |
| 6,245,807 B1 | 6/2001 | Pardee et al. | 514/454 |
| 2002/0169135 A1 | 11/2002 | Pardee et al. | 514/27 |
| 2003/0091639 A1 | 5/2003 | Jiang et al. | 424/486 |
| 2004/0071775 A1 | 4/2004 | Jiang et al. | 424/486 |
| 2004/0266857 A1 | 12/2004 | Jiang et al. | 514/437 |

FOREIGN PATENT DOCUMENTS

| | | |
|---|---|---|
| WO | WO 94/04145 | 3/1994 |
| WO | WO 99/47497 | 9/1999 |
| WO | WO 00/61142 | 10/2000 |
| WO | WO 03/011224 A2 | 2/2003 |
| WO | WO 2004/045557 A2 | 6/2004 |

OTHER PUBLICATIONS

Abell et al., "The Wittig and related reactions", in *Organophosphorus Reagents*, Chapter 4, pp. 99-127, Oxford University Press, Inc., New York (2004).
Adcock et al., "Substituent Effects. VIII. Synthesis of Substituted α- and β-Fluoronaphthalenes", *J. Am. Chem. Soc.*, 89(2):386-390 (1967).
Brittain et al., "Triphenylsilanethiol: A Solid H2S Equivalent in the Ring Openings of Epoxides", *Tetra. Let.*, 34(21):3363-3366 (1993).
Chuang et al., "Oxidative Free Radical Reaction of 2-Phenylthio-1,4-Naphthoquinones Initiated by Manganese(III) Acetate", *Heterocycles*, 43(10):2215-2221 (1996).
Cordero-Vargas et al., "Synthesis of substituted naphthalenes from α-tetralones generated by a xanthate radical addition-cyclisation sequence", *Org. Biomol. Chem.*, 2:3018-3025 (2004).
Edmonds et al., "The Wittig Reaction", in *Modern Carbonyl Olefination*, Chapter 1, pp. 1-17, Verlag GmbH & co. KGaA, Weinheim (2004).
Goncalves et al., "Evaluation of the Toxicity of 3-Allyl-β-Lapchone Against Trypa-Nosoma Cruzi Bloodstream Forms", *Mol. Biochem. Parasit.*, 1:167-176 (1980).
Hale et al., "1,3,4-Trisubstituted Pyrrolidine CCR5 Receptor Antagonists. Part 3: Polar Functionality and Its Effect on Anti-HIV-1 Activity", *Bioorg. Med. Chem. Lett.*, 12(20):2997-3000 (2002).
Huang et al., "β-Lapacone Induces Cell Cycle Arrest and Apoptosis in Human Colon Cancer Cells", *Mol. Med.*, 5:711-720 (1999).
Jambulingam et al., "Synthetic, Structural and Antimicrobial Studies of Some Substituted 2,6-dipehnyl-1-aza-7-oxa-4-spiro[2,5]octanes", *Asian J. Chem.*, 16(3-4):1261-1268 (2004).
Klapars et al., "Copper-Catalyzed Halogen Exchanged in Aryl Halides: An Aromatic Finkelstein Reaction", *J. Am. Chem. Soc.*, 124:14844-14845 (2002).
Krapcho et al., "Heterosubstituted Anthracene-9,10-dione Analogues. The Synthesis and Antitumor Evaluation of 5,8-Bis[(aminoalkyl)amino]naphtha[2,3-b]thiophen-4,9-diones", *J. Med. Chem.*, 33(9):2651-2655 (1990).
Krohn et al., "Transition Metal Catalyzed Oxidations; 4. Improved Method for the Oxidation of 1- and 2-Naphthols to 1,2-Napthoquinones", *Synthesis*, 12:1141-1143 (1990).
Kurokawa, S., "The reaction of Cadalene and Eudalen with Sulfur", *Bul. Chem. Soc. Jap.*, 43(5):1454-1459 (1970).
Lai et al., "β-lapachone induced cell death in human hepatoma (HepA2) cells", *Histol. Histopathol.*, 13:89-97 (1998).
Lawrence, N.J., "The Wittig reaction and related methods", in *Preparation of Alkenes*, Chapter 2, pp. 19-58 (1996).
Li et al., "β-Lapachone, a Novel DNA Topoisomerase I Inhibitor with a Mode of Action Different from Camptothecin", *J. Biol. Chem.*, 268(30):22463-22468 (1993).
Li et al., "Induction of Apoptosis by β-Lapachone in Human Prostate Cancer Cells", *Cancer Res.*, 55:3712-3715 (1995).
Li et al., "Potent Induction of Apoptosis by β-Lapachone in Human Multiple Myeloma Cell Lines and Patient Cells", *Mol. Med.*, 6(12):1008-1015 (2000).
Li et al., "Potent inhibition of tumor survival in vivo by β-lapachone plus taxol: Combining drugs imposes different artifical checkpoints", *PNAS*, 96(23):13369-13374 (1999).
Li et al., "Release of Mitochondiral Cytochrome C in Both Apoptosis and Necrosis Induced by β-Lapachone in Human Carcinoma Cells", *Mol. Med.*, 5:232-239 (1999).
Li et al., "Selective killing of cancer cells by β-lapachone: Direct checkpoint of activation as a strategy against cancer", *PNAS*, 100(5):2674-2678 (2003).

(Continued)

*Primary Examiner* — Taofiq A Solola
(74) *Attorney, Agent, or Firm* — Mintz Levin Cohn Ferris Glovsky and Popeo, P.C.; Ivor R. Elrifi, Esq.; Matthew Pavao, Esq.

(57) ABSTRACT

The present invention provides novel tricyclic spiro-oxathiine naphthoquinone derivatives, a synthetic method for making the derivatives, and the use of the derivatives to induce cell death and/or to inhibit proliferation of cancer or precancerous cells. The naphthoquinone derivatives of the present invention are related to the compound known as β-lapachone (3,4-dihydro-2,2-dimethyl-2H-naphtho(1,2-b)pyran-5,6-dione).

50 Claims, 4 Drawing Sheets

OTHER PUBLICATIONS

Paquet et al., "Reactions of polar dienes with o-quinones", *Can. J. Chem.*, 67(8):1354-1358 (1989).

Perumal et al., "Oxidation of Halophenols and Highly Substituted Phenols with Lead(IV)Acetate", *Synthesis*, 11:943-945 (1980).

Planchon et al., "β-Lapachone-mediated Apoptosis in Human Promyelocytic Leukemia (HL-60) and Human Prostate Cancer Cells: A p53-independent Response", *Cancer Res.*, 55:3706-3711 (1996).

Portela et al., "Redox Cycling of β-Lapchone and Related o-Naphthoquinones in the Presence of Dihydrolipoamide and Oxygen", *Biochem. Pharm.*, 51:275-283 (1996).

Prieto et al., "Arylboronic Acids and Arylpinacolboronate Esters in Suzuki Coupling Reactions Involving Indoles. Partner Role Swapping and Heterocycle Protection", *JOC*, 69(20):6812-6820 (2004).

Schaffner-Sabba et al., "β-Lapachone: Synthesis of Derivatives and Activities in Tumor Models", *J. Med. Chem.*, 27:990-994 (1984).

Schaus et al., "Highly Selective Hydrolytic Kinetic Resolution of Terminal Epoxides Catalyzed by Chiral (salen)Co$^{III}$ Complexes. Practical Syntheis of Enantioenriched Terminal Epoxides and 1,2-Diols", *J. Am. Chem. Soc.*, 124(7):1307-1315 (2002).

Steffan et al., "Novel Substituted 4-Aminomethylpiperidines as Potent and Selective Human β$_3$-Agonists. Part1: Aryloxypropanolaminomethylpiperidines", *Bioorg. Med. Chem. Lett.*, 12:2957-2961 (2002).

Suginome et al., "One-step Synthesis of 2,3-Dihydronaphtho[2,3-b]thiophene-4,9-diones by a New Regioselective [3+2] Photoaddition of Photogenerated 2-Mercapto-1,4-naphthoquinone with Alkenes", *J. Chem. Soc., Chem. Commun.*, 9:807-809 (1993).

Tapia et al., "Synthesis of 2H-Naphtho[2,3-b]Thiopyranoquinones and Density Functional Study for the Diels-Alder Reaction of a Benzothiopyranoquinone", *Heterocycles*, 53(3):585-598 (2000).

Tapia et al., "Synthesis of 3,4-Dihydro-4-hydroxy-9-methoxy-2H-naphtho[2,3-b]thiopyranoquinone", *Tetrahedron Letters*, 38(1):153-154 (1997).

Tonholo et al., "Electrochemical Properties of Biologically Active Heterocyclic Naphthoquinones", *J. Braz. Chem. Soc.*, 9(2):163-169 (1988).

Weller et al., "Topoisomerase-I Inhibitors for Human Malignant Glioma: Differential Modulation of p53, p21, bax and bcl-2 Expression and of CD95-Mediated Apoptosis by Camptothecin and β-Lapachone", *Int. J. Cancer*, 73:707-714 (1997).

Wuertzberger et al., "Induction of Apoptosis in MCF-7:WS8 Breast Cancer Cells by β-Lapachone", *Cancer Res.*, 58:1876-1885 (1998).

LAPACHONE COMPOUNDS AND METHODS OF USE THEREOF

RELATED APPLICATIONS

This application claims the benefit of, and priority to, U.S. Provisional Application No. 60/839,361 filed Aug. 21, 2006. The contents of this application is incorporated herein by reference in its entirety.

BACKGROUND OF THE INVENTION

β-lapachone (3,4-dihydro-2,2-dimethyl-2H-naphtho[1,2-b]pyran-5,6-dione), a quinone, is derived from lapachol (a naphthoquinone) which can be isolated from the lapacho tree (*Tabebuia avellanedae*), a member of the catalpa family (Bignoniaceae). Lapachol and β-lapachone (with numbering) have the following chemical structures:

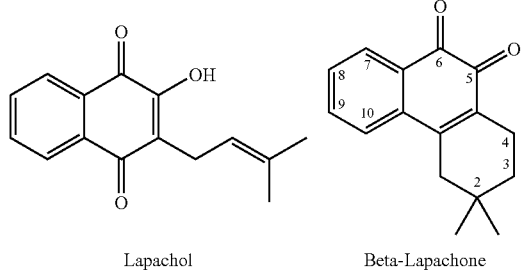

Lapachol                Beta-Lapachone

β-lapachone, as well as its intermediates, derivatives and analogs thereof, are described in Li, C. J. et al., (1993) *J. Biol. Chem.*, 268(30): 22463-22468. As a single agent, β-lapachone has demonstrated significant antineoplastic activity against human cancer cell lines at concentrations typically in the range of 1-10 μM (IC$_{50}$). Cytotoxicity has been demonstrated in transformed cell lines derived from patients with promyelocytic leukemia (Planchon et al., (1996) *Cancer Res.*, 55: 3706-3711), prostate (Li, C. J., et al., (1995) *Cancer Res.*, 55: 3712-3715), malignant glioma (Weller, M. et al., (1997) *Int. J. Cancer*, 73: 707-714), hepatoma (Lai, C. C., et al., (1998) *Histol Histopathol*, 13: 89-97), colon (Huang, L., et al., (1999) *Mol Med*, 5,: 711-720), breast (Wuertzberger, S. M., et al., (1998) *Cancer Res.*, 58: 1876), ovarian (Li, C. J. et al., (1999) *Proc. Natl. Acad. Sci. USA*, 96(23): 13369-13374), pancreatic (Li, Y., et al., (2000) *Mol Med*, 6: 1008-1015; Li, Y., (1999) *Mol Med*, 5: 232-239), and multiple myeloma cell lines, including drug-resistant lines (Li, Y., (2000) *Mol Med*, 6: 1008-1015). No cytotoxic effects were observed on normal fresh or proliferating human PBMC (Li, Y., (2000) *Mol Med*, 6:1008-1015).

β-lapachone appears to work by activating DNA damage response/checkpoint pathways, which may involve unscheduled expression of checkpoint molecules, e.g. E2F1, independent of DNA damage and cell cycle stages. Several studies have shown that β-lapachone activates checkpoint pathways and induces cell death in cancer cells from a variety of tissues without cell death of normal cells from these tissues (U.S. Patent Application Publication No. 2002/0169135, incorporated by reference herein). In normal cells with their intact regulatory mechanisms, such an imposed expression of a checkpoint molecule results in a transient expression pattern and causes little consequence. In contrast, cancer and pre-cancer cells have defective mechanisms, which result in unchecked and persistent expression of unscheduled checkpoint molecules, e.g. E2F1, leading to selective cell death in cancer and pre-cancer cells.

In addition to β-lapachone, a number of β-lapachone analogs having antiproliferative properties have been disclosed in the art, such as those described in PCT International Application PCT/US93/07878 (WO94/04145), which is incorporated by reference herein, and U.S. Pat. No. 6,245,807, incorporated by reference herein, in which a variety of substituents may be attached at positions 3- and 4-on the β-lapachone compound. PCT International Application PCT/US00/10169 (WO 00/61142), incorporated by reference herein, discloses β-lapachone, which may have a variety of substituents at the 3-position as well as in place of the methyl groups attached at the 2-position. U.S. Pat. Nos. 5,763,625, 5,824,700, and 5,969,163, each of which is incorporated by reference herein, disclose analogs and derivatives with a variety of substituents at the 2-, 3- and 4-positions. Furthermore, a number of journals report β-lapachone analogs and derivatives with substitutents at one or more of the following positions: 2-, 3-, 8- and/or 9-positions, (See, Sabba et al., (1984) *J Med Chem* 27:990-994 (substituents at the 2-, 8- and 9-positions); (Portela and Stoppani, (1996) *Biochem Pharm* 51:275-283 (substituents at the 2- and 9-positions); Goncalves et al., (1998) *Molecular and Biochemical Parasitology* 1:167-176 (substituents at the 2- and 3-positions)).

Moreover, U.S. Patent Application Publication No. 2004/0266857 and PCT Intentional Application PCT/US2003/037219 (WO 04/045557), incorporated in by reference herein, disclose and several journal reports describe structures having sulfur-containing hetero-rings in the "α" and "β" positions of lapachone (Kurokawa S, (1970) *Bulletin of The Chemical Society of Japan* 43:1454-1459; Tapia, R A et al., (2000) *Heterocycles* 53(3):585-598; Tapia, R A et al., (1997) *Tetrahedron Letters* 38(1):153-154; Chuang, C P et al., (1996) *Heterocycles* 40(10):2215-2221; Suginome H et al., (1993) *Journal of the Chemical Society, Chemical Communications* 9:807-809; Tonholo J et al., (1988) *Journal of the Brazilian Chemical Society* 9(2):163-169; and Krapcho A P et al., (1990) *Journal of Medicinal Chemistry* 33(9):2651-2655).

The references cited herein are not admitted to be prior art to the claimed invention.

SUMMARY OF THE INVENTION

The present invention provides a compound of Formula I:

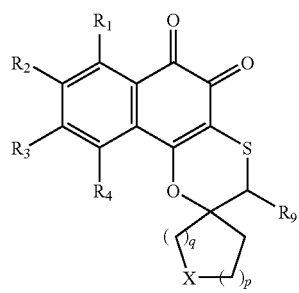

(I)

or a pharmaceutically acceptable salt and/or an individual diastereomer thereof,
wherein:
X=N-J$_1$,

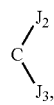

O, or S;
p=0, 1 or 2;
q=p or p+1, provided that if p is 0, q does not equal p;

$R_1$, $R_2$, $R_3$, and $R_4$, are each, independently, H, OH, F, Cl, Br, I, $CH_3$, $CF_3$, $C_2$-$C_6$ straight chain alkyl, substituted $C_1$-$C_6$ straight chain alkyl, $C_3$-$C_6$ branched alkyl, $C_3$-$C_8$ cycloalkyl, allyl, $C_2$-$C_6$ straight chain alkenyl, substituted $C_2$-$C_6$ straight chain alkenyl, $C_3$-$C_6$ branched alkenyl, $C_5$-$C_8$ cycloalkenyl, $C_2$-$C_6$ alkynyl, $NO_2$, CN, $NH_2$, alkylamine, substituted alkylamine, dialkylamine, arylamine, $C(O)NHR_{14}$, $NHC(O)R_{15}$, carbamoyl, aminesulfoxide, sulfonamide, sulfamoyl, sulfonic acid, phenyl, $C_5$-$C_8$ aryl, heteroaryl, heterocyclyl, $OCH_3$, $OCF_3$, $C_2$-$C_6$ alkoxy, alkoxycarbonyl, carboxyacid, carbonylalkoxy, SH, thioalkyl, thioaryl, alkylthioaryl, or $C_1$-$C_6$ hydroxyl alkyl;

$J_1$ is $-(CR_5R_6)_n-(CR_7R_8)_m-Y$, $-S(O)_o$-Z, amidine, substituted amidine, heterocyclyl, substituted heterocyclyl, 3,4-dioxo-3,4-dihydronaphthalenyl, heteroaryl, substituted heteroaryl, or

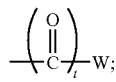

m=0, 1, 2, 3, 4, or 5;
n=0, 1, 2, 3, 4, or 5;
o=1 or 2;
t=1 or 2;

$R_5$ and $R_6$ are each, independently, H, OH, $CH_3$, $CF_3$, $C_2$-$C_6$ straight chain alkyl, $C_3$-$C_6$ branched alkyl, $C_3$-$C_8$ cycloalkyl, allyl, $C_2$-$C_6$ straight chain alkenyl, $C_3$-$C_6$ branched alkenyl, $C_5$-$C_8$ cycloalkenyl, $C_2$-$C_6$ alkynyl, phenyl, $C_5$-$C_8$ aryl, heteroaryl, heterocyclyl, carboxylate, or carbonylalkoxy; when $R_5$=$R_6$, $R_5$ cannot be OH, $NH_2$, SH, or $NO_2$;

$R_7$ and $R_8$ are each, independently, H, F, Cl, Br, I, OH, $CH_3$, $C_2$-$C_6$ straight chain alkyl, $CF_3$, $C_3$-$C_6$ branched alkyl, $C_3$-$C_8$ cycloalkyl, $C_2$-$C_6$ alkoxy, allyl, $C_2$-$C_6$ straight chain alkenyl, $C_3$-$C_6$ branched alkenyl, $C_5$-$C_8$ cycloalkenyl, $C_2$-$C_6$ alkynyl, $NO_2$, CN, amine, alkylamine, dialkylamine, arylamine, carbamoyl, aminesulfoxide, sulfonamide, sulfonic acid, phenyl, $C_5$-$C_8$ aryl, heteroaryl, heterocyclyl, $OCH_3$, $OCF_3$, alkoxycarbonyl, carboxyacid, carbonylalkoxy, SH, thioalkyl, thioaryl, or alkylthioaryl; when $R_7$=$R_8$, $R_7$ is not OH, $NH_2$, SH, or $NO_2$;

Y is H, F, Cl, Br, I, $CR_{10}$=$CHR_{11}$, $CF_3$, $CH_3$, $C_2$-$C_6$ straight chain alkyl, substituted $C_2$-$C_6$ straight chain alkyl, $C_3$-$C_6$ branched alkyl, $CH_2OR_{16}$, phenyl, substituted phenyl, $C_5$-$C_8$ aryl, substituted $C_5$-$C_8$ aryl, $C_3$-$C_8$ cycloalkyl, substituted $C_3$-$C_8$ cycloalkyl, $CH_2$-heterocycle, $C_5$-$C_8$ cycloalkenyl, aryloxy, substituted aryloxy, heteroaryl, substituted heteroaryl, heterocyclyl, substituted heterocyclyl, benzyl, alkylamine, substituted alkylamine, benzylamine, OH, $CH_3$, $CF_3$, $OCR_{12}$=$CHR_{13}$, $C_2$-$C_6$ alkynyl, amine, dialkylamine, arylamine, amide, carbamoyl, aminesulfoxide, sulfamide, sulfamoyl, sulfonic acid, heteroaryloxy, $OCH_3$, $OCF_3$, $C_2$-$C_6$ alkoxy, alkenoxy, phenoxy, benzyloxy, alkoxycarbonyl, carboxyacid, carboxyalkoxy, carbonylalkyl, thio, alkylthio, thioalkyl, arylthio, thioaryl, alkylthioaryl, or

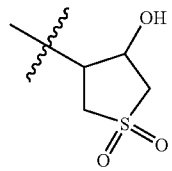

provided that, when n=0 and m=0, Y is H, heterocyclyl, heteroaryl, $C_3$-$C_8$ cycloalkyl, $C_5$-$C_8$ cycloalkyl, aryl, or

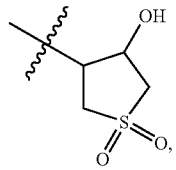

each of which may be substituted; if m=n=o, Y is not

W is $C_2$-$C_6$ straight chain alkyl, substituted $C_1$-$C_6$ straight chain alkyl, $OCH_3$, $C_2$-$C_6$ alkoxy, alkylthioalkyl, substituted alkylthioalkyl, $C_3$-$C_8$ cycloalkyl, substituted $C_3$-$C_8$ cycloalkyl, $C_5$-$C_8$ aryl, substituted aryl, phenyl, substituted phenyl, $CR_{10}$=$CHR_{11}$, alkylthio, benzyl, substituted benzyl, heterocyclyl, substituted heterocyclyl, phenoxy, aryloxy, substituted aryloxy, $OCR_{12}$=$CHR_{13}$, benzyloxy, heteroaryloxy, substituted heteroaryloxy, amine, substituted amine, arylamine, substituted arylamine, phenylamine, substituted phenylamine, $CH_3$, $CF_3$, $C_3$-$C_6$ branched alkyl, $C_5$-$C_8$ cycloalkenyl, $C_2$-$C_6$ alkynyl, alkylamine, dialkylamine, heteroaryl, $CH_2$-heterocyclyl, $CH_2$-substituted heterocyclyl, $OCF_3$, alkenoxy, $CH_2OR_{16}$, thioalkyl, arylthio, thioaryl, alkylthioaryl or alkylcarboxy, phenyl sulfonylamide, or substituted aryl sulfonylamide, chlorophenylacetyl;

Z is $CH_3$, $CF_3$, $C_2$-$C_6$ straight chain alkyl, heteroaryl, substituted heteroaryl, phenyl, substituted phenyl, $C_5$-$C_8$ aryl, substituted $C_5$-$C_8$ aryl, $C_3$-$C_6$ branched alkyl, $C_3$-$C_8$ cycloalkyl, $C_5$-$C_8$ cycloalkenyl, $C_2$-$C_6$ alkynyl, amine, alkylamine, dialkylamine, arylamine, benzyl, heteroaryloxy, heterocyclyl, $CH_2$-heterocycle, $OCH_3$, $OCF_3$, $C_2$-$C_6$ alkoxy, alkenoxy, phenoxy, aryloxy or benzyloxy;

$R_9$ is H, $CH_3$, $C_2$-$C_6$ straight chain alkyl, or $C_3$-$C_6$ branched alkyl;

$R_{10}$, $R_{11}$, $R_{12}$, and $R_{13}$ are each, independently, H, phenyl, $C_5$-$C_8$ aryl, $CH_3$, $CF_3$, $C_2$-$C_6$ straight chain alkyl, $C_3$-$C_8$ cycloalkyl, heteroaryl, or heterocyclyl;

$R_{14}$ and $R_{15}$ are each, independently H, $C_2$-$C_6$ straight alkyl, $C_3$-$C_6$ branched alkyl, $C_3$-$C_8$ cycloalkyl, allyl, $C_2$-$C_6$ straight alkenyl, branched alkenyl, $C_5$-$C_8$ cycloalkenyl, phenyl, $C_5$-$C_8$ aryl, benzyl, $CH_2C(OCH_3)_2$, heteroaryl, or heterocyclyl; and, $R_{16}$ is $C_3$-$C_6$ branched alkyl, $C_5$-$C_8$ aryl, substituted $C_5$-$C_8$ aryl, heteroaryl, phenyl, substituted phenyl, $CH_2$-aryl, benzyl, H, $CH_3$, $CF_3$, $C_2$-$C_6$ straight chain alkyl, $C_3$-$C_8$ cycloalkyl, heterocyclyl, or $CH_2$-heteroaryl.

$J_2$ and $J_3$ are each, independently, H, F, Cl, Br, I, $CR_{17}$=$CHR_{18}$, $CF_3$, $CH_3$, $C_2$-$C_6$ straight chain alkyl, substituted $C_1$-$C_6$ straight chain alkyl, $C_3$-$C_6$ branched alkyl, $CH_2OR_{21}$, phenyl, $C_5$-$C_8$ aryl, substituted $C_5$-$C_8$ aryl, $C_3$-$C_8$ cycloalkyl, substituted $C_3$-$C_8$ cycloalkyl, $CH_2$-heterocycle, $C_5$-$C_8$ cycloalkenyl, aryloxy, substituted aryloxy, heteroaryl, substituted heteroaryl, heterocyclyl, substituted heterocyclyl, benzyl, alkylamine, substituted alkylamine, benzylamine, OH, $CH_3$, $CF_3$, $OCR_{19}$=$CHR_{20}$, $C_2$-$C_6$ alkynyl, amine, dialkylamine, arylamine, amide, carbamoyl, aminesulfoxide, sulfamide, sulfamoyl, sulfonic acid, heteroaryloxy, $OCH_3$, $OCF_3$, $C_2$-$C_6$ alkoxy, alkenoxy, phenoxy, benzyloxy, alkoxycarbonyl, carboxyacid, carboxyalkoxy, carbonylalkyl, thio, alkylthio, thioalkyl, arylthio, thioaryl, alkylthioaryl, or

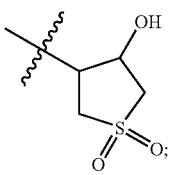

when $J_2=J_3$, $J_2$ is not OH, $NH_2$, SH, or $NO_2$; $J_2$ and $J_3$ can form a 4, 5; 6, 7, 8 membered spiro ring containing 0, 1, or 2 heteroatoms such as O, N, S;

$R_{17}$, $R_{18}$, $R_{19}$, and $R_{20}$ are each, independently, H, phenyl, $C_5$-$C_8$ aryl, $CH_3$, $CF_3$, $C_2$-$C_6$ straight chain alkyl, $C_3$-$C_8$ cycloalkyl, heteroaryl, or heterocyclyl;

$R_{21}$ is H, $C_2$-$C_6$ straight alkyl, $C_3$-$C_6$ branched alkyl, $C_3$-$C_8$ cycloalkyl, allyl, $C_2$-$C_6$ straight alkenyl, branched alkenyl, $C_5$-$C_8$ cycloalkenyl, phenyl, $C_5$-$C_8$ aryl, benzyl, $CH_2C(OCH_3)_2$, heteroaryl, or heterocyclyl.

In an embodiment, p=1 and q=1. In another embodiment, p=1 and q=2. In another embodiment, p=2 and q=2. In another embodiment, p=2 and q=3. In another embodiment, p=0 and q=1.

In an embodiment, $R_1$, $R_2$, $R_3$, and $R_4$ are each, independently, H, OH, F, Cl, Br, I, $CH_3$, $CF_3$, $OCH_3$, $C_2$-$C_6$ alkoxy, $C_2$-$C_6$ straight chain alkyl, substituted $C_2$-$C_6$ straight chain alkyl, phenyl, $C_5$-$C_8$ aryl, $NO_2$, CN, C(O)$NHR_{14}$ or NHC(O)$R_{15}$. In a further embodiment, $R_1$, $R_2$, $R_3$, and $R_4$ are each, independently, H, OH, F, Cl, Br, I, $CH_3$, $CF_3$, $OCH_3$, $C_2$-$C_6$ alkoxy. In an even further embodiment, $R_1$, $R_2$, $R_3$, and $R_4$ are each, independently, H or $OCH_3$. In an even further embodiment, $R_1$, $R_2$ and $R_4$ are each H and $R_3$ is $OCH_3$.

In an embodiment, X=O or S. In another embodiment

In another embodiment, X=N-$J_1$.

In an embodiment, $J_1$ is —$(CR_5R_6)_n$—$(CR_7R_8)_m$—Y.

In an embodiment, n=0 and m=0. In another embodiment, n=1 and m=0. In another embodiment, n=1 and m=1. In another embodiment, n=1 and m=2. In another embodiment, n=5 and m=5.

In an embodiment, $R_5$ and $R_6$ are each, independently, H or $CH_3$.

In an embodiment, $R_7$ and $R_8$ are each, independently, H, F, Cl, Br, I, OH, $CH_3$, $C_2$-$C_6$ straight chain alkyl, $CF_3$, $C_3$-$C_6$ branched alkyl, $C_3$-$C_8$ cycloalkyl, or $C_2$-$C_6$ alkoxy. In a further embodiment, $R_7$ and $R_8$ are each, independently, H or OH.

In an embodiment, Y is $CH_2OR_{16}$, phenyl, substituted $C_5$-$C_8$ aryl or benzyl.

In an embodiment, $R_5$ and $R_6$ are each H. In a further embodiment, Y is substituted or unsubstituted $C_5$-$C_8$ aryl. In an even further embodiment, the substituted $C_5$-$C_8$ aryl is substituted with from 1 to 5 substituents each of which is independently CN, Cl or F.

In an embodiment, $R_5$ and $R_6$ are each H and $R_7$ and $R_8$ are each, independently, H or OH. In a further embodiment, Y is $CH_2OR_{16}$. In a further embodiment, $R_{16}$ is substituted or unsubstituted $C_5$-$C_8$ aryl. In an even further embodiment, the substituted $C_5$-$C_8$ aryl is substituted with from 1 to 5 substituents each of which is independently $C_3$-$C_6$ branched alkyl, Cl, or F.

In an embodiment, $J_1$ is —S(O)$_o$-Z. In a further embodiment, o=1. In an alternative embodiment, o=2. In an embodiment, Z is $CH_3$, $CF_3$, $C_2$-$C_6$ straight chain alkyl, heteroaryl, substituted heteroaryl, phenyl, substituted phenyl, $C_5$-$C_8$ aryl, or substituted $C_5$-$C_8$ aryl.

In an embodiment, $J_1$ is

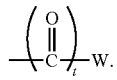

In an embodiment, t=1. In a further embodiment, W is substituted aryl, phenyl, phenoxy, aryloxy and substituted aryloxy. In an even further embodiment, the aryl and aryloxy is substituted with from 1 to 5 substituents each of which is independently CF3 or F.

In an alternative embodiment, t=2. In a further embodiment, t=2 and W is $C_2$-$C_6$ alkoxy.

In an embodiment, $R_9$ is H.
In an embodiment, $R_{10}$ and $R_{11}$ are both H.
In an embodiment, $R_{12}$ and $R_{13}$ are both H.
In an embodiment, $R_{12}$ is H and $R_{13}$ is phenyl.
In an embodiment, $R_{16}$ is $C_3$-$C_6$ branched alkyl, $C_5$-$C_8$ aryl, substituted $C_5$-$C_8$ aryl, heteroaryl, phenyl, substituted phenyl, $CH_2$-aryl, or benzyl.

In an embodiment, the compound of the present invention is selected from the following compounds, or a pharmaceutically acceptable salt and/or an individual diastereomer thereof:

1'-(3-chlorobenzoyl)spiro[naphtho[1,2-b][1,4]oxathiine-2,4'-piperidine]-5,6-dione (Compound 55);

1'-(3,4-dichlorobenzoyl)spiro[naphtho[1,2-b][1,4]oxathiine-2,4'-piperidine]-5,6-dione (Compound 53);

4-[(5,6-dioxo-5,6-dihydro-1'H-spiro[naphtho[1,2-b][1,4]oxathiine-2,4'-piperidine]-1'-yl)methyl]benzonitrile (Compound 123);

1'-(2-phenylethyl)spiro[naphtho[1,2-b][1,4]oxathiine-2,4'-piperidine]-5,6-dione (Compound 155);

1'-(4-fluorobenzyl)spiro[naphtho[1,2-b][1,4]oxathiine-2,4'-piperidine]-5,6-dione (Compound 125);

1'-[3-(4-tert-butylphenoxy)-2-hydroxypropyl]spiro[naphtho[1,2-b][1,4]oxathiine-2,4'-piperidine]-5,6-dione (Compound 157);

1'-(2-hydroxy-3-phenylpropyl)spiro[naphtho[1,2-b][1,4]oxathiine-2,4'-piperidine]-5,6-dione (Compound 163);

3-(trifluoromethyl)phenyl 5,6-dioxo-5,6-dihydro-1'H-spiro[naphtho[1,2-b][1,4]oxathiine-2,4'-piperidine]-1'-carboxylate (Compound 96);

4-fluorophenyl 5,6-dioxo-5,6-dihydro-1'H-spiro[naphtho[1,2-b][1,4]oxathiine-2,4'-piperidine]-1'-carboxylate (Compound 97);

1'-(2-chloro-6-fluorobenzyl)spiro[naphtho[1,2-b][1,4]oxathiine-2,4'-piperidine]-5,6-dione (Compound 129);

1'-(3-chloro-4-fluorobenzyl)spiro[naphtho[1,2-b][1,4]oxathiine-2,4'-piperidine]-5,6-dione (Compound 142);

1'-(3-phenoxypropyl)spiro[naphtho[1,2-b][1,4]oxathiine-2,4'-piperidine]-5,6-dione (Compound 144);

1'-[2-(4-chlorophenoxy)ethyl]spiro[naphtho[1,2-b][1,4]oxathiine-2,4'-piperidine]-5,6-dione (Compound 145);

1'-[(2S)-3-(4-fluorophenoxy)-2-hydroxypropyl]spiro[naphtho[1,2-b][1,4]oxathiine-2,4'-piperidine]-5,6-dione (Compound 180);

1'-[(2S)-3-(4-tert-butylphenoxy)-2-hydroxypropyl]spiro[naphtho[1,2-b][1,4]oxathiine-2,4'-piperidine]-5,6-dione (Compound 184);

1'-[(2R)-3-(4-tert-butylphenoxy)-2-hydroxypropyl]spiro[naphtho[1,2-b][1,4]oxathiine-2,4'-piperidine]-5,6-dione (Compound 185);

1'-[(2R)-3-(4-fluorophenoxy)-2-hydroxypropyl]spiro[naphtho[1,2-b][1,4]oxathiine-2,4'-piperidine]-5,6-dione (Compound 181);

1'-[(2S)-3-(4-chlorophenoxy)-2-hydroxypropyl]spiro[naphtho[1,2-b][1,4]oxathiine-2,4'-piperidine]-5,6-dione (Compound 182);

1'-[(2R)-3-(4-chlorophenoxy)-2-hydroxypropyl]spiro[naphtho[1,2-b][1,4]oxathiine-2,4'-piperidine]-5,6-dione (Compound 183);

1'-[(2R)-2-hydroxy-3-phenylpropyl]spiro[naphtho[1,2-b][1,4]oxathiine-2,4'-piperidine]-5,6-dione (Compound 186);

1'-[(2S)-2-hydroxy-3-phenylpropyl]spiro[naphtho[1,2-b][1,4]oxathiine-2,4'-piperidine]-5,6-dione (Compound 187);

1'-[(2S)-2-hydroxy-3-(2-methylphenoxy)propyl]spiro[naphtho[1,2-b][1,4]oxathiine-2,4'-piperidine]-5,6-dione (Compound 200);

1'-isopropylspiro[naphtho[1,2-b][1,4]oxathiine-2,4'-piperidine]-5,6-dione (Compound 152);

1'-[(2S)-3-(4-ethylphenoxy)-2-hydroxypropyl]spiro[naphtho[1,2-b][1,4]oxathiine-2,4'-piperidine]-5,6-dione (Compound 207);

1'-[(2R)-3-(4-ethylphenoxy)-2-hydroxypropyl]spiro[naphtho[1,2-b][1,4]oxathiine-2,4'-piperidine]-5,6-dione (Compound 228);

1'-[(2R)-2-hydroxy-3-(2-methylphenoxy)propyl]spiro[naphtho[1,2-b][1,4]oxathiine-2,4'-piperidine]-5,6-dione (Compound 224).

The present invention also provides a pharmaceutical composition that comprises a compound of Formula I in combination with a pharmaceutically acceptable carrier or excipient. In an embodiment, the pharmaceutical composition further comprises a second chemotherapeutic agent. In a further embodiment, said second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

The present invention further provides a method of treating a cell proliferative disorder. The method comprises administering to a subject in need thereof a therapeutically effective amount of a compound of formula I as defined in claim 1, or a pharmaceutically acceptable salt thereof, or a prodrug or metabolite thereof, in combination with a pharmaceutically acceptable carrier, wherein said cell proliferative disorder is treated.

In an embodiment, the cell proliferative disorder is a pre-cancerous condition.

In another embodiment, the cell proliferative disorder is a cancer. In an embodiment, the cancer is adenocarcinoma, squamous carcinoma, sarcoma, lymphoma, multiple myeloma, or leukemia. In a further embodiment, the cancer is lung cancer, colon cancer, breast cancer, pancreatic cancer, prostate cancer, acute leukemia, chronic leukemia, multiple melanoma, ovarian cancer, malignant glioma, leiomyosarcoma, hepatoma, or head and neck cancer.

In an embodiment, the compound of formula I or a pharmaceutically acceptable salt thereof, or a prodrug or metabolite thereof, is administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In an embodiment, the treating cancer comprises a reduction in tumor size, a delay of tumor growth, an improvement in the survival of patients, or an improvement in the quality of patient life, or at least two of the above.

In another embodiment, the cancer is primary cancer or metastatic cancer, or both.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 shows that the treatments with the test compounds reduced the mean tumor volume of human colon cancer xenograft.

DETAILED DESCRIPTION OF THE INVENTION

1. The Lapachone Compounds

Figure 1A:
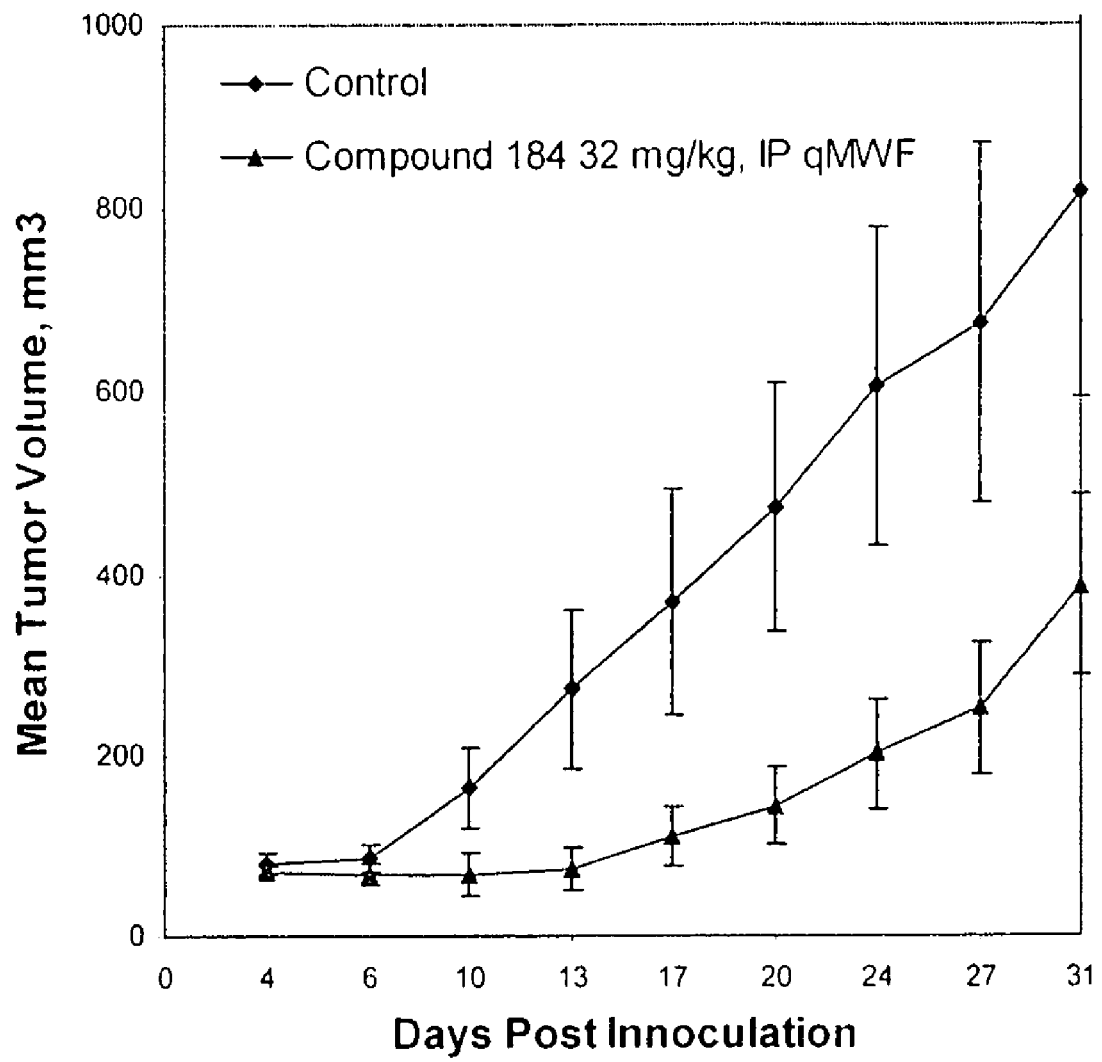
FIG. 1A shows the treatment with Compound 184

The present invention provides novel tricyclic spiro-oxathiine naphthoquinone derivatives, a synthetic method for making the derivatives, and the use of the derivatives to inhibit proliferation and/or inducing cell death of neoplastic cells. The naphthoquinone derivatives of the present invention are related to the compounds known as β-lapachone (3,4-dihydro-2,2-dimethyl-2H-naphtho(1,2-b)pyran-5,6-dione). The structure of β-lapachone is described above.

The β-lapachone analogs of the present invention include spiro-oxathiine hetero-rings. There are no known naphthoquinone derivatives that have dihydrospiro-oxathiine hetero-rings in the "β" position, i.e. analogous to the positioning for the tetrahydropyran ring in β-lapachone.

In one embodiment, the present invention provides the compounds of Formula I:

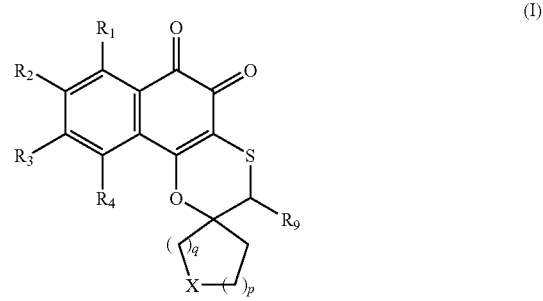

(I)

or a pharmaceutically acceptable salt and/or an individual diastereomer thereof, wherein:

X=N-J$_1$,

O, or S;

p=0, 1 or 2;

q=p or p+1, provided that if p is 0, q does not equal p;

R$_1$, R$_2$, R$_3$, and R$_4$, are each, independently, H, OH, F, Cl, Br, I, CH$_3$, CF$_3$, C$_2$-C$_6$ straight chain alkyl, substituted C$_1$-C$_6$ straight chain alkyl, C$_3$-C$_6$ branched alkyl, C$_3$-C$_8$ cycloalkyl, allyl, C$_2$-C$_6$ straight chain alkenyl, substituted C$_2$-C$_6$ straight chain alkenyl, C$_3$-C$_6$ branched alkenyl, C$_5$-C$_8$ cycloalkenyl, C$_2$-C$_6$ alkynyl, NO$_2$, CN, NH$_2$, alkylamine, substituted alkylamine, dialkylamine, arylamine, C(O)NHR$_{14}$, NHC(O)R$_{15}$, carbamoyl, aminesulfoxide, sulfonamide, sulfamoyl, sulfonic acid, phenyl, C$_5$-C$_8$ aryl, heteroaryl, heterocyclyl, OCH$_3$, OCF$_3$, C$_2$-C$_6$ alkoxy, alkoxycarbonyl, carboxyacid, carbonylalkoxy, SH, thioalkyl, thioaryl, alkylthioaryl, or C$_1$-C$_6$ hydroxyl alkyl;

J$_1$ is —(CR$_5$R$_6$)$_n$—(CR$_7$R$_8$)$_m$, —Y, —S(O)$_o$-Z, amidine, substituted amidine, heterocyclyl, substituted heterocyclyl, 3,4-dioxo-3,4-dihydronaphthalenyl, heteroaryl, substituted heteroaryl, or

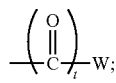

m=0, 1, 2, 3, 4, or 5;
n=0, 1, 2, 3, 4, or 5;
o=1 or 2;
t=1 or 2;

R$_5$ and R$_6$ are each, independently, H, OH, CH$_3$, CF$_3$, C$_2$-C$_6$ straight chain alkyl, C$_3$-C$_6$ branched alkyl, C$_3$-C$_8$ cycloalkyl, allyl, C$_2$-C$_6$ straight chain alkenyl, C$_3$-C$_6$ branched alkenyl, C$_5$-C$_8$ cycloalkenyl, C$_2$-C$_6$ alkynyl, phenyl, C$_5$-C$_8$ aryl, heteroaryl, heterocyclyl, carboxylate, or carbonylalkoxy; when R$_5$=R$_6$, R$_5$ cannot be OH, NH$_2$, SH, or NO$_2$;

R$_7$ and R$_8$ are each, independently, H, F, Cl, Br, I, OH, CH$_3$, C$_2$-C$_6$ straight chain alkyl, CF$_3$, C$_3$-C$_6$ branched alkyl, C$_3$-C$_8$ cycloalkyl, C$_2$-C$_6$ alkoxy, allyl, C$_2$-C$_6$ straight chain alkenyl, C$_3$-C$_6$ branched alkenyl, C$_5$-C$_8$ cycloalkenyl, C$_2$-C$_6$ alkynyl, NO$_2$, CN, amine, alkylamine, dialkylamine, arylamine, carbamoyl, aminesulfoxide, sulfonamide, sulfonic acid, phenyl, C$_5$-C$_8$ aryl, heteroaryl, heterocyclyl, OCH$_3$, OCF$_3$, alkoxycarbonyl, carboxyacid, carbonylalkoxy, SH, thioalkyl, thioaryl, or alkylthioaryl; when R$_7$=R$_8$, R$_7$ is not OH, NH$_2$, SH, or NO$_2$;

Y is H, F, Cl, Br, I, CR$_{10}$=CHR$_{11}$, CF$_3$, CH$_3$, C$_2$-C$_6$ straight chain alkyl, substituted C$_2$-C$_6$ straight chain alkyl, C$_3$-C$_6$ branched alkyl, CH$_2$OR$_{16}$, phenyl, substituted phenyl, C$_5$-C$_8$ aryl, substituted C$_5$-C$_8$ aryl, C$_3$-C$_8$ cycloalkyl, substituted C$_3$-C$_8$ cycloalkyl, CH$_2$-heterocycle, C$_5$-C$_8$ cycloalkenyl, aryloxy, substituted aryloxy, heteroaryl, substituted heteroaryl, heterocyclyl, substituted heterocyclyl, benzyl, alkylamine, substituted alkylamine, benzylamine, OH, CH$_3$, CF$_3$, OCR$_{12}$=CHR$_{13}$, C$_2$-C$_6$ alkynyl, amine, dialkylamine, arylamine, amide, carbamoyl, aminesulfoxide, sulfamide, sulfamoyl, sulfonic acid, heteroaryloxy, OCH$_3$, OCF$_3$, C$_2$-C$_6$ alkoxy, alkenoxy, phenoxy, benzyloxy, alkoxycarbonyl, carboxyacid, carboxyalkoxy, carbonylalkyl, thio, alkylthio, thioalkyl, arylthio, thioaryl, alkylthioaryl, or

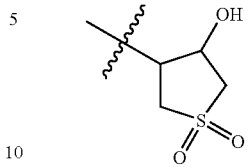

provided that, when n=0 and m=0, Y is H, heterocyclyl, heteroaryl, C$_3$-C$_8$ cycloalkyl, C$_5$-C$_8$ cycloalkyl, aryl, or

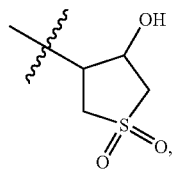

each of which may be substituted;

W is C$_2$-C$_6$ straight chain alkyl, substituted C$_1$-C$_6$ straight chain alkyl, OCH$_3$, C$_2$-C$_6$ alkoxy, alkylthioalkyl, substituted alkylthioalkyl, C$_3$-C$_8$ cycloalkyl, substituted C$_3$-C$_8$ cycloalkyl, C$_5$-C$_8$ aryl, substituted aryl, phenyl, substituted phenyl, CR$_{10}$=CHR$_{11}$, alkylthio, benzyl, substituted benzyl, heterocyclyl, substituted heterocyclyl, phenoxy, aryloxy, substituted aryloxy, OCR$_{12}$=CHR$_{13}$, benzyloxy, heteroaryloxy, substituted heteroaryloxy, amine, substituted amine, arylamine, substituted arylamine, phenylamine, substituted phenylamine, CH$_3$, CF$_3$, C$_3$-C$_6$ branched alkyl, C$_5$-C$_8$ cycloalkenyl, C$_2$-C$_6$ alkynyl, alkylamine, dialkylamine, heteroaryl, CH$_2$-heterocyclyl, CH$_2$-substituted heterocyclyl, OCF$_3$, alkenoxy, CH$_2$OR$_{16}$, thioalkyl, arylthio, thioaryl, alkylthioaryl or alkylcarboxy, phenyl sulfonylamide, or substituted aryl sulfonylamide, chlorophenylacetyl;

Z is CH$_3$, CF$_3$, C$_2$-C$_6$ straight chain alkyl, heteroaryl, substituted heteroaryl, phenyl, substituted phenyl, C$_5$-C$_8$ aryl, substituted C$_5$-C$_8$ aryl, C$_3$-C$_6$ branched alkyl, C$_3$-C$_8$ cycloalkyl, C$_5$-C$_8$ cycloalkenyl, C$_2$-C$_6$ alkynyl, amine, alkylamine, dialkylamine, arylamine, benzyl, heteroaryloxy, heterocyclyl, CH$_2$-heterocycle, OCH$_3$, OCF$_3$, C$_2$-C$_6$ alkoxy, alkenoxy, phenoxy, aryloxy or benzyloxy;

R$_9$ is H, CH$_3$, C$_2$-C$_6$ straight chain alkyl, or C$_3$-C$_6$ branched alkyl;

R$_{10}$, R$_{11}$, R$_{12}$, and R$_{13}$ are each, independently, H, phenyl, C$_5$-C$_8$ aryl, CH$_3$, CF$_3$, C$_2$-C$_6$ straight chain alkyl, C$_3$-C$_8$ cycloalkyl, heteroaryl, or heterocyclyl;

R$_{14}$ and R$_{15}$ are each, independently H, C$_2$-C$_6$ straight alkyl, C$_3$-C$_6$ branched alkyl, C$_3$-C$_8$ cycloalkyl, allyl, C$_2$-C$_6$ straight alkenyl, branched alkenyl, C$_5$-C$_8$ cycloalkenyl, phenyl, C$_5$-C$_8$ aryl, benzyl, CH$_2$C(OCH$_3$)$_2$, heteroaryl, or heterocyclyl; and, R$_{16}$ is C$_3$-C$_6$ branched alkyl, C$_5$-C$_8$ aryl, substituted C$_5$-C$_8$ aryl, heteroaryl, phenyl, substituted phenyl, CH$_2$-aryl, benzyl, H, CH$_3$, CF$_3$, C$_2$-C$_6$ straight chain alkyl, C$_3$-C$_8$ cycloalkyl, heterocyclyl, or CH$_2$-heteroaryl.

J$_2$ and J$_3$ are each, independently, H, F, Cl, Br, I, CR$_{17}$=CHR$_{18}$, CF$_3$, CH$_3$, C$_2$-C$_6$ straight chain alkyl, substituted C$_1$-C$_6$ straight chain alkyl, C$_3$-C$_6$ branched alkyl, CH$_2$OR$_{21}$, phenyl, C$_5$-C$_8$ aryl, substituted C$_5$-C$_8$ aryl, C$_3$-C$_8$ cycloalkyl, substituted C$_3$-C$_8$ cycloalkyl, CH$_2$-heterocycle, C$_5$-C$_8$ cycloalkenyl, aryloxy, substituted aryloxy, heteroaryl, substituted heteroaryl, heterocyclyl, substituted heterocyclyl, benzyl, alkylamine, substituted alkylamine, benzylamine, OH, CH$_3$, CF$_3$, OCR$_{19}$=CHR$_{20}$, C$_2$-C$_6$ alkynyl, amine, dialkylamine, arylamine, amide, carbamoyl, aminesulfoxide, sulfamide, sulfamoyl, sulfonic acid, heteroaryloxy, OCH₃, OCF₃, C₂-C₆ alkoxy, alkenoxy, phenyloxy, benzyloxy, alkoxycarbonyl, carboxyacid, carboxyalkoxy, carbonylalkyl, thio, alkylthio, thioalkyl, arylthio, thioaryl, alkylthioaryl, or

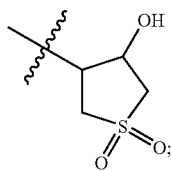

when $J_2=J_3$, $J_2$ is not OH, NH₂, SH, or NO₂; $J_2$ and $J_3$ can form a 4, 5; 6, 7, 8 membered spiro ring containing 0, 1, or 2 heteroatoms such as O, N, S;

$R_{17}$, $R_{18}$, $R_{19}$, and $R_{20}$ are each, independently, H, phenyl, $C_5$-$C_8$ aryl, CH₃, CF₃, $C_2$-$C_6$ straight chain alkyl, $C_3$-$C_8$ cycloalkyl, heteroaryl, or heterocyclyl;

$R_{21}$ is H, $C_2$-$C_6$ straight alkyl, $C_3$-$C_6$ branched alkyl, $C_3$-$C_8$ cycloalkyl, allyl, $C_2$-$C_6$ straight alkenyl, branched alkenyl, $C_5$-$C_8$ cycloalkenyl, phenyl, $C_5$-$C_8$ aryl, benzyl, CH₂C(OCH₃)₂, heteroaryl, or heterocyclyl.

In one embodiment, $X=N$-$J_1$, the compound of Formula I has the structure of Formula Ia:

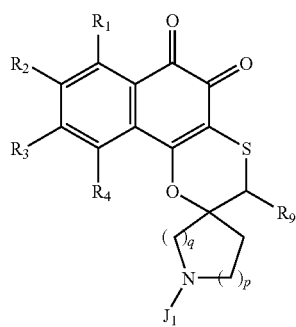
(Ia)

In another embodiment,

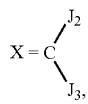

the compound of Formula I has the structure of Formula Ib:

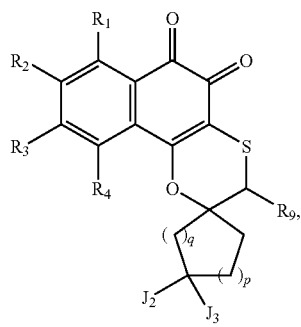
(Ib)

In another embodiment, X=O or S, the compound of Formula I has the structure of Formula Ic or Ib:

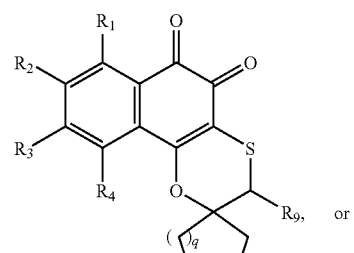
(Ic)

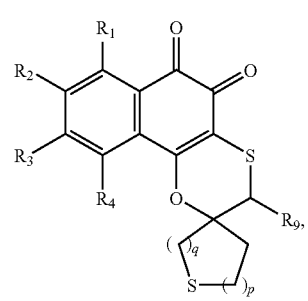
(Id)

In one embodiment, p is 0 and q is 1 and the compound of Formula I has the structure of Formula A:

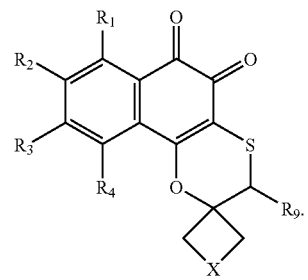
(A)

In another embodiment, p is 2 and q is 2 and the compound of Formula I has the structure of Formula B:

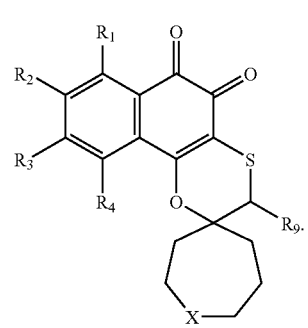
(B)

In another embodiment, p is 2 and q is 3 and the compound of Formula I has the structure of Formula C:

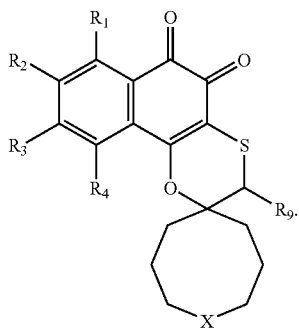
(C)

In another embodiment, p is 1 and q is 1 and the compound of Formula I has the structure of Formula D:

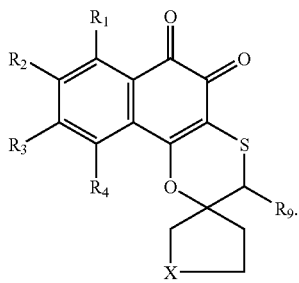
(D)

In another embodiment, p is 1 and q is 2 and the compound of Formula I has the structure of Formula E:

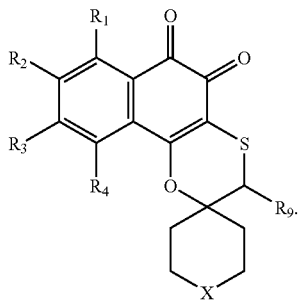
(E)

In another embodiment, p is 2 and q is 1 and the compound of Formula I has the structure of Formula F:

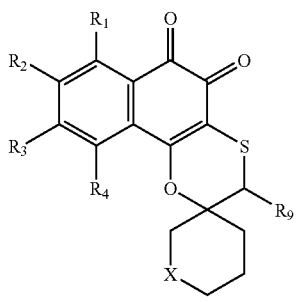
(F)

Compounds of Formula Ia include those in which $R_1$, $R_2$, $R_3$, and $R_4$ are each, independently, H, OH, F, Cl, Br, I, $CH_3$, $CF_3$, $OCH_3$, $C_2$-$C_6$ alkoxy, $C_2$-$C_6$ straight chain allyl, substituted $C_2$-$C_6$ straight chain alkyl, phenyl, $C_5$-$C_8$ aryl, $NO_2$, CN, $C(O)NHR_{14}$ or $NHC(O)R_{15}$. For example, $R_1$, $R_2$, $R_3$, and $R_4$ are each, independently, H, OH, F, Cl, Br, I, $CH_3$, $CF_3$, $OCH_3$, $C_2$-$C_6$ alkoxy. In another embodiment, $R_1$, $R_2$, $R_3$, and $R_4$ are each, independently, H or $OCH_3$. For example, $R_1$, $R_2$ and $R_4$ are each H and $R_3$ is $OCH_3$.

Compounds of Formula Ia include those in which $J_1$ is —$(CR_5R_6)_n$—$(CR_7R_8)_m$—Y. For example, n=1 and m=0. In another embodiment, n=1 and m=1. In another embodiment, n=0 and m=0. In another embodiment, n=1 and m=2. In another embodiment, n=5 and m=5.

Compounds of Formula Ia include those in which $R_5$ and $R_6$ are each, independently, H or $CH_3$. For example, $R_5$ and $R_6$ are each H.

Compounds of Formula Ia include those in which $R_7$ and $R_8$ are each, independently, H, F, Cl, Br, I, OH, $CH_3$, $C_2$-$C_6$ straight chain alkyl, $CF_3$, $C_3$-$C_6$ branched alkyl, $C_3$-$C_8$ cycloalkyl, or $C_2$-$C_6$ alkoxy. For example, $R_7$ and $R_8$ are each, independently, H or OH.

Compounds of Formula Ia include those in which $R_5$ and $R_6$ are each H and $R_7$ and $R_8$ are each, independently, H or OH.

Compounds of Formula Ia include those in which Y is $CH_2OR_{16}$, phenyl, substituted $C_5$-$C_8$ aryl or benzyl. In one embodiment, Y is $CH_2OR_{16}$. For example, Y is substituted or unsubstituted $C_5$-$C_8$ aryl. In one embodiment, the substituted $C_5$-$C_8$ aryl is substituted with from 1 to 5 substituents each of which is independently CN, Cl or F. For example, $R_{16}$ is substituted or unsubstituted $C_5$-$C_8$ aryl. In another embodiment, the substituted $C_5$-$C_8$ aryl is substituted with from 1 to 5 substitutents each of which is independently $C_3$-$C_6$ branched alkyl, Cl, or F.

Compounds of Formula Ia include those in which $J_1$ is —$S(O)_o$-Z. For example, o=1 or o=2. In one embodiment, Z is $CH_3$, $CF_3$, $C_2$-$C_6$ straight chain alkyl, heteroaryl, substituted heteroaryl, phenyl, substituted phenyl, $C_5$-$C_8$ aryl, or substituted $C_5$-$C_8$ aryl.

Compounds of Formula Ia include those in which $J_1$ is

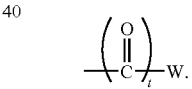

For example, t=1 or t=2. In one embodiment, W is substituted aryl, phenyl, phenoxy, aryloxy and substituted aryloxy. In another embodiment, the aryl and aryloxy is substituted with from 1 to 5 substituents each of which is independently $CF_3$ or F. In another embodiment, t=2 and W is $C_2$-$C_6$ alkoxy.

Additional compounds of Formula Ia include those in which $R_9$ is H; $R_{10}$ and $R_{11}$ are both H; $R_{12}$ and $R_{13}$ are both H; $R_{16}$ is $C_3$-$C_6$ branched alkyl, $C_5$-$C_8$ aryl, substituted $C_5$-$C_8$ aryl, heteroaryl, phenyl, substituted phenyl, $CH_2$-aryl, or benzyl. In one embodiment, $R_{12}$ is H and $R_{13}$ is phenyl.

Some representative compounds of Formula I are shown as follows:
1'-(3-chlorobenzoyl)spiro[naphtho[1,2-b][1,4]oxathiine-2,4'-piperidine]-5,6-dione (Compound 55);
1'-(3,4-dichlorobenzoyl)spiro[naphtho[1,2-b][1,4]oxathiine-2,4'-piperidine]-5,6-dione (Compound 53);
4-[(5,6-dioxo-5,6-dihydro-1H-spiro[naphtho[1,2-b][1,4]oxathiine-2,4'-piperidine]-1'-yl)methyl]benzonitrile (Compound 123);
1'-(2-phenylethyl)spiro[naphtho[1,2-b][1,4]oxathiine-2,4'-piperidine]-5,6-dione (Compound 155);
1'-(4-fluorobenzyl)spiro[naphtho[1,2-b][1,4]oxathiine-2,4'-piperidine]-5,6-dione (Compound 125);

1'-[3-(4-tert-butylphenoxy)-2-hydroxypropyl]spiro[naphtho[1,2-b][1,4]oxathiine-2,4'-piperidine]-5,6-dione (Compound 157);

1'-(2-hydroxy-3-phenylpropyl)spiro[naphtho[1,2-b][1,4]oxathiine-2,4'-piperidine]-5,6-dione (Compound 163);

3-(trifluoromethyl)phenyl 5,6-dioxo-5,6-dihydro-1'H-spiro[naphtho[1,2-b][1,4]oxathiine-2,4'-piperidine]-1'-carboxylate (Compound 96);

4-fluorophenyl 5,6-dioxo-5,6-dihydro-1'H-spiro[naphtho[1,2-b][1,4]oxathiine-2,4'-piperidine]-1'-carboxylate (Compound 97);

1'-(2-chloro-6-fluorobenzyl)spiro[naphtho[1,2-b][1,4]oxathiine-2,4'-piperidine]-5,6-dione (Compound 129);

1'-(3-chloro-4-fluorobenzyl)spiro[naphtho[1,2-b][1,4]oxathiine-2,4'-piperidine]-5,6-dione (Compound 142);

1'-(3-phenoxypropyl)spiro[naphtho[1,2-b][1,4]oxathiine-2,4'-piperidine]-5,6-dione (Compound 144);

1'-[2-(4-chlorophenoxy)ethyl]spiro[naphtho[1,2-b][1,4]oxathiine-2,4'-piperidine]-5,6-dione (Compound 145);

1'-[(2S)-3-(4-fluorophenoxy)-2-hydroxypropyl]spiro[naphtho[1,2-b][1,4]oxathiine-2,4'-piperidine]-5,6-dione (Compound 180);

1'-[(2S)-3-(4-tert-butylphenoxy)-2-hydroxypropyl]spiro[naphtho[1,2-b][1,4]oxathiine-2,4'-piperidine]-5,6-dione (Compound 184);

1'-[(2R)-3-(4-tert-butylphenoxy)-2-hydroxypropyl]spiro[naphtho[1,2-b][1,4]oxathiine-2,4'-piperidine]-5,6-dione (Compound 185);

1'-[(2R)-3-(4-fluorophenoxy)-2-hydroxypropyl]spiro[naphtho[1,2-b][1,4]oxathiine-2,4'-piperidine]-5,6-dione (Compound 181);

1'-[(2S)-3-(4-chlorophenoxy)-2-hydroxypropyl]spiro[naphtho[1,2-b][1,4]oxathiine-2,4'-piperidine]-5,6-dione (Compound 182);

1'-[(2R)-3-(4-chlorophenoxy)-2-hydroxypropyl]spiro[naphtho[1,2-b][1,4]oxathiine-2,4'-piperidine]-5,6-dione (Compound 183);

1'-[(2R)-2-hydroxy-3-phenylpropyl]spiro[naphtho[1,2-b][1,4]oxathiine-2,4'-piperidine]-5,6-dione (Compound 186);

1'-[(2S)-2-hydroxy-3-phenylpropyl]spiro[naphtho[1,2-b][1,4]oxathiine-2,4'-piperidine]-5,6-dione (Compound 187);

1'-[(2S)-2-hydroxy-3-(2-methylphenoxy)propyl]spiro[naphtho[1,2-b][1,4]oxathiine-2,4'-piperidine]-5,6-dione (Compound 200);

1'-isopropyl spiro[naphtho[1,2-b][1,4]oxathiine-2,4'-piperidine]-5,6-dione (Compound 152);

1'-[(2S)-3-(4-ethylphenoxy)-2-hydroxypropyl]spiro[naphtho[1,2-b][1,4]oxathiine-2,4'-piperidine]-5,6-dione (Compound 207);

1'-[(2R)-3-(4-ethylphenoxy)-2-hydroxypropyl]spiro[naphtho[1,2-b][1,4]oxathiine-2,4'-piperidine]-5,6-dione (Compound 228);

1'-[(2R)-2-hydroxy-3-(2-methylphenoxy)propyl]spiro[naphtho[1,2-b][1,4]oxathiine-2,4'-piperidine]-5,6-dione (Compound 224).

Representative compounds of the present invention are also shown in the Examples.

Unless defined otherwise, all technical and scientific terms used herein have the same meaning as commonly understood by one of ordinary skill in the art to which this invention belongs. In case of a conflict in terminology, the present specification controls. The following terms generally have the following meanings.

1.1. Definitions

As used herein, the term "alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl). "Alkyl" further includes alkyl groups that have oxygen, nitrogen, or sulfur atoms replacing one or more hydrocarbon backbone carbon atoms. In certain embodiments, a straight chain or branched alkyl has six or fewer carbon atoms in its backbone (e.g., $C_1$-$C_6$ for straight chain, $C_3$-$C_6$ for branched chain), and more preferably four or fewer.

The term "alkyl" also includes both "unsubstituted" and "substituted alkyls", the latter of which refers to alkyl moieties having substituents replacing a hydrogen on one or more carbon of the hydrocarbon backbone. Such substitutents can include, for example, alkyl, alkenyl, alkynyl, hydroxyl, alkylcarbonyl, arylcarbonyl, alkoxycarbonyl, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl ($S(O)_2NH_2$), aminesulfoxide (NHS(O) or S(O)NH), sulfonamide ($NHS(O)_2$ or $S(O)_2NH$), nitro, —$CF_3$, halogen, cyano, azido, heterocyclyl, alkylaryl, or an aromatic or heteroaromatic moiety. An "alkylaryl" or aralkyl moiety is an alkyl moiety substituted with an aryl (e.g., methylphenyl (benzyl)). "Alkyl" also includes the side chains of natural and unnatural amino acids.

Aryl includes groups with aromaticity, including 5- and 6-membered "unconjugated", or single-ring aromatic groups that may include from one to four heteroatoms, as well as "conjugated", or multicyclic systems with at least one aromatic ring. Examples of aryl groups include phenyl, pyrrole, furan, thiophene, thiazole, isothiazole, imidazole, triazole, tetrazole, pyrazole, oxazole, isoxazole, pyridine, pyrazine, pyridazine, and pyrimidine, and the like. Furthermore, the term aryl includes multicyclic groups, e.g., tricyclic, bicyclic, e.g., naphthalene, benzoxazole, benzodioxazole, benzothizole, benzoimidazole, benzothiophene, methylenedioxyphenyl, quinoline, isoquinoline, napthridine, indole, benzofuran, purine, benzofuran, deazapureine, or indolizine. Those aryl groups having heteroatoms in the ring structure may also be referred to as "aryl heterocycles", "heterocycles", "heterocyclyls", "heteroaryls" or "heteroaromatics" e.g., pyridine, pyrazole, pyrimidine, furan, isoxazole, imidazole[2,1,b]thiazole, triazole, pyrazine, benzothiophene, imidazole, or thiophene.

The aromatic ring can be substituted at one or more ring positions with such substituents as described above, as for example, halogen, hydroxyl, alkyl, alkoxy, alkylcarbonyloxy, arylcarbonyloxy, alkoxycarbonyloxy, aryloxycarbonyloxy, carboxylate, carboxyacid, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, carboxyalkyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, or sulfur replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, phenyl, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example "alkynyl" includes straight chain alkynyl groups (e.g., ethyl, propynyl, butynyl, pentynyl, hexynyl, heptynyl, octynyl, nonynyl, decynyl), branched chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

As used herein, "amine" or "amino" includes compounds where a nitrogen atom is covalently bonded to at least one carbon or heteroatom. "Alkylamino" includes groups of compounds wherein nitrogen is bound to at least one additional alkyl group. Examples of alkylamino groups include benzylamino, methylamino, ethylamino, and phenethylamino. "Dialkylamino" includes groups wherein the nitrogen atom is bound to at least two additional alkyl groups. Examples of dialkylamino groups include dimethylamino and diethylamino. "Arylamino" and "diarylamino" include groups wherein the nitrogen is bound to at least one or two aryl groups, respectively. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substitutents such as straight chain alkyl, branched alkyl, cycloalkyl, aryl, heteroaryl, or heterocycle. Substitutents on amide groups may be further substituted.

"Acyl" includes compounds and moieties that contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "cycloalkyl" includes saturated acyclic groups (e.g., cyclopropyl, cyclopentyl, cyclohexyl, cyclohexyl, cycloheptyl, cyclooctyl). Preferred cycloalkyls have from three to eight carbon atoms in their ring structure, and more preferably have five or six carbon atoms in the ring structure. Cycloalkyls includes both "unsubstituted cycloalkyls" and "substituted cycloalkyls", the latter of which refers to replacing a hydrogen on one or more of the carbons in the ring structure. Such substituents can include, for example, alkyl, alkenyl, alkynyl, halogen; hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The terms "heterocyclyl" or "heterocyclic group" include closed ring structures, e.g. 3- to 10-, or 4- to 7-membered rings, which include one or more heteroatoms. "Heteroatom" includes atoms of any element other than carbon or hydrogen. Examples of heteroatoms include nitrogen, oxygen, or sulfur.

Heterocyclyl groups can be saturated or unsaturated and include pyrrolidine, pyrazine, pyrimidine, oxolane, 1,3-dioxolane, thiolane, tetrahydrofuran, tetrahydropyran, piperidine, piperazine, pyrrolidine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, carboxyacid, alkylcarbonyl, alkoxycarbonyl, aminocarbonyl, alkylthiocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF$_3$, or —CN, or the like.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The term "C1-C6" includes one to six carbon atoms (C1, C2, C3, C4, C5 or C6). The term "C2-C6" includes two to six carbon atoms (C2, C3, C4, C5 or C6). The term "C3-C6" includes three to six carbon atoms (C3, C4, C5 or C6). The term "C3-C8" includes two to eight carbon atoms (C3, C4, C5, C6, C7 or C8). The term "C5-C8" includes five to eight carbon atoms (C5, C6, C7 or C8).

It should be noted that any heteroatom or carbon atom with unsatisfied valences is assumed to have the hydrogen atom to satisfy the valences.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a stricture are intended, unless the specific stereochemistry or isomeric form is specifically indicated. All tautomers of shown or described compounds are also considered to be part of the present invention.

It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g. C=C, C=N, or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substitutents and/or variables are permissible, but only if such combinations result in stable compounds.

In the specification, the singular forms also include the plural, unless the context clearly dictates otherwise.

2. The Synthesis of Lapachone Compounds

The present invention also provides methods for the synthesis of the compounds of Formula I. In one embodiment, the present invention provides a method for the synthesis of compounds according to the following schemes, and the protocols shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the invention can be prepared in a variety of ways, some of which are known in the art. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$.; John Wiley & Sons: New York, 1999, incorporated by reference herein, are useful and recognized reference textbooks of organic synthesis known to those in the art. The following descriptions of synthetic methods are designed to illustrate, but not limit, general procedures for the preparation of compounds of the invention.

The compounds of this invention with general formula (I) may be prepared according to the following schemes from commercially available starting materials or starting materials, which can be prepared using literature procedures. These schemes show the preparation of representative compounds of this invention.

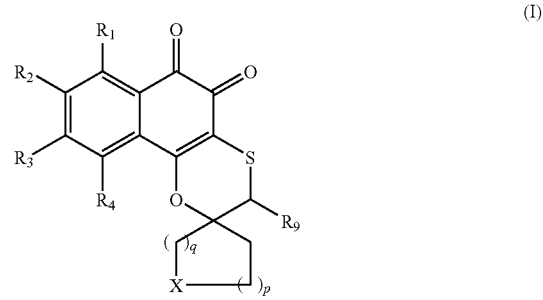

(I)

The compounds of the present invention can be prepared from the reaction of spiro-1,2-quinone (Ia) and appropriate intermediate/commercial reagents. (Scheme 9)

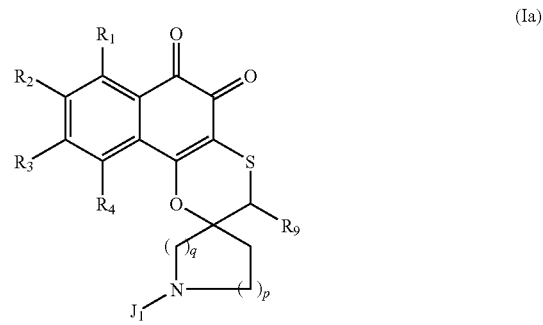

(Ia)

Scheme 1

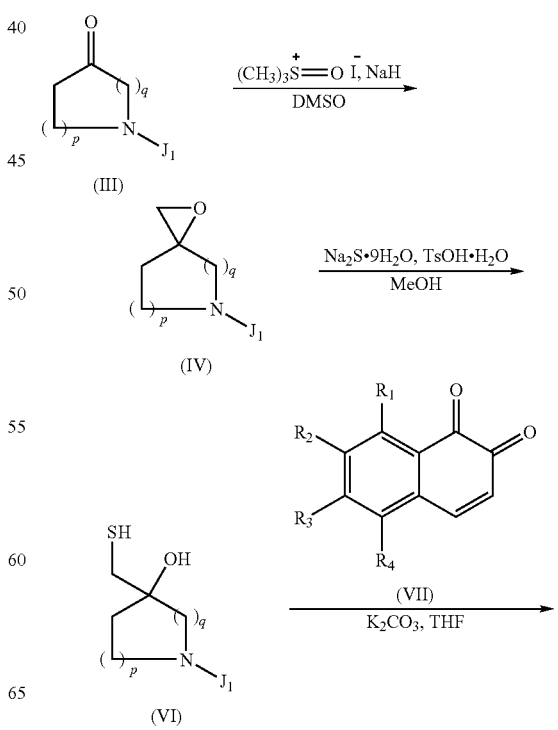

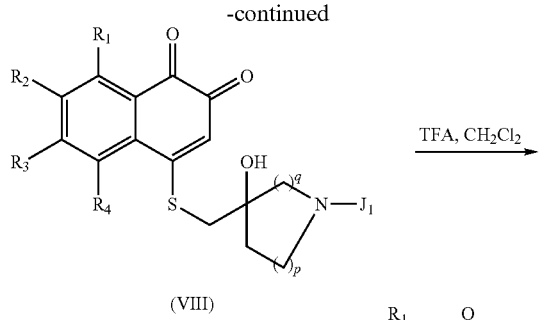

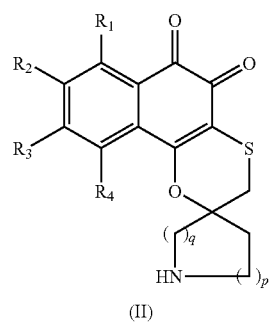

Compounds of formula (Ia) can be conveniently prepared by a variety of methods familiar to those skilled in the art. One common route is illustrated in Scheme 1. Epoxide compounds such as formula (IV) may be conveniently prepared from ketones of formula (III) where $J_1$ is a protecting group such as tert-butyl carbamate (t-BOC). Trimethylsulfoxonium ylide is prepared by treating trimethylsulfoxonium iodide with bases such as sodium hydride in a polar solvent such as anhydrous dimethylsulfoxide. Other bases such as potassium t-butoxide may also be used instead of sodium hydride. The trimethylsulfoxonium ylide is treated with ketone of formula (III) at 0° C. initially and the reaction warmed to room temperature for 4-24 hours to provide epoxide (IV). (Hale, J. et al, Bioorganic & Medicinal Chemistry Letters, 2002, 12(20), 297; Jambulingam M et al, Asian Journal of Chemistry, 2004, 16(3-4), 1261) Many ketones are commercially available or readily prepared by methods described in the literature and known to those skilled in art. Alternatively, the epoxide (IV) can also be conveniently prepared from alkenes (V) by treatment with peroxy acids such m-chloroperoxybenzoic acid. Many alkenes are commercially available or readily prepared from ketones (III) by methods described in the literature [Abell A. et al, Organophosphorus Reagents, 2004, 99; Lawrence N. et al, Preparation of Alkenes, 1996, 19; Edmonds M. et al, Modern Carbonyl Olefination 2004, 1] and known to those skilled in art.

The epoxides (IV) are used to prepare thioalcohol compounds of formula (VI). These can be conveniently prepared by a variety of methods familiar to those skilled in the art. The epoxide (IV) is treated with a pretreated mixture of sodium sulfide and acids such as p-toluene sulfonic acid in polar protic solvent such as methanol for 0.5-4 hours at a temperature of 0-25° C. to provide the thioalcohol (VI). Another common route to prepare thialcohols (VI) is by treating epoxide (IV) with triphenylsilane thiol, tertiary amine bases such as triethyl amine and in polar protic solvent such as methanol for 0.5-4 hours at ambient temperatures (Brittain J. et al, Tetrahedron Letters, 1993, 34(21), 3363).

The thioalcohols (VI) are used to prepare 1,2-quinone alcohol compounds of formula (VIII). These can be conveniently prepared by methods familiar to those skilled in the alt. The thioalcohol (VI) is treated with 1,2-quinones (VII), bases such as potassium carbonate and solvents such as tetrahydrofuran for 0.5-4 hours at ambient temperatures to provide the 1,2-quinone alcohols with formula (VIII). Alternatively bases such as triethylamine, sodium carbonate, cesium carbonate and solvents such as acetonitrile dichloromethane can also be utilized.

1,2-Quinone alcohols (VIII) are used to prepare spiro-1,2-quinone compounds with formula (II). These can be conveniently prepared by methods familiar to those skilled in the art. 1,2-Quinone alcohols with formula (VIII) are treated with acid such as trifluoroacetic acid and solvents such as dichloromethane in open air at ambient temperature for 24-96 hours. Alternatively acids such as p-toluenesulfonic acid, sulfuric acid can also be used and air or oxygen can also be bubbled through the reaction.

Scheme 2

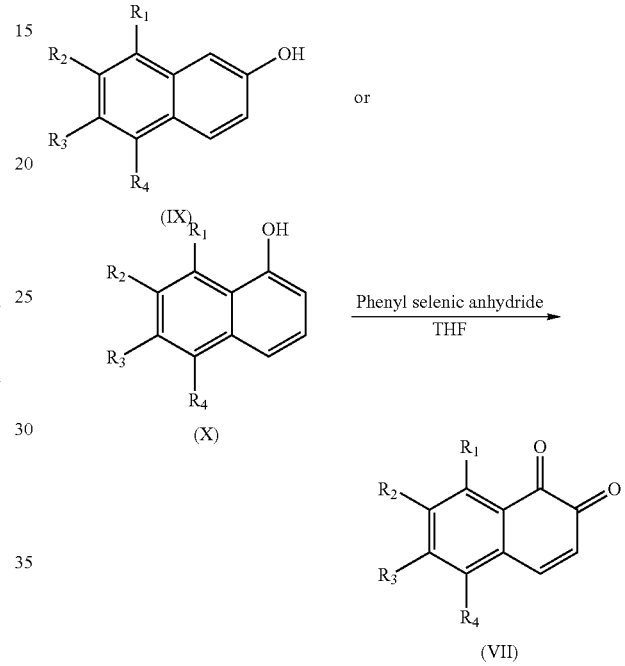

Compounds of formula (VII) can be conveniently prepared by a variety of methods familiar to those skilled in the art. One common route is illustrated in Scheme 2. Naphthols (IX-X) are treated with a solution of phenylselenic anhydride in solvent such as tetrahydrofuran for 15-30 minutes at a temperature of 60-80° C. to provide the 1,2-quinones with formula (VII). Many naphthols are commercially available or readily prepared by methods described in the literature and known to those skilled in art. (Cordero-Vargas, A. et al, Org. Biomol. Chem. 2004, 2, 3018; Adcock, W. et al, J. Am. Chem. Soc. 1967, 89(2), 386; Gareau, Y. et al, WO 99/47497)

Scheme 3

(i) $K_2CO_3$, THF

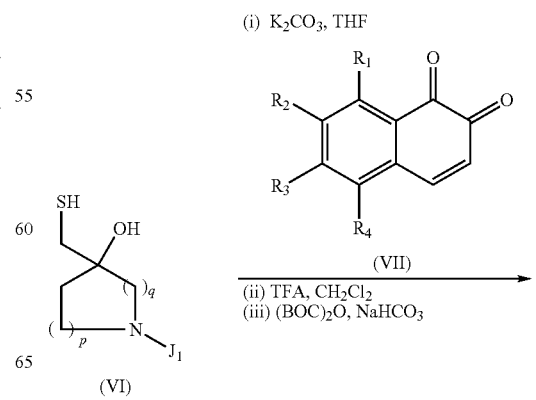

(ii) TFA, $CH_2Cl_2$
(iii) $(BOC)_2O$, $NaHCO_3$

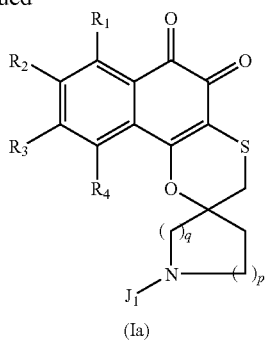

(Ia)

Compounds of formula (Ia) where $J_1$ is a protecting group such as tert-butyl carbamate (t-BOC) can be conveniently prepared by methods familiar to those skilled in the art. One common route is illustrated in Scheme 3. Thioalcohol (VI) is treated with 1,2-quinones (VII), bases such as potassium carbonate and solvents such as tetrahydrofuran for 0.5-4 hours at ambient temperatures to provide the 1,2-quinone alcohols (VIII). The resulting crude 1,2-quinone alcohols (VIII) is treated with acid such as trifluoroacetic acid and solvents such as dichloromethane in open air at ambient temperature for 24-96 hours to provide the spiro-1,2-quinone compounds with formula (II). The resulting crude spiro-1,2-quinone compounds (II) are treated with di-tert-butyl dicarbonate in bases such as aqueous sodium bicarbonate, solvent such as dichloromethane for 0.25-4 hours at ambient temperature to provide the t-butoxycarbamate (t-BOC) protected spiro-1,2-quinones compounds with formula (Ia).

Scheme 4

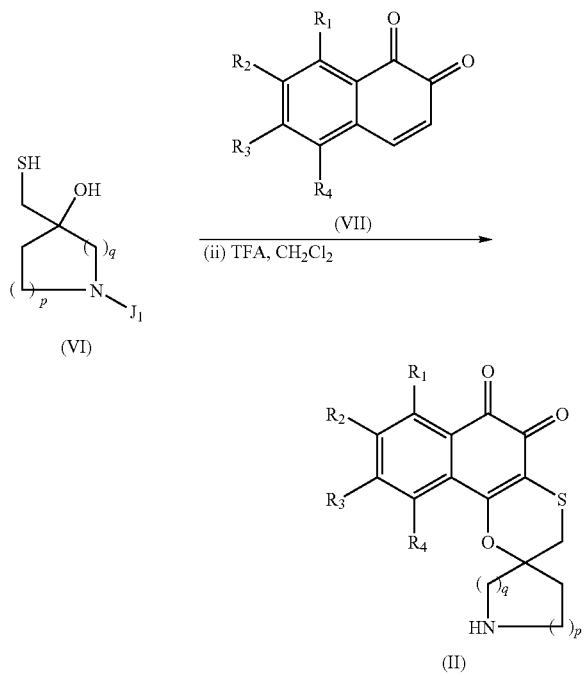

Compounds of formula (II) can also be prepared as shown in Scheme 4. Thioalcohol (VI) where $J_1$ is a protecting group such as tert-butyl carbamate (t-BOC) is treated with 1,2-quinones (VII), bases such as potassium carbonate and solvents such as tetrahydrofuran for 0.5-4 hours at ambient temperatures to provide the 1,2-quinone alcohols (VIII). The resulting crude 1,2-quinone alcohols (VIII) are treated with acid such as trifluoroacetic acid and solvents such as dichloromethane in open air at ambient temperature for 24-96 hours to provide the spiro-1,2-quinone compounds with formula (II).

Scheme 5

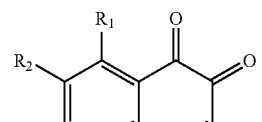

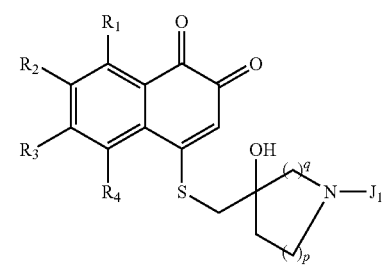

(VIII)

Another common route for the preparation of compounds of formula (VIII) where $J_1$ is a protecting group such as tert-butyl carbamate (t-BOC) is shown in Scheme 5. Thioalcohol (VI) is treated with 4-chloro-1,2-quinone (XI), bases such as potassium carbonate and solvents such as tetrahydrofuran for 0.5-4 hours at ambient temperatures to provide the 1,2-quinone alcohols with formula (VIII). Alternatively other 4-halo-1,2-quinones such as 4-bromo-1,2-quinone, bases such as triethylamine, sodium carbonate, cesium carbonate and solvents such as acetonitrile, dichloromethane can also be utilized. Many 4-halo-1,2-quinones are readily prepared by methods described in the literature and known to those skilled in art. (Paquet, J. et al, Canadian Journal of Chemistry, 1989, 67(8), 1354; Perumal, T. et al, 1980, 11, 943; Krohn K. et al, Synthesis, 1990, 12, 1141).

Scheme 6

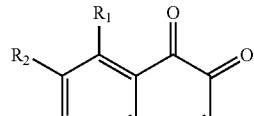

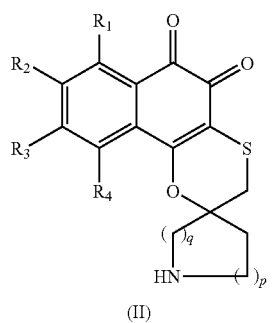

(II)

Another common route for the preparation of compounds of formula (II) is shown in Scheme 6. Thioalcohol (VI) where $J_1$ is a protecting group such as t-butyl carbamate (t-BOC) is treated with 4-chloro-1,2-quinone (XI), tertiary amine bases such as triethylamine and solvents such as dichloromethane for 0.5-4 hours at ambient temperatures. To the reaction is added acids such as trifluoroacetic acid to provide the spiro-1,2-quinone (II). This example illustrates how spiro-1,2-quinone (II) can be conveniently prepared without isolating 1,2-quinone alcohols (VIII).

Another common route for the preparation of compounds of formula (Ia and II) where $J_1$ is a protecting group such as tert-butyl carbamate (t-BOC) is illustrated in Scheme 7. 1,2-Quinone alcohols (VIII) are treated with 1-3 equivalents of acids such as trifluoroacetic acid, oxidants such as sodium iodate and solvents such as dichloromethane at ambient temperature for 24-96 hours to provide the spiro-1,2-quinones compounds with formula (Ia and II). Alternatively acids such as p-toluenesulfonic acid can also be used.

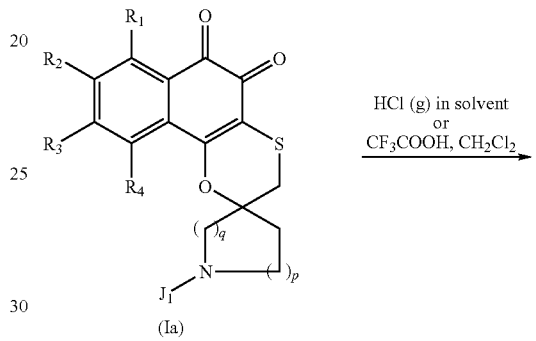

Scheme 8

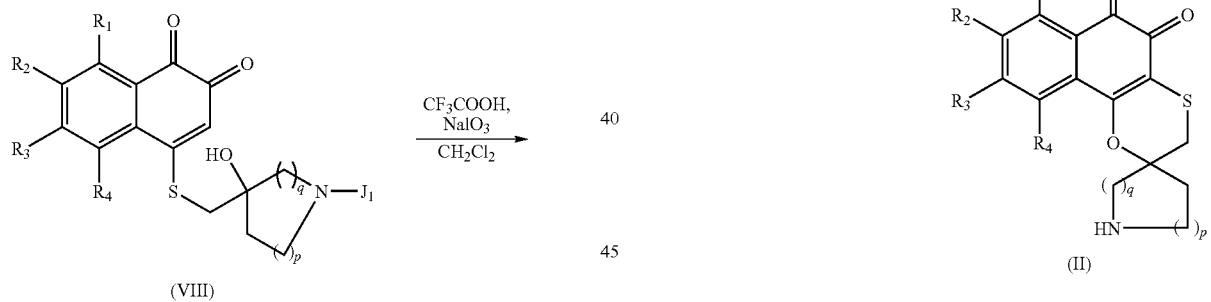

Scheme 7

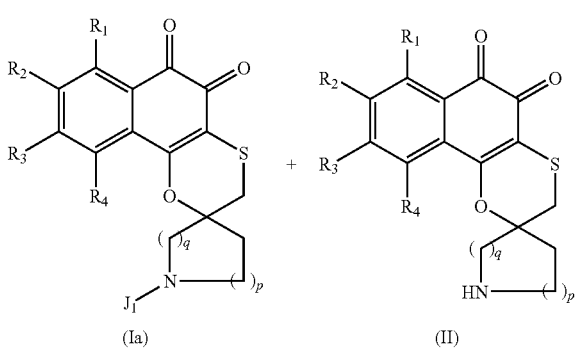

Compounds of formula (II) where can also be prepared as shown in Scheme 8. Spiro-1,2-quinones (II) can be prepared by treating spiro-1,2-quinones (Ia) where $J_1$ is a protecting group such as tert-butyl carbamate (t-BOC) with acids such as trifluoroacetic acid in solvents such as dichloromethane or solution of hydrogen chloride gas in solvents such as ethyl acetate, 1,2-dioxane, diethyl ether at ambient temperature for 1-24 hours. The product spiro-1,2-quinones (II) can be isolated as free base, hydrochloride or trifluoroacetic acid salt. To obtain the free base an aqueous workup with sodium bicarbonate is carried out on either acid salt. The above condition also describes a method to remove the protecting group tert-butyl carbamate (t-BOC) group from amines.

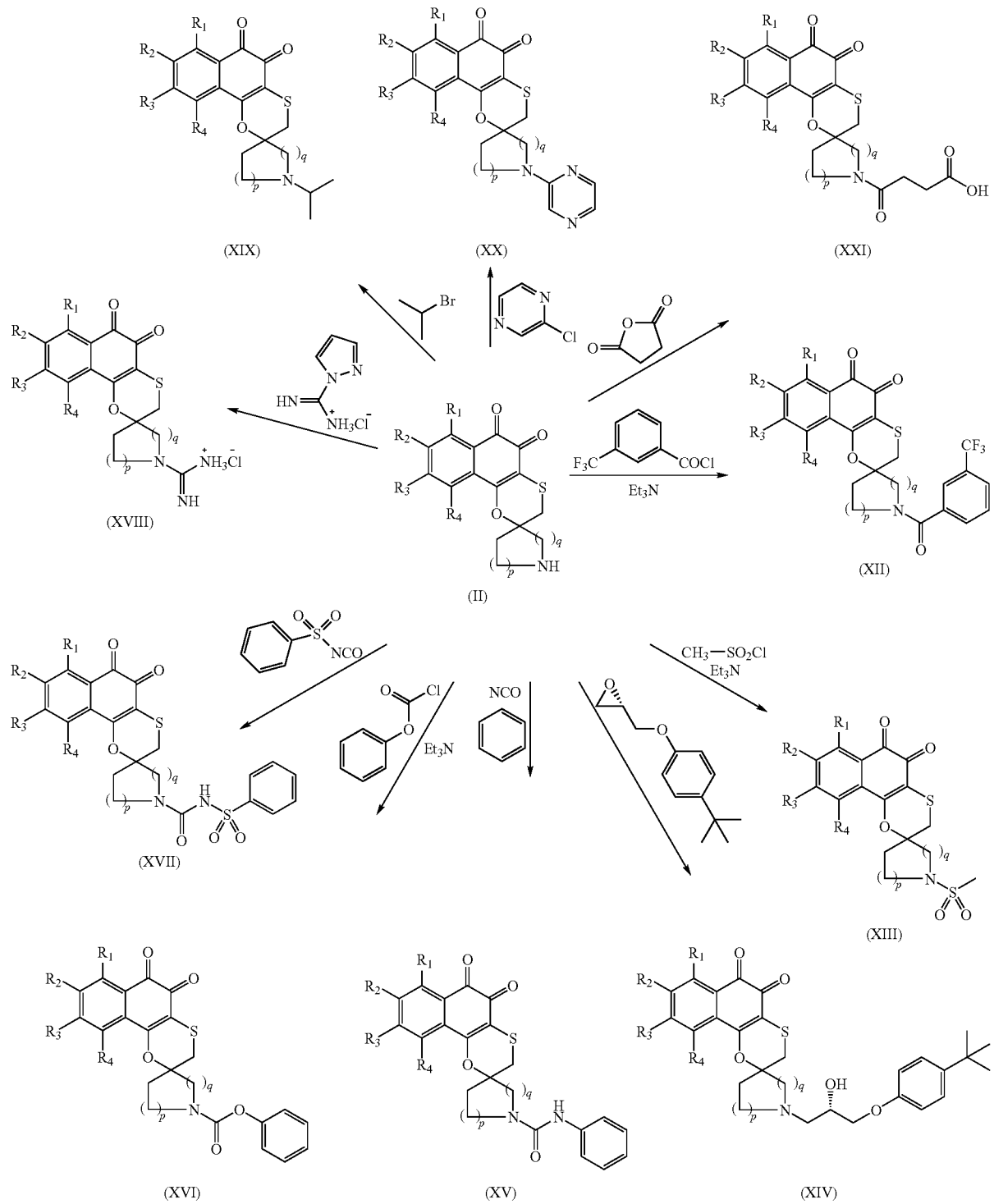

Scheme 9 illustrates a variety of chemical transformation of spiro-1,2-quinone (II) to provide compounds (XII-XXI). The following methods are provided by way of exemplification. Alternative methods may be employed and are described in reference text's such as Comprehensive Organic Transformations, Richard C. Larock, Second Edition, Wiley-VCH, 1999; Protective Groups in Organic Synthesis, Third Edition, Theodora W. Greene and Peter M. Wuts, Wiley Interscience, 1999; The Practice of Peptide Synthesis, M. Bodanszky and A. Bodanzsky, Springer-Verlag, 1984.

The spiro-1,2-quinone amide (XII) can be conveniently prepared by treating spiro-1,2-quinone (II) with acid chlorides such as m-trifluoromethylbenzoyl chloride in presence of tertiary anine bases such as triethylamine, diisopropylethyl amine and solvents such as dichloromethane at ambient temperature for 1-12 hours. Many acid chlorides are commercially available or readily prepared by methods described in the literature and known to those skilled in art.

Alternatively spiro-1,2-quinone amide (XII) can be conveniently prepared by treating spiro-1,2-quinone (II) with the corresponding carboxylic acid in presence of amide coupling agents such as HBTU (O-(benzotriazo-1-yl)-N,N,N',N'-tetramethyluronium hexafluorophosphate), tertiary amine bases such as dimethylaminopyridine and solvents such as dimethylformamide at ambient temperature for 4-24 hours. Alternatively amide coupling agents such as DCC (dicylcohexycarbodiimide), BOP ((benzotriazo-1-yloxy)tris(dimethylamino) phosphonium hexafluorophosphate, EDCI.HCl (1-(3-Dimethyl aminopropyl)-3-ethylcarbodiimide hydrochloride), DMC (2-chloro-1,3-dimethylimidazolinium chloride) and tertiary amines bases such as triethylamine, diisopropylethyl amine can also be used. Many carboxylic acids are commercially available or readily prepared by methods described in the literature and known to those skilled in art.

Spiro-1,2-quinone sulfonamide (XIII) can be conveniently prepared by treating spiro-1,2-quinone (II) with sulfonyl chlorides such as methanesulfonyl chloride in presence of tertiary amine bases such as triethylamine and solvents such as dichloromethane at ambient temperature for 1-12 hours. Alternatively tertiary amines bases such as diisopropylethyl amine can also be used. Many sulfonyl chlorides are commercially available or readily prepared by methods described in the literature and known to those skilled in art.

Spiro-1,2-quinone amino alcohol (XIV) can be conveniently prepared by treating spiro-1,2-quinone (II) with epoxides such as (2S)-2-[(4-t-butyl-phenoxy)methyl]oxathiine in solvents such as acetonitrile, ethanol and with or without lithium perchlorate at 50-100° C. for 1-12 hours. The above conditions can be used with both chiral and racemic epoxide to prepare both chiral and racemic amino alcohols, respectively. Many epoxide both chiral and racemic are commercially available or readily prepared by methods described in the literature and known to those skilled in art. (Schaus et. al J. Am. Chem. Soc. 124 (7) 2002, 1307-1315; Steffan et. al. Bioorg. Med. Chem. Lett. 2002, 12, 2957-2961)

Spiro-1,2-quinone urea (XV) can be conveniently prepared by treating spiro-1,2-quinone (II) with isocyanates such as phenylisocyanate in solvents such as dichloromethane at ambient temperature for 1-12 hours. Many isocyanates are commercially available or readily prepared by methods described in the literature and known to those skilled in art. Isocyantes can also be prepared in situ from carboxylic acids by a variety of methods familiar to those skilled in the art. Carboxylic acids are treated with diphenyl phosphoryl azide in solvents such as toluene at reflux for 1-5 hours. The isocyanates are used in situ as solution to react with the spiro-1,2-quinones (II) to prepare spiro-1,2-quinone ureas (XV) as described above.

Spiro-1,2-quinone carbamate (XVI) can be conveniently prepared by treating spiro-1,2-quinone (II) with carbamoyl chlorides such as phenylchlorido carbonate, bases such as triethylamine, diisopropylethyl amine, aqueous sodium carbonate in solvents such as ethyl acetate, dichloromethane at ambient temperature for 1-12 hours. Many carbamates are commercially available or readily prepared by methods described in the literature and known to those skilled in art. Carbamoyl chlorides can also be prepared in situ from carboxylic acids by a variety of methods familiar to those skilled in the art. Carboxylic acids are treated with oxalyl chloride, triphosgenes in solvents such as dichloromethane at 0° C. to ambient temperature for 1-5 hours. The resulting carbamoyl are used in situ as solution to react with the spiro-1,2-quinones (II) to prepare spiro-1,2-quinone carbamates with formula (XVI) as described above.

Spiro-1,2-quinone sulfonyl urea (XVII) where X is nitrogen can be conveniently prepared by treating spiro-1,2-quinone (II) with sulfonyl isocyanates such as phenylsulfonyl isocyanate (XVIII) in solvents such as dichloromethane at 0° C. to ambient temperature for 1-12 hours. Many sulfonyl isocyanates are commercially available or readily prepared by methods described in the literature and known to those skilled in art.

Spiro-1,2-quinone guanidine with formula (XVIII) can be conveniently prepared by treating spiro-1,2-quinone (II) with pyrazole carboxamidine hydrochloride, tertiary amine bases such as triethylamine, diisopropylethyl amine and in solvents such as dimethylformamide at 50-90° C. for 1-12 hours. The crude spiro-1,2-quinone guanidine (XVIII) are titurated with diethyl ether to provide pure spiro-1,2-quinone guanidine (XVIII) isolated as HCl salts.

Alternatively alkyl substituted spiro-1,2-quinone guanidines can be conveniently prepared by treating spiro-1,2-quinone (II) with bis(tert-butoxycarbonyl)-S-methylisothiourea, mercuric (II) chloride, tertiary amine bases such as triethylamine, diisopropylethyl amine and in solvents such as dimethylformamide at 50-90° C. for 1-12 hours. The resulting bis(tert-butoxycarbonyl) protected guanidine can be treated with benzyl bromide or other alkyl halides in presence of phase transfer catalyst such as tert-butyl ammonium iodide, bases such as potassium hydroxide in water and organic solvent such as toluene at 40-70° C. for 1-8 hours to provide alkyl substituted bis(tert-butoxycarbonyl) protected guanidine. Treatment of the alkyl substituted bis(tert-butoxycarbonyl) protected guanidine with acids such as trifluoroacetic acid in solvents such as dichloromethane or solution of hydrogen chloride gas in solvents such as ethyl acetate, 1,2-dioxane, diethyl ether at ambient temperature for 1-24 hours provided alkyl substituted guanidine as hydrochloride salt. Many alkyl halides such as alkyl chloride, bromide and iodides are commercially available or readily prepared by methods described in the literature and known to those skilled in art.

Spiro-1,2-quinone alkyl amines (XIX) can be conveniently prepared by treating spiro-1,2-quinone (II) with alkyl halides such as 2-bromopropane, bases such as potassium carbonate, cesium carbonate, triethylamine, diisopropylethyl amines in solvent such as acetonitrile, dimethylformamide at 70-90° C. for 1-12 hours. Alternatively alkyl chloride can be treated with the spiro-1,2-quinone (II) in presence of sodium iodide (to in situ prepare alkyl iodide) to provide spiro-1,2-quinone alkyl amines (XIX). Many alkyl halides are commercially available or readily prepared by methods described in the literature and known to those skilled in art.

Spiro-1,2-quinone amine heterocycle (XX) can be conveniently prepared by treating spiro-1,2-quinone (II) with heterocyclic halides such as 2-chloropyrazine, tertiary amine bases such as triethylamine, diisopropylethyl amines in polar aprotic solvent such as dimethylsulfoxide dimethylformamide at 80-110° C. for 1-12 hours. Many heterocyclic halides are commercially available or readily prepared by methods described in the literature and known to those skilled in art.

Spiro-1,2-quinone amide acids (XXI) can be conveniently prepared by treating spiro-1,2-quinone (II) with anhydrides such as dihydrofuran-2,5-dione in solvent such as acetonitrile, dimethylsulfoxide at 70-90° C. for 1-12 hours. Many anhydrides are commercially available or readily prepared by methods described in the literature and known to those skilled in art.

Scheme 10

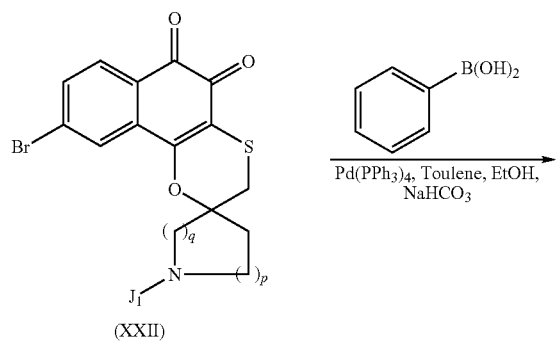

(XXII)

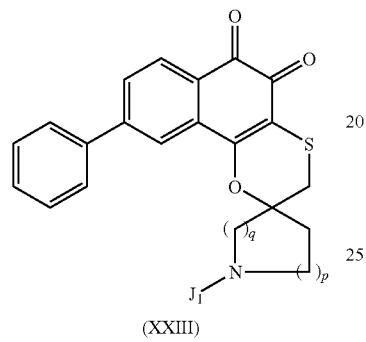

(XXIII)

Scheme 11

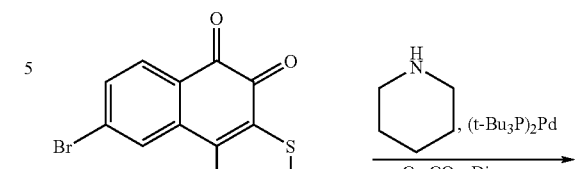

(XXII)

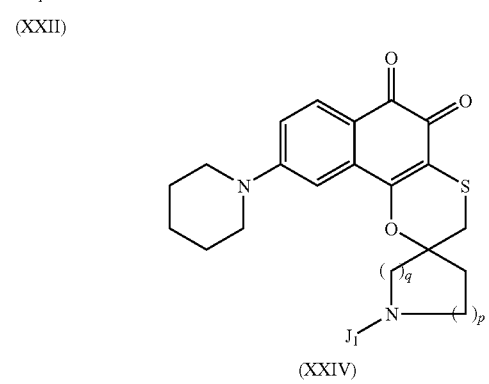

(XXIV)

As shown in Scheme 10, phenyl spiro-1,2-quinones (XXII) where $J_1$ is a protecting group such as tert-butyl carbamate (t-BOC) can be conveniently prepared by treating tert-butoxy carbamate protected bromo-spiro-1,2-quinone amine (XXII) with boronic acids such as phenyl boronic acid Pd(0) catalyst such as Pd(Ph$_3$P)$_4$, bases such as sodium bicarbonate, cesium carbonate in solvent such as ethanol, toluene at 70-100° C. for 1-12 hours. Many aromatic boronic acids are commercially available or readily prepared by methods described in the literature and known to those skilled in art. (Prieto M. et al, JOC, 2004, 69(20), 6812)

As shown in Scheme 11, phenyl amino substituted spiro-1,2-quinones (XXIV) where $J_1$ is a protecting group such as tert-butyl carbamate (t-BOC) can be conveniently prepared by treating tert-butoxy carbamate protected bromo-spiro-1,2-quinone amine (XXII) with amines such as piperidine, Pd(0) catalyst such as bis(tri-tert-butyl phosphine)palladium (0), bases such as cesium carbonate, sodium bicarbonate in solvent such as dioxane at 70-130° C. for 1-12 hours. Many secondary amines are commercially available or readily prepared by methods described in the literature and known to those skilled in art. (J. Am. Chem. Soc., 2002, 124, 14844)

Scheme 12

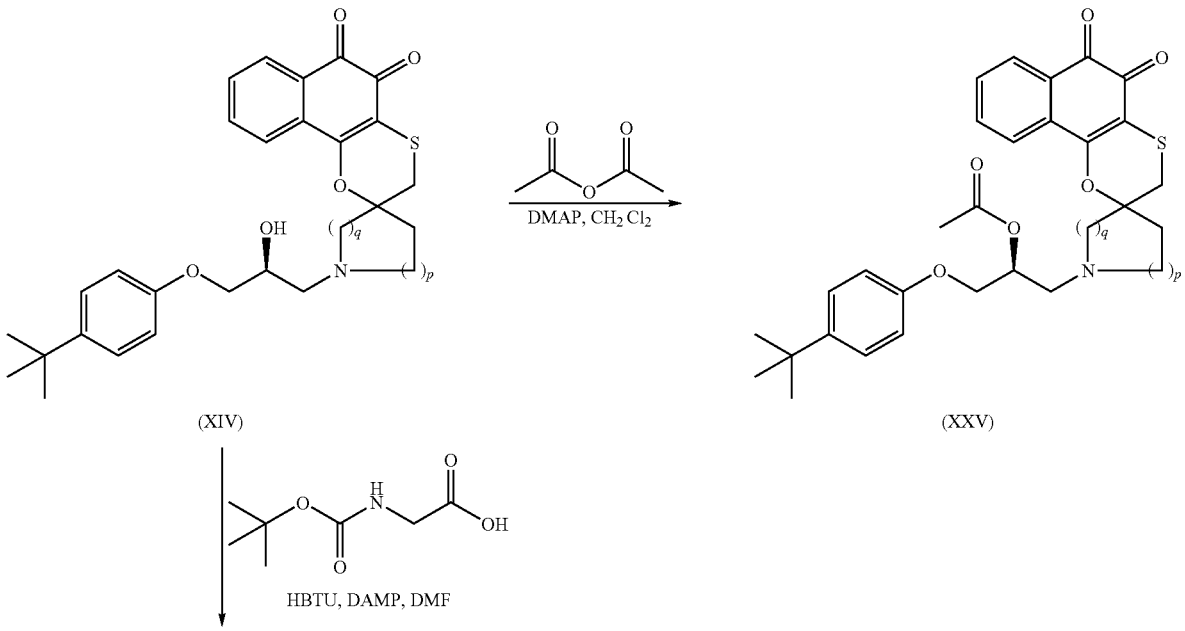

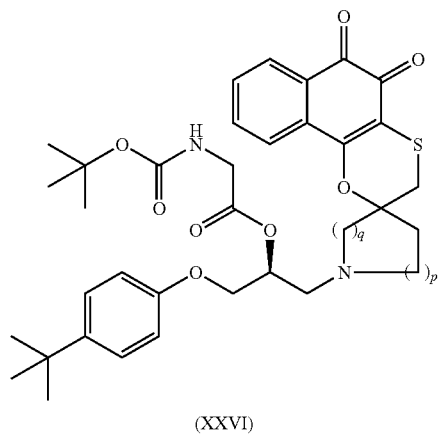

(XXVI)

As shown in Scheme 12, spiro-1,2-quinone amino alcohol esters (XXV) can be conveniently prepared by treating spiro-1,2-quinone amino alcohols (XIV) with anhydride such as acetic anhydride, tertiary amine base such as dimethylamino pyridine, triethylamine, diisopropylethylamine in solvent such as dichloromethane at 0° C. to ambient temperatures for 1-12 hours. Many anhydrides are commercially available or readily prepared by methods described in the literature and known to those skilled in art.

Alternatively the spiro-1,2-quinone amino alcohol esters with formula (XXVI) can be conveniently prepared by treating spiro-1,2-quinone amino alcohols (XIV) with carboxylic acids such as N-(tert-butoxycarbonyl)glycine, in presence of ester coupling agents such as HBTU (O-(benzotriazo-1-yl)-N,N,N',N'-tetramethyluronium hexafluorophosphate), tertiary amine bases such as dimethylaminopyridine, solvents such as dimethylformamide at ambient temperatures for 4-24 hours. Many carboxylic acids including protected amino acids both chiral and racemic are commercially available or readily prepared by methods described in the literature and known to those skilled in art.

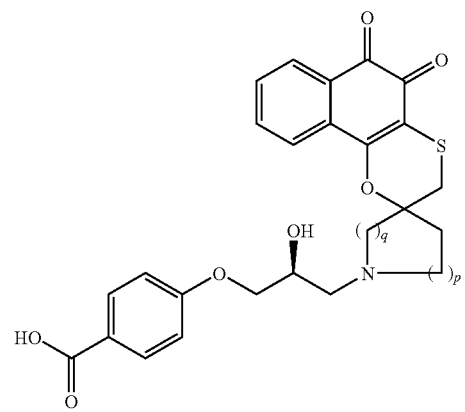

(XXVII)

As shown in Scheme 13, spiro-1,2-quinone acid (XXVIII) can be conveniently prepared by treating spiro-1,2-quinone benzyl ester (XXVII) with Pd (0) on carbon, in an atmosphere of hydrogen and with solvents such as ethyl acetate at ambient temperatures for 4-24 hours.

Scheme 13

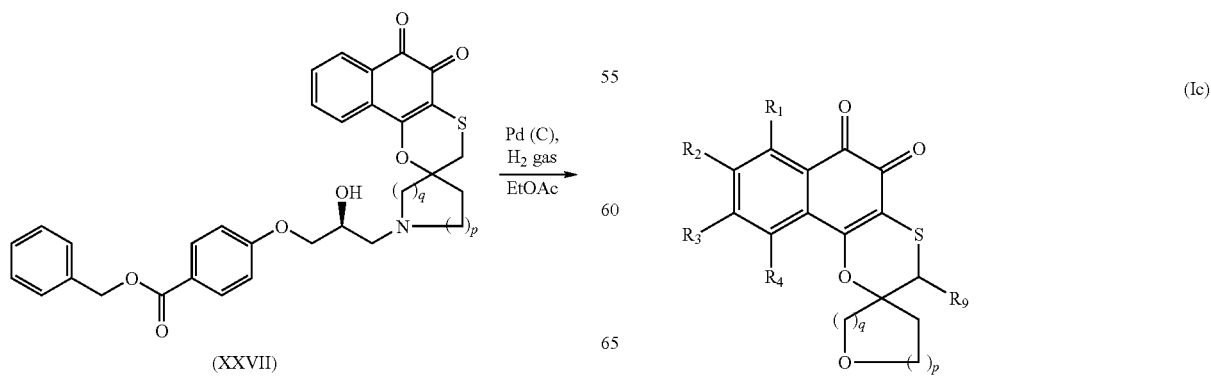

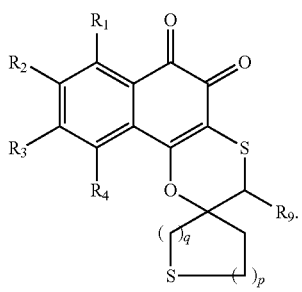

Scheme 14

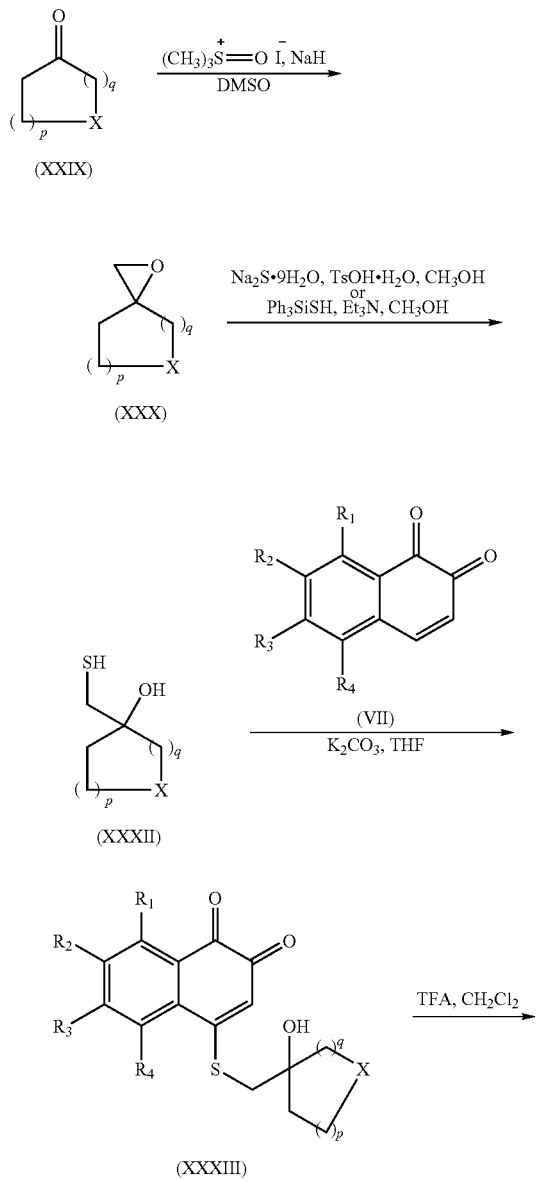

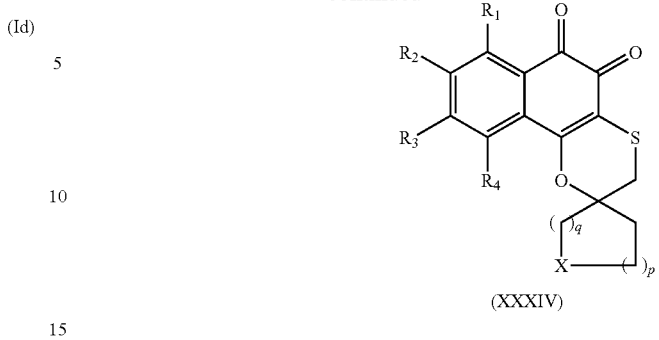

(XXXIV)

The compounds of the present invention having the formula (Ic and Id) where X is oxygen and sulfur can be conveniently prepared as shown in Scheme 14. Epoxide compounds (XXX) where X is oxygen and sulfur may be conveniently prepared from ketones (XXIX) where X is oxygen and sulfur. Trimethylsulfoxonium ylide is prepared by treating trimethylsulfoxonium iodide with bases such as sodium hydride in a polar solvent such as anhydrous dimethylsulfoxide. Other bases such as potassium t-butoxide may also be used instead of sodium hydride. The trimethylsulfoxonium ylide is treated with ketone (XXIX) at 0° C. initially and the reaction warmed to room temperature for 4-24 hours to provide epoxide (XXX). Many ketones are commercially available or readily prepared by methods described in the literature and known to those skilled in art. Alternatively, the epoxide (XXX) where X is oxygen or sulfur substituted with phenyl can also be conveniently prepared from alkenes (XXIX) by treatment with peroxy acids such m-chloroperoxybenzoic acid. Many alkenes are commercially available or readily prepared from ketones (XXIX) by methods described in the literature (such as wittig reaction) and known to those skilled in art.

The epoxides (XXX) are used to prepare thioalcohol compounds of formula (XXXII). These can be conveniently prepared by a variety of methods familiar to those skilled in the art. The epoxide (XXX) is treated with a pretreated mixture of sodium sulfide and acids such as p-toluene sulfonic acid in polar protic solvent such as methanol for 0.5-4 hours at a temperature of 0-25° C. to provide the Thioalcohol (XXXII). Another common route to prepare Thioalcohols (XXXII) is by treating epoxide (XXX) with triphenylsilane thiol, tertiary anine bases such as triethyl amine and in polar protic solvent such as methanol for 0.54 hours at ambient temperatures.

Thioalcohols (XXXII) are used to prepare 1,2-quinone alcohol (XXXIII). These can be conveniently prepared by methods familiar to those skilled in the art. Thioalcohol (XXXII) is treated with 1,2-quinones (VII), bases such as potassium carbonate and solvents such as tetrahydrofuran ambient temperatures to provide the 1,2-quinone alcohols with formula (XXXIII). Alternatively bases such as triethylamine, sodium carbonate, cesium carbonate and solvents such as acetonitrile dichloromethane can also be utilized.

1,2-Quinone alcohols (XXXIII) are used to prepare spiro-1,2-quinone compounds with formula (XXXIV). These can be conveniently prepared by methods familiar to those skilled in the art. 1,2-Quinone alcohols with formula (XXXIII) are treated with acid such as trifluoroacetic acid and solvents such as dichloromethane in open air at ambient temperature for 24-96 hours. Alternatively acids such as p-toluenesulfonic acid can also be used and air or oxygen can also be bubbled through the reaction.

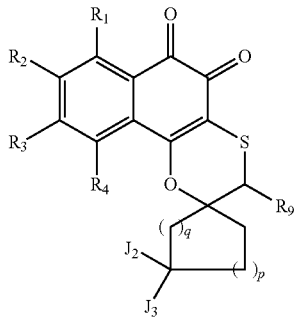

(Ib)

The compounds of the present invention having the formula (Ib) where $J_2$ and $J_3$ can be protecting group such as dioxolane ring, ketone or when $J_2$ is hydrogen, $J_3$ is phenyl or N-$J_1$, and $J_1$ is a protecting group such as tert-butyl carbamate (t-BOC) or selected from additional groups described in the detailed description of the invention, can be conveniently prepared as shown in Scheme 9 and 15.

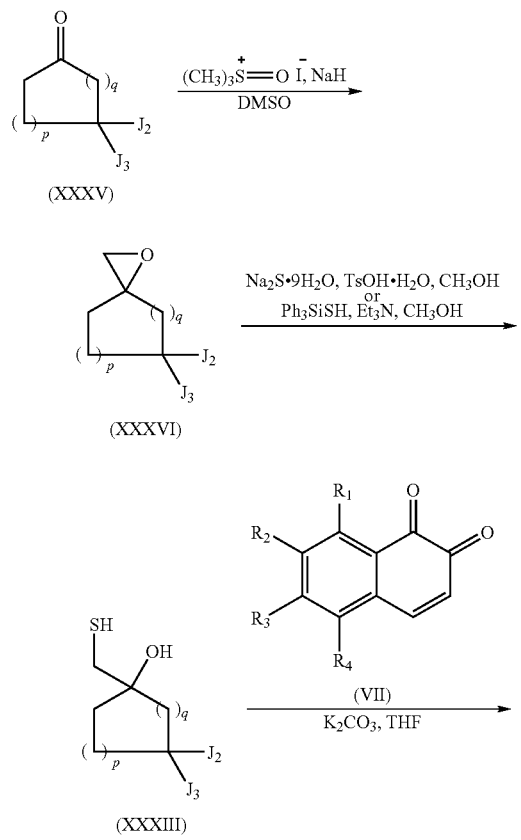

Scheme 15

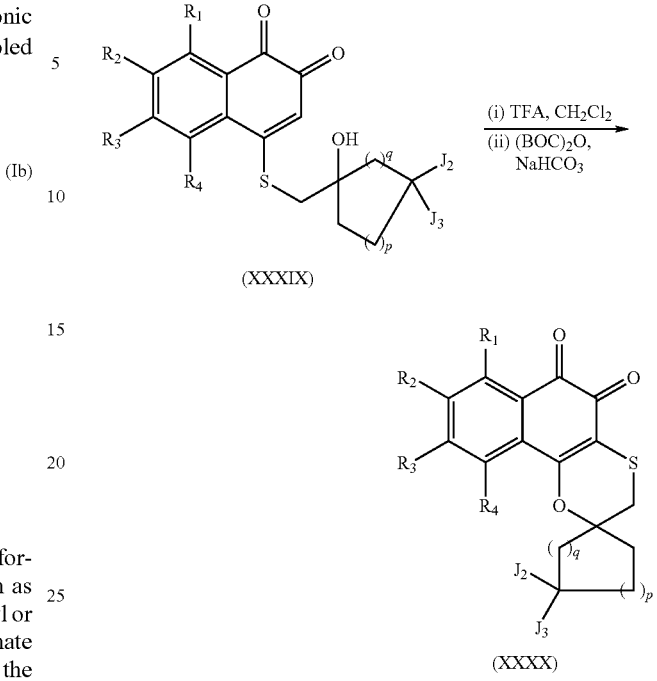

Epoxide compounds (XXXVI) may be conveniently prepared from ketones (XXXV). Trimethylsulfoxnium ylide is prepared by treating trimethlylsulfoxonium iodide with bases such as sodium hydride in a polar solvent such as anhydrous dimethylsulfoxide. Other bases such as potassium t-butoxide may also be used instead of sodium hydride. The trimethlylsulfoxonium ylide is treated with ketone (XXXV) at 0° C. initially and the reaction warmed to room temperature for 4-24 hours to provide epoxide (XXXVI). Many ketones are commercially available or readily prepared by methods described in the literature and known to those skilled in art. Alternatively, the epoxide (XXXVI) can also be conveniently prepared from alkenes (XXXVII) by treatment with peroxy acids such m-chloroperoxybenzoic acid. Many alkenes are commercially available or readily prepared from ketone (XXXV) by methods described in the literature (such as wittig reaction) and known to those skilled in art.

The epoxides (XXXVI) are used to prepare thioalcohol compounds of formula (XXXVIII). These can be conveniently prepared by a variety of methods familiar to those skilled in the art. The epoxide (XXXVI) is treated with a pretreated mixture of sodium sulfide and acids such as p-toluene sulfonic acid in polar protic solvent such as methanol for 0.5-4 hours at a temperature of 0-25° C. to provide the thioalcohol (XXXVIII). A preferred common route to prepare thioalcohols (XXXVIII) where $J_2$ and $J_3$ are a part of the dioxolane ring, which is an acid sensitive moiety is by treating epoxide (XXXVI) with triphenylsilane thiol, tertiary amine bases such as triethyl amine and in polar protic solvent such as methanol for 0.5-4 hours at ambient temperatures.

The thioalcohols (XXXVIII) are used to prepare 1,2-quinone alcohol compounds of formula (XXXIX). These can be conveniently prepared by methods familiar to those skilled in the art. Thioalcohol (XXXVIII) is treated with 1,2-quinones (VII), bases such as potassium carbonate and solvents such as tetrahydrofuran for 0.5-4 hours at ambient temperatures to provide the 1,2-quinone alcohols with formula (XXXIX). Alternatively bases such as triethylamine, sodium carbonate, cesium carbonate and solvents such as acetonitrile dichloromethane can also be utilized.

1,2-Quinone alcohols (XXXIX) are used to prepare spiro-1,2-quinone compounds (XXXX). These can be conveniently prepared by methods familiar to those skilled in the art. 1,2-Quinone alcohols (XXXIX) are treated with acid such as trifluoroacetic acid and solvents such as dichloromethane in open air at ambient temperature for 24-96 hours to prepare spiro-1,2-quinone (XXXX). Alternatively acids such as p-toluenesulfonic acid can also be used and air or oxygen can also be bubbled through the reaction. In the reaction where $J_2$ and $J_3$ is dioxolane protecting group, spiro-1,2-quinone ketone (XXXX) is also formed. In the reaction where $J_2$ is hydrogen, $J_3$ is N-$J_1$ where $J_1$ is a protecting group such as tert-butyl carbamate (t-BOC), the crude spiro-1,2-quinone is isolated in which $J_1$ is hydrogen. The crude spiro-1,2-quinone where $J_1$ is hydrogen is treated with di-tert-butyl dicarbonate in bases such as aqueous sodium bicarbonate, solvent such as dichloromethane for 0.25-4 hours at ambient temperature to provide the spiro-1,2-quinones (XXXX) where $J_1$ is tert-butyl carbamate (t-BOC) protecting group.

sodium borohydride in solvents such as methanol at ambient temperatures for 4-24 hours. Alternatively reducing agents such as sodium triacetoxyborohydride in solvents such as tetrahydrofuran, dichloromethane can also be used to prepare spiro-1,2-quinone alcohol with formula (XXXXI)

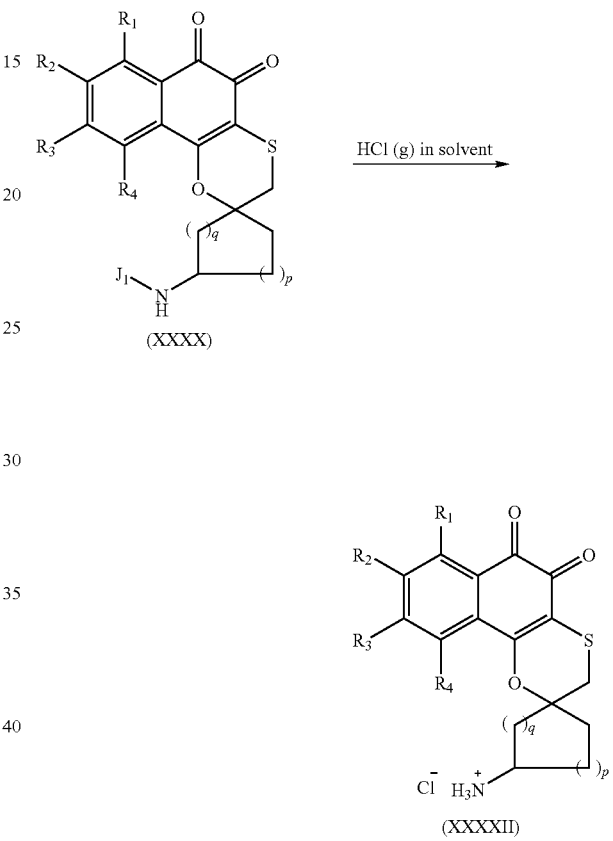

Scheme 17

Compounds of formula (XXXXII) can be prepared as shown in Scheme 17. Spiro-1,2-quinones (XXXXII) can be prepared by treating spiro-1,2-quinones (XXXX) where and $J_1$ is a protecting group such as t-butyl carbamate (t-BOC) with acids such as a solution of hydrogen chloride gas in solvents such as ethyl acetate, 1,2-dioxane, diethyl ether at ambient temperature for 1-24 hours to give the product as an hydrochloride salt. Alternatively trifluoroacetic acid in solvents such as dichloromethane can also be used in the above reaction. The product spiro-1,2-quinones (XXXXII) can be isolated as free base, hydrochloride or trifluoroacetic acid salt. To obtain the free base an aqueous workup with sodium bicarbonate is carried out on either acid salt. The above condition also describes the method to deprotect amines protected with t-butoxycarbamoyl (t-BOC) group.

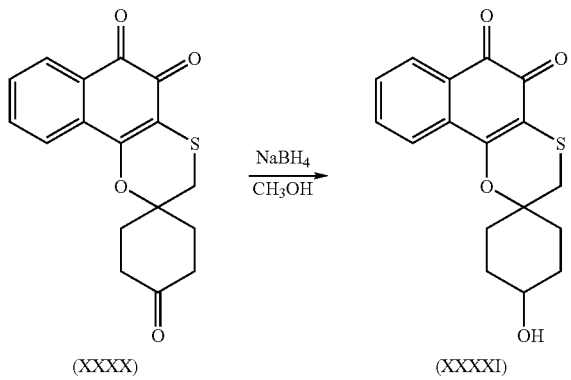

As shown in Scheme 16, spiro-1,2-quinone alcohol (XXXXI) can be conveniently prepared by treating spiro-1,2-quinone ketone (XXXX) with reducing agents such as Scheme 18

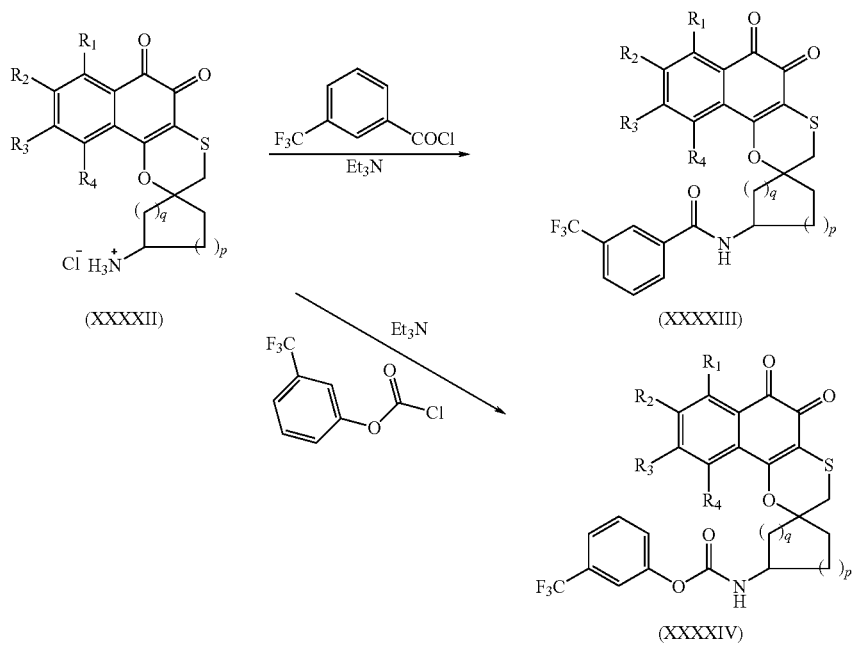

Scheme 18 illustrates a variety of chemical transformation of spiro-1,2-quinone (XXXXI) to provide compounds (XXXXII-XXXXIII). The following methods are provided by way of exemplification. Furthermore, the spiro-1,2-quinone (XXXXII) can also be functionalized to prepare compounds with functional groups in an analogous fashion as illustrated in Scheme 9. Alternative methods may be employed and are described in reference text's such as Comprehensive Organic Transformations, Richard C. Larock, Second Edition, Wiley—VCH, 1999; Protective Groups in Organic Synthesis, Third Edition, Theodora W. Greene and Peter M. Wuts, Wiley Interscience, 1999; The Practice of Peptide Synthesis, M. Bodanszky and A. Bodanzsky, Springer-Verlag, 1984.

The spiro-1,2-quinone amides (XXXXII) can be conveniently prepared by treating spiro-1,2-quinone (XXXXI) with acid chlorides such as m-trifluoromethylbenzoyl chlorides in presence of tertiary amine bases such as triethylamine, diisopropylethyl amine and solvents such as dichloromethane at ambient temperature for 1-12 hours. Many acid chlorides are commercially available or readily prepared by methods described in the literature and known to those skilled in art.

Alternatively spiro-1,2-quinone amides (XXXXIII) can be conveniently prepared by treating spiro-1,2-quinone (XXXII) with carboxylic acids with formula in presence of amide coupling agents such as HBTU (O-(benzotriazo-1-yl)-N,N,N',N'-tetramethyluronium hexafluorophosphate), tertiary amine bases such as dimethylaminopyridine and solvents such as dimethylformamide at ambient temperature for 4-24 hours. Alternatively amide coupling agents such as DCC (dicylcohexycarbodiimide), BOP ((benzotriazo-1-yloxy)tris (dimethylamino) phosphonium hexafluorophosphate, EDCI-.HCl (1-(3-Dimethyl aminopropyl)-3-ethylcarbodiimide hydrochloride), DMC (2-chloro-1,3-dimethylimidazolinium chloride) and tertiary amines bases such as triethylamine, diisopropylethyl amine can also be used. Many carboxylic acids are commercially available or readily prepared by methods described in the literature and known to those skilled in art.

Spiro-1,2-quinone carbamates (XXXXIV) can be conveniently prepared by treating spiro-1,2-quinone (XXXXII) with carbamoyl chlorides such as 3-(trifluoromethyl)phenyl chloroformate, bases such as triethylamine, diisopropylethyl amine, aqueous sodium carbonate in solvents such as ethyl acetate, dichloromethane at ambient temperature for 1-12 hours. Many carbamates are commercially available or readily prepared by methods described in the literature and known to those skilled in art.

Compounds encompassed in the invention can be produced according to this or other synthetic processes without departing from the spirit or essential characteristics of the invention. All changes that come within the meaning and range of equivalency of the compounds are intended to be embraced herein. Thus, it is expected that one of ordinary skill in the art would know how to alter the synthetic schemes illustrated herein so as to produce a desired substitution pattern on a compound, produce an increased or decreased product yield, minimize reaction side products, eliminate the use of dangerous or toxic chemical reactants, and/or to produce a desired amount of product (e.g., scale-up reaction size for commercial manufacture), and the like.

The present invention further provides a compound prepared by one of the synthetic processes disclosed herein, such as those disclosed in the Examples.

3. Methods of Treatment

The present invention also provides a method for the treatment of a cell proliferative disorder in a mammal comprising administering to a mammal in need of such treatment, a therapeutically effective amount of a compound of Formula I. The invention further provides the use of a compound of Formula I for the preparation of a medicament useful for the treatment of a cell proliferative disorder. In one embodiment, the invention provides for the treatment of cancer or precancerous conditions in a mammal comprising administering to a mammal in need of such treatment, a therapeutically effective amount of a compound of Formula I. The mammal can be e.g., any mammal, e.g., a human, a primate, mouse, rat, dog, cat, cow, horse, pig. For example, the mammal is a human.

An effective amount of a compound of Formula I is used in a method to treat a cell proliferative disorder in a mammal without affecting normal cells of the mammal. For example, a therapeutically effective amount of a compound of Formula I is used in a method for treating cancer in a mammal by inducing cell death in cancer cells without affecting normal cells in the normal. Cell death can occur by either apoptosis or necrosis mechanisms. In another example, administration of a therapeutically effective amount of a compound of Formula I induces sustained (non-transient) activity (e.g. elevation of the level) of a checkpoint molecule in abnormally proliferating cells without affecting checkpoint molecule activity in normal cells. For example, administration of a therapeutically effective amount of a compound of Formula I induces activation of E2F1 checkpoint pathway in abnormally proliferating cells without significantly affecting normal cells. In another example, administration induces sustained E2F pathway activity (e.g. elevation of E2F levels) in cancer cells without affecting E2F pathway activity (e.g. E2F levels) in normal cells. Methods of measuring induction of E2F activity and elevation of E2F levels are as shown in Li et al., (2003) *Proc Natl Acad Sci USA.* 100(5): 2674-8. In another example, administration of a therapeutically effective amount of a compound of Formula I induces cell death in abnormally proliferating cells without inducing cell death in normal cells.

The invention also provides a method of protecting against a cell proliferative disorder in a mammal by administering a therapeutically effective amount of a compound of Formula I to a mammal. The invention also provides the use of a compound of Formula I for the preparation of a medicament useful for the prevention of a cell proliferative disorder. In one embodiment, the invention provides for the prevention of cancer in a mammal comprising administering to a mammal in need of such treatment, a therapeutically effective amount of a compound of Formula I.

The compounds of the invention are administered in the form of pharmaceutical compositions, e.g., as described herein.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

As used herein, "monotherapy" refers to administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention is more effective than combination therapy in inducing a desired biological effect.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating cancer results in a reduction in size of a tumor. In another aspect, treating cancer results in a reduction in tumor volume. In another aspect, treating cancer results in a decrease in number of tumors. In another aspect, treating cancer results in a decrease in number of metastatic lesions in other tissues or organs distant from the primary tumor site. In another aspect, treating cancer results in an increase in average survival time of a population of treated subjects in comparison to a population receiving carrier alone. In another aspect, treating cancer results in an increase in average survival time of a population of treated subjects in comparison to a population of untreated subjects. In another aspect, treating cancer results in increase in average survival time of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in tumor growth rate. In another aspect, treating cancer results in a decrease in tumor regrowth.

In another aspect, treating or preventing a cell proliferative disorder results in a reduction in the rate of cellular proliferation. In another aspect, treating or preventing a cell proliferative disorder results in a reduction in the proportion of proliferating cells. In another aspect, treating or preventing a cell proliferative disorder results in a decrease in size of an area or zone of cellular proliferation. In another aspect, treating or preventing a cell proliferative disorder results in a decrease in the number or proportion of cells having an abnormal appearance or morphology.

In additional aspects, β-lapachone, or a pharmaceutically acceptable salt, metabolite, analog or derivative thereof, can be administered in combination with a chemotherapeutic agent. Exemplary chemotherapeutics with activity against cell proliferative disorders are known to those of ordinary skill in the art, and may be found in reference texts such as the *Physician's Desk Reference*, 59th Edition, Thomson PDR (2005). For example, the chemotherapeutic agent can be a taxane, an aromatase inhibitor, an anthracycline, a microtubule targeting drug, a topoisomerase poison drug, a targeted monoclonal or polyclonal antibody, an inhibitor of a molecular target or enzyme (e.g., a kinase inhibitor), or a cytidine analogue drug. In preferred aspects, the chemotherapeutic agent can be, but is not restricted to, tamoxifen, raloxifene, anastrozole, exemestane, letrozole, cisplatin, carboplatin, TAXOL® (paclitaxel), cyclophosphamide, lovastatin, minosine, GEMZAR® (gemcitabine HCl), araC, 5-fluorouracil (5-FU), methotrexate (MTX), TAXOTERE® (docetaxel), ZOLADEX® (goserelin), vincristin, vinblastin, nocodazole, teniposide, etoposide, epothilone, navelbine, camptothecin, daunonibicin, dactinomycin, mitoxantrone, amsacrine, doxorubicin (adriamycin), epirubicin, idarubicin, or GLEEVEC® (imatanib), IRESSA® (gefitinib), TARCEVA® (erlotinib), NEXAVAR® (sorafenib), SUTENT® (sunitinib malate), HERCEPTIN® (trastuzumab), RITUXAN® (Rituximab), ERBITUX® (cetuximab), AVASTIN® (bevacizumab), or agents listed in http://www.cancer.org/docroot/cdg/cdg_0.asp. In another aspect, the chemotherapeutic agent can be a cytokine such as G-CSF (granulocyte colony stimulating factor). In another aspect, β-lapachone, or a pharmaceutically acceptable salt, metabolite, analog or derivative thereof may be administered in combination with radiation therapy. In yet another aspect, β-lapachone, or a pharmaceutically acceptable salt, metabolite, analog or derivative thereof may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

4. The Pharmaceutical Compositions and Formulations

A "pharmaceutically acceptable salt" or "salt" of the disclosed compound is a product of the disclosed compound that contains an ionic bond, and is typically produced by reacting the disclosed compound with either an acid or a base, suitable for administering to a subject. Pharmaceutically acceptable salt can include, but is not limited to, acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca, or organic amine salts.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The present invention also provides pharmaceutical formulations comprising a compound of Formula I in combination with at least one pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in "Remington: The Science and Practice of Pharmacy, Twentieth Edition." Lippincott Williams & Wilkins, Philadelphia, Pa., which is incorporated herein by reference. Examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Methods for formulation are disclosed in PCT International Application PCT/US02/24262 (WO03/011224), U.S. Patent Application Publication No. 2003/0091639 and U.S. Patent Application Publication No. 2004/0071775, each of which is incorporated by reference herein.

A compound of Formula I is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of Formula I (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation. In another embodiment, a therapeutically effective amount of a compound of Formula I is administered in a suitable dosage form without standard pharmaceutical carriers or diluents.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include tune-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active compounds into preparations that can be used pharmaceutically. Of course, the appropriate formulation is dependent upon the route of administration chosen.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. For treatment of psoriatic conditions, systemic administration (e.g., oral administration), or topical administration to affected areas of the skin, are preferred routes of administration. The dose chosen should be sufficient to constitute effective treatment but not so high as to cause unacceptable side effects. The state of the disease condition (e.g., cancer, psoriasis, and the like) and the health of the patient should be closely monitored during and for a reasonable period after treatment.

EXAMPLES

Examples are provided below to further illustrate different features of the present invention. The examples also illustrate useful methodology for practicing the invention. These examples do not limit the claimed invention.

Example 1

Procedure A

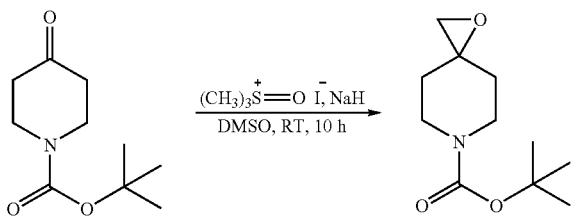

E1.1. Synthesis of tert-butyl 1-oxa-6-azaspiro[2.5]octane-6-carboxylate (Compound 1)

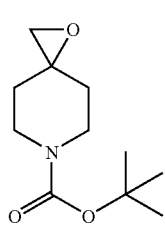

A mixture of trimethylsulfoxonium iodide (65.2 g, 29.6 mmol) and anhydrous DMSO (300 ml) was stirred at room temperature for 1 hour under a nitrogen atmosphere. The reaction was then cooled to 0° C. and NaH (60% in mineral oil) (14.2 g, 35.5 mmol) was added in small portions over the course of 1 hour. The reaction mixture was allowed to warm to room temperature and stirred for 4 hours. The reaction mixture was then cooled to 0° C., tert-butyl 4-oxo-1-piperidinecarboxylate (59.0 g, 29.6 mmol) added, then allowed to react at room temperature for 16 hours. The reaction mixture was then poured onto 1.2 liters of ice water and extracted with ether (4×400 ml). The organic layers were washed with water (2×500 ml) and brine (2×500 ml). The organic extract was dried with $Na_2SO_4$ and concentrated under reduced pressure. The crude product was purified by flash column chromatography ($SiO_2$, 5% EtOAc in hexanes to 40% EtOAc in hexanes) to afford the product as white crystalline solid (35.3 g, 56%). M.p.=48-50° C.; 400 MHz $^1$H NMR ($CDCl_3$) δ: 3.77-3.68 (m, 2H), 3.45-3.36 (m, 2H), 2.68 (s, 2H), 1.83-1.74 (m, 2H), 1.5-1.4 (m, 11H); LCMS: 214 [M+H].

E1.2. Synthesis of tert-butyl 1-oxa-6-azaspiro[2.6]nonane-6-carboxylate (Compound 2)

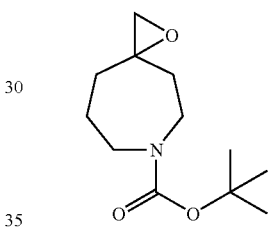

Compound 2 was synthesized using tert-butyl 4-oxoazepane-1-carboxylate using conditions outlines in procedure A. 400 MHz $^1$H NMR ($CDCl_3$) δ: 3.70-3.50 (m, 2H), 3.36-3.28 (m, 2H), 2.66-2.61 (m, 2H), 2.00-1.67 (m, 6H), 1.47 (s, 9H).

E1.3. Synthesis of tert-butyl 1-oxa-5-azaspiro[2.5]octane-5-carboxylate (Compound 3)

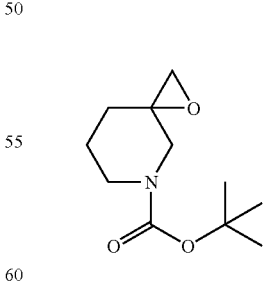

Compound 3 was synthesized using tert-butyl 3-oxopiperidine-1-carboxylate using conditions outlines in procedure A. 400 MHz $^1$H NMR ($CDCl_3$) δ: 3.47-3.44 (m, 3H), 3.37-3.33 (m, 1H), 2.76 (brs, 1H), 2.66 (d, J=4.4 Hz, 1H), 1.9-1.79 (m, 1H), 1.77-1.61 (m, 3H), 1.4 (s, 9H).

Example 2

Procedure B

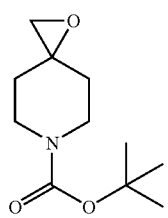
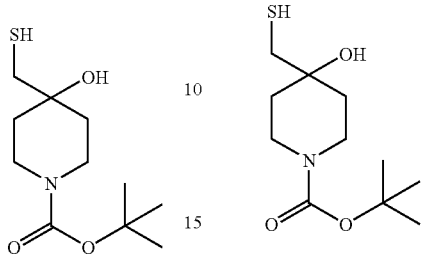

E2.1. Synthesis of tert-butyl 4-hydroxy-4-(mercaptomethyl)piperidine-1-carboxylate (Compound 4)

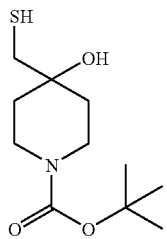

To a mixture of tert-butyl 1-oxa-6-azaspiro[2.5]octane-6-carboxylate (35.3 g, 16.55 mmol) and triphenylsilanethiol (48.4 g, 16.55 mmol) in anhydrous methanol (1.0 L) was added triethylamine (23.1 ml, 16.55 mmol) drop-wise over the course of 30 minutes. The reaction was stirred for 1 hour at room temperature and the methanol was evaporated under reduced pressure. The crude product was purified by flash column chromatography ($SiO_2$, 5% EtOAc in hexanes to 40% EtOAc in hexanes) to afford 81% (33.1 g) pure final product. M.p.=54-55° C.; 400 MHz $^1$H NMR ($CDCl_3$) δ: 3.97-3.78 (m, 2H), 3.19-3.08 (m, 2H), 2.61 (d, J=4.4 Hz, 2H), 1.70-1.55 (m, 2H), 1.50-1.38 (m, 11H); LCMS: 248 [M+H].

Example 3

Procedure C

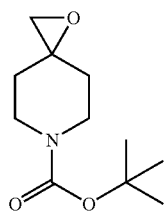
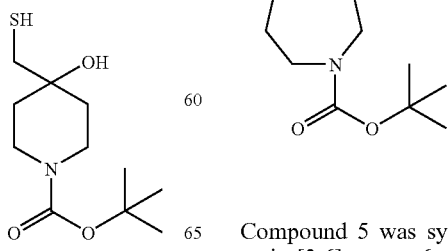

E3.1. Synthesis of tert-butyl 4-hydroxy-4-(mercaptomethyl)piperidine-1-carboxylate (Compound 4)

Sodium sulfide nonahydrate (60 g, 0.25 mol) was dissolved in MeOH (1.25 L), and the resulting solution was degassed by applying vacuum and filling nitrogen three times. The solution was then cooled to 0° C. with an ice-water bath. To the above solution was added p-toluenesulfonic acid hydrate (76 g, 0.4 mol) and the resulting mixture was stirred at 0° C. for 10 min. A yellowish colored solution was formed. The tert-butyl 1-oxa-6-azaspiro[2.5]octane-6-carboxylate (21.2 g, 0.1 mol) was added to the reaction mixture and stirred at 0° C. for 1 h and then at room temperature for 1.5 h. Saturated sodium bicarbonate solution (200 mL) was added to the reaction, and the methanol was evaporated under reduced pressure. To the residue was added water (500 mL) and extracted with EtOAc (1×400 mL and 2×250 mL), the combined organic layer was washed with brine (250 mL) and dried over sodium sulfate. After concentration, the crude product (26.2 g) was obtained as an oil. The crude product was purified by flash column chromatography ($SiO_2$, 5% to 40% EtOAc in hexanes) to afford the product as a white solid. (19.2 g, 78%). M.p.=54-55° C.; 400 MHz $^1$H NMR ($CDCl_3$) δ: 3.97-3.80 (m, 2H), 3.19-3.08 (m, 2H), 2.61 (d, J=4.4 Hz, 2H), 2.22 (s, 1H), 1.68-1.60 (m, 2H), 1.50-1.40 (m, 11H); LCMS: 248 [M+H].

E3.2. Synthesis of tert-butyl 4-hydroxy-4-(mercaptomethyl)azepane-1-carboxylate (Compound 5)

Compound 5 was synthesized using tert-butyl 1-oxa-6-azaspiro[2.6]nonane-6-carboxylate using conditions outlined in procedure C.

E3.3. Synthesis of tert-butyl 3-hydroxy-3-(mercaptomethyl)piperidine-1-carboxylate (Compound 6)

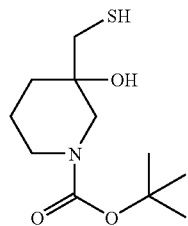

Compound 6 was synthesized using tert-butyl 1-oxa-5-azaspiro[2.5]octane-5-carboxylate and conditions outlined in procedure C.

Example 4

Procedure D

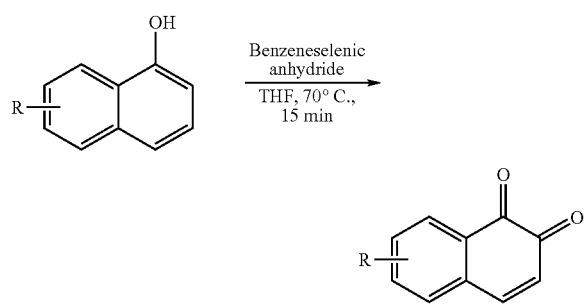

E4.1. Synthesis of 6-chloronaphthalene-1,2-dione (Compound 7)

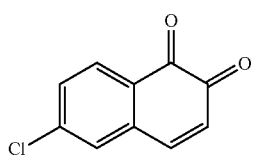

To a solution of benzeneselenic anhydride (3.18 g, 8.8 mmol) in tetrahydrofuran (30 ml), which had been heated to 70° C. was added a solution of 6-chloro-1-naphthol (1.5 g, 8.4 mmol) in tetrahydrofuran (5 ml). The reaction was maintained at 70° C. for 15 minutes. The mixture was then concentrated under reduced pressure. The residue was suspended in hexanes (100 ml) and filtered. This was repeated 5 times. The residue was dissolved in dichloromethane (100 ml), filtered and concentrated under reduced pressure to afford the product as an orange solid (1.33 g, 82%); 400 MHz $^1$H NMR (CDCl$_3$) δ: 8.06 (d, J=8.4 Hz, 1H), 7.49 (dd, J=2 and 8.4 Hz. 1H), 7.41-7.38 (m, 2H), 6.50 (d, J=10 Hz, 1H).

E4.2. Synthesis of 7-methoxynaphthalene-1,2-dione (Compound 8)

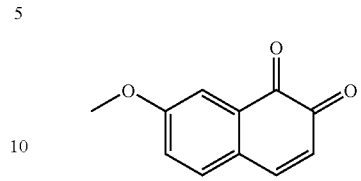

Compound 8 was synthesized using 7-methoxy-2-naphthol and conditions outlined in procedure D. M.p.=78-80° C.; 400 MHz $^1$H NMR (DMSO-d$_6$) δ: 7.86-7.42 (m, 4H), 6.37 (d, J=9.6 Hz, 1H), 3.93 (s, 3H); LCMS: 189 [M+H]

E4.3. Synthesis of 6-fluoronaphthalene-1,2-dione (Compound 9)

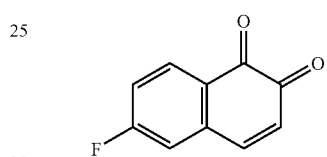

Compound 9 was synthesized using 6-fluoro-1-naphthol and conditions outlined in procedure D. 400 MHz $^1$H NMR (CDCl$_3$) δ: 8.18-8.15 (dd, J=8.60, 5.47 Hz, 1H), 7.41-7.38 (d, J=10.17 Hz, 1H), 7.21-7.16 (m, 1H), 7.09-7.06 (dd, J=8.21, 2.34 Hz, 1H), 6.51-6.49 (d, J=10.17 Hz, 1H).

E4.4. Synthesis of 6-bromonaphthalene-1,2-dione (Compound 10)

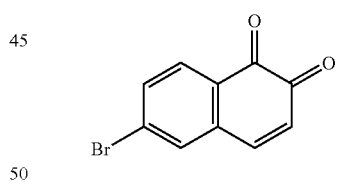

Compound 10 was synthesized using 6-bromo-1-naphthol and conditions outlined in procedure D.

E4.5. Synthesis of 6-methoxy-1,2-dione (Compound 11)

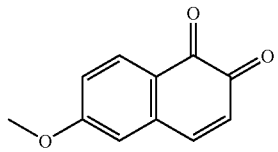

Compound 11 was synthesized using 6-methoxy-1-naphthol and conditions outlined in procedure D.

Example 5

Procedure E

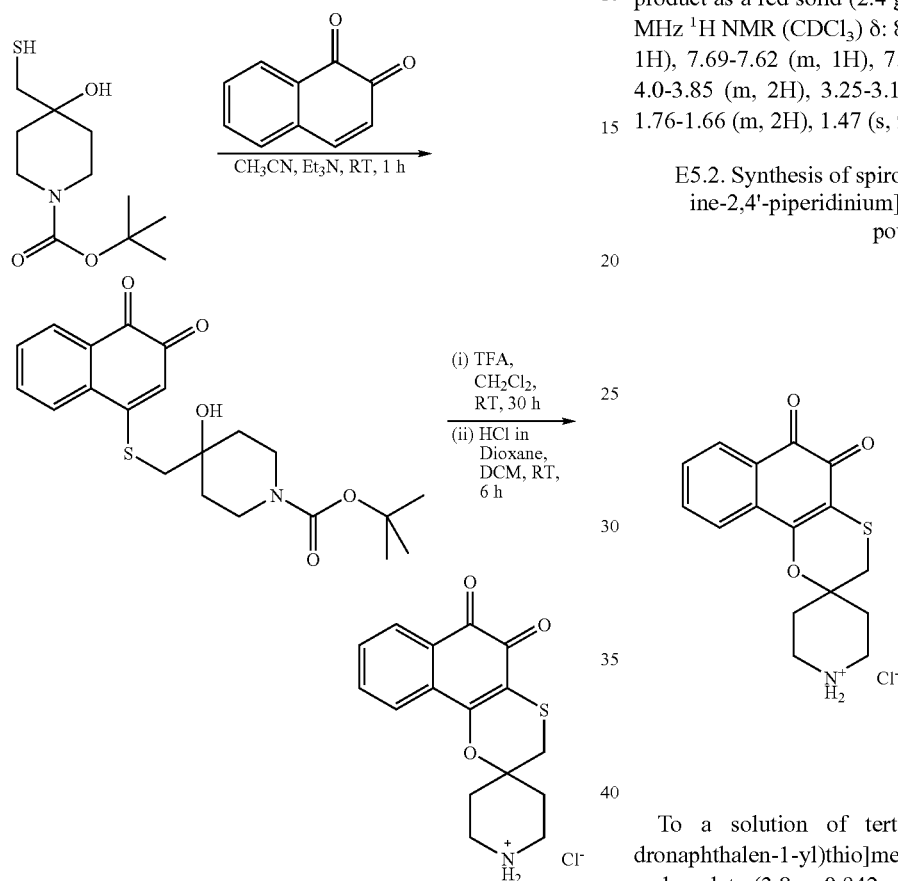

E5.1. Synthesis of tert-butyl 4-{[(3,4-dioxo-3,4-dihydronaphthalen-1-yl)thio]methyl}-4-hydroxypiperidine-1-carboxylate (Compound 12)

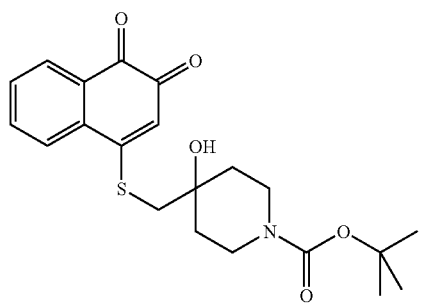

To a solution of naphthalene-1,2-dione (3.2 g, 2.02 mmol) and tert-butyl 4-hydroxy-4-(mercaptomethyl)piperidine-1-carboxylate (5.0 g, 2.02 mmol) in anhydrous acetonitrile (400 ml) was added triethylamine (2.82 ml, 2.02 mmol). The reaction mixture was allowed to stir for 1 hour at room temperature and the solvents were evaporated under reduced pressure. The crude product was purified by flash column chromatography (SiO$_2$, 40% EtOAc in hexanes to 70% EtOAc in hexanes). Fractions containing the product were concentrated and tritrated with ethyl acetate/ether to afford the desired product as a red solid (2.4 g, 29%). M.p.=156-157° C.; 400 MHz $^1$H NMR (CDCl$_3$) δ: 8.17-8.12 (m, 1H), 7.87-7.83 (m, 1H), 7.69-7.62 (m, 1H), 7.59-7.52 (m, 1H), 6.49 (s, 1H), 4.0-3.85 (m, 2H), 3.25-3.14 (m, 4H), 1.84-1.78 (m, 2H), 1.76-1.66 (m, 2H), 1.47 (s, 9H); LCMS: 404 [M+H].

E5.2. Synthesis of spiro[naphtho[1,2-b][1,4]oxathiine-2,4'-piperidinium]-5,6-dione chloride (Compound 13)

To a solution of tert-butyl 4-{[(3,4-dioxo-3,4-dihydronaphthalen-1-yl)thio]methyl}-4-hydroxypiperidine-1-carboxylate (3.8 g, 0.942 mmol) in 50 ml dichloromethane which was cooled to 0° C. was added trifluoroacetic acid (200 ml). The reaction mixture was stirred at room temperature for 30 hours and the solvent removed under reduced pressure. The mixture was dissolved in dichloromethane (150 ml) and pouted over a 0° C. mixture of saturated sodium carbonate (500 ml) and water (200 ml). Methanol (500 ml) was then added to the reaction mixture and allowed to stir overnight. The mixture was extracted with dichloromethane (4×400 ml). The organic extracts were combined and washed with a mixture of 2.0M sodium carbonate and brine (5×500 ml). The organic layer was separated, dried with Na$_2$SO$_4$, and concentrated under reduced pressure to give a purple solid. To a stirred solution of the purple solid in dichloromethane (100 ml), 4.0 M HCl in dioxane (20 ml) was added dropwise. The precipitate was filtered, washed with dichloromethane and ether, and recrystallized from ethanol to give a purple crystalline solid (1.84 g, 58%). M.p.=229-232° C.; 400 MHz $^1$H NMR (DMSO-d$_6$) δ: 9.19 (br, s, 2H), 7.90-7.86 (m, 1H), 7.84-7.80 (m, 1H), 7.76-7.71 (m, 1H), 7.58-7.53 (m, 1H), 3.33-3.25 (m, 2H), 3.16-3.07 (m, 4H), 2.22-2.15 (m, 2H), 2.20-1.50 (m, 2H); LCMS: 302 [M+H].

E5.3. Synthesis of spiro[naphtho[1,2-b][1,4]oxathiine-2,4'-piperidinium]-5,6-dione cis-2-carboxycyclohexanecarboxylate (Compound 14)

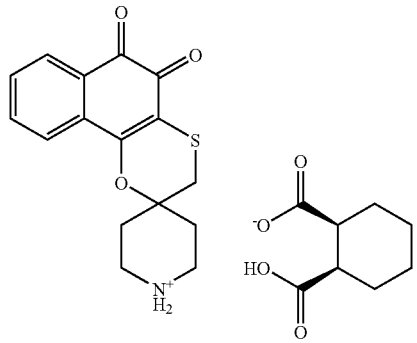

To a mixture of spiro[naphtho[1,2-b][1,4]oxathiine-2,4'-piperidine]-5,6-dione (0.5 g, 1.66 mmol) and acetonitrile (20 ml) which had been preheated to 80° C. was added a preheated (80° C.) solution of cis-cyclohexane-1,2-dicarboxylic acid (0.286 ml, 1.66 mmol) in acetonitrile (20 ml). The reaction mixture was stirred overnight at 80° C. The resulting purple precipitate was filtered, washed with acetonitrile, and dried under reduced pressure to afford the product as a purple solid (0.472 g, 60%). M.p.=204-207° C.; 400 MHz $^1$H NMR (DMSO-$d_6$) δ: 7.90-7.87 (m, 1H), 7.83-7.81 (m, 1H), 7.78-7.73 (m, 1H), 7.58-7.54 (m, 1H), 3.16-3.11 (m, 4H), 3.07-3.00 (m, 2H), 2.53-2.48 (m, 2H), 2.11-2.05 (m, 2H), 1.88-1.75 (m, 4H), 1.52-1.40 (m, 4H), 1.33-1.29 (m, 2H); LCMS: 302 [M+H].

E5.4. Synthesis of spiro[naphtho[1,2-b][1,4]oxathiine-2,4'-piperidinium]-5,6-dione trains-2-carboxycyclohexanecarboxylate (Compound 15)

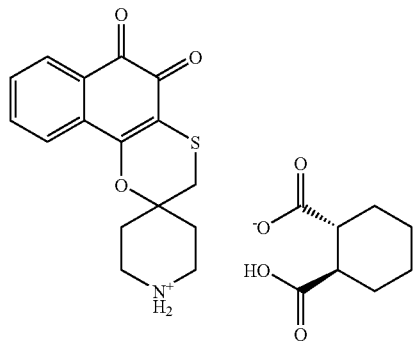

Compound 15 was synthesized using spiro[naphtho[1,2-b][1,4]oxathiine-2,4'-piperidine]-5,6-dione, trans-cyclohexane-1,2-dicarboxylic acid and conditions outlined for compound 14. M.p.=208-211° C.; 400 MHz $^1$H NMR (DMSO-$d_6$) δ: 7.90-7.87 (m, 1H), 7.82-7.73 (m, 2H), 7.58-7.53 (m, 1H), 3.06 (s, 2H), 2.96-2.86 (m, 4H), 2.29-2.26 (m, 2H), 1.98-1.91 (m, 4H), 1.77-1.65 (m, 4H), 1.23-1.17 (m, 4H); LCMS: 302 [M+H].

Example 6

Procedure F

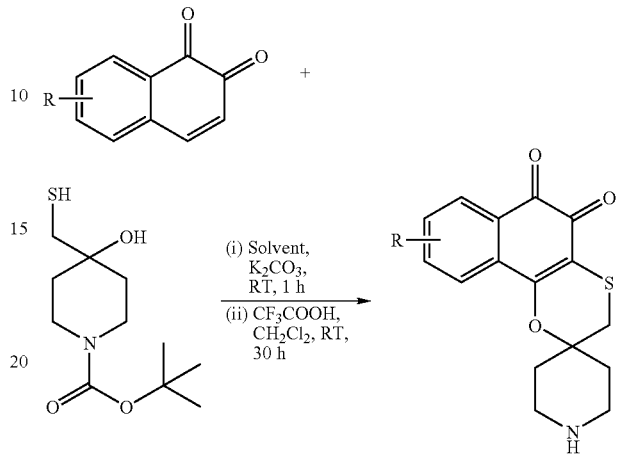

E6.1. Synthesis of spiro[naphtho[1,2-b][1,4]oxathiine-2,4'-piperidine]-5,6-dione (Compound 16)

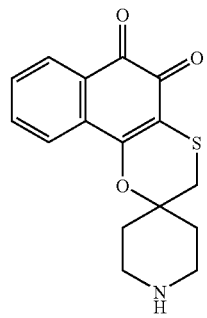

Step (i): To a 2 L round-bottomed flask containing the crude tert-butyl 4-hydroxy-4-(mercaptomethyl)piperidine-1-carboxylate (25.5 g, 0.1 mol) was added THF (1.1 L) followed by naphthalene-1,2-dione (13.0 g, 85 mmol) and granular $K_2CO_3$ (21 g). The reaction was allowed to proceed for 1 h at room temperature. The reaction mixture was filtered to remove all solids and the filtrate concentrated under reduced pressure. The crude residue obtained was used in step (ii) without any further purification.

Step (ii): The crude residue was dissolved in dichloromethane (400 mL) and trifluoroacetic acid (250 mL) was added in three portions. The reaction mixture was allowed to proceed at room temperature in an open flask. After the reaction was stirred overnight, air was bubbled into the reaction and the reaction was continued to stir for additional 48 h. The solvent was then removed under reduced pressure and the residue was dissolved in 1:9 methanol/dichloromethane (800 mL). The organics were extracted twice with water (2×400 mL). The pH of the combined aqueous extracts were adjusted to pH 8 using saturated $NaHCO_3$. The aqueous layer was then extracted with 1:9 methanol/dichloromethane (5×300 mL). The combined organic extracts was washed with brine, dried (with $Na_2SO_4$), filtered and concentrated under reduced pressure to afford the product as a dark purple solid (combined yield for two steps: 12.4 g, 51%). M.p.=234-240° C.; 400 MHz $^1$H NMR (CDCl$_3$) δ: 8.08-8.03 (m, 1H), 7.82-7.78 (m, 1H), 7.68-7.63 (m, 1H), 7.51-7.46 (m, 1H), 3.12-3.00 (m, 4H), 2.94 (s, 2H), 2.13-2.06 (m, 2H), 1.81-1.72 (m, 2H); LCMS: 302 [M+H].

E6.2. Synthesis of spiro[naphtho[1,2-b][1,4]oxathiine-2,3'-piperidine]-5,6-dione (Compound 17)

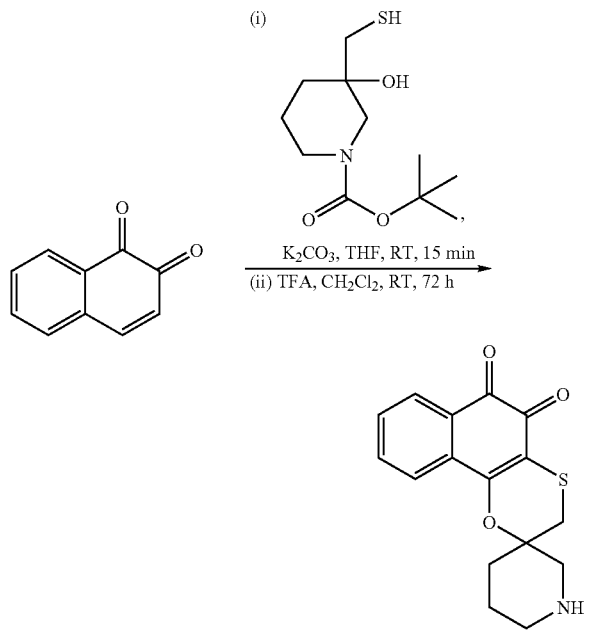

Step (i): It was carried out using tert-butyl 3-hydroxy-3-(mercaptomethyl)piperidine-1-carboxylate, naphthalene-1,2-dione, tetrahydrofuran as the solvent and conditions outlined in procedure F [step (i)]. The intermediate was used in step (ii) without any purification.

Step (ii): Compound 17 was synthesized using conditions as outlined in procedure F [step (ii)]. M.p.=128-134° C.; 400 MHz $^1$H NMR (CDCl$_3$) δ: 8.04 (dd, J=1.2 and 7.6 Hz, 1H), 7.78 (dd, J=0.8 and 7.6 Hz, 1H), 7.65 (dt, J=1.2 and 7.6 Hz, 1H), 7.48 (dt, J=1.2 and 7.6 Hz, 1H), 3.18 (d, J=13.2 Hz, 1H), 3.05-2.92 (m, 4H), 2.85-2.79 (m, 1H), 2.18-2.11 (m, 1H), 1.88-1.88-1.65 (m, 3H); LCMS: 302 [M+H].

E6.3. Synthesis of 9-chlorospiro[naphtho[1,2-b][1,4]oxathiine-2,4'-piperidine]-5,6-dione (Compound 18)

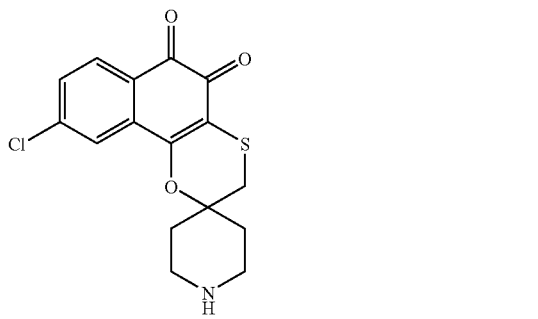

Step (i): tert-butyl 4-{[(7-chloro-3,4-dioxo-3,4-dihydronaphthalen-1-yl)thio]methyl}-4-hydroxypiperidine-1-carboxylate was synthesized using tert-butyl 4-hydroxy-4-(mercaptomethyl)piperidine-1-carboxylate, 6-chloronaphthalene-1,2-dione, acetonitrile as the solvent and conditions outlined in procedure F [step(i)]. The intermediate was purified by flash column chromatography (SiO$_2$, 30% EtOAc in hexanes to 50% EtOAc in hexanes).

Step (ii): Compound 18 was synthesized using conditions as outlined in procedure F [step (ii)]. M.p.=>300° C.; 400 MHz $^1$H NMR (DMSO-d$_6$) δ: 7.91-7.86 (m, 1H), 7.67-7.62 (m, 2H), 3.07 (s, 2H), 2.86-2.77 (m, 4H), 1.93-1.89 (m, 2H), 1.71-1.64 (m, 2H); LCMS: 336 [M+H].

E6.4. Synthesis of 9-fluorospiro[naphtho[1,2-b][1,4]oxathiine-2,4'-piperidine]-5,6-dione (Compound 19)

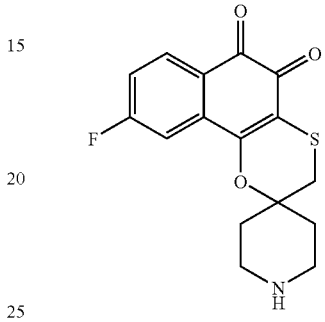

Step (i): tert-butyl 4-{[(7-fluoro-3,4-dioxo-3,4-dihydronaphthalen-1-yl)thio]methyl}-4-hydroxypiperidine-1-carboxylate was synthesized using tert-butyl 4-hydroxy-4-(mercaptomethyl)piperidine-1-carboxylate, 6-fluoronaphthalene-1,2-dione, acetonitrile as the solvent and conditions outlined in procedure F [step(i)]. The intermediate was purified by flash column chromatography (SiO$_2$, 30% EtOAc in hexanes to 50% EtOAc in hexanes).

Step (ii): Compound 19 was synthesized using conditions as outlined in procedure F [step(ii)]. 400 MHz $^1$H NMR (CDCl$_3$) δ: 8.10-8.07 (m, 1H), 7.45-7.42 (dd, J=9.39, 2.34 Hz, 1H), 7.17-7.2 (dt, J=16.43, 8.21 Hz, 1H), 3.07-3.05 (m, 4H), 2.11-1.76 (m, 6H); LCMS: 320 [M+H]

E6.5. Synthesis of 9-methoxyspiro[naphtho[1,2-b][1,4]oxathiine-2,4'-piperidine]-5,6-dione (Compound 20)

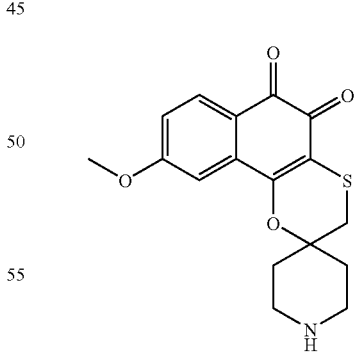

Step (i): tert-butyl 4-hydroxy-4-{[(7-methoxy-3,4-dioxo-3,4-dihydronaphthalen-1-yl)thio]methyl}piperidine-1-carboxylate was synthesized using tert-butyl 4-hydroxy-4-(mercaptomethyl)piperidine-1-carboxylate, 6-methoxynaphthalene-1,2-dione, acetonitrile as the solvent and conditions outlined in procedure F [step(i)]. The crude intermediate was used in step (ii) without any further purification.

Step (ii): Compound 20 was synthesized using conditions as outlined in procedure F and purified by preparative thin layer chromatography (SiO$_2$) to afford the desired product as a purple solid (combined yield for two steps: 0.054 g, 22%). M.p.=224-226° C.; 400 MHz $^1$H NMR (DMSO-d$_6$) δ: 7.88 (d, J=8.8 Hz, 1H), 7.20 (s, 1H), 7.08 (d, J=8.4 Hz, 1H), 3.89 (s, 3H), 3.11 (s, 2H), 2.82 (brs, 4H), 1.88 (m, 2H), 1.65 (m, 2H); LCMS: 332 [M+H].

Example 7

Procedure G

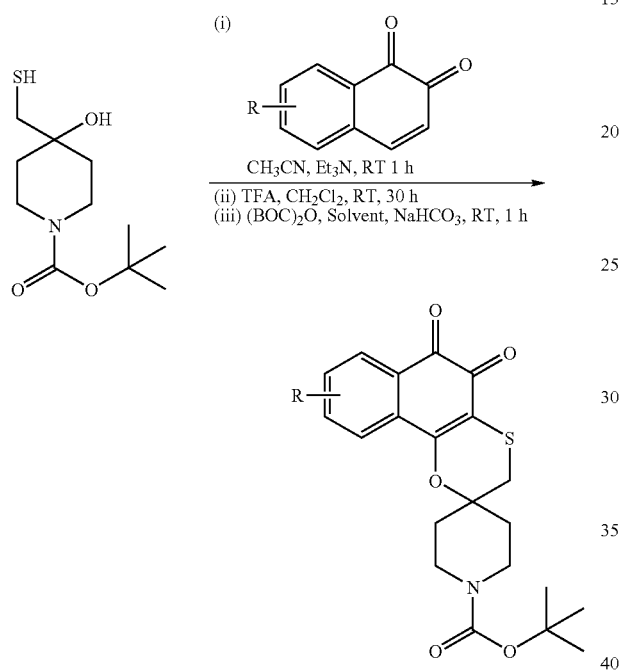

E7.1. Synthesis of tert-butyl 8-methoxy-5,6-dioxo-5,6-dihydro-1'H-spiro[naphtho[1,2-b][1,4]oxathiine-2,4'-piperidine]-1'-carboxylate (Compound 21)

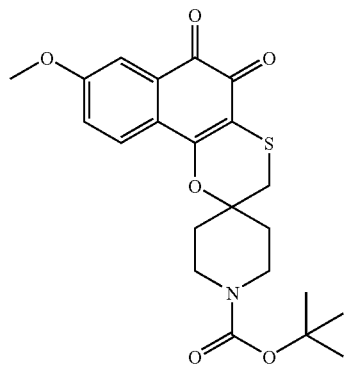

Step (i): To a solution of 7-methoxynaphthalene-1,2-dione (3.88 g, 20.3 mmol) and tert-butyl 4-hydroxy-4-(mercaptomethyl)piperidine-1-carboxylate (5.70 g, 23.1 mmol) in acetonitrile (120 mL) was added potassium carbonate (5.71 g, 41.3 mmol). The reaction was stirred at room temperature for 1.5 hours. The solvent was removed under reduced pressure and the crude product used in step (ii) without any further purification.

Step (ii): The crude intermediate from step (i) (7.1 g) was dissolved in dichloromethane (100 mL) and trifluoroacetic acid (75 mL) was added drop-wise over the course of 1 hour. The reaction was stirred at room temperature for 24 hours and the solvent removed under reduced pressure. The crude product was dissolved in methanol and dichloromethane (1:9) (40 mL) and washed with water (3×40 mL). The aqueous layers were combined, neutralized with saturated NaHCO$_3$, and washed with methanol and dichloromethane (1:9) (4×20 mL). The organic layers were combined, dried over MgSO$_4$, and the concentrated under reduced pressure to yield a purple solid (2.9 g). This product was carried out on to step (iii) without any further purification.

Step (iii): The crude intermediate from step (ii) (2.88 g, 8.69 mmol) was dissolved in saturated NaHCO$_3$ (25 mL) and dichloromethane (60 mL). To the stirring solution was then added di-tert-butyl dicarbonate (3.50 g, 16.0 mmol) and the reaction was stirred for 15 minutes at room temperature. The reaction mixture was poured into a seperatory funnel and the layers were allowed to separate. The aqueous layer was washed with DCM (4×20 mL). The organic extracts were combined, dried over MgSO$_4$, and concentrated under reduced pressure to yield a purple solid (4.2 g). The crude product was purified by flash column chromatography (SiO$_2$, 50% EtOAc in hexanes) to afford the product as a purple solid (combined yield for three steps: 3.62 g, 41%). M.p.=231-232° C.; 400 MHz $^1$H NMR (DMSO-d$_6$) δ: 7.76 (d, J=7.8 Hz, 1H), 7.37 (d, J=1.2 Hz, 1H), 7.26 (dd, J=2.2, 8.0 Hz, 1H), 3.87 (s, 3H), 3.08 (s, 2H), 2.06-1.93 (m, 2H), 1.76-1.67 (m, 2H), 1.42 (s, 9H). LCMS: 432 [M+H]

E7.2. Synthesis of tert-butyl 9-bromo-5,6-dioxo-5,6-dihydro-1'H-spiro[naphtho[1,2-b][1,4]oxathiine-2,4'-piperidine]-1'-carboxylate (Compound 22)

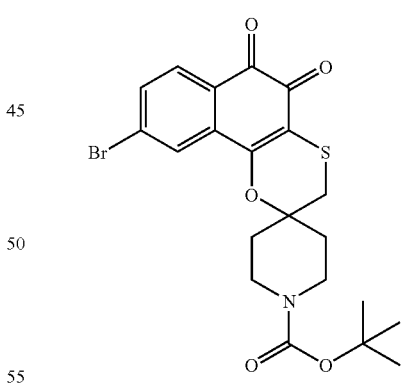

Step (i): tert-butyl 4-{[(7-bromo-3,4-dioxo-3,4-dihydronaphthalen-1-yl)thio]methyl}-4-hydroxypiperidine-1-carboxylate was synthesized using 6-bromonaphthalene-1,2-dione, tert-butyl 4-hydroxy-4-(mercaptomethyl)piperidine-1-carboxylate, acetonitrile as a solvent and conditions outlined in procedure G [Step (i)].

Step (ii): 9-bromospiro[naphtho[1,2-b][1,4]oxathiine-2,4'-piperidine]-5,6-dione was synthesized using conditions as outlined in procedure G [Step (ii)].

Step (iii): Compound 22 was synthesized using conditions as outlined in procedure G [Step (iii)]. M.p.=199-201° C.;

400 MHz $^1$H NMR (DMSO-d$_6$) δ: 7.84 (d, J=1.2 Hz, 1H), 7.79 (m, 2H), 3.81 (d, J=14 Hz, 2H), 3.20 (br, 2H), 3.11 (s, 2H), 2.01 (br, 1H), 1.97 (br, 1H), 1.78-1.70 (m, 2H), 1.42 (s, 9H); LCMS: 482 [M+H].

E7.3. Synthesis of tert-butyl 5',6'-dioxo-5',6'-dihydro-1H-spiro[azepane-4,2'-naphtho[1,2-b][1,4]oxathiine]-1-carboxylate (Compound 23)

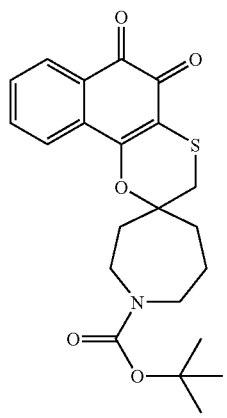

Step (i): tert-butyl 4-{[(3,4-dioxo-3,4-dihydronaphthalen-1-yl)thio]methyl}-4-hydroxypiperidine-1-carboxylate was synthesized using 6-naphthalene-1,2-dione, tert-butyl 4-hydroxy-4-(mercaptomethyl)azepane-1-carboxylate, tetrahydrofuran as a solvent and conditions outlined in procedure G [Step (i)].

Step (ii): spiro[azepane-4,2'-naphtho[1,2-b][1,4]oxathiine]-5',6'-dione was synthesized using conditions as outlined in procedure G [Step (ii)].

Step (iii): Compound 23 was synthesized using conditions as outlined in procedure G [Step (iii)]. M.p.=62-65° C.; 400 MHz $^1$H NMR (CDCl$_3$) δ: 8.05 (dd, J=1.2 and 8 Hz, 1H), 7.73 (dd, J=1.2, 8 Hz, 1H), 7.65 (t, J=8 Hz, 1H), 7.49 (t, J=8 Hz, 1H), 3.89-3.32 (m, 4H), 2.99-2.89 (m, 2H), 2.30-1.55 (m, 6H), 1.46 (d, J=11.6 Hz, 9H); LCMS: 416 [M+H]

Example 8

General Procedure H

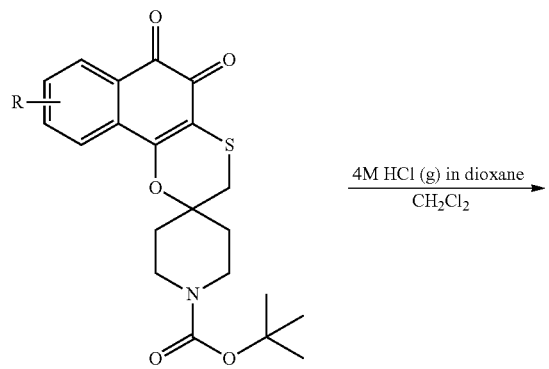

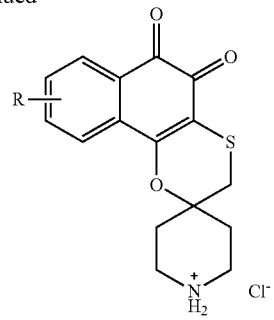

E8.1. Synthesis of spiro[azepane-4,2'-naphtho[1,2-b][1,4]oxathiine]-5',6'-dione hydrochloride (Compound 24)

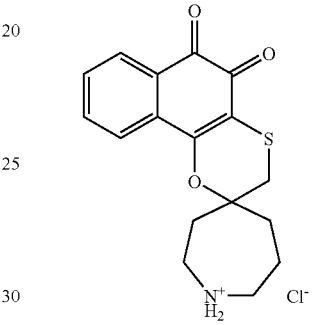

To a solution of tert-butyl 5',6'-dioxo-5',6'-dihydro-1H-spiro[azepane-4,2'-naphtho[1,2-b][1,4]oxathiine]-1-carboxylate (0.275 g, 0.66 mmol) in dichloromethane (8 ml) was added a 4M solution of HCl (g) in dioxane (3 ml). The reaction mixture was stirred at room temperature for 4 hours followed by addition of diethylether (50 ml). The resulting precipitate was filtered and washed with diethyl ether (3×10 mL) to afford the product as a purple solid (0.2 g, 85%). M.p.=201-205° C.; 400 MHz $^1$H NMR (DMSO-d$_6$) δ: 9.11 (brs, 2H), 7.90 (d, J=7.6 Hz, 1H), 7.82-7.75 (m, 2H), 7.58 (t, J=7.2 Hz, 1H), 3.57 (s, 2H), 3.34-3.11 (m, 4H), 2.36 (dd, J=7.2 and 15.6 Hz 1H), 2.27-2.21 (m, 2H), 2.08-1.98 (m, 2H), 1.90-1.80 (m, 1H); LCMS: 316 [M+H]

E8.2. Synthesis of 1'-(piperidin-4-ylcarbonyl)spiro[naphtho[1,2-b][1,4]oxathiine-2,4'-piperidine]-5,6-dione hydrochloride (Compound 25)

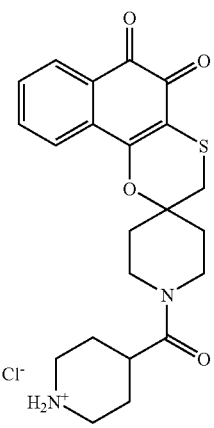

Compound 25 was synthesized using tert-butyl 4-[(5,6-dioxo-5,6-dihydro-1'H-spiro[naphtho[1,2-b][1,4]oxathiine- 2,4'-piperidin]-1'-yl)carbonyl]piperidine-1-carboxylate, ethyl acetate as a solvent instead of dichloromethane and conditions outlined in procedure H. M.p.=94-100° C., 400 MHz $^1$H NMR (DMSO-d$_6$) δ 9.0-8.86 (br.s, 1H), 8.7-8.5 (br.s, 1H), 7.94-7.88 (m, 1H), 7.88-7.82 (m, 1H), 7.78-7.72 (m, 1H), 7.62-7.54 (m, 1H), 4.3-4.2 (m, 1H), 3.98-3.8 (m, 1H), 3.55-3.4 (m, 1H), 3.35-3.2 (m, 2H), 3.11 (s, 2H), 3.15-2.84 (m, 4H), 2.12-1.97 (m, 2H), 1.85-1.62 (m, 6H); LCMS=413 [M+H].

E8.3. Synthesis of 1'-(piperidin-4-ylacetyl)spiro [naphtho[1,2-b][1,4]oxathiine-2,4'-piperidine]-5,6-dione hydrochloride (Compound 26)

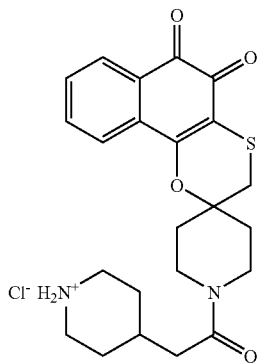

Compound 26 was synthesized using tert-butyl 4-[2-(5,6-dioxo-5,6-dihydro-1'H-spiro[naphtho[1,2-b][1,4]oxathiine-2,4'-piperidin]-1'-yl)-2-oxoethyl]piperidine-1-carboxylate, ethyl acetate as a solvent instead of dichloromethane and conditions outlined in procedure H. M.p.=200-202° C., 400 MHz $^1$H NMR DMSO-D$_6$ δ 8.98-8.8 (br. s, 1H), 8.77-8.6 (br. s, 1H), 7.9-7.86 (m, 1H), 7.85-7.8 (m, 1H), 7.78-7.65 (m, 1H), 7.6-7.53 (m, 1H), 4.36-4.22 (m, 1H), 3.93-3.8 (m, 1H), 3.75-3.35 (m, 4H), 3.28-3.18 (m 2H), 3.11 (s, 2H), 3.15-3.0 (m, 1H), 2.96-2.8 (m, 2H), 2.34 (d, J=3.3 Hz, 2H), 2.1-1.92 (m, 3H), 1.85-1.6 (m, 3H), 1.43-1.24 (m, 2H); LCMS=427 [M+H].

E8.4. Synthesis of 9-morpholin-4-ylspiro[naphtho[1,2-b][1,4]oxathiine-2,4'-piperidine]-5,6-dione bis-hydrochloride (Compound 27)

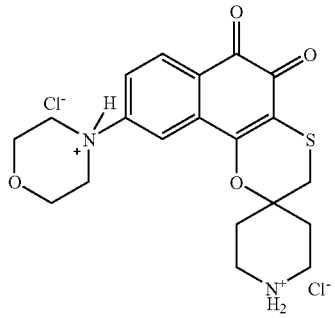

Compound 27 was synthesized using tert-butyl 9-morpholin-4-yl-5,6-dioxo-5,6-dihydro-1'H-spiro[naphtho[1,2-b][1,4]oxathiine-2,4'-piperidine]-1'-carboxylate and conditions outlined in procedure H. M.p.=>300° C.; 400 MHz $^1$H NMR (DMSO-d$_6$) δ: 7.76 (d, J=8.8 Hz, 1H), 7.20 (s, 1H), 7.08 (dd, J=2 and 8.8 Hz, 1H), 3.74 (m, 4H), 3.43 (m, 4H), 3.29 (m, 2H), 3.14 (s, 2H), 2.82 (brm, 2H), 1.88 (m, 2H), 1.65 (m, 2H); LCMS: 387 [M+H].

E.8.5. Synthesis of 1'-piperidin-4-ylspiro[naphtho[1,2-b][1,4]oxathiine-2,4'-piperidine]-5,6-dione bis-hydrochloride (Compound 28)

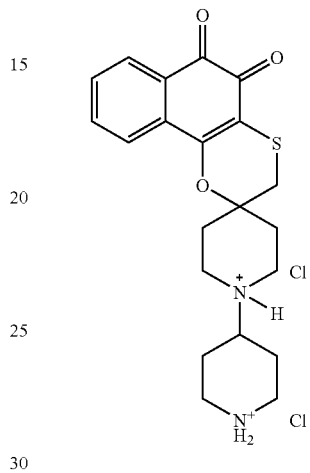

Compound 28 was synthesized using tert-butyl 4-(5,6-dioxo-5,6-dihydro-1'H-spiro[naphtho[1,2-b][1,4]oxathiine-2,4'-piperidine]-1'-yl)piperidine-1-carboxylate, 3.0 M HCl gas as a solution in ethylacetate instead of dioxane, ethyl acetate as a solvent instead of dichloromethane and conditions outlined in procedure H. M.p.=214-216° C.; 400 MHz $^1$H NMR (DMSO-d$_6$) δ: 11.49 (d, 1H), 9.17 (s, 1H), 9.01 (s, 1H), 7.90-7.87 (m, 2H), 7.76-7.72 (m, 1H), 7.59-7.55 (m, 1H), 3.62-3.55 (m, 4H), 3.42 (d, 2H), 3.12 (s, 3H), 2.90-2.86 (m, 2H), 2.48 (d, 2H), 2.35-2.29 (m, 4H), 2.05-1.97 (m, 2H); LCMS: 385 [M+H].

E.8.6. Synthesis of 4-aminospiro[cyclohexane-1,2'-naphtho[1,2-b][1,4]oxathiine]-5',6'-dione hydrochloride (Compound 29)

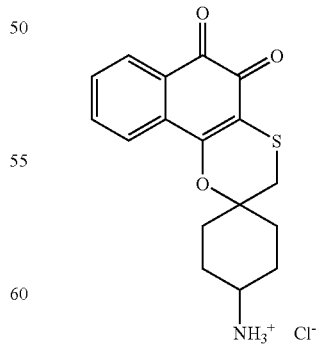

Compound 29 was synthesized tert-butyl (5',6'-dioxo-5',6'-dihydrospiro[cyclohexane-1,2'naphtho[1,2-b][1,4]oxathiin]-4-yl)carbamate as described in procedure H. M.p.=256-257° C.; 400 MHz $^1$H NMR (DMSO-d$_6$) δ: 8.10 (br, 3H), 7.91 (dd, J=7.6 Hz, 1.2 Hz, 1H), 7.86 (d, J=7.6 Hz, 1H), 7.76 (td, J=8.0 Hz, 1.2 Hz, 1H), 7.58 (td, J=7.6 Hz, 0.8 Hz, 1H), 3.14 (br, 1H), 3.03 (s, 2H), 2.12 (d, J=12.8 Hz, 2H), 1.96-1.88 (m, 2H), 1.83-1.63 (m, 4H); LCMS: 316 [M+H].

Example 9

Procedure I

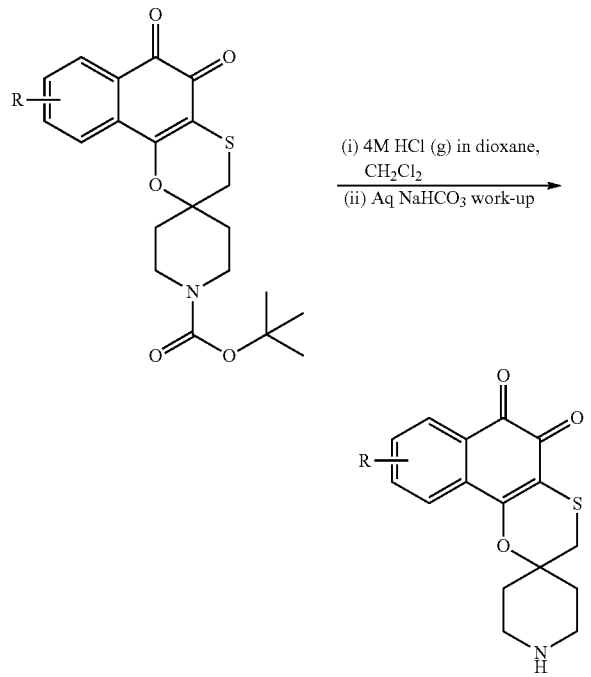

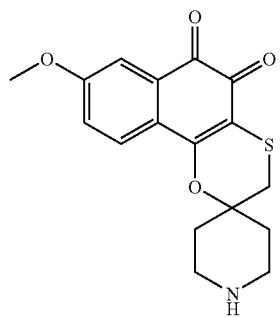

E9.1. Synthesis of 8-methoxyspiro[naphtho[1,2-b][1,4]oxathiine-2,4'-piperidine]-5,6-dione (Compound 30)

To a solution of tert-butyl 8-methoxy-5,6-dioxo-5,6-dihydro-1'H-spiro[naphtho[1,2-b][1,4]oxathiine-2,4'-piperidine]-1'-carboxylate (1.11 g, 2.60 mmol) in dichloromethane (80 mL) was added a 4.0M solution of HCl (g) in dioxane (20 mL, 80 mmol). The reaction was stirred at room temperature for 1 hour and the solvent was evaporated under reduced pressure. The residue was dissolved in a mixture of dichloromethane (40 mL) and saturated NaHCO₃ (40 mL). The organic layer was separated and the aqueous layer extracted with dichloromethane (3×20 mL). The organic extracts were combined, dried over MgSO₄, and evaporated under reduced pressure to afford the product as a purple solid (0.728 g, 84%). M.p.=130° C. (dec); 400 MHz $^1$H NMR (DMSO-d₆) δ: 7.96-7.82 (m, 1H), 7.60-7.12 (m, 2H), 3.87 (s, 3H), 3.12-2.94 (m, 2H), 1.94-1.82 (m, 2H), 1.72-1.60 (m, 2H); LCMS: 332 [M+H].

E9.2. Synthesis of 9-piperidin-1-ylspiro[naphtho[1,2-b][1,4]oxathiine-2,4'-piperidine]-5,6-dione (Compound 31)

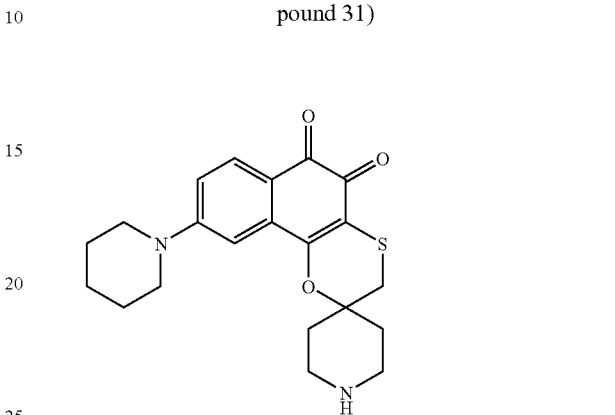

Compound 31 was synthesized using tert-butyl 5,6-dioxo-9-piperidin-1-yl-5,6-dihydro-1'H-spiro[naphtho[1,2-b][1,4]oxathiine-2,4'-piperidine]-1'-carboxylate and conditions outlined in procedure 1. M.p.=300° C. (dec); 400 MHz $^1$H NMR (DMSO-d) δ: 7.76 (dd, J=2, 9.2 Hz, 1H), 7.17 (s, 1H), 6.95 (d, J=8.4 Hz, 1H), 3.51 (brs, 4H), 3.02 (s, 2H), 2.81 (brm, 4H), 1.88 (m, 2H), 1.65 (brm, 81-1); LCMS: 385 [M+H].

Example 10

General Procedure J

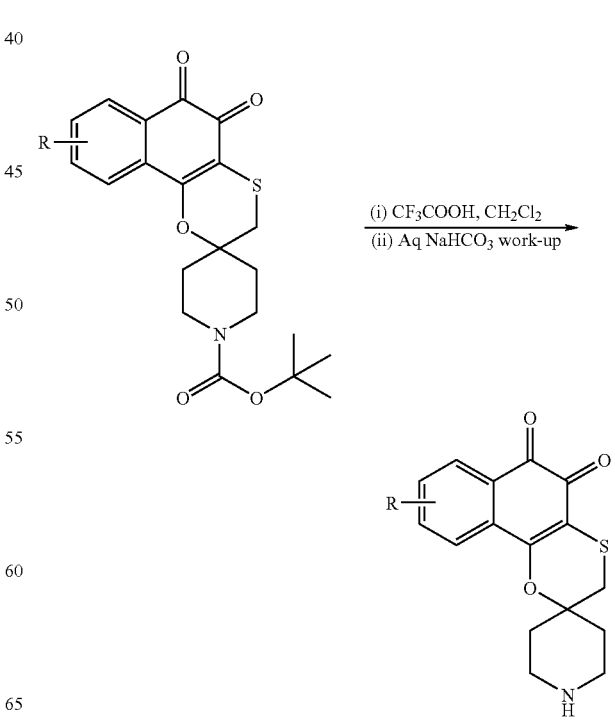

E10.1. Synthesis of 9-bromospiro[naphtho[1,2-b][1,4]oxathiine-2,4'-piperidine]-5,6-dione (Compound 32)

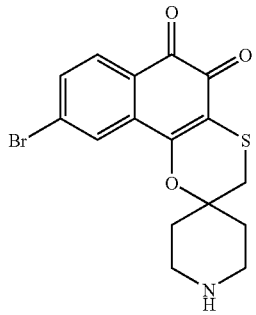

To a solution of tert-butyl 9-bromo-5,6-dioxo-5,6-dihydro-1'H-spiro[naphtho[1,2-b][1,4]oxathiine-2,4'-piperidine]-1'-carboxylate (0.5 g, 1.03 mmol) in dichloromethane (35 mL) was added trifluoroacetic acid (25 mL). The resulting solution was stirred at room temperature for 16 hours. The solvent was removed under reduced pressure and the residue dissolved in dichloromethane (50 mL). To the reaction mixture was then added a saturated solution of sodium bicarbonate until the pH was 8. The organic layer was separated and the aqueous layer extracted with dichloromethane (3×50 mL). The combined organic extracts were dried over sodium sulfate and concentrated under reduced pressure to afford the product as red solid in quantitative yield. M.p.=315-320° C.; 400 MHz $^1$H NMR (DMSO-$d_6$) δ: 7.82 (s, 1H), 7.79 (s, 2H), 3.07 (s, 2H), 2.86-2.77 (m, 4H), 1.91 (d, J=13.2 Hz, 2H), 1.71-1.63 (m, 2H); LCMS: 382 [M+H].

E10.2. Synthesis of 9-pyridin-4-yispiro[naphtho[1,2-b][1,4]oxathiine-2,4'-piperidine]-5,6-dione (Compound 33)

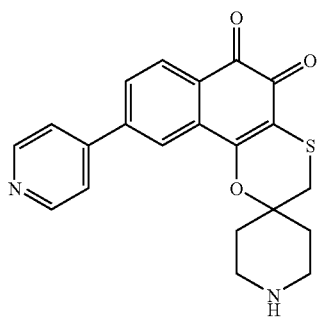

Compound 33 was synthesized using tert-butyl 5,6-dioxo-9-pyridin-4-yl-5,6-dihydro-1'H-spiro[naphtho[1,2-b][1,4]oxathiine-2,4'-piperidine]-1'-carboxylate and conditions outlined in procedure J. M.p.=223-228° C.; 400 MHz $^1$H NMR (DMSO-$d_6$) δ 8.75 (d, J=5.2 Hz, 2H), 8.05 (s, 1H), 8.04-7.96 (m, 2H), 7.78 (d, J=4.4 Hz, 2H), 3.10 (s, 2H), 2.90-2.84 (m, 4H), 1.98 (d, J=12.8 Hz, 2H), 1.75-1.67 (m, 2H); LCMS: 379 [M+H].

E10.3. Synthesis of 9-pyridin-3-ylspiro[naptho[1,2-b][1,4]oxathiine-2,4'-piperidine]-5,6-dione (Compound 34)

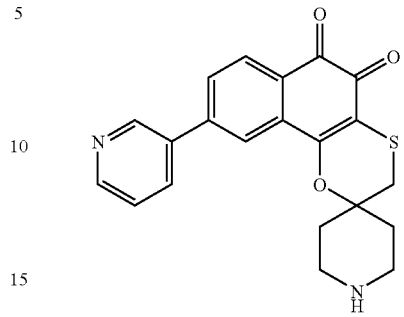

Compound 34 was synthesized using tert-butyl 5,6-dioxo-9-pyridin-3-yl-5,6-dihydro-1'H-spiro[naphtho[1,2-b][1,4]oxathiine-2,4'-piperidine]-1'-carboxylate and conditions outlined in procedure J. M.p.=213-215° C.; 400 MHz $^1$H NMR (DMSO-$d_6$) δ: 8.96 (s, 1H), 8.69 (m, 1H), 8.17 (d, J=6.8 Hz, 1H), 8.04-7.90 (m, 3H), 7.62-7.57 (m, 1H), 3.09 (s, 2H), 2.85 (m, 4H), 1.96 (d, J=13.2 Hz, 2H), 1.74-1.66 (m, 2H); LCMS: 379 [M+H].

E10.4. Synthesis of 9-[3-(trifluoromethyl)phenyl]spiro[naphtho[1,2-b][1,4]oxathiine-2,4'-piperidine]-5,6-dione (Compound 35)

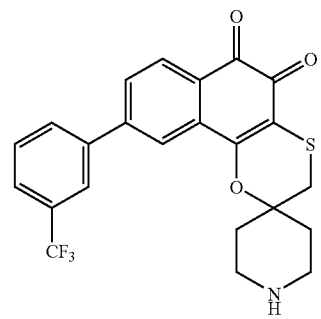

Compound 35 was synthesized using of tert-butyl 5,6-dioxo-9-[3-(trifluoromethyl)phenyl]-5,6-dihydro-1'H-spiro[naphtho[1,2-b][1,4]oxathiine-2,4'-piperidine]-1'-carboxylate and conditions outlined in procedure J. M.p.=199-203° C.; 400 MHz $^1$H NMR (DMSO-$d_6$) δ: 8.08-7.95 (m, 5H), 7.89-7.79 (m, 2H), 3.09 (s, 2H), 2.86-2.82 (m, 4H), 1.96 (d, J=13.2 Hz, 2H), 1.74-1.65 (m, 2H); LCMS: 446 [M+H].

E10.5. Synthesis of 9-[4-(trifluoromethyl)phenyl]spiro[naphtho[1,2-b][1,4]oxathiine-2,4'-piperidine]-5,6-dione (Compound 36)

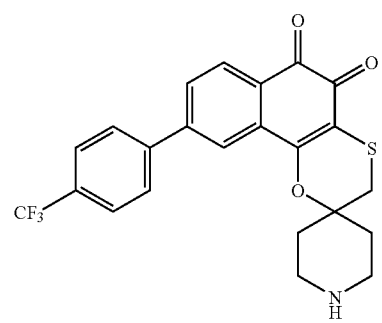

Compound 36 was synthesized using tert-butyl 5,6-dioxo-9-[4-(trifluoromethyl)phenyl]-5,6-dihydro-1'H-spiro[naphtho[1,2-b][1,4]oxathiine-2,4'-piperidine]-1'-carboxylate and conditions outlined in procedure J. M.p.=190-240° C.; 400 MHz $^1$H NMR (DMSO-d$_6$) δ: 8.02-7.90 (m, 7H), 3.12 (s, 2H), 2.99-2.89 (m, 4H), 2.03 (d, J=13.6 Hz, 2H), 1.80-1.72 (m, 2H); LCMS: 446 [M+H].

E10.6. Synthesis of 9-[2-(trifluoromethyl)phenyl]spiro[naphtho[1,2-b][1,4]oxathiine-2,4'-piperidine]-5,6-dione (Compound 37)

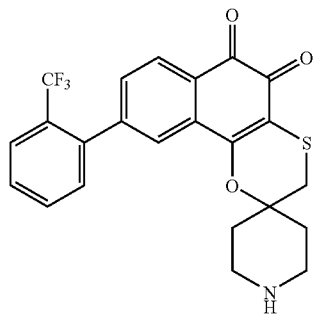

Compound 37 was synthesized using tert-butyl 5,6-dioxo-9-[2-(trifluoromethyl)phenyl]-5,6-dihydro-1'H-spiro[naphtho[1,2-b][1,4]oxathiine-2,4'-piperidine]-1'-carboxylate and conditions outlined in procedure J. M.p.=125-127° C.; 400 MHz $^1$H NMR (DMSO-d$_6$) δ: 7.99 (d, J=8.0 Hz, 1H), 7.92 (d, J=8.0 Hz, 1H), 7.81 (dd, J=7.6, 7.6 Hz, 1H), 7.75-7.69 (m, 2H), 7.54 (d, J=8.0 Hz, 1H), 7.50 (d, J=8.0 Hz, 1H), 3.06 (s, 2H), 2.84-2.67 (m, 4H), 1.89 (d, J=13.2 Hz, 2H), 1.69-1.60 (m, 2H); LCMS: 446 [M+H].

E10.7. Synthesis of 9-phenylspiro[naphtho[1,2-b][1,4]oxathiine-2,4'-piperidine]-5,6-dione (Compound 38)

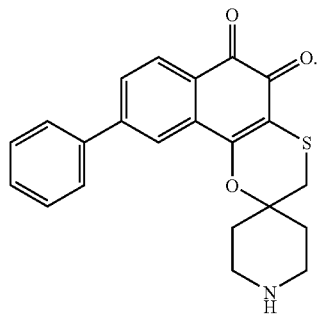

Compound 38 was synthesized using tert-butyl 5,6-dioxo-9-phenyl-5,6-dihydro-1'H-spiro[naphtho[1,2-b][1,4]oxathiine-2,4'-piperidine]-1'-carboxylate and conditions outlined in procedure J. M.p.=83-87° C.; 400 MHz $^1$H NMR (DMSO-d$_6$) δ: 8.00-7.96 (m, 2H), 7.86 (dd, J=1.6, 7.6 Hz, 1H), 7.75 (d, J=7.6 Hz, 2H), 7.59-7.47 (m, 3H), 3.09 (s, 2H), 2.88-2.83 (m, 4H), 1.96 (d, J=13.2 Hz, 2H), 1.73-1.60 (m, 2H); LCMS: 378 [M+H].

Example 11

Procedure K

E11.1. Synthesis of tert-butyl 4-{[(3,4-dioxo-3,4-dihydronaphthalen-1-yl)thio]methyl}-4-hydroxypiperidine-1-carboxylate (Compound 12)

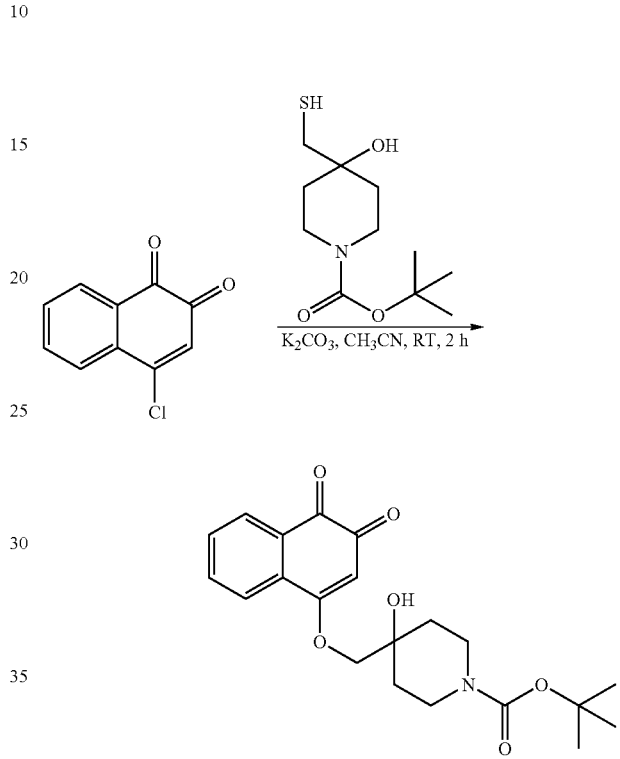

To a solution of 4-chloronaphthalene-1,2-dione (1.0 g, 5.2 mmol) and tert-butyl 4-hydroxy-4-(mercaptomethyl)piperidine-1-carboxylate (1.348 g, 5.45 mmol) in acetonitrile (20 mL) was added potassium carbonate (2.16 g, 15.6 mmol). The reaction was stirred at room temperature for 2 hours. To the reaction mixture was then added EtOAc (40 mL) and the reaction mixture filtered through celite. The solvent was then removed under reduced pressure. The crude foamy residue was dissolved in EtOAc (40 mL) and the solvent once again removed under reduced pressure. To the crude foamy solid was added EtOAc (7 mL) and the reaction mixture stirred for 10 min. An orange solid separated out. Diethyl ether (20 mL) was then added and the solution was left in the refrigerator to ensure that most of the product crashed out. The solid was filtered and washed with diethyl ether to afford the product as an orange solid. The mother liquor was concentrated under reduced pressure and purified by flash column chromatography (SiO$_2$, 40% EtOAc in hexanes) to recover the product (1.66 g, 80%) as an orange solid. M.p.=156-157° C.; 400 MHz $^1$H NMR (CDCl$_3$) δ: 8.2-8.14 (m, 1H), 7.9-7.86 (m, 1H), 7.72-7.66 (m, 1H), 7.61-7.55 (m, 1H), 6.50 (s, 1H), 4.05-3.85 (m, 2H), 3.25-3.1 (m, 2H), 3.19 (s, 2H), 1.9-1.7 (m, 5H), 1.47 (s, 9H); LCMS: 404 [M+H].

Example 12

Procedure L

E12.1 Synthesis of spiro[naphtha[1,2-b][1,4]oxathiine-2,4'-piperidine]-5,6-dione (Compound 16)

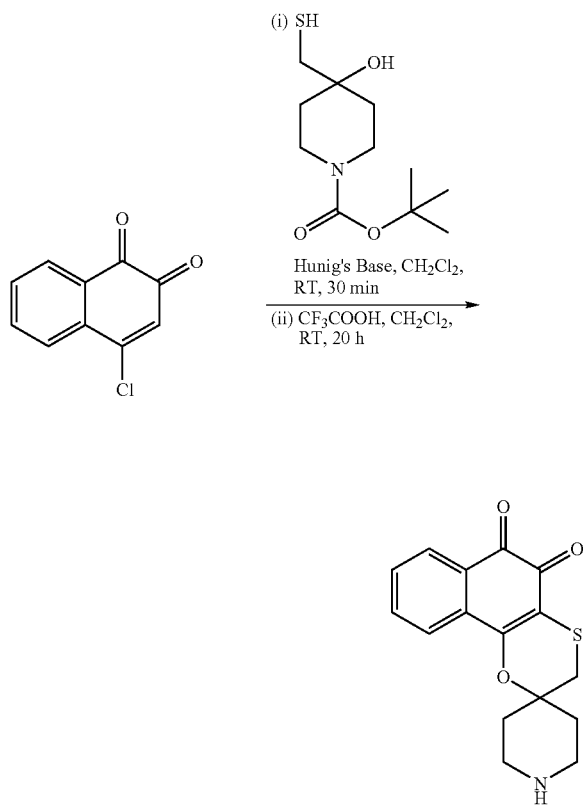

To a solution of 4-chloronapthaquinone (1.0 g, 5.20 mmol) in dichloromethane (40 mL) was added tert-butyl 4-hydroxy-4-(mercaptomethyl)piperidine-1-carboxylate (1.26 g, 5.20 mmol) followed by Hunig's Base (0.91 mL, 5.20 mmol). The reaction mixture was stirred at room temperature for 30 min. To it was then added trifluoroacetic acid (14 mL) and the reaction mixture stirred at room temperature for 20 hours. The reaction mixture was then extracted with water (3×100 mL). The combined aqueous layers were basified with solid sodium bicarbonate to pH 8 and then extracted with dichloromethane (3×100 mL). The combined organic extracts was washed with brine (2×100 mL), dried with sodium sulfate and concentrated under reduced pressure. The resulting solid was dissolved in 50% dichloromethane in EtOAc and concentrated under reduced pressure to afford the product (0.75 g, 48%) as a purple solid. M.p.=230-236° C.; 400 MHz $^1$H NMR (CDCl$_3$) δ: 8.04 (m, 1H), 7.79 (m, 1H), 7.66 (m, 1H), 7.49 (m, 1H), 3.10 (m, 4H), 2.95 (m, 2H), 2.13 (m, 2H), 1.83 (m, 2H); LCMS: 302 [M+H].

Example 13

Procedure M

13.1. Synthesis of tert-butyl 5,6-dioxo-5,6-dihydro-1'H-spiro[naphtho[1,2-b][1,4]oxathiine-2,4'-piperidine]-1'-carboxylate and spiro[naphtho[1,2-b][1,4]oxathiine-2,4'-piperidine]-5,6-dione (Compound 109 and 16)

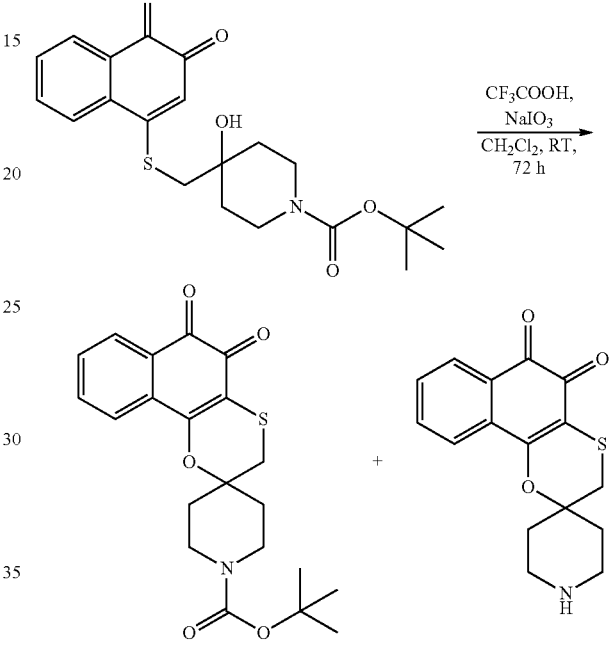

To a solution of tert-butyl 4-{[(3,4-dioxo-3,4-dihydronaphthalen-1-yl)thio]methyl}-4-hydroxypiperidine-1-carboxylate (0.50 g, 1.24 mmol) in dichloromethane (12.5 mL) was added sodium iodate (0.736 g, 3.72 mmol) followed by trifluoroacetic acid (238 μL 3.1 mmol). The reaction mixture was stirred at room temperature for 72 hr. The reaction mixture was then diluted with dichloromethane (75 mL) and washed with water (2×50 mL). The combined aqueous layer was then extracted with dichloromethane (25 mL). The resulting aqueous layer after dichloromethane extraction contained and spiro[naphtha[1,2-b][1,4]oxathiine-2,4'-piperidine]-5,6-dione was stored for further workup. The combined dichloromethane extracts were washed with brine (50 mL), dried with sodium sulfate and concentrated under reduced pressure. The crude tert-butyl 5,6-dioxo-5,6-dihydro-1'H-spiro[naphtho[1,2-b][1,4]oxathiine-2,4'-piperidine]-1'-carboxylate was purified by flash column chromatography (SiO$_2$, 30% EtOAc in hexanes) to afford the product (0.304 g, 62%) as a purple solid. 400 MHz $^1$H NMR (CDCl$_3$) δ 8.05-8.07 (m, 1H), 7.73-7.75 (m, 1H), 7.64-7.68 (m, 1H), 7.48-7.52 (m, 1H), 4.04 (br.s 2H), 3.21-3.29 (m, 2H), 2.94 (s, 2H), 2.10-2.13 (m, 2H), 1.72-1.80 (m, 2H), 1.48 (s, 9H); LCMS: 402 [M+H]. The aqueous layer containing spiro[naphtha[1,2-b][1,4]oxathiine-2,4'-piperidine]-5,6-dione was basified to pH 8 using sodium bicarbonate and extracted with dichloromethane (2×20 mL). The combined organic extracts were washed with bring (20 mL), dried with sodium sulfate and concentrated under reduced pressure. The presence of spiro

[naphtha[1,2-b][1,4]oxathiine-2,4'-piperidine]-5,6-dione (0.034 g, 7%) was identified by LCMS: 302 [M+H].

Other embodiments are within the following claims. While several embodiments have been shown and described, various modifications may be made without departing from the spirit and scope of the present invention.

Example 14

Procedure N

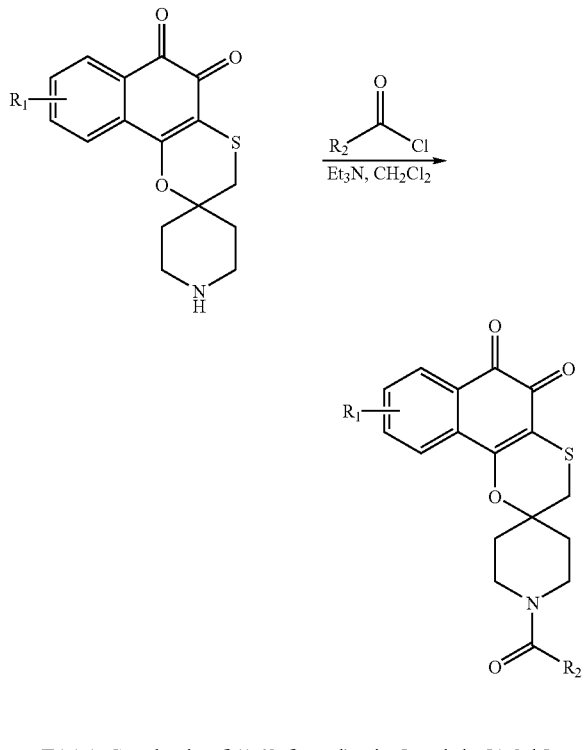

E14.1. Synthesis of 1'-(2-furoyl)spiro[naphtho[1,2-b][1,4]oxathiine-2,4'-piperidine]-5,6-dione (Compound 39)

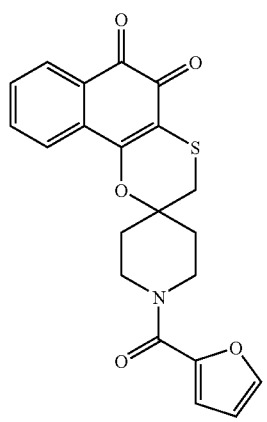

To a solution of spiro[naphtho[1,2-b][1,4]oxathiine-2,4'-piperidine]-5,6-dione (0.1 g, 0.33 mmol) in dichloromethane (3.0 mL) was added 2-furoyl chloride (0.050 g, 0.40 mmol) followed by triethylamine (0.114 mL, 0.79 mmol). The reaction mixture was stirred for 1 h at room temperature. The organic layer was separated, washed with water (2.0 mL), dried with sodium sulfate and concentrated under vacuum. The crude product was crystallized from EtOAc and hexanes to give the desired product as a purple solid (0.08 g, 61%). M.p.=165° C.; 400 MHz $^1$H NMR (DMSO-d$_6$) δ 7.89-7.85 (m, 3H), 7.78 (t, 1H), 7.57 (t, 1H), 7.02 (d, J=3.6 Hz, 1H), 6.63 (d, J=3.6 Hz, 1H), 4.24 (d, 2H), 3.13 (s, 2H), 2.15 (brs, 2H), 2.08 (brs, 2H), 1.95 (m, 2H). LCMS: 396 [M+H].

E14.2. Synthesis of 1'-[(3,5-dimethylisoxazol-4-yl)carbonyl]spiro[naphtho[1,2-b][1,4]oxathiine-2,4'-piperidine]-5,6-dione (Compound 40)

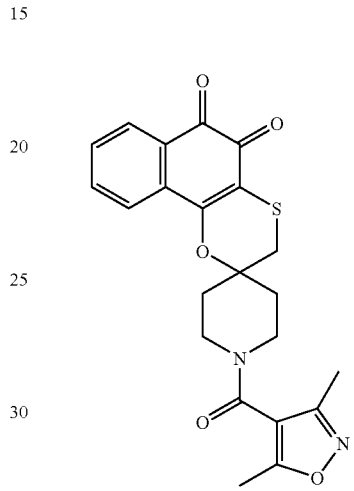

Compound 40 was synthesized using spiro[naphtho[1,2-b][1,4]oxathiine-2,4'-piperidine]-5,6-dione, 3,5-dimethylisoxazole-4-carbonyl chloride and conditions outlined in procedure N. M.p.=274-275° C.; 300 MHz $^1$H NMR (DMSO-d$_6$) δ 8.08 (d, 1H), 7.73 (m, 2H), 7.54 (t, 1H), 3.42 (t, 2H), 2.99 (s, 2H), 2.45 (s, 3H), 2.31 (s, 3H), 2.21 (m, 2H), 1.90 (brm 2H), 1.58 (s, 2H); LCMS: 425 [M+H].

E14.3. Synthesis of 1'-(2,5-dimethyl-3-furoyl)spiro[naphtho[1,2-b][1,4]oxathiine-2,4'-piperidine]-5,6-dione (Compound 41)

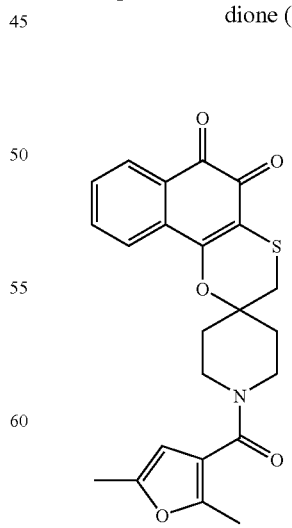

Compound 41 was synthesized using spiro[naphtho[1,2-b][1,4]oxathiine-2,4'-piperidine]-5,6-dione, 2,5-dimethyl-3- furoyl chloride and conditions outlined in procedure N. M.p.=234-235° C.; 300 MHz ¹H NMR (DMSO-d₆) δ 8.15 (d, 1H), 7.81 (d, 1H), 7.63 (t, 1H), 7.54 (t, 1H), 5.92 (s, 1H), 3.40 (m, 2H), 3.05 (s, 2H), 2.40 (s, 3H), 2.21 (s, 3H), 2.18 (m, 2H), 1.90 (m, 2H), 1.60 (s, 2H); LCMS: 424 [M+H].

E14.4. Synthesis of 1'-[(1,3-dimethyl-1H-pyrazol-5-yl)carbonyl]spiro[naphtho[1,2-b][1,4]oxathiine-2,4'-piperidine]-5,6-dione (Compound 42)

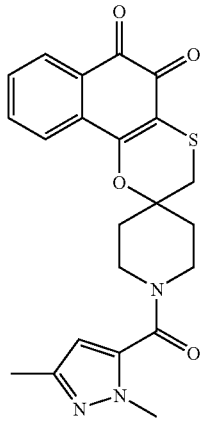

Compound 42 was synthesized using spiro[naphtho[1,2-b][1,4]oxathiine-2,4'-piperidine]-5,6-dione, 1,3-dimethyl-1H-pyrazole-5-carbonyl chloride and conditions outlined in procedure N. M.p.=244-245° C.; 300 MHz ¹H NMR (DMSO-d₆) δ 8.07 (d, 1H), 7.67 (d, 1H), 7.65 (t, 1H), 7.56 (t, 1H), 6.16 (s, 1H), 3.40 (m, 2H), 3.86 (s, 3H), 3.01 (s, 2H), 2.26 (s, 3H), 2.24 (m, 2H), 1.92 (m, 2H), 1.62 (m, 2H); LCMS: 424 [M+H].

E14.5. Synthesis of 1'-(3-furoyl)spiro[naphtho[1,2-b][1,4]oxathiine-2,4'-piperidine]-5,6-dione (Compound 43)

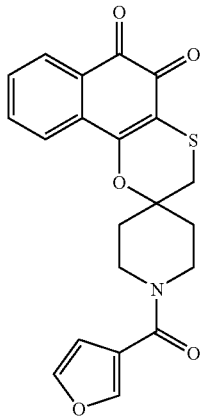

Compound 43 was synthesized using spiro[naphtho[1,2-b][1,4]oxathiine-2,4'-piperidine]-5,6-dione, 3-furoyl chloride and conditions outlined in procedure N. M.p.=234-235° C.; 300 MHz ¹H NMR (DMSO-d₆) δ 8.05 (d, 1H), 7.67 (d, 1H), 7.65 (t, 1H), 7.50 (t, 1H), 7.24 (s, 2H), 6.58 (s, 1H), 3.46 (m, 2H), 2.96 (s, 2H), 2.20 (m, 2H), 1.92 (m, 2H), 1.58 (brs, 2H); LCMS: 396 [M+H].

E14.6. Synthesis of 1'-[4-(1H-pyrazol-1-yl)benzoyl]spiro[naphtho[1,2-b][1,4]oxathiine-2,4'-piperidine]-5,6-dione (Compound 44)

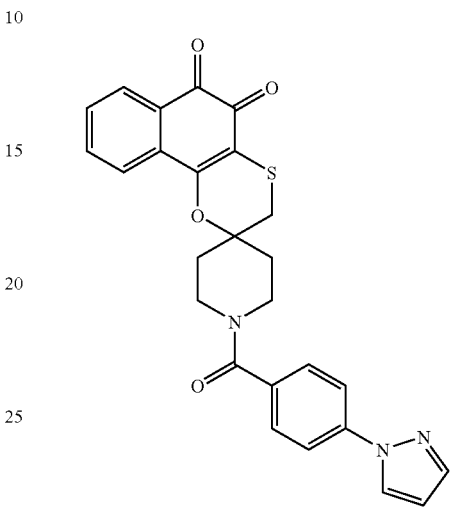

Compound 44 was synthesized using spiro[naphtho[1,2-b][1,4]oxathiine-2,4'-piperidine]-5,6-dione, 4-(1H-pyrazol-1-yl)benzoyl chloride and conditions outlined in procedure N. M.p.=299-300° C.; 300 MHz ¹H NMR (DMSO-d₆) δ 8.06 (d, 1H), 8.0 (s, 1H), 7.64 (m, 4H), 7.65 (t, 1H), 7.50 (m, 3H), 6.52 (s, 1H), 3.42 (m, 2H), 2.96 (s, 2H), 2.22 (m, 2H), 1.92 (m 2H), 1.58 (s, 2H); LCMS: 472 [M+H].

E14.7. Synthesis of 1'-[(1,5-dimethyl-1H-pyrazol-3-yl)carbonyl]spiro[naphtho[1,2-b][1,4]oxathiine-2,4'-piperidine]-5,6-dione (Compound 45)

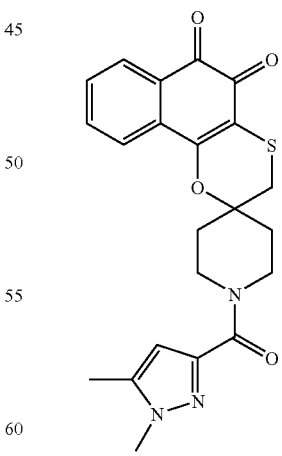

Compound 45 was synthesized using spiro[naphtho[1,2-b][1,4]oxathiine-2,4'-piperidine]-5,6-dione, 1,5-dimethyl-1H-pyrazole-3-carbonyl chloride and conditions outlined in procedure N. M.p.=184-185° C.; 300 MHz ¹H NMR (DMSO-d₆) δ 8.04 (d, 1H), 7.80 (m, 1H), 7.65 (m, 1H), 7.46 (m, 1H), 6.42

(s, 1H), 3.80 (s, 3H), 3.47 (m, 2H), 2.98 (s, 2H), 2.26 (s, 3H), 2.18 (m, 2H), 1.90 (m 2H), 1.62 (brs, 2H); LCMS: 424 [M+H].

E14.8. Synthesis of 1'-[3-(dimethylamino)benzoyl]spiro[naphtho[1,2-b][1,4]oxathiine-2,4'-piperidine]-5,6-dione (Compound 46)

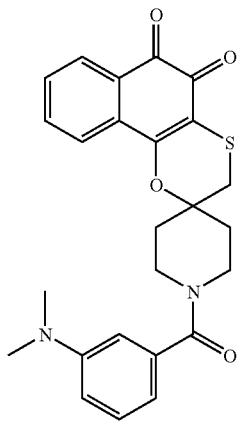

Compound 46 was synthesized using spiro[naphtho[1,2-b][1,4]oxathiine-2,4'-piperidine]-5,6-dione, 3-(dimethylamino)benzoyl chloride and conditions outlined in procedure N. M.p.=170-172° C.; LCMS: 449 [M+H].

E14.9. Synthesis of 1'-[(4-chlorophenyl)acetyl]spiro[naphtho[1,2-b][1,4]oxathiine-2,4'-piperidine]-5,6-dione (Compound 47)

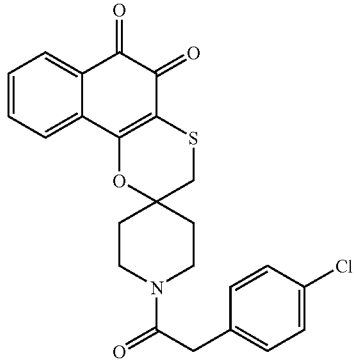

Compound 47 was synthesized using spiro[naphtho[1,2-b][1,4]oxathiine-2,4'-piperidine]-5,6-dione, (4-chlorophenyl)acetyl chloride and conditions outlined in procedure N. M.p.=120-125° C.; 300 MHz $^1$H NMR (DMSO-$d_6$) δ 7.91 (m, 2H), 7.74 (t, 1H), 7.56 (t, 1H), 7.35 (m, 2H), 7.25 (m, 2H), 4.10 (dd, 1H), 3.94 (m, 1H), 3.77 (dd, J=3.3 Hz, 2H), 3.57 (s, 2H), 3.09 (s, 2H), 2.05 (m, 2H), 1.67 (m, 2H); LCMS: 454 [M+H].

E14.9. Synthesis of 1'-[(phenylthio)acetyl]spiro[naphtho[1,2-b][1,4]oxathiine-2,4'-piperidine]-5,6-dione (Compound 48)

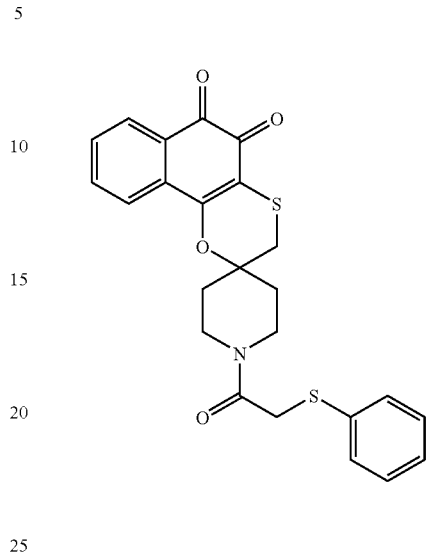

Compound 48 was synthesized using spiro[naphtho[1,2-b][1,4]oxathiine-2,4'-piperidine]-5,6-dione (phenylthio)acetyl chloride and conditions outlined in procedure N. M.p.=155-157° C.; 300 MHz $^1$H NMR (DMSO-$d_6$) δ 7.89 (m, 2H), 7.76 (t, 1H), 7.60 (t, 1H), 7.39 (m, 2H), 7.29 (m, 2H), 7.20 (m, 1H), 4.11 (dd, 2H), 4.05 (s, 2H), 3.42 (t, 2H), 3.11 (s, 2H), 2.05 (m, 2H), 1.80 (m, 2H); LCMS: 452 [M+H].

E14.10. Synthesis of 1'-(2-iodobenzoyl)spiro[naphtho[1,2-b][1,4]oxathiine-2,4'-piperidine]-5,6-dione (Compound 49)

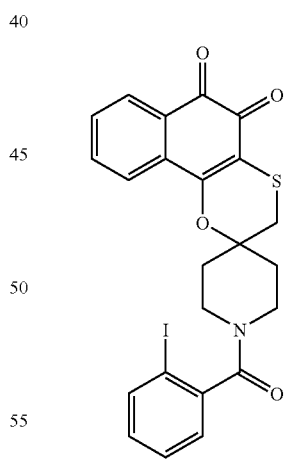

Compound 49 was synthesized using spiro[naphtho[1,2-b][1,4]oxathiine-2,4'-piperidine]-5,6-dione, 2-iodobenzoyl chloride and conditions outlined in procedure N. M.p.=165-166° C.; 300 MHz $^1$H NMR (DMSO-$d_6$) δ 7.90 (m, 2H), 7.78 (t, 1H), 7.58 (m, 2H), 7.39 (m, 3H), 4.31 (dd, 2H), 3.50 (m, 1H), 3.20 (m, 1H), 3.13 (s, 2H), 2.05 (d, 2H), 1.82 (m, 2H); LCMS: 532 [M+H].

E14.11. Synthesis of 1'-[chloro(phenyl)acetyl]spiro[naphtho[1,2-b][1,4]oxathiine-2,4'-piperidine]-5,6-dione (Compound 50)

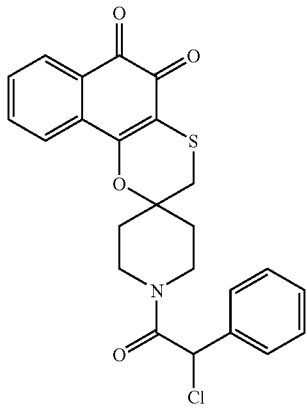

Compound 50 was synthesized using spiro[naphtho[1,2-b][1,4]oxathiine-2,4'-piperidine]-5,6-dione, chloro(phenyl)acetyl chloride and conditions outlined in procedure N. M.p.=125-126° C.; 300 MHz $^1$H NMR (DMSO-$d_6$) δ 7.62-7.88 (m, 3H), 7.35-7.55 (m, 6H), 6.44 (d, 1H), 4.15 (m, 2H), 3.30 (m, 2H), 3.0-3.13 (2 s, 2H), 2.0 (m, 2H), 1.65 (m, 2H); LCMS: 454 [M+H].

E14.12. Synthesis of 1'-(1-benzothien-2-ylcarbonyl)spiro[naphtho[1,2-b][1,4]oxathiine-2,4'-piperidine]-5,6-dione (Compound 51)

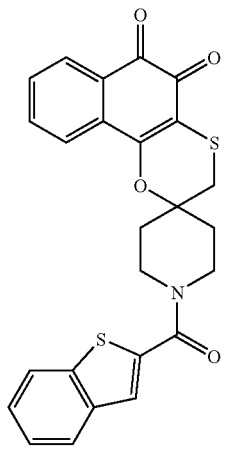

Compound 51 was synthesized using spiro[naphtho[1,2-b][1,4]oxathiine-2,4'-piperidine]-5,6-dione, 1-benzothiophene-2-carbonyl chloride and conditions outlined in procedure N. M.p.=110-112° C.; 300 MHz $^1$H NMR (DMSO-$d_6$) δ 8.20 (m, 1H), 7.93 (m, 3H), 7.77 (m, 2H), 7.58 (t, 1H), 7.45 (m, 2H), 4.22 (brm, 2H), 3.41 (brm, 2H), 3.15 (s, 2H), 2.17 (m, 2H), 1.88 (m, 2H); LCMS: 462 [M+H].

E14.13. Synthesis of methyl (5,6-dioxo-5,6-dihydro-1'H-spiro[naphtho[1,2-b][1,4]oxathiine-2,4'-piperidine]-1'-yl)(oxo)acetate (Compound 52)

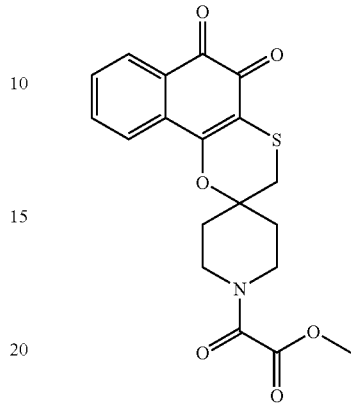

Compound 52 was synthesized using spiro[naphtho[1,2-b][1,4]oxathiine-2,4'-piperidine]-5,6-dione, methyl oxalyl chloride and conditions outlined in procedure N. M.p.=240-241° C.; 300 MHz $^1$H NMR (DMSO-$d_6$) δ 7.88 (d, J=7.8 Hz, 2H), 7.68 (t, 1H), 7.57 (t, 1H), 4.18 (m, 1H), 3.83 (s, 3H), 3.41 (brm, 2H), 3.20 (m, 1H), 3.14 (s, 2H), 2.07 (m, 2H), 1.80 (m, 2H); LCMS: 388 [M+H].

E14.14. Synthesis of 1'-(3,4-dichlorobenzoyl)spiro[naphtho[1,2-b][1,4]oxathiine-2,4'-piperidine]-5,6-dione (Compound 53)

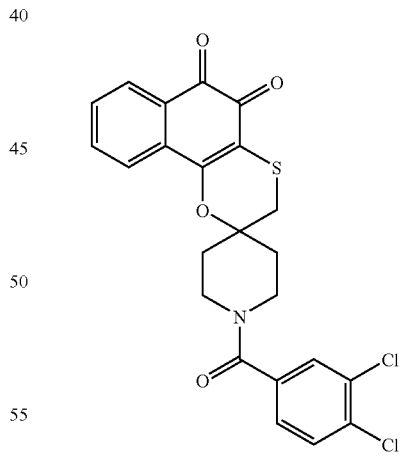

Compound 53 was synthesized using spiro[naphtho[1,2-b][1,4]oxathiine-2,4'-piperidine]-5,6-dione, 3,4-dichlorobenzoyl chloride and conditions outlined in procedure N. M.p.=221° C.; 300 MHz $^1$H NMR (DMSO-$d_6$) δ 7.89 (m, 2H), 7.74 (m, 3H), 7.58 (t, 1H), 7.46 (d, J=8.1 Hz, 1H), 4.40 (m, 1H), 3.56 (brm, 2H), 3.30 (m, 1H), 3.10 (s, 2H), 2.08 (m, 2H), 1.85 (m, 2H); LCMS: 474 [M+H].

E14.15. Synthesis of 1'-[3-(trifluoromethyl)benzoyl]spiro[naphtho 1,2-b][1,4]oxathiine-2,4'-piperidine-5,6-dione (Compound 54)

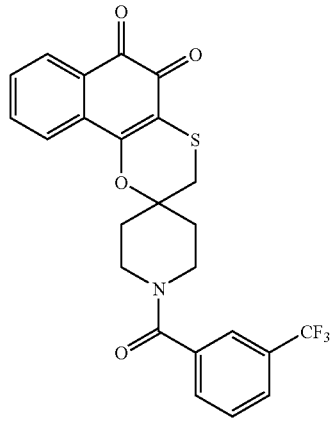

Compound 54 was synthesized using spiro[naphtho[1,2-b][1,4]oxathiine-2,4'-piperidine]-5,6-dione, 3-(trifluoromethyl)benzoyl chloride and conditions outlined in procedure N. M.p.=165-166° C.; 300 MHz $^1$H NMR (DMSO-d$_6$) δ 7.70-7.98 (m, 7H), 7.57 (m, 1H), 4.40 (m, 1H), 3.55 (brm, 2H), 3.30 (m, 1H), 3.11 (s, 2H), 2.10 (m, 1H), 1.85 (m, 3H); LCMS: 474 [M+H].

E14.16. Synthesis of 1'-(3-chlorobenzoyl)spiro[naphtho[1,2-b][4]oxathiine-2,4'-piperidine]-5,6-dione (Compound 55)

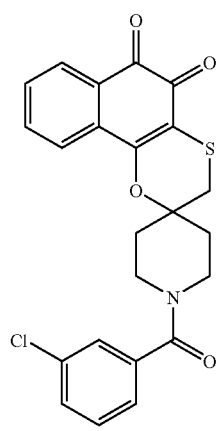

Compound 55 was synthesized using spiro[naphtho[1,2-b][1,4]oxathiine-2,4'-piperidine]-5,6-dione, 3-chlorobenzoyl chloride and conditions outlined in procedure N. M.p.=155-158° C.; 300 MHz $^1$H NMR (DMSO-d$_6$) δ 7.89 (m, 2H), 7.69 (t, 1H), 7.52 (m, 4H), 7.40 (m, 1H), 4.40 (m, 1H), 3.50 (brm, 2H), 3.24 (m, 1H), 3.11 (s, 2H), 2.08 (m, 1H), 1.90 (m, 3H); LCMS: 440 [M+H].

E14.17. Synthesis of 1'-(3-nitrobenzoyl)spiro[naphtho[1,2-b][1,4]oxathiine-2,4'-piperidine]-5,6-dione (Compound 56)

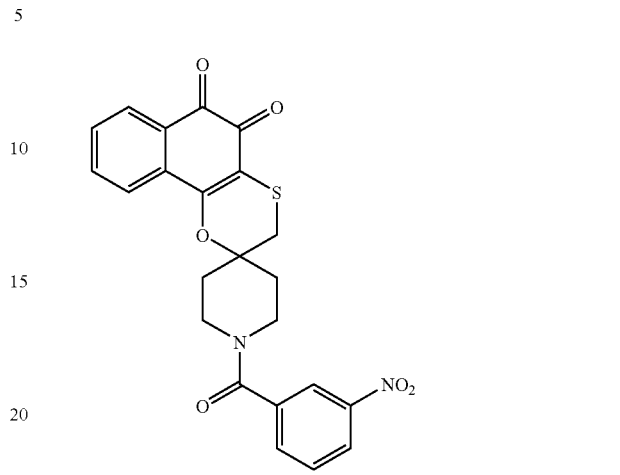

Compound 56 as synthesized using spiro[naphtho[1,2-b][1,4]oxathiine-2,4'-piperidine]-5,6-dione, 3-nitrobenzoyl chloride and conditions outlined in procedure N. M.p.=160-162° C.; 300 MHz $^1$H NMR (DMSO-d$_6$) δ 8.30 (m, 2H), 7.92 (m, 3H), 7.77 (t, 2H), 760 (m, 1H), 4.40 (m, 1H), 3.52 (brm, 2H), 3.24 (m, 1H), 3.12 (s, 2H), 2.08 (m, 1H), 1.90 (m, 3H); LCMS: 451 [M+H].

E14.18. Synthesis of 1'-isonicotinoylspiro[naphtho[1,2-b]1,4]oxathiine-2,4'-piperidine-5,6-dione (Compound 57)

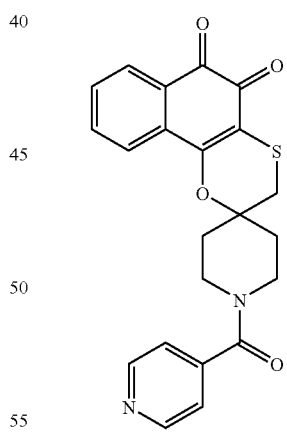

Compound 57 was synthesized using spiro[naphtho[1,2-b][1,4]oxathiine-2,4'-piperidine]-5,6-dione, isonicotinoyl chloride and conditions outlined in procedure N. M.p.=267-269° C.; 400 MHz $^1$H NMR (CDCl$_3$) δ 8.73 (d, J=6 Hz, 2H), 8.08 (d, J=8 Hz, 1H), 7.75 (m, 1H), 7.70 (m, 1H), 7.66 (t, 1H), 7.52 (t, J=7.6 Hz, 2H), 4.68 (d, J=12 Hz, 1H), 3.63 (m, 1H), 3.50 (m 1H), 3.37 (m, 1H), 2.98 (d, 7.6 Hz, 2H), 2.28 (brm, 1H), 2.14 (brm, 1H), 1.91 (brm, 1H), 1.73 (brm, 1H); LCMS: 407 [M+H].

E14.19. Synthesis of 1'-[(5-methyl-2-phenyl-2H-1,2,3-triazol-4-yl)carbonyl]spiro[naphtho[1,2-b][1,4]oxathiine-2,4'-piperidine]-5,6-dione (Compound 58)

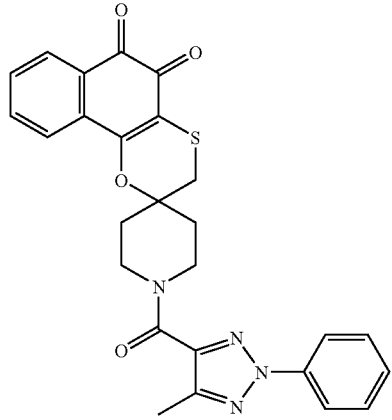

Compound 58 was synthesized using spiro[naphtho[1,2-b][1,4]oxathiine-2,4'-piperidine]-5,6-dione, 5-methyl-2-phenyl-2H-1,2,3-triazole-4-carbonyl chloride and conditions outlined in procedure N. M.p.=275-280° C.; 300 MHz $^1$H NMR (CDCl$_3$) δ 8.07 (d, J=7.5 Hz, 1H), 7.99 (d, J=7.5 Hz, 2H), 7.80 (d, J=7.5 Hz, 1H), 7.68 (t, J=8.4 Hz, 1H), 7.48 (m, 3H), 7.37 (m, 1H), 4.65 (m, 2H), 3.67 (t, 1H), 3.39 (m 1H), 3.01 (s, 2H), 2.57 (s, 3H), 2.30 (brm, 2H), 1.96 (m, 2H); LCMS: 487 [M+H].

E14.20. Synthesis of 1'-(pyridin-3-ylcarbonyl)spiro[naphtho[1,2-b][1,4]oxathiine-2,4'-piperidine]-5,6-dione (Compound 59)

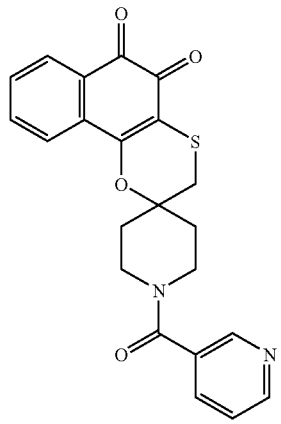

Compound 59 was synthesized using spiro[naphtho[1,2-b][1,4]oxathiine-2,4'-piperidine]-5,6-dione, nicotinoyl chloride and conditions outlined in procedure N. M.p.=218-220° C.; 300 MHz $^1$H NMR (CDCl$_3$) δ 8.71 (brs, 2H), 8.08 (d, J=7.5 Hz, 1H), 7.77 (m, 3H), 7.53 (t, J=7.5 Hz, 1H), 7.40 (m, 1H), 4.62 (m, 1H), 3.78 (m, 1H), 3.42 (m 2H), 2.99 (s, 2H), 2.24 (s, 2H), 1.90 (m, 2H); LCMS: 407 [M+H].

E14.21. Synthesis of 1'-(3-methylbenzoyl)spiro[naphtho[1,2-b][1,4]oxathiine-2,4'-piperidine]-5,6-dione (Compound 60)

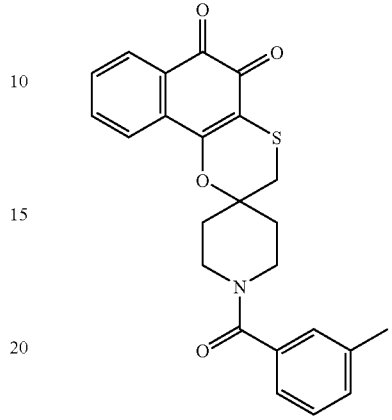

Compound 60 was synthesized using spiro[naphtho[1,2-b][1,4]oxathiine-2,4'-piperidine]-5,6-dione, 3-methylbenzoyl chloride and conditions outlined in procedure N. M.p.=188-190° C.; 300 MHz $^1$H NMR (CDCl$_3$) δ 8.08 (d, J=7.8 Hz, 1H), 7.77 (d, J=6.9 Hz, 1H), 7.68 (m, 1H), 7.51 (m, 1H), 7.25 (m, 4H), 4.60 (m, 1H), 3.80 (m, 1H), 3.42 (m 2H), 2.98 (s, 2H), 2.38 (s, 3H), 2.24 (brm, 2H), 1.90 (brm, 2H); LCMS: 420 [M+H].

E14.22. Synthesis of 1'-[(2E)-3-(2-chlorophenyl)prop-2-enoyl]spiro[naphtho[1,2-b][1,4]oxathiine-2,4'-piperidine]-5,6-dione (Compound 61)

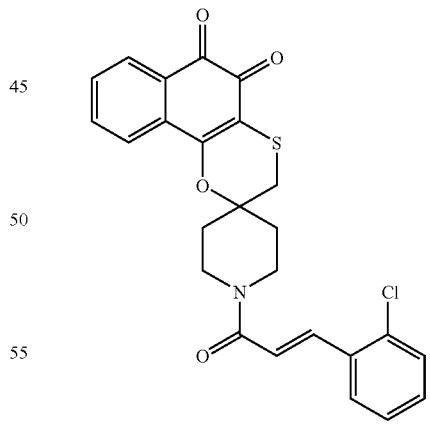

Compound 61 was synthesized using spiro[naphtho[1,2-b][1,4]oxathiine-2,4'-piperidine]-5,6-dione, 2-chlorocinnamoyl chloride and conditions outlined in procedure N. M.p.=110-115° C.; 300 MHz $^1$H NMR (DMSO) δ 8.0-7.75 (m, 5H), 7.6-7.4 (m, 3H), 7.4-7.25 (m, 1H), 7.2-7.1 (m, 1H), 4.5-4.35 (m, 1H), 3.45-3.05 (m, 5H), 2.25-1.7 (m, 4H); LCMS: 466 [M+H].

E14.23. Synthesis of 1-(3-chlorobenzoyl)spiro[azepane-4,2'-naphtho[1,2-b][1,4]oxathiine]-1-5',6'-dione (Compound 62)

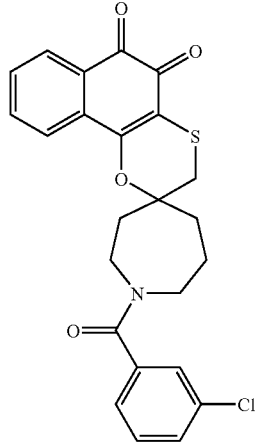

Compound 62 was synthesized using spiro[azepane-4,2'-naphtho[1,2-b][1,4]oxathiine]-5',6'-dione, 3-chlorobenzoyl chloride and conditions outlined in procedure N. M.p.=98-100° C., 400 MHz $^1$H NMR (CDCl$_3$) δ: 8.08-8.06 (m, 1H), 7.76-7.66 (m, 2H), 7.52-7.48 (m, 1H), 7.42-7.21 (m, 4H), 3.87-3.86 (m, 1H), 3.67-3.49 (m, 3H), 3.05-2.92 (m, 2H), 2.39-2.17 (m, 4H), 2.04-1.96 (m, 1H), 1.89-1.76 (m, 1H); LCMS: 454 [M+H].

E14.24. Synthesis of 1'-(3-chlorobenzoyl)-8-methoxyspiro[naphtho[1,2-b][1,4]oxathiine-2,4'-piperidine]-5,6-dione (Compound 63)

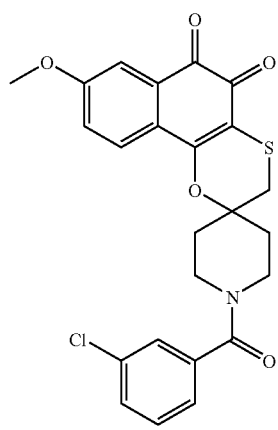

Compound 63 was synthesized using 8-methoxyspiro[naphtho[1,2-b][1,4]oxathiine-2,4'-piperidine]-5,6-dione, 3-chlorobenzoyl chloride and conditions outlined in procedure N. M.p.=130° C. (dec); 400 MHz $^1$H NMR (DMSO-d) δ: 7.82 (d, J=8.6 Hz, 1H), 7.55-7.40 (m, 3H), 7.38 (d, J=7.6 Hz, 2H), 7.34 (d, J=7.4 Hz, 1H), 4.42 (bs, 1H), 3.87 (s, 3H), 3.58-3.20 (m, 4H), 3.03 (s, 2H), 2.08-2.02 (m, 2H), 1.96-1.88 (m, 2H), 1.86-1.78 (m, 2H); LCMS: 470 [M+H].

E14.25. Synthesis of 1'-(3-chlorobenzoyl)-9-phenylspiro[naphtho[1,2-b][1.4]oxathiine-2,4'-piperidine]-5,6-dione (Compound 64)

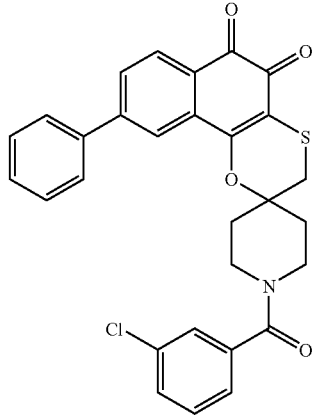

Compound 64 was synthesized using 9-phenylspiro[naphtho[1,2-b][1,4]oxathiine-2,4'-piperidine]-5,6-dione, 3-chlorobenzoyl chloride and conditions outlined in procedure N. Mp.: 240-241° C.; 400 MHz $^1$H NMR (DMSO-d$_6$) δ: 8.01 (d, J=1.6 Hz, 1H), 7.99 (d, J=8.0 Hz, 1H), 7.87 (dd, J=1.6, 7.6 Hz, 1H), 7.83-7.76 (m, 2H), 7.60-7.46 (m, 6H), 7.41 (dt, J=1.6, 7.6 Hz, 1H), 4.32 (br, 1H), 3.49 (br, 2H), 3.14 (s, 2H), 3.35-3.28 (m, 1H), 2.15 (br, 1H), 2.03 (br, 1H), 1.90 (br, 2H); LCMS: 516 [M+H].

E14.26. Synthesis of 1'-(3-chlorobenzoyl)-9-pyridin-3-ylspiro[naphtho[1,2-b][1,4]oxathiine-2,4'-piperidine]-5,6-dione (Compound 65)

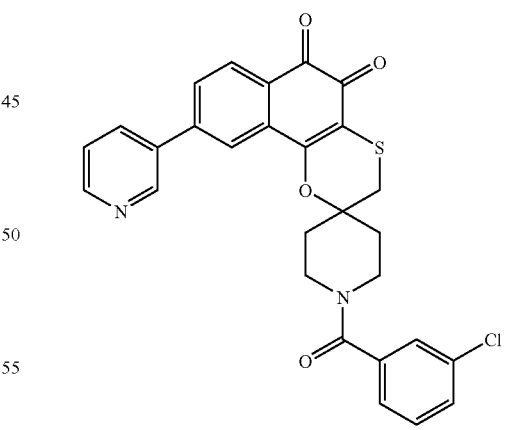

Compound 65 was synthesized using 9-pyridin-3-ylspiro[naphtho[1,2-b][1,4]oxathiine-2,4'-piperidine]-5,6-dione, 3-chlorobenzoyl chloride and conditions outlined in procedure N. Mp.: 240-242° C.; 400 MHz $^1$H NMR (DMSO-d$_6$) δ 9.04 (d, J=2.0 Hz, 1H), 8.69 (dd, J=1.6, 4.8 Hz, 1H), 8.24 (dt, J=1.6, 8.8 Hz, 1H), 8.05 (d, J=1.6 Hz, 1H), 8.01 (d, J=8.0 Hz, 1H), 7.93 (dd, J=1.6, 8.4 Hz, 1H), 7.59 (dd, J=4.8, 8.0 Hz, 1H), 7.55-7.47 (m, 3H), 7.41 (d, J=7.6 Hz, 1H), 4.32 (br, 1H), 3.50 (br, 2H), 3.38-3.30 (m, 1H), 3.14 (s, 2H), 2.15 (m, 1H), 2.03 (m, 1H), 1.90 (nm 2H); LC MS: 519 [M+H].

E14.27. Synthesis of 1'-(3-chlorobenzoyl)-9-pyridin-4-ylspiro[naphtho[1,2-b][1,4]oxathiine-2,4'-piperidine]-5,6-dione (Compound 66)

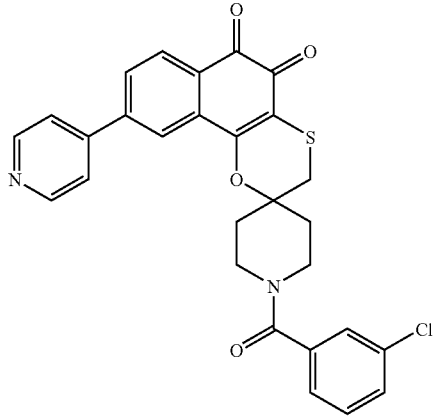

Compound 66 was synthesized using 9-pyridin-4-ylspiro[naphtho[1,2-b][1,4]oxathiine-2,4'-piperidine]-5,6-dione, 3-chlorobenzoyl chloride and conditions outlined in procedure N. Yield: 99%. Mp.: 265-267° C.; 400 MHz $^1$H NMR (DMSO-d$_6$) δ 8.75 (m, 2H), 8.08 (d, J=1.6 Hz, 1H), 8.03 (d, J=8.4 Hz, 1H), 7.98 (dd, J=1.6, 8.0 Hz, 1H), 7.83 (m, 2H), 7.56-7.47 (m, 3H), 7.41 (dt, J=1.2, 7.6 Hz, 1H), 4.32 (br, 1H), 3.50 (br, 2H), 3.38-3.30 (m, 1H), 3.14 (s, 2H), 2.15 (m, 1H), 2.02 (m, 1H), 1.91 (m, 2H); LCMS: 517 [M+H].

E14.28. Synthesis of 9-chloro-1'-(3-chlorobenzoyl)spiro[naphtho[1,2-b][1,4]oxathiine-2,4'-piperidine]-5,6-dione (Compound 67)

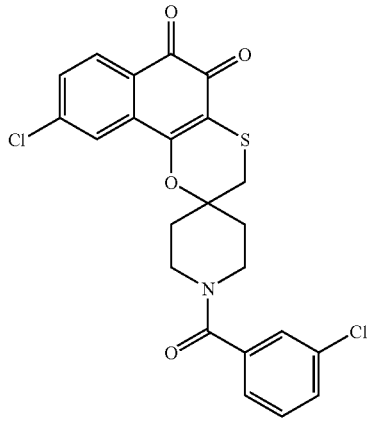

Compound 67 was synthesized using 9-chlorospiro[naphtho[1,2-b][1,4]oxathiine-2,4'-piperidine]-5,6-dione, 3-chlorobenzoyl chloride and conditions outlined in procedure N. (81 mg, 95%); M.p.=125-130° C.; 400 MHz $^1$H NMR (DMSO-d$_6$) δ: 7.90 (d, J=8.4 Hz, 1H), 7.76 (d, J=1.6 Hz, 1H), 7.63 (dd, J=1.2 and 8.4 Hz, 1H), 7.55-7.48 (m, 3H), 7.42 (d, J=7.2 Hz, 1H), 4.4-4.2 (m, 1H), 3.84 (brs, 2H), 3:34-3.24 (m, 1H), 3.12 (s, 2H), 2.19-2.08 (m, 1H), 2.02-1.8 (m, 3H); LCMS: 474 [M+H].

E14.29. Synthesis of 9-bromo-1'-(3-chlorobenzoyl)spiro[naphtho[1,2-b][1,4]oxathiine-2,4'-piperidine]-5,6-dione (Compound 68)

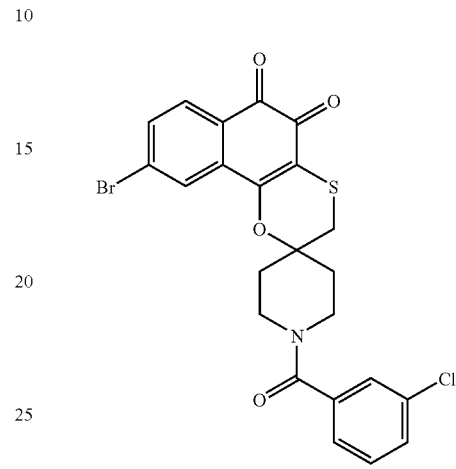

Compound 68 was synthesized using 9-bromospiro[naphtho[1,2-b][1,4]oxathiine-2,4'-piperidine]-5,6-dione, 3-chlorobenzoyl chloride and conditions outlined in procedure N. M.p.=135-140° C.; 400 MHz $^1$H NMR (CDCl$_3$) δ: 7.93-7.91 (m, 1H), 7.83-7.82 (m, 1H), 7.67-7.64 (m, 1H), 7.45-7.25 (m, 4H), 4.65-4.5 (bs, 1H), 3.80-3.65 (bs, 1H), 3.55-3.35 (m, 2H), 2.98 (s, 2H), 2.30-2.05 (m, 2H), 2.00-1.67 (m, 2H); LCMS: 518 [M+H].

E14.30. Synthesis of 1'-(3-chlorobenzoyl)-9-methoxyspiro[naphtho[1,2-b][1,4]oxathiine-2,4'-piperidine]-5,6-dione (Compound 69)

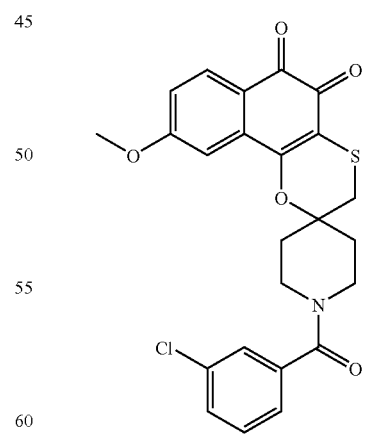

Compound 69 was synthesized using 9-methoxyspiro[naphtho[1,2-b][1,4]oxathiine-2,4'-piperidine]-5,6-dione, 3-chlorobenzoyl chloride and conditions outlined in procedure N. M.p.=125-127° C.; 400 MHz $^1$H NMR (CDCl$_3$) δ: LCMS: 7.90 (d, 1H), 7.55-7.47 (m, 3H), 7.41 (m, 1H), 7.25

(d, 1H), 7.11 (dd, 1H), 3.94, (s, 3H), 3.55-3.40 (m, 2H), 3.11 (s, 2H), 2.18-1.92 (m, 4H), 1.89-1.82 (m, 2H); LCMS: 470 [M+H].

E14.31. Synthesis of N-(5',6'-dioxo-5',6'-dihydrospiro[cyclohexane-1,2'-naphtho[1,2-b][1,4]oxathiin]-4-yl)-3-(trifluoromethyl)benzamide (Compound 70)

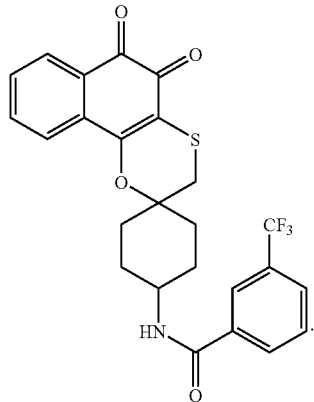

Compound 70 was synthesized using 4-aminospiro[cyclohexane-1,2'-naphtho[1,2-b][1,4]oxathiine]-5',6'-dione hydrochloride, 3-(trifluoromethyl)benzoyl chloride, triethylamine to neutralize the hydrochloride and conditions outlined in procedure N. M.p.=266-267° C.; 400 MHz $^1$H NMR (DMSO-d$_6$) δ: 8.66 (d, J=7.8 Hz, 1H), 8.21-8.16 (m, 2H), 7.92 (d, J=7.4 Hz, 1H), 7.85 (t, J=7.1 Hz, 1H), 7.80 (t, J=7.1 Hz, 1H), 7.74 (t, J=7.1 Hz, 1H), 7.58 (t, J=7.1 Hz, 1H), 4.08-3.94 (m, 1H), 3.06 (s, 2H), 2.20-2.10 (m, 2H), 1.94-1.72 (m, 7H), LCMS: 488 [M+H].

Example 15

Procedure O

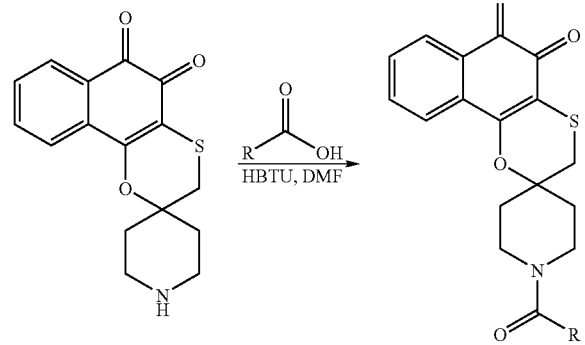

E15.1. Synthesis of tert-butyl 4-[(5,6-dioxo-5,6-dihydro-1'H-spiro[naphtho[1,2-b][1,4]oxathiine-2,4'-piperidine]-1'-yl)carbonyl]piperidine-1-carboxylate (Compound 71)

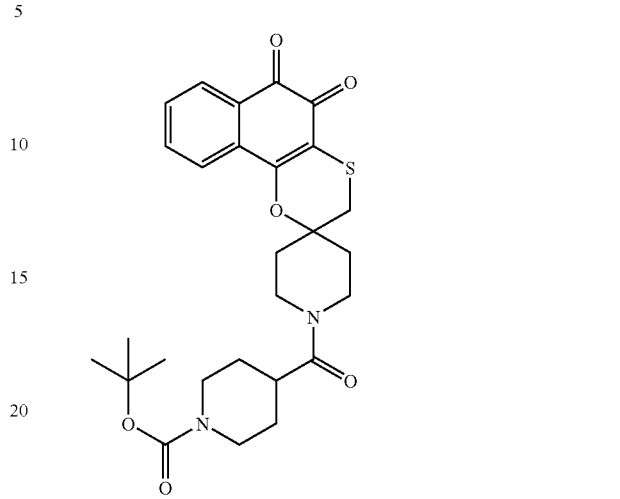

To a solution of 1-(tert-butoxycarbonyl)piperidine-4-carboxylic acid (0.628 g, 2.74 mmol) in dimethyl formamide (20 mL) was added HBTU (1.039 g, 2.74 mmol), dimethylamino pyridine (0.335 g, 2.74 mmol) followed by spiro[naphtho[1,2-b][1,4]oxathiine-2,4-piperidine]-5,6-dione (0.75 g, 2.49 mmol). The reaction mixture was stirred at room temperature for 16 hours. To the reaction was added water (100 mL) and the aqueous layer extracted with EtOAc (3×50 mL). The combined organic extract was washed with 1.0N HCl (2×100 mL), saturated sodium bicarbonate (2×100 mL), saturated sodium chloride (2×100 mL), dried with sodium sulfate and concentrated under reduced pressure. The crude product was purified by flash column chromatography (SiO$_2$, 20% EtOAc in dichloromethane) to afford the product as a purple solid (0.81 g, 63%). M.p.=94-100° C., (DMSO-d$_6$) δ: 7.93-7.84 (m, 2H), 7.8-7.72 (m, 1H), 7.6-7.52 (m, 1H), 4.33-4.22 (m, 1H), 4.0-3.85 (m, 3H), 3.5-3.4 (m, 1H), 3.11 (s, 2H), 3.1-3.0 (m, 1H), 2.98-2.7 (m, 31-1), 2.13-1.96 (m, 2H), 1.88-1.58 (m, 5H), 1.5-1.4 (m, 1H), 1.4 (s, 9H); LCMS=513 [M+H].

E15.2. Synthesis of tert-butyl 4-[2-(5,6-dioxo-5,6-dihydro-1'H-spiro[naphtho[1,2-b][1,4]oxathiine-2,4'-piperidine]-1'-yl)-2-oxoethyl]piperidine-1-carboxylate (Compound 72)

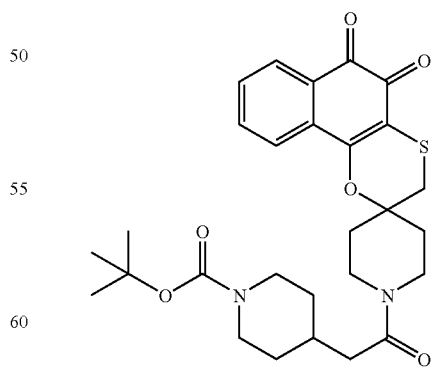

Compound 72 was synthesized using spiro[naphtho[1,2-b][1,4]oxathiine-2,4'-piperidine]-5,6-dione, [1-(tert-butoxycarbonyl)piperidin-4-yl]acetic acid and conditions outlined in procedure O. M.p.=110-113° C., (DMSO-d$_6$) δ:7.94-7.88 (m, 1H), 7.87-7.8 (m, 1H), 7.78-7.71 (m, 1H), 7.6-7.52 (m, 1H), 4.36-4.22 (m, 1H), 4.0-3.8 (m, 2H), 3.48-3.28 (m, 2H), 3.1 (s, 2H), 3.1-3.0 (m, 1H), 2.8-2.6 (m, 2H), 2.29 (d, J=3.6 Hz, 2H), 2.1-1.96 (m, 2H), 1.95-1.6 (m, 4H), 1.39 (s, 9H), 1.15-0.98 (m, 2H); LCMS=527 [M+H].

E15.3. Synthesis of 1'-(5,6-dihydro-4H-pyrrolo[3,2,1-ij]quinolin-1-ylcarbonyl)spiro[naphtho[1,2-b][1,4]oxathiine-2,4'-piperidine]-5,6-dione (Compound 73)

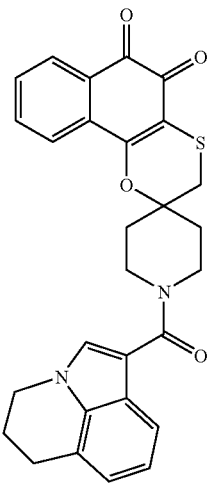

Compound 73 was synthesized using spiro[naphtho[1,2-b][1,4]oxathiine-2,4'-piperidine]-5,6-dione, 5,6-dihydro-4H-pyrrolo[3,2,1-ij]quinone-1-carboxylic acid conditions outlined in procedure O. M.p.=265-267° C.; 400 MHz $^1$H NMR (DMSO-$d_6$) δ: 7.92 (dd, J=0.78, 7.4 Hz, 2H), 7.76-7.80 (m, 2H), 7.59 (t, J=7.4 Hz, 1H), 7.49 (d, J=8.2 Hz, 1H), 7.05 (t, J=7.8 Hz, 1H), 6.93 (d, J=7.0 Hz, 1H), 4.22 (m, 4H), 3.45 (t, J=11.4 Hz, 2H), 3.16 (s, 2H), 2.95 (t, J=5.8 Hz, 2H), 2.06-2.16 (m, 4H), 1.87 (m 2H); LCMS=485 [M+H].

E15.4. Synthesis of 1'-(1H-benzimidazol-2-ylcarbonyl)spiro[naphtho[1,2-b][1,4]oxathiine-2,4'-piperidine]-5,6-dione (Compound 74)

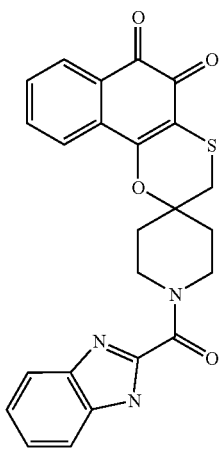

Compound 74 was synthesized using spiro[naphtho[1,2-b][1,4]oxathiine-2,4'-piperidine]-5,6-dione, 1H-benzimidazole-2-carboxylic acid and conditions outlined in procedure O. M.p.=266-268° C.; 400 MHz $^1$H NMR (DMSO-$d_6$) δ: 13.17 (s, 1H), 7.92 (m, 2H), 7.76 (m, 2H), 7.56 (m, 2H), 7.24-7.35 (m, 2H), 5.46 (d, 1H), 4.48 (d, 1H), 3.82 (t, 0H), 3.33 (m, 1H), 3.18 (d, 2H), 2.17 (m, 2H), 1.85-2.04 (m, 2H); LCMS=446 [M+H].

Example 16

Procedure P

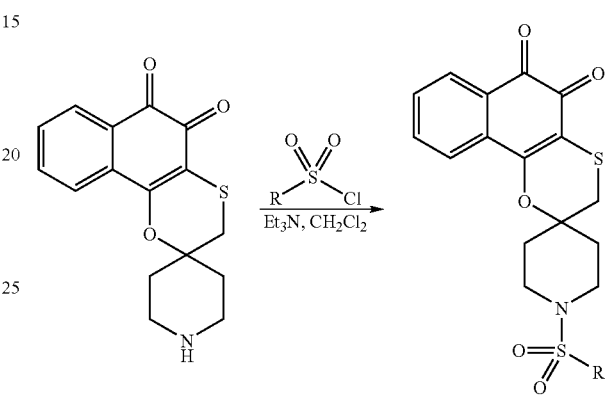

E16.1. Synthesis of 1'-(methylsulfonyl)spiro[naphtho[1,2-b][1,4]oxathiine-2,4'-piperidine]-5,6-dione (Compound 75)

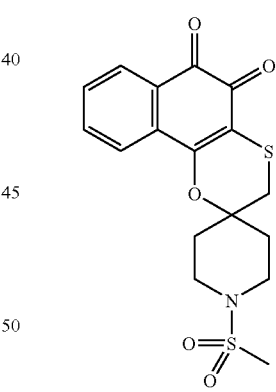

To a mixture of spiro[naphtho[1,2-b][1,4]oxathiine-2,4'-piperidine]-5,6-dione (0.5 g, 1.66 mmol) in dichloromethane (50 mL) was added methanesulfonyl chloride (0.129 ml, 1.67 mmol) followed by triethylamine (1.2 ml, 8.61 mmol). The reaction was stirred at room temperature for 3 h followed by addition of water (50 mL). The organic layer was separated, dried with $Na_2SO_4$ and concentrated under reduced pressure. The crude product was purified by flash column chromatography ($SiO_2$, 5% EtOAc in dichloromethane) to afford the product as a purple solid (0.458 g, 72.7%). M.p.=258° C.; 400 $^1$H NMR (CDCl$_3$) δ: 8.09-8.06 (m, 1H), 7.71-7.64 (m, 2H), 7.54-7.49 (m, 1H), 3.84-3.78 (m, 2H), 3.22-3.14 (m, 2H), 2.97 (s, 2H), 2.88 (s, 3H), 2.30-2.23 (m, 2H), 2.00-1.90 (m, 2H); LCMS: 380 [M+H]; Calc. for $C_{17}H_{17}NO_5S_2$ 0.07 CHCl$_3$: C, 53.15; H, 4.48; N, 3.633; Found C, 52.37; H, 4.44; N, 3.44.

E16.2. Synthesis of 1'-[(3,4-dichlorophenyl)sulfonyl]spiro[naphtho[1,2-b][1,4]oxathiine-2,4'-piperidine]-5,6-dione (Compound 76)

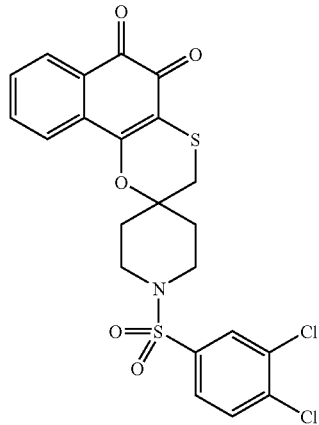

Compound 76 was synthesized using spiro[naphtho[1,2-b][1,4]oxathiine-2,4'-piperidine]-5,6-dione, 3,4-dichlorobenzenesulfonyl chloride and conditions outlined in procedure P. M.p.=275-276° C.; 400 $^1$H NMR (DMSO-d$_6$) δ: 8.00-7.95 (m, 2H), 7.86-7.83 (m, 1H), 7.78-7.74 (m, 1H), 7.55-7.49 (m, 1H), 7.45-7.40 (m, 1H), 7.15-7.11 (m, 1H), 3.62-3.53 (m, 2H), 3.09 (s, 2H), 2.66-2.57 (m, 2H), 2.13-2.03 (m, 2H), 1.94-1.84 (m, 2H) LCMS: 510 [M+H].

E16.3. Synthesis of 1'-[(6-chloroimidazo[2,1-b][1,3]thiazol-5-yl)sulfonyl]spiro[naphtho[1,2-b][1,4]oxathiine-2,4'-piperidine]-5,6-dione (Compound 77)

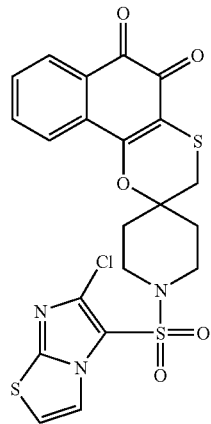

Compound 77 was synthesized using spiro[naphtho[1,2-b][1,4]oxathiine-2,4'-piperidine]-5,6-dione, 6-chloroimidazo[2,1-b][1,3]thiazole-5-sulfonyl chloride and conditions outlined in procedure P. M.p.=265-267° C.; 400 MHz $^1$H NMR (DMSO-d$_6$) δ: 8.08-8.05 (m, 1H), 7.87-7.84 (m, 1H), 7.61-7.50 (m, 3H), 7.33-7.29 (m, 1H), 3.66-3.60 (m, 2H), 3.11 (s, 2H), 3.02-2.95 (m, 2H), 2.12-2.06 (m, 2H), 1.95-1.84 (m, 2H); LCMS: 522 [M+H].

E16.4. Synthesis of 1'-(2-thienylsulfonyl)spiro[naphtho[1,2-b][1,4]oxathiine-2,4'-piperidine]-5,6-dione (Compound 78)

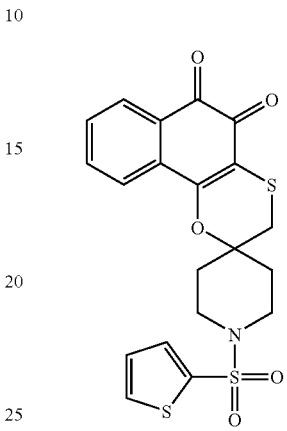

Compound 78 was synthesized using spiro[naphtho[1,2-b][1,4]oxathiine-2,4'-piperidine]-5,6-dione, thiophene-2-sulfonyl chloride and conditions outlined in procedure P. M.p.=245-248° C.; 400 MHz $^1$H NMR (CDCl$_3$) δ: 8.02-8.05 (m, 1H), 7.70-7.67 (m, 1H), 7.61-7.59 (m, 1H), 7.48-7.44 (m, 2H), 7.27-7.22 (m, 1H), 7.22-7.18 (m, 1H), 3.79-3.72 (m, 2H), 2.94 (s, 2H), 2.91-2.84 (m, 2H), 2.26-2.18 (m, 2H), 2.02-1.91 (m, 2H); LCMS: 448 [M+H].

E16.5. Synthesis of 1'-[(1-methyl-1H-imidazol-4-yl)sulfonyl]spiro[naphtho[1,2-b][1,4]oxathiine-2,4'-piperidine]-5,6-dione (Compound 79)

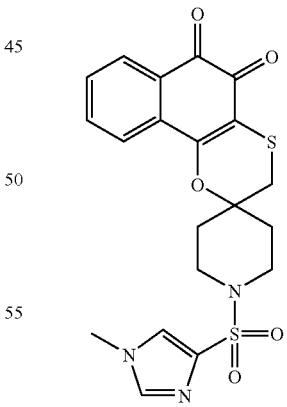

Compound 79 was synthesized using spiro[naphtho[1,2-b][1,4]oxathiine-2,4'-piperidine]-5,6-dione, 1-methyl-1H-imidazole-4-sulfonyl chloride and conditions outlined in procedure P. M.p.=256-257° C.; 400 MHz $^1$H NMR (CDCl$_3$) δ: 8.06-8.03 (m, 1H), 7.64-7.56 (m, 2H), 7.53-7.45 (m, 3H), 3.84-3.78 (m, 5H), 3.30-3.22 (m, 2H), 2.93 (s, 2H), 2.22-2.13 (m, 2H), 2.0-1.90 (m, 2H); LCMS: 446 [M+H].

E16.6. Synthesis of 1'-[(1,3,5-trimethyl-1H-pyrazol-4-yl)sulfonyl]spiro[naphtho[1,2-b][1,4]oxathiine-2,4'-piperidine]-5,6-dione (Compound 80)

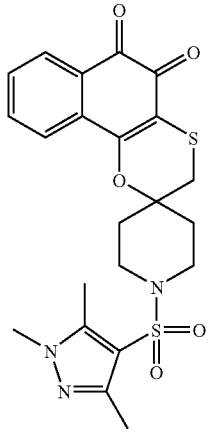

Compound 80 was synthesized using spiro[naphtho[1,2-b][1,4]oxathiine-2,4'-piperidine]-5,6-dione, 1,3,5-trimethyl-1H-pyrazole-4-sulfonyl chloride and conditions outlined in procedure P. M.p.=273-275° C.; 400 MHz $^1$H NMR (DMSO-$d_6$) δ: 7.88-7.85 (m, 1H), 7.64-7.58 (m, 1H), 7.56-7.52 (m, 1H), 7.32-7.29 (m, 1H), 3.72 (s, 3H), 3.50-3.44 (m, 2H), 3.09 (s, 2H), 2.71-2.65 (m, 2H), 2.38 (s, 3H), 2.22 (s, 3H), 2.11-2.05 (m, 2H), 1.91-1.82 (m, 2H); LCMS: 474 [M+H].

E16.7. Synthesis of 1'-[(5-chloro-1,3-dimethyl-1H-pyrazol-4-yl)sulfonyl]spiro[naphtho[1,2-b][1,4]oxathiine-2,4'-piperidine]-5,6-dione (Compound 81)

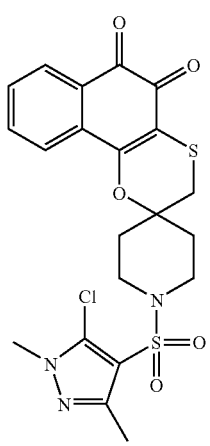

Compound 81 was synthesized using spiro[naphtho[1,2-b][1,4]oxathiine-2,4'-piperidine]-5,6-dione, 5-chloro-1,3-dimethyl-1H-pyrazole-4-sulfonyl chloride and conditions outlined in procedure P. M.p.=247-249° C.; 400 MHz $^1$H NMR (DMSO-d) δ: 7.89-7.86 (m, 1H), 7.66-7.61 (m, 1H), 7.57-7.52 (m, 1H), 7.41-7.38 (m, 1H), 3.80 (s, 3H), 3.56-3.51 (m, 2H), 3.11 (s, 2H), 2.88-2.81 (m, 2H), 2.29 (s, 3H), 2.13-2.06 (m, 2H), 1.93-1.84 (m, 2H); LCMS: 494 [M+H].

E16.8. Synthesis of 1'-[(3-chlorophenyl)sulfonyl]spiro[naphtho[1,2-b][1,4]oxathiine-2,4'-piperidine]-5,6-dione (Compound 82)

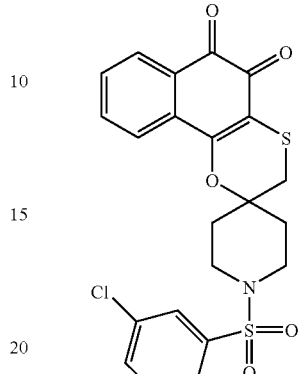

Compound 82 was synthesized using spiro[naphtho[1,2-b][1,4]oxathiine-2,4'-piperidine]-5,6-dione, 3-chlorobenzenesulfonyl chloride and conditions outlined in procedure P. M.p.=255-256° C.; 400 $^1$H NMR (DMSO-d) δ: 7.98-7.9 (m, 1H), 7.89-7.82 (m, 1H), 7.8-7.7 (m, 3H), 7.58-7.4 (m, 2H), 7.3 (d, J=7.6 Hz, 1H), 3.65-3.58 (m, 2H), 3.1 (s, 2H), 2.6-2.5 (m, 2H), 2.15-2.05 (m, 2H), 1.95-1.84 (m, 2H) LCMS: 476 [M+H].

E16.9. Synthesis of N,N-dimethyl-5,6-dioxo-5,6-dihydro-1'H-spiro[naphtho[1,2-b][1,4]oxathiine-2,4'-piperidine]-1'-sulfonamide (Compound 83)

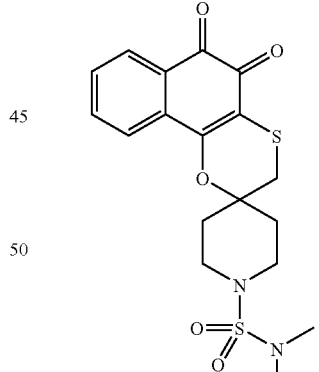

Compound 83 was synthesized using spiro[naphtho[1,2-b][1,4]oxathiine-2,4'-piperidine]-5,6-dione, dimethylsulfamoyl chloride and conditions outlined in procedure P. M.p.=215-218° C.; 400 MHz $^1$H NMR (DMSO-$d_6$) δ 7.89-7.91 (dd. J=0.78, 7.4 Hz, 1H,), 7.76-7.83 (m, J=1.5, 7.4, 7.4 Hz, 2H), 7.55-7.59 (ddd, J=1.5, 7.4, 7.4 Hz, 1H), 3.54 (dt, J=3.5, 12.9 Hz, 2H), 3.18-3.21 (t, 2H), 3.14 (s, 2H), 2.78 (s, 6H), 2.06-2.10 (m, 2H), 1.82-1.90 (br m 2H); LCMS: 409 [M+H].

Example 17

Procedure Q

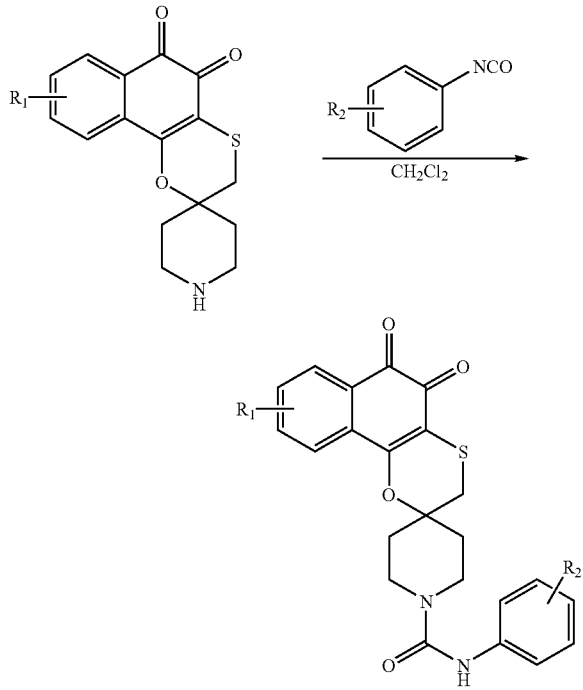

E17.1. Synthesis of 5,6-dioxo-N-phenyl-5,6-dihydro-1'H-spiro[naphtho[1,2-b][1,4]oxathiine-2,4'-piperidine]-1'-carboxamide (Compound 84)

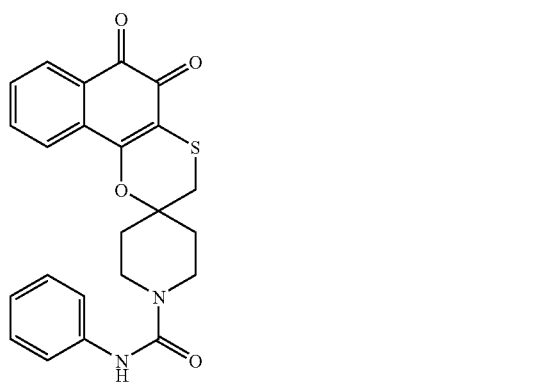

To a solution of spiro[naphtho[1,2-b][1,4]oxathiine-2,4'-piperidine]-5,6-dione (0.1 g, 0.33 mmol) in dichloromethane (4.0 mL) was added the isocyanatobenzene (0.043 g, 0.37 mmol). The reaction mixture was stirred at room temperature for 30 min. The solvent was then removed under vacuum. The crude product was purified by flash column chromatography (SiO$_2$, 100% dichloromethane to 10% EtOAc in dichloromethane) to give the desired product as a purple solid (0.085 g, 61%). M.p.=228-230° C.; 400 MHz $^1$H NMR (CDCl$_3$) δ: 8.08 (d, J=6.8 Hz, 1H), 7.8-7.7 (m, 1H) 7.67 (t, J=7.6 Hz, 1H), 7.55-7.48 (m, 1H), 7.4-7.27 (m, 4H), 7.1-7.03 (m, 1H), 6.40 (s, 1H), 4.1-4.0 (m, 2H), 3.5-3.35 (m, 2H), 2.98 (s, 2H), 2.27-2.0 (m, 2H), 1.95 1.8 (m, 2H); LCMS: 421 [M+H].

E17.2. Synthesis of N-(4-fluorophenyl)-5,6-dioxo-5,6-dihydro-1'H-spiro[naphtho[1,2-b][1,4]oxathiine-2,4'-piperidine]-1'-carboxamide (Compound 85)

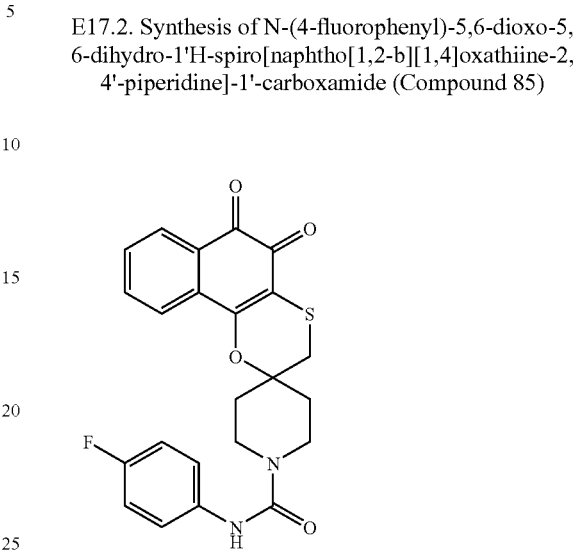

Compound 85 was synthesized using spiro[naphtho[1,2-b][1,4]oxathiine-2,4'-piperidine]-5,6-dione, 1-fluoro-4-isocyanatobenzene and conditions outlined in procedure Q. M.p.=218-220° C.; 400 MHz $^1$H NMR (DMSO-d$_6$) δ: 8.64 (s, 1H), 7.95-7.8 (m, 2H), 7.8-7.7 (m, 1H), 7.6-7.5 (m, 1H), 7.5-7.4 (m, 2H), 7.15-7.0 (m, 2H), 4.15-4.0 (m, 2H), 3.4-3.2 (m, 2H), 3.13 (s, 2H), 2.1-1.95 (m, 2H), 1.9-1.7 (m, 2H); LCMS: 439 [M+H].

E17.3. Synthesis of 5,6-dioxo-N-[3-(trifluoromethyl)phenyl]-5,6-dihydro-1'H-spiro[naphtho[1,2-b][1,4]oxathiine-2,4'-piperidine]-1'-carboxamide (Compound 86)

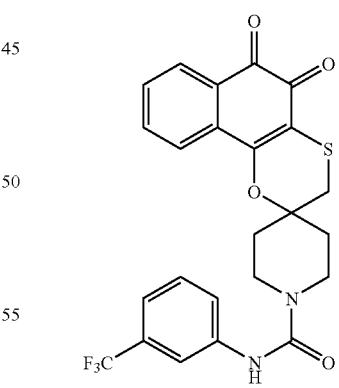

Compound 86 was synthesized using spiro[naphtho[1,2-b][1,4]oxathiine-2,4'-piperidine]-5,6-dione, 1-isocyanato-3-(trifluoromethyl)benzene and conditions outlined in procedure Q. M.p.=216-218° C.; 400 MHz $^1$H NMR (DMSO-d$_6$) δ: 8.95 (s, 1H), 8.0-7.82 (m, 3H), 7.8-7.72 (m, 2H), 7.61-7.54 (m, 1H), 7.5-7.4 (m, 1H), 7.28-7.22 (m, 1H), 4.17-4.0 (m, 2H), 3.38-3.22 (m, 2H), 3.14 (s, 2H), 2.1-2.0 (m, 2H), 1.9-1.75 (m, 2H); LCMS: 489 [M+H].

E17.4. Synthesis of N-(3,4-dichlorophenyl)-5,6-dioxo-5,6-dihydro-1'H-spiro[naphtho[1,2-b][1,4]oxathiine-2,4'-piperidine]-1'-carboxamide (Compound 87)

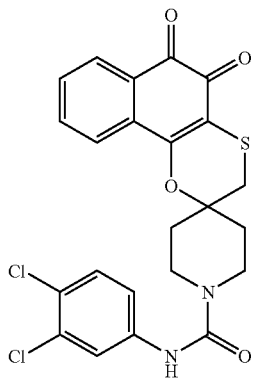

Compound 87 was synthesized using spiro[naphtho[1,2-b][1,4]oxathiine-2,4'-piperidine]-5,6-dione, 1,2-dichloro-4-isocyanatobenzene and conditions outlined in procedure Q. M.p.=245-246° C.; 400 MHz $^1$H NMR (DMSO-$d_6$) δ: 8.90 (s, 1H), 7.94-7.84 (m, 3H), 7.79-7.73 (m, 1H), 7.6-7.55 (m, 1H), 7.52-7.44 (m, 2H), 4.1-4.0 (m, 2H), 3.34-3.22 (m, 2H), 3.13 (s, 2H), 2.1-2.0 (m, 2H), 1.86-1.76 (m, 2H); LCMS: 489 [M+H].

E17.5. Synthesis of N-[4-(dimethylamino)phenyl]-5,6-dioxo-5,6-dihydro-1'H-spiro[naphtho[1,2-b][1,4]oxathiine-2,4'-piperidine]-1'-carboxamide (Compound 88)

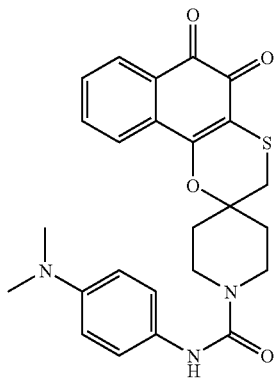

Compound 88 was synthesized using spiro[naphtho[1,2-b][1,4]oxathiine-2,4'-piperidine]-5,6-dione, 4-isocyanato-N,N-dimethylaniline and conditions outlined in procedure Q. M.p.=222-224° C.; 400 MHz $^1$H NMR (DMSO-$d_6$) δ: 8.31 (s, 1H), 7.95-7.85 (m, 2H), 7.8-7.72 (m, 1H), 7.6-7.55 (m, 1H), 7.27-7.20 (m, 2H), 6.7-6.6 (m, 2H), 4.1-3.97 (m, 2H), 3.3-3.18 (m, 2H), 3.13 (s, 2H), 2.82 (s, 6H), 2.08-1.98 (m, 2H), 1.85-1.75 (m, 2H); LCMS: 464 [M+H].

E17.6. Synthesis of 5,6-dioxo-5,6-dihydro-1'H-spiro[naphtho[1,2-b][1,4]oxathiine-2,4'-piperidine]-1'-carboxamide (Compound 89)

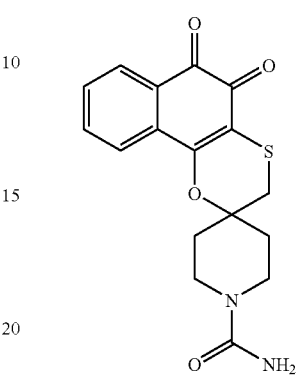

Compound 89 was synthesized using spiro[naphtha[1,2-b][1,4]oxathiine-2,4'-piperidine]-5,6-dione, isocyanato(trimethyl)silane and conditions outlined in procedure Q. M.p.=218-220° C.; 400 MHz $^1$H NMR (DMSO-$d_6$) δ: 7.90 (d, J=6.8 Hz, 1H), 7.83 (d, J=8.0 Hz, 1H), 7.75 (t, J=7.6 Hz, 1H), 7.56 (t, J=8.0 Hz, 1H), 6.05 (s, 2H), 3.86 (d, J=13.6 Hz, 2H), 3.15-3.10 (m, 4H), 1.95 (d, J=13.6 Hz, 2H), 1.73-1.67 (m, 2H); LCMS: 345 [M+H].

Example 18

Procedure R

E18.1. Synthesis of 5,6-dioxo-N-pyridin-3-yl-5,6-dihydro-1'H-spiro[naphtho[1,2-b][1,4]oxathiine-2,4'-piperidine]-1'-carboxamide (Compound 90)

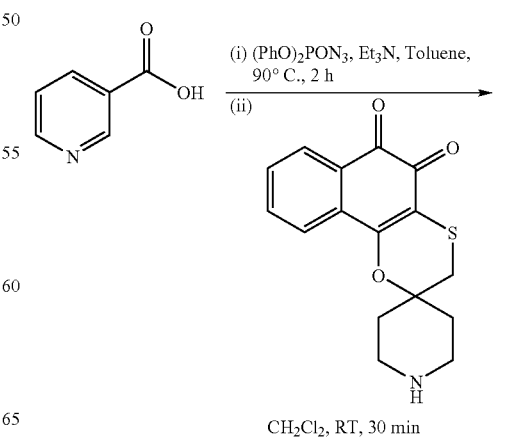

-continued

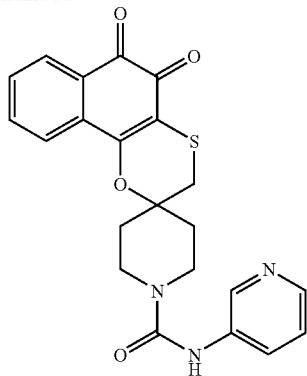

Step (i): To a mixture of nicotinic acid (0.3 g, 2.19 mmol) in toluene (8.0 mL) was added diphenylphosphoryl azide (0.47 mL, 2.19 mmol) followed by triethylamine (0.61 mL, 4.38 mmol). The reaction mixture was stirred at 90° C. for 2 hours.

Step (ii): The reaction was cooled to room temperature and the resulting solution of 3-isocyanatopyridine in toluene (3 mL) was then added to another flask containing a solution of spiro[naphtho[1,2-b][1,4]oxathiine-2,4'-piperidine]-5,6-dione (0.15 g, 0.5 mmol) in dichloromethane (5.0 mL). The reaction was stirred at room temperature for 30 minutes. The solvent was removed under vacuum. The crude product was purified by flash column chromatography (SiO$_2$, 100% EtOAc to 2% methanol in EtOAc) to give the desired product as a purple solid (0.182 g, 84%). M.p.=155-160° C.; 400 MHz $^1$H NMR (DMSO-d$_6$) δ: 8.81 (s, 1H), 8.65 (s, 1H), 8.18-8.13 (m, 1H), 7.95-7.83 (m, 3H), 7.8-7.71 (m, 1H), 7.62-7.55 (m, 1H), 7.31-7.24 (m, 1H), 4.15-4.0 (m, 2H), 3.4-3.2 (m, 2H), 3.14 (s, 2H), 2.15-2.0 (m, 2H), 1.9-1.76 (m, 2H); LCMS: 422 [M+H].

E18.2. Synthesis of N-(6-methylpyridin-3-yl)-5,6-dioxo-5,6-dihydro-1'H-spiro[naphtho[1,2-b][1,4]oxathiine-2,4'-piperidine]-1'-carboxamide (Compound 91)

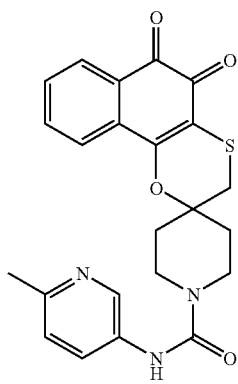

Compound 91 was synthesized using 6-methylnicotinic acid to synthesize 5-isocyanato-2-methylpyridine [Step (i)] followed by [step (ii)] using spiro[naphtho[1,2-b][1,4]oxathiine-2,4'-piperidine]-5,6-dione as outlined in procedure R. M.p.=231-233° C.; 400 MHz $^1$H NMR (DMSO-d$_6$) δ: 8.7 (s, 1H), 8.5 (s, 1H), 7.97-7.85 (m, 2H), 7.8-7.72 (m, 2H), 7.6-7.53 (m, 1H), 7.16-7.1 (m, 1H), 4.15-4.0 (m, 2H), 3.4-3.2 (m, 2H), 3.14 (s, 2H), 2.39 (s, 3H), 2.1-2.0 (m, 2H), 1.9-1.76 (m, 2H); LCMS: 436 [M+H].

Example 19

Procedure S

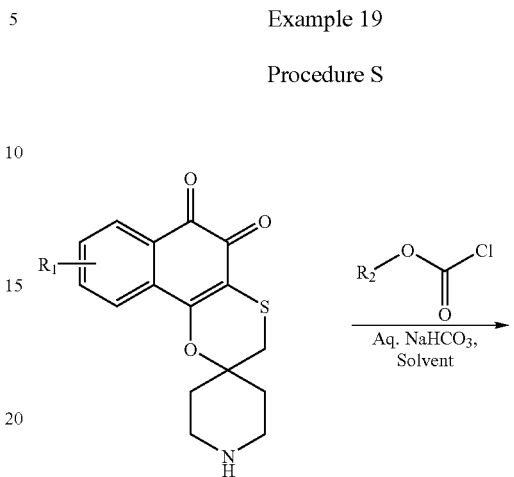

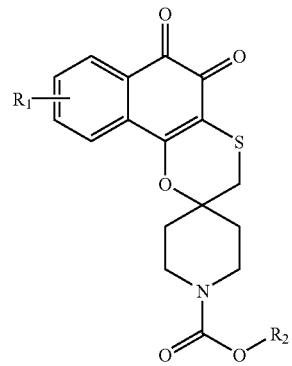

E19.1. Synthesis of phenyl 5,6-dioxo-5,6-dihydro-1'H-spiro[naphtho[1,2-b][1,4]oxathiine-2,4'-piperidine]-1'-carboxylate (Compound 92)

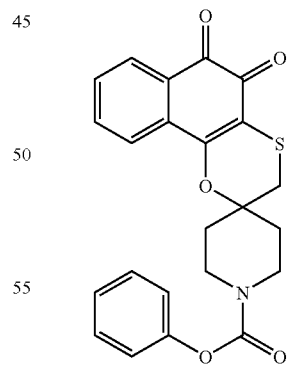

To a mixture of spiro[naphtho[1,2-b][1,4]oxathiine-2,4'-piperidine]-5,6-dione (0.1 g, 0.33 mmol) in ethyl acetate (2.0 mL) and aqueous saturated sodium bicarbonate (2.0 mL) was added phenyl chloridocarbonate (0.057 g). The reaction mixture was stirred at room temperature for 5 min. The organic layer was separated, washed with water (2.0 mL), dried with sodium sulfate and concentrated under vacuum. The crude product was crystallized from EtOAc/hexanes to give the desired product as a purple solid (0.08 g, 57%). M.p.=259-261° C.; 400 MHz ¹H NMR (DMSO-d₆) δ: 7.88 (t, J=7.2 Hz, 2H), 7.75 (t, J=7.2 Hz, 1H), 7.56 (t, J=7.6 Hz, 1H), 7.38 (t, J=7.2 Hz, 2H), 7.21 (t, J=7.2 Hz, 1H), 7.12 (d, J=8 Hz, 2H), 4.04 (m, 2H), 3.34 (m, 2H), 3.13 (s, 2H), 2.07 (m, 2H), 1.89 (m, 2H); LCMS: 422 [M+H].

E19.2. Synthesis of isobutyl 5,6-dioxo-5,6-dihydro-1'H-spiro[naphtho[1,2-b][1,4]oxathiine-2,4'-piperidine]-1'-carboxylate (Compound 93)

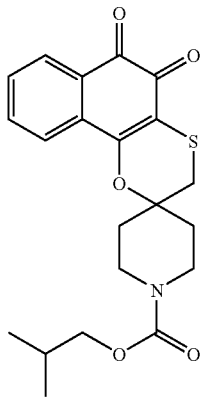

Compound 93 was synthesized using spiro[naphtho[1,2-b][1,4]oxathiine-2,4'-piperidine]-5,6-dione, isobutyl chloridocarbonate, EtOAc as the solvent and conditions outlined in procedure S. M.p.=154-155° C.; 400 MHz ¹H NMR (DMSO-d₆) δ: 7.88 (d, J=8 Hz, 1H), 7.83 (d, J=8 Hz, 1H), 7.733 (t, J=7.2 Hz, 1H), 7.55 (t, J=7.2 Hz, 1H), 3.92 (d, J=13.6 Hz, 2H), 3.78 (d, J=6.4 Hz, 2H), 3.20 (br. s, 2H), 3.08 (s, 2H), 2.0 (d, J=15.4 Hz, 2H), 1.96 (m, 1H), 1.73 (t, J=12 Hz, 2H), 0.88 (d, J=6.8 Hz, 6H); LCMS: 402 [M+H].

E19.3. Synthesis of vinyl 5,6-dioxo-5,6-dihydro-1'H-spiro[naphtho[1.2-b][1,4]oxathiine-2,4'-piperidine]-1'-carboxylate (Compound 94)

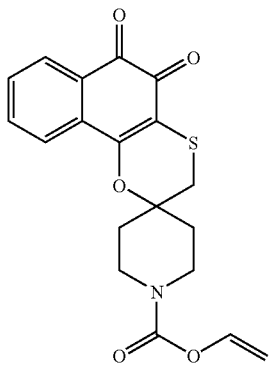

Compound 94 was synthesized using spiro[naphtho[1,2-b][1,4]oxathiine-2,4'-piperidine]-5,6-dione, vinyl chloridocarbonate, EtOAc as the solvent and conditions outlined in procedure S. M.p.=191-193° C.; 400 MHz ¹H NMR (DMSO-d₆) δ: 7.85 (m, 2H), 7.72 (t, J=7.6 Hz, 1H), 7.55 (t, J=7.2 Hz, 1H), 7.14 (m, 1H), 4.80 (d, J=13.6 Hz, 1H), 4.51 (d, J=5.6 Hz, 1H), 3.95 (m, 2H), 3.26 (m, 2H), 3.08 (s, 2H), 2.01 (m, 2H), 1.80 (m, 2H); LCMS: 372 [M+H].

E19.4. Synthesis of 2-ethylhexyl 5,6-dioxo-5,6-dihydro-1'H-spiro[naphtho[1,2-b][1,4]oxathiine-2,4'-piperidine]-1'-carboxylate (Compound 95)

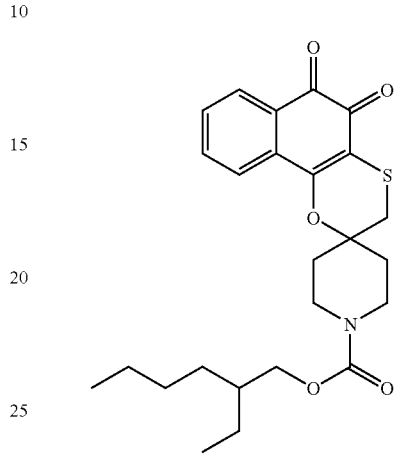

Compound 95 was synthesized using spiro[naphtho[1,2-b][1,4]oxathiine-2,4'-piperidine]-5,6-dione, 2-ethylhexyl chloridocarbonate, EtOAc as the solvent and conditions outlined in procedure S. M.p.=92-93° C.; 400 MHz ¹H NMR (DMSO-d₆) δ: 7.88 (d, J=6.8 Hz 1H), 7.82 (d, J=7.6 Hz, 1H), 7.73 (t, J=7.6 Hz, 1H), 7.54 (t, J=7.6 Hz, 1H), 3.91 (m, 4H), 3.24 (brm, 2H), 3.08 (s, 2H), 2.0 (d, J=13.6 Hz, 2H), 1.73 (m, 2H), 1.52 (m, 1H), 1.28 (m, 8H), 0.84 (t, J=7.2 Hz, 6H); LCMS: 458 [M+H].

E19.5. Synthesis of 3-(trifluoromethyl)phenyl 5,6-dioxo-5,6-dihydro-1'H-spiro[naphtho[1,2-b][1,4]oxathiine-2,4'-piperidine]-1'-carboxylate (Compound 96)

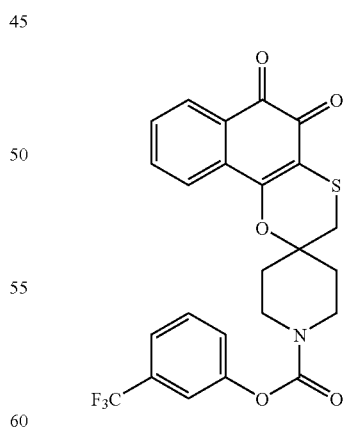

Compound 96 was synthesized using spiro[naphtho[1,2-b][1,4]oxathiine-2,4'-piperidine]-5,6-dione, 3-(trifluoromethyl)phenyl chloridocarbonate, EtOAc as the solvent and conditions outlined in procedure S. M.p.=225-226° C.; 400 MHz ¹H NMR (DMSO-d₆) δ: 7.88 (t, J=8.8 Hz, 2H), 7.76 (t, J=7.2 Hz, 1H), 7.55-7.66 (m, 3H), 7.48 (d, J=8 Hz, 1H), 7.04

(m, 1H), 4.09 (m, 2H), 3.46 (t, J=12.4, 2H), 3.13 (s, 2H), 2.09 (m, 2H), 1.92 (m, 2H); LCMS: 490 [M+H].

E19.6. Synthesis of 4-fluorophenyl 5,6-dioxo-5,6-dihydro-1'H-spiro[naphtho[1,2-b][1,4]oxathiine-2,4'-piperidine]-1'-carboxylate (Compound 97)

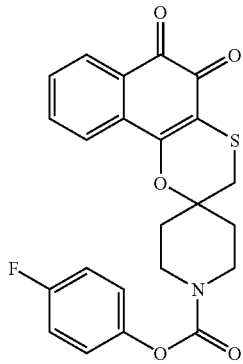

Compound 97 was synthesized using spiro[naphtho[1,2-b][1,4]oxathiine-2,4'-piperidine]-5,6-dione, 4-fluorophenyl chloridocarbonate, EtOAc as the solvent and conditions outlined in procedure S. M.p.=212-214° C.; 400 MHz $^1$H NMR (DMSO-d$_6$) δ: 7.88 (m, 2H), 7.75 (t, J=8 Hz, 1H), 7.56 (t, J=8 Hz, 1H), 7.15-7.23 (m, 4H), 4.10 (m, 2H), 3.40 (m, 2H), 3.13 (s, 2H); 2.09 (m, 2H), 1.90 (m, 2H); LCMS: 440 [M+H].

E19.7. Synthesis of benzyl 5,6-dioxo-5,6-dihydro-1'H-spiro[naphtho[1,2-b][1,4]oxathiine-2,4'-piperidine]-1'-carboxylate (Compound 98)

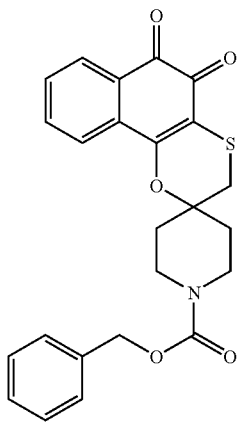

Compound 98 was synthesized using spiro[naphtho[1,2-b][1,4]oxathiine-2,4'-piperidine]-5,6-dione, benzyl chloridocarbonate, EtOAc as the solvent and conditions outlined in procedure S. M.p.=222-224° C.; 400 MHz $^1$H NMR (DMSO-d$_6$) δ: 7.87 (d, J=8 Hz, 1H), 7.82 (d, J=8 Hz, 1H), 7.73 (t, J=7.2 Hz, 1H), 7.54 (t, J=7.2 Hz, 1H), 7.15-7.30 (m, 5H), 4.23 (d, J=5.6 Hz, 2H), 3.90 (d, J=13.6 Hz, 2H), 3.15 (t, J=11.6 Hz, 2H), 3.08 (s, 2H), 1.95 (d, J=12.4 Hz, 2H), 1.70 (m, 2H); LCMS: 436 [M+H].

E19.8. Synthesis of 3-(trifluoromethyl)phenyl 9-bromo-5,6-dioxo-5,6-dihydro-1'H-spiro[naphtho[1,2-b][1,4]oxathiine-2,4'-piperidine]-1'-carboxylate (Compound 99)

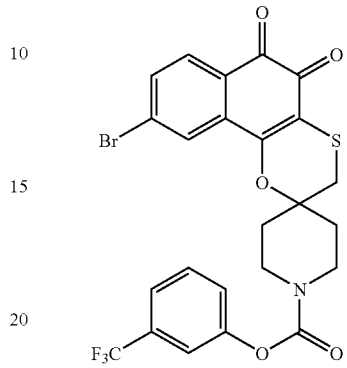

Compound 99 was synthesized using 9-bromospiro[naphtho[1,2-b][1,4]oxathiine-2,4'-piperidine]-5,6-dione, 3-(trifluoromethyl)phenyl chloridocarbonate, EtOAc as the solvent and conditions outlined in procedure S. M.p.=210-211° C.; 400 MHz $^1$H NMR (CDCl$_3$) δ: 7.95-7.92 (m, 1H), 7.85-7.84 (m, 1H), 7.68-7.65 (m, 1H), 7.52-7.49 (m, 2H), 7.43-7.41 (m, 1H), 7.36-7.32 (m, 1H), 4.33-4.18 (m, 2H), 3.55-3.35 (m, 2H), 3.00 (s, 2H), 2.30-2.20 (m, 2H), 1.95-1.86 (m, 2H); LCMS: 568 [M+H].

E19.9. Synthesis of 3-(trifluoromethyl)phenyl 9-fluoro-5,6-dioxo-5,6-dihydro-1'H-spiro[naphtho[1,2-b][1,4]oxathiine-2,4'-piperidine]-1'-carboxylate (Compound 100)

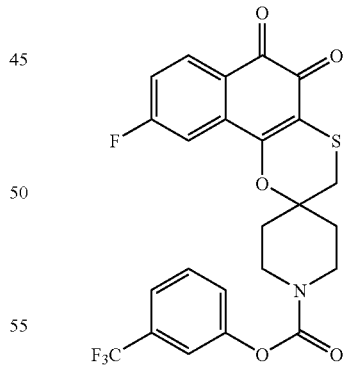

Compound 100 was synthesized using 9-fluorospiro[naphtho[1,2-b][1,4]oxathiine-2,4'-piperidine]-5,6-dione, 3-(trifluoromethyl)phenyl chloridocarbonate, EtOAc as the solvent and conditions outlined in procedure S. M.p.=101-105° C., 400 MHz $^1$H NMR (DMSO-d$_6$) δ: 8.00-7.97 (m, 1H), 7.67-7.57 (m, 4H), 7.51-7.49 (d, J=7.82 Hz, 1H), 7.43-7.38 (dt, J=8.21, 16.82 Hz, 1H), 4.11-3.92 (m, 2H), 3.54-3.48 (m, 2H), 3.15 (s, 2H), 2.11-1.87 (m, 4H); LCMS: 508 [M+H]

E19.10. Synthesis of 3-(trifluoromethyl)phenyl 9-chloro-5,6-dioxo-5,6-dihydro-1'H-spiro[naphtho[1,2-b][1,4]oxathiine-2,4'-piperidine]-1'-carboxylate (Compound 101)

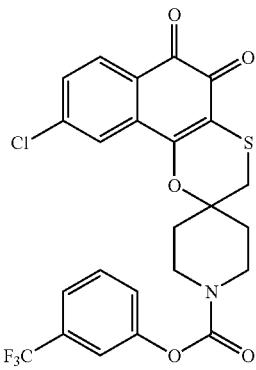

Compound 101 was synthesized using 9-chlorospiro[naphtho[1,2-b][1,4]oxathiine-2,4'-piperidine]-5,6-dione, 3-(trifluoromethyl)phenyl chloridocarbonate, triethylamine instead of aqueous sodium bicarbonate, dichloromethane as a solvent and conditions outlined in procedure S. M.p.=109-112° C.; 400 MHz $^1$H NMR (DMSO-d$_6$) δ: 7.90 (d, J=8 Hz, 1H), 7.77 (d, J=2 Hz, 1H), 7.68-7.59 (m, 4H), 7.50 (d, J=7.6 Hz, 1H), 4.08 (d, J=13.2 Hz, 1H), 3.94 (d, J=12.4 Hz, 1H), 3.51 (t, J=11.6 Hz, 1H), 3.39-3.34 (m, 1H), 3.16 (s, 2H), 2.15-2.09 (m, 2H), 2.00-1.85 (m, 2H); LCMS: 524 [M+H].

E19.11. Synthesis of 3-(trifluoromethyl)phenyl 5',6'-dioxo-5',6'-dihydro-1H-spiro[azepane-4,2'-naphtho[1,2-b][1,4]oxathiine]-1-carboxylate (Compound 102)

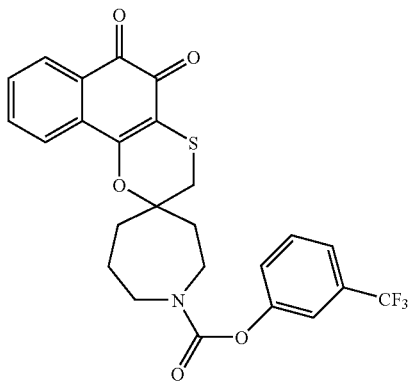

Compound 102 was synthesized using spiro[azepane-4,2'-naphtho[1,2-b][1,4]oxathiine]-5',6'-dione, 3-(trifluoromethyl)phenyl chloridocarbonate, triethylamine instead of aqueous sodium bicarbonate, dichloromethane as a solvent and conditions outlined in procedure S. M.p.=111-114° C.; 400 MHz $^1$H NMR (DMSO-d$_6$) δ: 7.91-7.89 (d, J=7.43 Hz, 1H), 7.83-7.79 (m, 1H), 7.73-7.68 (m, 1H), 7.67-7.49 (m, 5H), 3.81-3.52 (m, 4H), 3.28-3.09 (m, 2H), 2.33-1.86 (m, 6H); LCMS: 504 [M+H].

E19.12. Synthesis of 3-(trifluoromethyl)phenyl 5,6-dioxo-5,6-dihydro-1'H-spiro[naphtho[1,2-b][1,4]oxathiine-2,3'-piperidine]-1'-carboxylate (Compound 103)

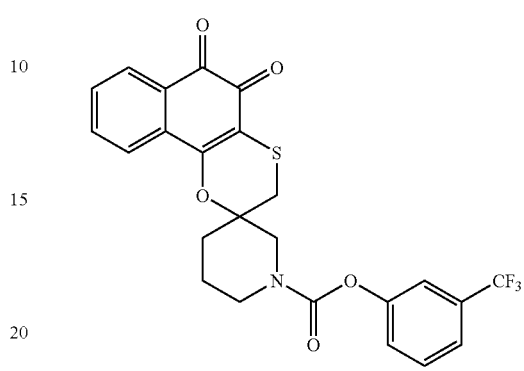

Compound 103 was synthesized using spiro[naphtho[1,2-b][1,4]oxathiine-2,3'-piperidine]-5,6-dione, 3-(trifluoromethyl)phenyl chloridocarbonate, triethylamine instead of aqueous sodium bicarbonate, dichloromethane as a solvent and conditions outlined in procedure S. M.p.=95-99° C., 400 MHz $^1$H NMR (CDCl$_3$) δ: 8.05-7.99 (m, 1H), 7.74-7.66 (m, 2H), 7.52-7.43 (m, 2H), 7.38-7.33 (m, 2H), 6.88-6.87 (m, 1H); LCMS: 490 [M+H].

E19.13. Synthesis of 3-(trifluoromethyl)phenyl 8-methoxy-5,6-dioxo-5,6-dihydro-1'H-spiro[naphtho[1,2-b][1,4]oxathiine-2,4'-piperidine]-1'-carboxylate (Compound 104)

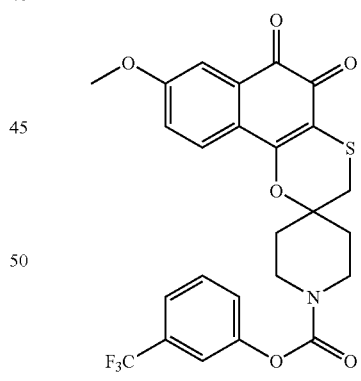

Compound 104 was synthesized using 8-methoxyspiro[naphtho[1,2-b][1,4]oxathiine-2,4'-piperidine]-5,6-dione, 3-(trifluoromethyl) phenyl chloroformate, triethylamine instead of aqueous sodium bicarbonate, dichloromethane as a solvent and conditions outlined in procedure S. M.p.=233-234° C.; 400 MHz $^1$H NMR (DMSO-d$_6$) δ: 7.82 (d, J=8.4 Hz, 1H), 7.62 (m, 3H), 7.50 (brd, J=8 Hz, 1H), 7.38 (d, J=2.8 Hz, 1H), 7.27 (dd, J=2.4 and 8.4 Hz, 1H), 4.11 (m, 1H), 3.99 (m, 1H), 3.88 (s, 3H), 3.40 (m, 2H), 3.13 (s, 2H), 2.11 (m, 2H), 1.93 (m, 2H); LCMS: 520 [M+H].

E19.14. Synthesis of 3-(trifluoromethyl)phenyl 5,6-dioxo-9-phenyl-5,6-dihydro-1'H-spiro[naphtho[1,2-b][1,4]oxathiine-2,4'-piperidine]-1'-carboxylate (Compound 105)

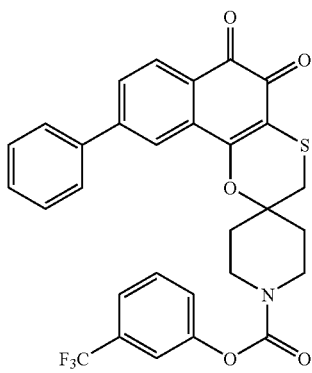

Compound 105 was synthesized using 9-phenylspiro[naphtho[1,2-b][1,4]oxathiine-2,4'-piperidine]-5,6-dione, 3-(trifluoromethyl)phenyl chloroformate, triethylamine instead of aqueous sodium bicarbonate, dichloromethane as a solvent and conditions outlined in procedure S. M.p.=188-190° C.; 400 MHz $^1$H NMR (DMSO-$d_6$) δ: 8.03 (d, J=1.6 Hz, 1H), 8.00 (d, J=8.0 Hz, 1H), 7.88 (dd, J=1.6, 8.4 Hz, 1H), 7.82 (d, J=7.2 Hz, 2H), 7.67-7.55 (m, 5H), 7.50 (dd, J=8.0, 8.0 Hz, 2H), 4.10 (br, 1H), 3.97 (br, 1H), 3.56-3.44 (br, 1H), 3.42-3.34 (br, 1H), 3.18 (s, 2H), 2.16 (d, J=12.8 Hz, 2H), 2.04-1.88 (m, 2H); LCMS: 566 [M+H].

E19.15. Synthesis of 3-(trifluoromethyl)phenyl 9-methoxy-5,6-dioxo-5,6-dihydro-1'H-spiro[naphtho[1,2-b][1,4]oxathiine-2,4'-piperidine]-1'-carboxylate (Compound 106)

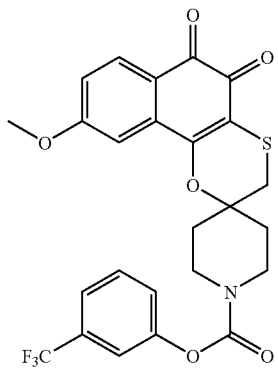

Compound 106 was synthesized using 9-methoxyspiro[naphtho[1,2-b][1,4]oxathiine-2,4'-piperidine]-5,6-dione, 3-(trifluoromethyl)phenyl chloroformate, triethylamine instead of aqueous sodium bicarbonate, dichloromethane as a solvent and conditions outlined in procedure S. M.p.=88-89° C.; 400 MHz $^1$H NMR (DMSO-$d_6$) δ: 7.91 (d, J=8.4 Hz, 1H), 7.62 (m, 2H), 7.50 (brd, J=8.0 Hz, 1H), 7.24 (d, J=2.4 Hz, 1H), 7.11 (dd, J=2.4 and 8.4 Hz, 1H), 4.10 (m, 1H), 3.98 (m, 1H), 3.94 (s, 3H), 3.45 (m, 2H), 3.15 (s, 2H), 2.10 (m, 2H), 1.95 (m, 2H); LCMS: 520 [M+H].

E19.16. Synthesis of 3-(trifluoromethyl)phenyl 4-(5,6-dioxo-5,6-dihydro-1'H-spiro[naphtho[1,2-b][1,4]oxathiine-2,4'-piperidin]-1'-yl)piperidine-1-carboxylate (Compound 107)

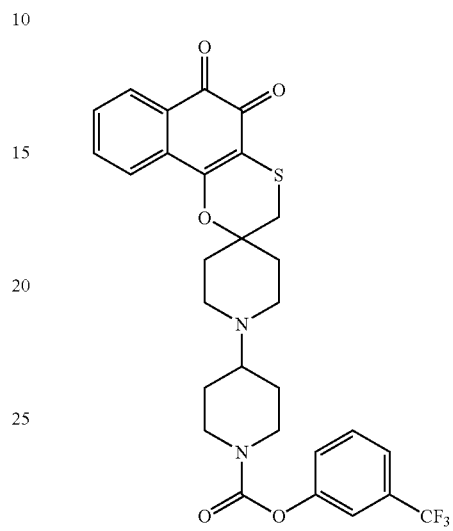

Compound 107 was synthesized using 1'-piperidin-4-yl-spiro[naphtho[1,2-b][1,4]oxathiine-2,4'-piperidine]-5,6-dione bis hydrochloride, triethylamine instead of aqueous sodium bicarbonate, dichloromethane as a solvent and conditions outlined in procedure S. M.p.=70-73° C.; 400 MHz $^1$H NMR (CDCl$_3$) δ: 8.05-8.03 (m, 1H), 7.51-7.31 (m, 1H), 7.67-7.63 (m, 1H), 7.50-7.46 (m, 3H), 7.39 (s, 1H), 7.32-7.29 (m, 1H), 4.36 (t, 2H), 3.98-3.89 (m, 1H), 3.63-3.62 (m, 1H), 3.39-3.29 (m, 1H), 3.03-2.87 (m, 4H), 2.84-2.58 (m, 2H), 2.18-2.07 (m, 2H), 1.95-1.84 (m, 4H), 1.65-1.60 (m, 2H); LCMS: 573 [M+H].

E19.17. Synthesis of 3-(trifluoromethyl)phenyl (5',6'-dioxo-5',6'-dihydrospiro[cyclohexane-1,2'-naphtho[1,2-b][1,4]oxathiin]-4-yl)carbamate (Compound 108)

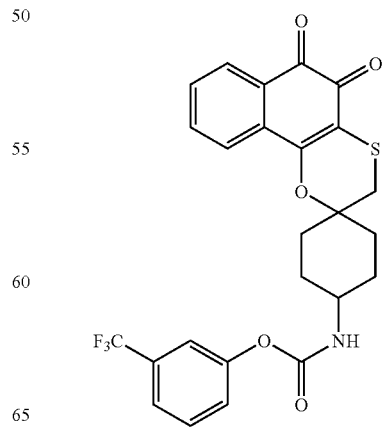

Compound 108 was synthesized using 4-aminospiro[cyclohexane-1,2'-naphtho[1,2-b][1,4]oxathiine]-5',6'-dione hydrochloride, 3-(trifluoromethyl)phenyl chloroformate, triethyl amine to neutralize the hydrochloride and conditions outlined in procedure S. M.p.=198-199° C.; 400 MHz $^1$H NMR (DMSO-d$_6$) δ: 8.08 (d, J=7.8 Hz, 1H), 7.92 (d, J=7.4 Hz, 1H), 7.83 (t, J=7.1 Hz, 1H), 7.78 (t, J=7.1 Hz, 1H), 7.66-7.43 (m, 4H), 3.56-3.47 (m, 1H), 3.04 (s, 2H), 2.16-2.05 (m, 2H), 1.94-1.80 (m, 2H), 1.78-1.66 (m, 7H), LCMS: 504 [M+H].

Example 20

Procedure T

E20.1. Synthesis of tert-butyl 5,6-dioxo-5,6-dihydro-1'H-spiro[naphtho[1,2-b][1,4]oxathiine-2,4'-piperidine]-1'-carboxylate (Compound 109)

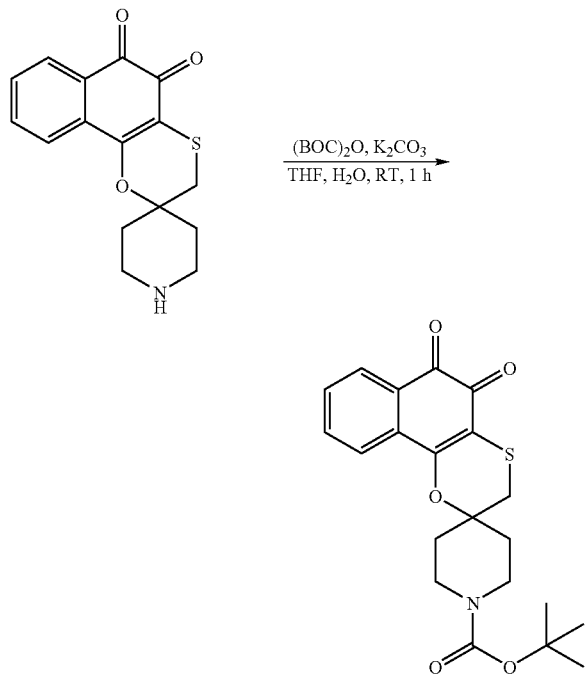

To a mixture of spiro[naphtho[1,2-b][1,4]oxathiine-2,4'-piperidine]-5,6-dione (10.0 g, 3.32 mmol) and di-tert-butyl dicarbonate (7.25 g, 3.32 mmol) in THF (150 ml) was added 100 ml H$_2$O and 50 ml concentrated aqueous K$_2$CO$_3$. The reaction was stirred at room temperature for 1 hour. The mixture was poured onto H$_2$O (250 mL) and extracted with ethyl acetate (3×250 ml). The organic extract was combined, dried with Na$_2$SO$_4$ and concentrated under reduced pressure. The crude product was purified by flash column chromatography (SiO$_2$, 30% EtOAc in hexanes to 50% EtOAc in hexanes) to afford the product as a purple solid. The solid was then recrystallized from EtOAc and hexanes to give the product as purple crystals (3.26 g, 24%). 400 MHz $^1$H NMR (CDCl$_3$) δ: 8.08-8.05 (m, 1H), 7.76-7.73 (m, 1H), 7.68-7.65 (m, 1H), 7.52-7.49 (m, 1H), 4.08-3.95 (m, 2H), 3.29-3.21 (m, 2H), 2.94 (s, 2H), 2.14-2.09 (m, 2H), 1.80-1.70 (m, 2H), 1.48 (s, 9H); LCMS: 402.

Example 21

Procedure U

E21.1. Synthesis of pyridin-3-yl 5,6-dioxo-5,6-dihydro-1'H-spiro[naphtho[1,2-b][1,4]oxathiine-2,4'-piperidine]-1'-carboxylate (Compound 110)

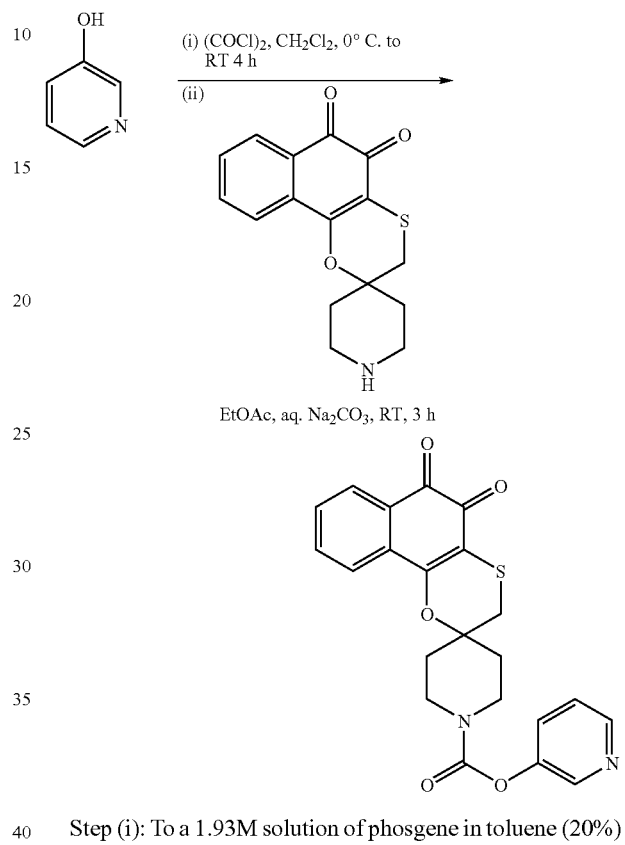

Step (i): To a 1.93M solution of phosgene in toluene (20%) (9.92 ml, 19.1 mmol) was added anhydrous dichloromethane (5 mL). The mixture was stirred at 0° C. under an argon atmosphere. A solution of pyridin-3-ol (0.364 g, 3.83 mmol) in anhydrous pyridine (0.413 ml, 5.1 mmol) and anhydrous dichloromethane (10 ml) was added drop-wise to the stirred phosgene solution at 0° C. over a period of 15 minutes. The mixture was then allowed to warm to room temperature and stirred for an additional 4 h. A stream of nitrogen was passed through the solution to remove the phosgene and solvents. The product was suspended in EtOAc (40 mL) and used as a stock solution in step (ii) without any further purification.

Step (ii): To a solution of spiro[naphtho[1,2-b][1,4]oxathiine-2,4'-piperidine]-5,6-dione (0.5 g, 1.66 mmol) in EtOAc (10 mL) was added pyridin-3-yl chloridocarbonate (40 ml of a stock solution) in 100 ml EtOAc was added 2M aqueous sodium carbonate (200 ml). The reaction mixture was stirred for three hours at room temperature. The organics layer was separated, washed with water (1×100 ml), dried with sodium sulfate and concentrated under reduced pressure. The crude product was purified by flash column chromatography (SiO$_2$, 10% EtOAc in dichloromethane to 40% EtOAc in dichloromethane) to afford the product as a purple solid (0.246 g, 33%). M.p.=246-247° C.; 400 MHz $^1$H NMR (DMSO-d$_6$) δ: 8.31-8.34 (m, 1H), 7.91-7.86 (m, 3H), 7.77-7.71 (m, 1H), 7.52-7.58 (m, 1H), 7.29-7.33 (m, 1H), 7.16-7.18 (m, 1H), 4.15-4.22 (m, 1H), 3.93-4.02 (m, 1H), 3.42-3.51 (m, 1H), 3.26-3.38 (m, 1H), 3.12-3.16 (m, 2H), 2.05-2.13 (m, 2H), 1.82-1.96 (m, 2H); LCMS: 423 [M+H].

E21.2. Synthesis of 6-methyllpyridin-3-yl 5,6-dioxo-5,6-dihydro-1'H-spiro[naphtho[1,2-b][1,4]oxathiine-2,4'-piperidine]-1'-carboxylate (Compound 111)

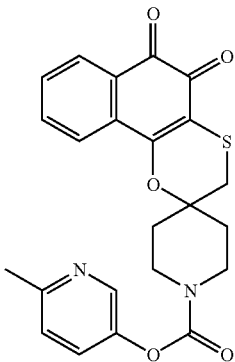

Step (i): 6-Methylpyridin-3-yl chloridocarbonate was synthesized using 6-methylpyridin-3-ol and conditions outlined in procedure U [Step (i)]. The product was used in step (ii) without any further purification.

Step (ii): Compound 111 was synthesized using spiro[naphtho[1,2-b][1,4]oxathiine-2,4'-piperidine]-5,6-dione, 6-methylpyridin-3-yl chloridocarbonate and conditions outlined in procedure U [step (ii)]. M.p.=220-222° C.; 400 MHz $^1$H NMR (DMSO-$d_6$) δ: 8.25-8.27 (m, 1H), 7.85-7.91 (m, 2H), 7.72-7.78 (m, 1H), 7.53-7.59 (m, 1H), 7.46-7.51 (m, 1H), 7.26-7.30 (m, 1H), 4.07-4.16 (m, 1H), 3.92-3.95 (m, 1H), 3.40-3.50 (m, 1H), 3.25-3.36 (m, 1H), 3.13 (s, 2H), 2.44 (s, 3H), 2.05-2.15 (m, 2H), 1.80-1.98 (m, 2H); LCMS: 437 [M+H].

E21.3. Synthesis of pyridin-2-yl 5,6-dioxo-5,6-dihydro-1'H-spiro[naphtho[1,2-b][1,4]oxathiine-2,4'-piperidine]-1'-carboxylate (Compound 112)

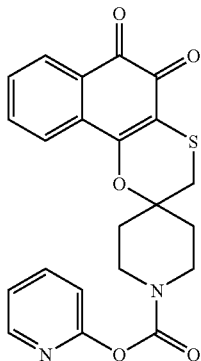

Step (i): Pyridin-2-yl chloridocarbonate was synthesized using pyridin-2-ol and conditions outlined in procedure U [step(i)]. The product was used in step (ii) without any further purification.

Step (ii): Compound 112 was synthesized using spiro[naphtho[1,2-b][1,4]oxathiine-2,4'-piperidine]-5,6-dione, pyridin-2-yl chloridocarbonate and conditions outlined in procedure U [step (ii)]. M.p.=203-205° C.; 400 MHz $^1$H NMR (DMSO-$d_6$) δ: 8.41-8.44 (m, 1H), 7.86-7.91 (m, 3H), 7.73-7.78 (m, 1H), 7.61-7.65 (m, 1H), 7.54-7.59 (m, 1H), 7.43-7.47 (m, 1H), 4.08-4.16 (m, 1H), 3.93-4.02 (m, 1H), 3.40-3.52 (m, 1H), 3.26-3.38 (m, 1H), 3.13 (s, 2H), 2.04-2.13 (m, 2H), 1.82-1.98 (m, 2H); LCMS: 423 [M+H].

E21.4. Synthesis of pyrrolidin-3-yl 5,6-dioxo-5,6-dihydro-1'H-spiro[naphtho[1,2-b][1,4]oxathiine-2,4'-piperidine]-1'-carboxylate hydrochloride (Compound 113)

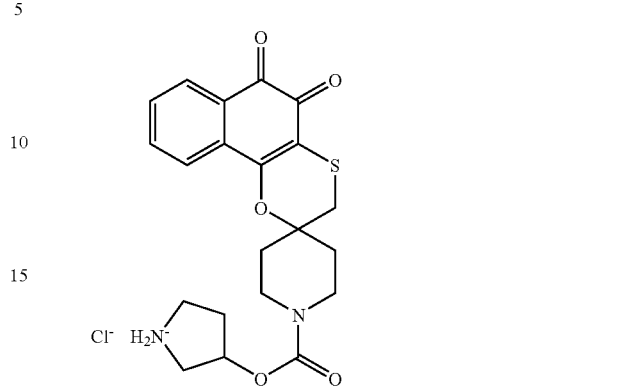

Step (i): tert-Butyl 3-[(chlorocarbonyl)oxy]pyrrolidine-1-carboxylate was synthesized using tert-butyl 3-hydroxypyrrolidine-1-carboxylate and conditions outlined in procedure U [step(i)]. The product was used in step (ii) without any further purification.

Step (ii): 1-(tert-Butoxycarbonyl)pyrrolidin-3-yl 5,6-dioxo-5,6-dihydro-1'H-spiro[naphtho[1,2-b][1,4]oxathiine-2,4'-piperidine]-1'-carboxylate was synthesized using spiro[naphtho[1,2-b][1,4]oxathiine-2,4'-piperidine]-5,6-dione, tert-butyl 3-[(chlorocarbonyl)oxy]pyrrolidine-1-carboxylate and conditions outlined in procedure U [step (ii)].

Step (iii): Compound 113 was synthesized using 1-(tert-butoxycarbonyl)pyrrolidin-3-yl 5,6-dioxo-5,6-dihydro-1'H-spiro[naphtho[1,2-b][1,4]oxathiine-2,4'-piperidine]-1'-carboxylate and conditions outlined in procedure H. M.p.=90-100° C.; 400 MHz $^1$H NMR (DMSO-$d_6$) δ: 9.22-9.0 (br.s, 2H), 7.92-7.89 (m, 1H), 7.85-7.83 (m, 1H), 7.78-7.73 (m, 1H), 7.59-7.55 (m, 1H), 5.33 (d, J=3.2 Hz, 2H), 5.22 (m, 1H), 4.38 (m, 2H), 3.94 (m, 2H), 3.2 (m, 2H), 3.11 (m, 2H), 3.00 (m, 2H), 2.01 (m, 2H), 1.86 (m, 2H); LCMS: 415 [M+H].

E21.5. Synthesis of 3-(dimethylamino)phenyl 5,6-dioxo-5,6-dihydro-1'H-spiro-[naphtho[1,2-b][1,4]oxathiine-2,4'-piperidine]-1'-carboxylate (Compound 114)

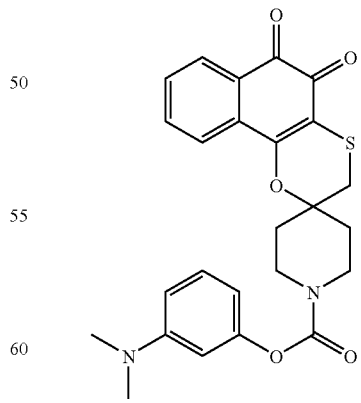

Step (i): 3-(Dimethylamino)phenyl chloridocarbonate was synthesized using 3-(dimethylamino)phenol and conditions outlined in procedure U [step(i)]. The product was used in step (ii) without any further purification.

Step (ii): The compound 114 was synthesized using spiro[naphtho[1,2-b][1,4]oxathiine-2,4'-piperidine]-5,6-dione, 3-(dimethylamino)phenyl chloridocarbonate and conditions outlined in procedure U [step (ii)]. M.p.=244-246° C.; 400 MHz $^1$H NMR (DMSO-d$_6$) δ: 7.90-7.89 (m, 2H), 7.80-7.75 (m, 1H), 7.60-7.57 (m, 1H), 7.18-7.14 (m, 1H), 6.58-6.55 (m, 1H), 6.43-6.38 (m, 2H), 4.09-3.99 (m, 2H), 3.45-3.30 (m, 2H), 3.15 (s, 2H), 2.89 (s, 6H), 2.07-2.11 (m, 2H), 1.90 (brs, 2H); LCMS: 465 [M+H].

E21.6. Synthesis of piperidin-3-yl 5,6-dioxo-5,6-dihydro-1'H-spiro[naphtho[1,2-b][1,4]oxathiine-2,4'-piperidine]-1'-carboxylate hydrochloride (Compound 115)

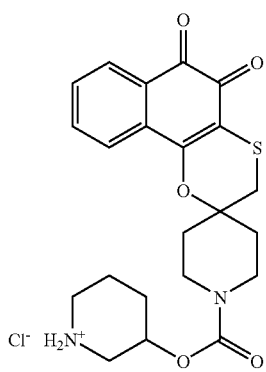

Step (i): tert-Butyl 3-[(chlorocarbonyl)oxy]piperidine-1-carboxylate was synthesized using tert-butyl 3-hydroxypiperidine-1-carboxylate and conditions outlined in procedure U [step(i)]. The crude product was used in step (ii) without any further purification.

Step (ii): 1-(tert-Butoxycarbonyl)piperidin-3-yl 5,6-dioxo-5,6-dihydro-1'H-spiro[naphtho[1,2-b][1,4]oxathiine-2,4'-piperidine]-1'-carboxylate was synthesized using spiro[naphtho[1,2-b][1,4]oxathiine-2,4'-piperidine]-5,6-dione, tert-butyl 3-[(chlorocarbonyl)oxy]piperidine-1-carboxylate and conditions outlined in procedure U [step (ii)].

Step (iii): Compound 115 was synthesized using 1-(tert-butoxycarbonyl)piperidin-3-yl 5,6-dioxo-5,6-dihydro-1'H-spiro[naphtho[1,2-b][1,4]oxathiine-2,4'-piperidine]-1'-carboxylate and conditions outlined in procedure H. M.p.=194-198° C.; 400 MHz $^1$H NMR (DMSO-d$_6$) δ: 9.20 (br.s 1H), 8.75 (br.s 1H), 7.92-7.90 (m, 1H), 7.83 (m, 1H), 7.78-7.74 (m, 1H), 7.60-7.56 (m, 1H), 4.90 (br.s, 1H), 4.14 (m, 1H), 3.91 (m, 1H), 3.30-3.07 (m, 7H), 2.98 (m, 1H), 2.04-2.01 (m, 2H), 1.83-1.66 (m, 6H); LCMS: 429 [M+H].

Example 22

Procedure V

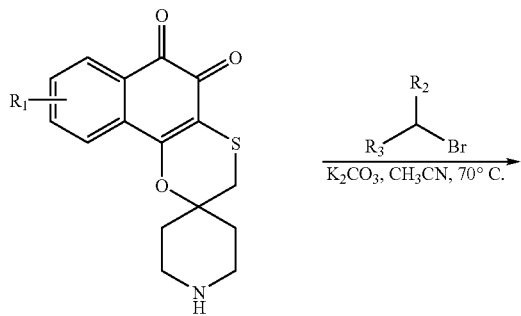

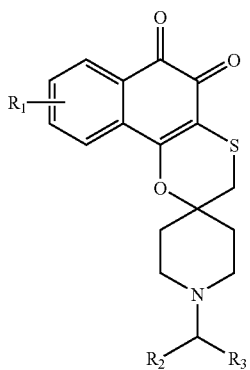

E22.1. Synthesis of 1'-[4-(1H-pyrazol-4-yl)benzyl]spiro[naphtho[1,2-b][1,4]oxathiine-2,4'-piperidine]-5,6-dione (Compound 116)

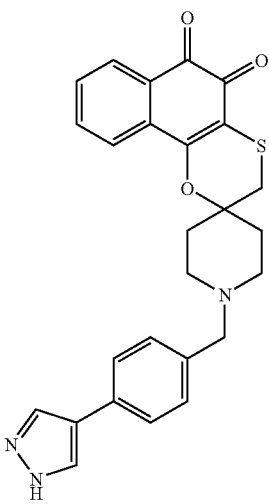

To a mixture of spiro[naphtho[1,2-b][1,4]oxathiine-2,4'-piperidine]-5,6-dione (0.15 g, 0.5 mmol) in anhydrous acetonitrile (5.0 mL) was added 4-[4-(bromomethyl)phenyl]-1H-pyrazole (0.24 g, 1.0 mmol) followed by potassium carbonate (0.20 g, 1.5 mmol). The reaction mixture was stirred at 70° C. for 16 h. The reaction mixture was filtered to remove all the solids and the solvent removed under vacuum. The crude product was purified by reverse phase HPLC to give the desired product as a purple solid (0.005 g, 2.3%). M.p.=190-192° C.; 400 MHz $^1$H NMR (CDCl$_3$) δ: 8.1 (d, 1H), 7.9 (s, 1H), 7.8 (d, 1H), 7.6-7.7 (m, 4H), 7.5 (t, 1H), 7.4 (d, 2H), 6.5 (s, 1H), 3.6 (s, 2h), 2.9 (s, 2h), 2.8 (d, 2H), 2.5 (t, 2H), 2.1 (d, 2H), 1.9 (t, 2H); LCMS: 458 [M+H].

E22.2. Synthesis of 1'-(tetrahydrofuran-2-ylmethyl)spiro[naphtho[1,2-b][1,4]oxathiine-2,4'-piperidine]-5,6-dione (Compound 117)

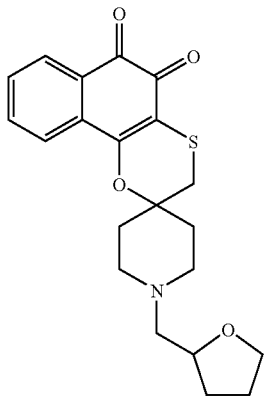

Compound 117 was synthesized using spiro[naphtho[1,2-b][1,4]oxathiine-2,4'-piperidine]-5,6-dione, 2-(bromomethyl)tetrahydrofuran and conditions outlined in procedure V. M.p.=155-159° C.; 400 MHz $^1$H NMR (CDCl$_3$) δ: 8.05 (d, 1H), 7.75 (d, 1H), 7.65 (t, 1H), 7.5 (t, 1H), 4.1 (m, 1H), 3.9 (m, 1H), 3.75 (m, 1H), 3.0-2.8 (m, 4H), 2.6-2.4 (m, 4H), 2.2-2.1 (m, 2H), 2.1-1.8 (m, 5H), 1.5 (m, 1H); LCMS: 386 [M+H].

E22.3. Synthesis of 1'-(2-fluorobenzyl)spiro[naphtho[1,2-b][1,4]oxathiine-2,4'-piperidine]-5,6-dione (Compound 118)

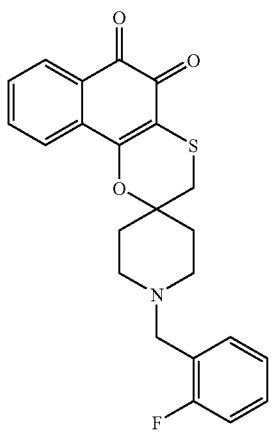

Compound 118 was synthesized using spiro[naphtho[1,2-b][1,4]oxathiine-2,4'-piperidine]-5,6-dione, 1-(bromomethyl)-2-fluorobenzene and conditions outlined in procedure V. M.p.=118-122° C.; 400 MHz $^1$H NMR (CDCl$_3$) δ: 8.05 (d, 1H), 7.65 (m, 2H), 7.5 (t, 1H), 7.4 (t, 1H), 7.3 (m, 1H), 7.15 (t, 1H), 7.05 (t, 1H), 3.7 (s, 2H), 2.9 (s, 2H), 2.8 (d, 2H), 2.55 (t, 2H), 2.1 (d, 2H), 1.9 (t, 2H); LCMS: 410 [M+H].

E22.4. Synthesis of 1'-(tetrahydro-2H-pyran-2-ylmethyl)spiro[naphtho[1,2-b][1,4]oxathiine-2,4'-piperidine]-5,6-dione (Compound 119)

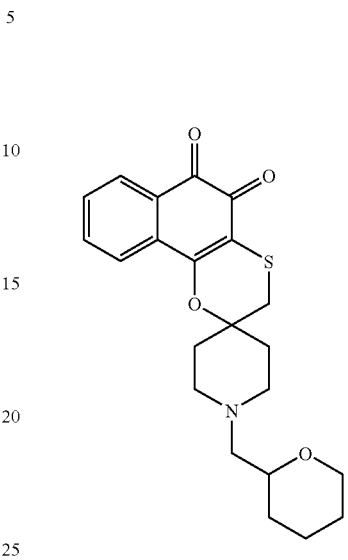

Compound 119 was synthesized using spiro[naphtho[1,2-b][1,4]oxathiine-2,4'-piperidine]-5,6-dione, 2-(bromomethyl)tetrahydro-2H-pyran and conditions outlined in procedure V. M.p.=135-137° C.; 400 MHz $^1$H NMR (CDCl$_3$) δ: 8.05 (d, 1H), 7.8 (d, 1H), 7.65 (t, 1H), 7.5 (t, 1H), 4.0 (d, 1H), 3.5 (dt, 2H), 2.9 (m, 3H), 2.65-2.3 (m, 4H), 2.1 (m, 2H), 1.9 (m, 3H), 1.5 (m, 4H), 1.3 (m, 2H); LCMS: 400 [M+H].

E22.5. Synthesis of 1'-(4-methylbenzyl)spiro[naphtho[1,2-b][1,4]oxathiine-2,4'-piperidine]-5,6-dione (Compound 120)

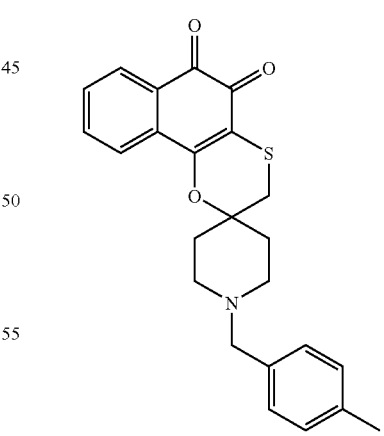

Compound 120 was synthesized using spiro[naphtho[1,2-b][1,4]oxathiine-2,4'-piperidine]-5,6-dione, 1-(bromomethyl)-4-methylbenzene and conditions outlined in procedure V. M.p.=156-158° C.; 400 MHz $^1$H NMR (CDCl$_3$) δ: 8.05 (d, 1H), 7.75 (d, 1H), 7.65 (t, 1H), 7.5 (t, 1H), 7.2 (dd, 4H), 3.55 (s, 2H), 2.9 (s, 2H), 2.75 (d, 2H), 2.5 (t, 2H), 2.35 (s, 3H), 2.1 (d, 2H), 1.85 (t, 2H); LCMS: 406 [M+H].

E22.6. Synthesis of 1'-(3-methoxybenzyl)spiro[naphtho[1,2-b][1,4]oxathiine-2,4'-piperidine]5,6-dione (Compound 121)

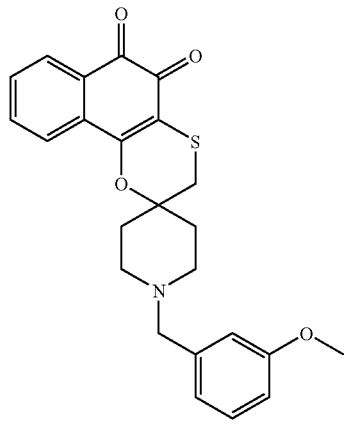

Compound 121 was synthesized using spiro[naphtho[1,2-b][1,4]oxathiine-2,4'-piperidine]-5,6-dione, 1-(bromomethyl)-3-methoxybenzene and conditions outlined in procedure V. M.p.=129-131° C.; 400 MHz $^1$H NMR (CDCl$_3$) δ: 8.05 (d, 1H), 7.75 (d, 1H), 7.65 (t, 1H), 7.5 (t, 1H), 7.25 (m, 2H), 6.9 (s, 1H), 6.8 (d, 1H), 3.8 (s, 3H), 3.55 (s, 2H), 2.9 (s, 2H), 2.75 (d, 2H), 2.5 (t, 2H), 2.1 (d, 2H), 1.9 (t, 2H); LCMS: 422 [M+H].

E22.7. Synthesis of 1'-(cyclopropylmethyl)spiro[naphtho[1,2-b][1,4]oxathiine-2,4'-piperidine]-5,6-dione (Compound 122)

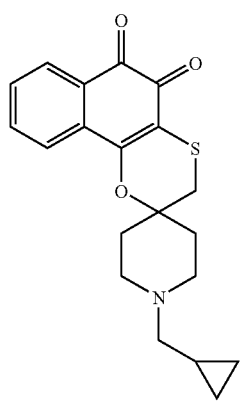

Compound 122 was synthesized using spiro[naphtho[1,2-b][1,4]oxathiine-2,4'-piperidine]-5,6-dione, (bromomethyl)cyclopropane and conditions outlined in procedure V. M.p.=161-164° C.; 400 MHz $^1$H NMR (CDCl$_3$) δ: 8.05 (d, 1H), 7.75 (d, 1H), 7.65 (t, 1H), 7.5 (t, 1H), 2.95 (m, 4H), 2.5 (t, 2H), 2.35 (d, 2H), 2.15 (d, 2H), 1.9 (t, 2H), 0.9 (s, 1H), 0.55 (d, 2H), 0.15 (s, 2H); LCMS: 356 [M+H].

E22.8. Synthesis of 4-[(5,6-dioxo-5,6-dihydro-1'H-spiro[naphtho[1,2-b][1,4]oxathiine-2,4'-piperidin]-1'-yl)methyl]benzonitrile (Compound 123)

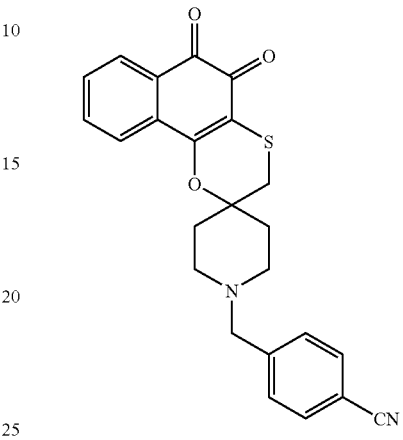

Compound 123 was synthesized using spiro[naphtho[1,2-b][1,4]oxathiine-2,4'-piperidine]-5,6-dione, 4-(bromomethyl)benzonitrile and conditions outlined in procedure V. M.p.=207-211° C.; 400 MHz $^1$H NMR (CDCl$_3$) δ: 8.05 (d, 1H), 7.75 (d, 1H), 7.65-7.6 (m, 3H), 7.55-7.45 (m, 3H), 3.6 (s, 2H), 2.9 (s, 2H), 2.7 (m, 2H), 2.5 (t, 2H), 2.15 (d, 2H), 1.9 (t, 2H); LCMS: 417 [M+H].

E22.9. Synthesis of 1'-(2,4-difluorobenzyl)spiro[naphtho[1,2-b][1,4]oxathiine-2,4'-piperidine]-5,6-dione (Compound 124)

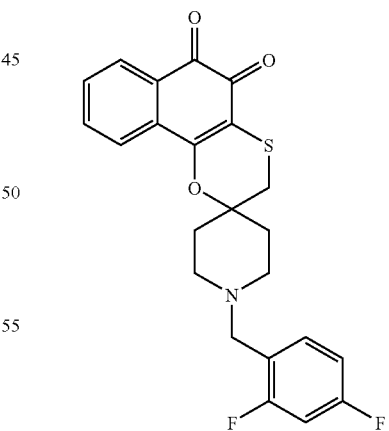

Compound 124 was synthesized using spiro[naphtho[1,2-b][1,4]oxathiine-2,4'-piperidine]-5,6-dione, 1-(bromomethyl)-2,4-difluorobenzene and conditions outlined in procedure V. M.p.=104-107° C.; 400 MHz $^1$H NMR (CDCl$_3$) δ: 8.05 (d, 1H), 7.65 (m, 2H), 7.5 (t, 1H), 7.35 (q, 1H), 6.85 (m, 2H), 3.65 (s, 2H), 2.9 (s, 2H), 2.8 (d, 2H), 2.5 (t, 2H), 2.15 (d, 2H), 1.85 (t, 2H); LCMS: 428 [M+H].

E22.10. Synthesis of 1'-(4-fluorobenzyl)spiro[naphtho[1,2-b][1,4]oxathiine-2,4'-piperidine]-5,6-dione (Compound 125)

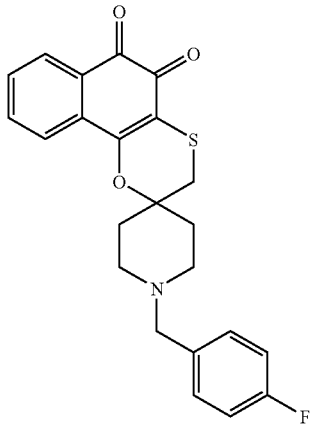

Compound 125 was synthesized using spiro[naphtho[1,2-b][1,4]oxathiine-2,4'-piperidine]-5,6-dione, 1-(bromomethyl)-2,4-difluorobenzene and conditions outlined in procedure V. M.p.=104-106° C.; 400 MHz $^1$H NMR (CDCl$_3$) δ 8.05 (d, 1H), 7.75 (d, 1H), 7.65 (t, 1H), 7.5 (t, 1H), 7.3 (m, 2H), 7.0 (t, 2H), 3.55 (s, 2H), 2.9 (s, 2H), 2.75 (d, 2H), 2.45 (t, 2H), 2.1 (d, 2H), 1.85 (t, 2H); LCMS: 410 [M+H].

E22.11. Synthesis of 1'-isobutylspiro[naphtho[1,2-b][1,4]oxathiine-2,4'-piperidine]-5,6-dione (Compound 126)

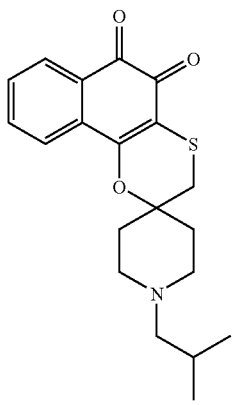

Compound 126 was synthesized using spiro[naphtho[1,2-b][1,4]oxathiine-2,4'-piperidine]-5,6-dione, 1-bromo-2-methylpropane and conditions outlined in procedure V. M.p.=158-161° C.; 400 MHz $^1$H NMR (CDCl$_3$) δ 8.05 (d, 1H), 7.75 (d, 1H), 7.65 (t, 1H), 7.5 (t, 1H), 2.9 (s, 2H), 2.75 (d, 2H), 2.4 (t, 2H), 2.15 (d, 2H), 2.1 (d, 2H), 1.75-1.9 (m, 3H), 0.9 (s, 6H); LCMS: 358 [M+H].

E22.12. Synthesis of 1'-(1-methylbutyl)spiro[naphtho[1,2-b][1,4]oxathiine-2,4'-piperidine]-5,6-dione (Compound 127)

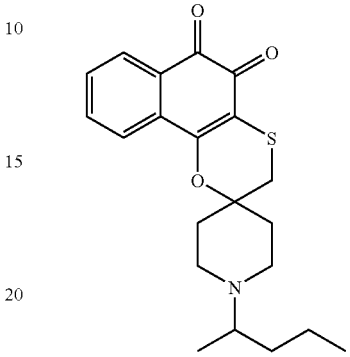

Compound 127 was synthesized using spiro[naphtho[1,2-b][1,4]oxathiine-2,4'-piperidine]-5,6-dione, 2-bromopentane and conditions outlined in procedure V. M.p.=109-111° C.; 400 MHz $^1$H NMR (CDCl$_3$) δ 8.05 (d, 1H), 7.75 (d, 1H), 7.65 (t, 1H), 7.5 (t, 1H), 2.9 (s, 2H), 2.8-2.6 (m, 5H), 2.1 (d, 2H), 1.85 (q, 2H), 1.55 (m, 1H), 1.4-1.15 (m, 3H), 1.0 (t, 3H), 0.9 (t, 3H); LCMS: 372 [M+H].

E22.13. Synthesis of 1'-decylspiro[naphtho[1,2-b][1,4]oxathiine-2,4'-piperidine]-5,6-dione (Compound 128)

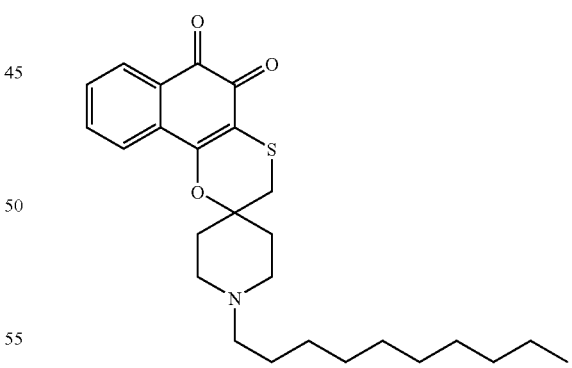

Compound 128 was synthesized using spiro[naphtho[1,2-b][1,4]oxathiine-2,4'-piperidine]-5,6-dione, 1-bromodecane and conditions outlined in procedure V. M.p.=110-111° C.; 400 MHz $^1$H NMR (CDCl$_3$) δ 8.06 (d, J=1.2 Hz, 1H), 7.8-7.75 (m, 1H), 7.75-7.6 (m, 1H), 7.53-7.43 (m, 1H), 2.93 (s, 2H) 2.85-2.75 (m, 2H), 2.5-2.35 (m, 4H), 2.2-2.05 (m, 2H), 1.95-1.8 (m, 2H), 1.6-1.43 (m, 2H), 1.4-1.18 (m, 14H), 0.9-0.8 (m, 3H); LCMS: 442 [M+H].

E22.14. Synthesis of 1'-(2-chloro-6-fluorobenzyl)spiro[naphtho[1,2-b][1,4]oxathiine-2,4'-piperidine]-5,6-dione (Compound 129)

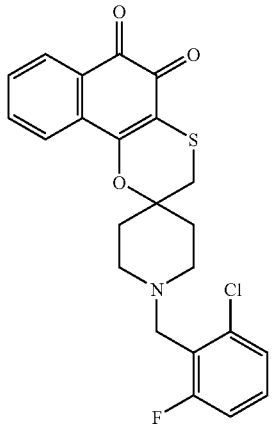

Compound 129 was synthesized using spiro[naphtho[1,2-b][1,4]oxathiine-2,4'-piperidine]-5,6-dione, 2-(bromomethyl)-1-chloro-3-fluorobenzene and conditions outlined in procedure V. M.p.=90-92° C.; 300 MHz $^1$H NMR (CDCl$_3$) δ 8.08-8.02 (m, 1H), 7.76-7.72 (m, 1H), 7.69-7.62 (m, 1H), 7.52-7.44 (m, 1H), 7.28-7.2 (m, 2H), 7.06-6.97 (m, 1H), 3.78 (d, J=2.1 Hz, 2H), 2.91 (s, 2H), 2.9-2.8 (m, 2H), 2.7-2.58 (m, 2H), 2.16-2.04 (m, 2H), 1.92-1.78 (m, 2H); LCMS: 444 [M+H].

E22.15. Synthesis of 1'-benzylspiro[naphtho[1,2-b][1,4]oxathiine-2,4'-piperidine]-5,6-dione (Compound 130)

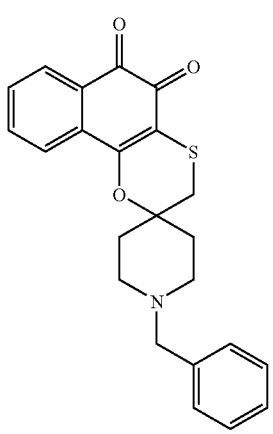

Compound 130 was synthesized using spiro[naphtho[1,2-b][1,4]oxathiine-2,4'-piperidine]-5,6-dione, (bromomethyl)benzene and conditions outlined in procedure V. M.p.=170-172° C.; 400 MHz $^1$H NMR (DMSO-d$_6$) δ: 7.9 (d, 1H), 7.8-7.7 (m, 2H), 7.55 (t, 1H), 7.35-7.2 (m, 5H), 3.55 (s, 2H), 3.05 (s, 2H), 2.7 (d, 2H), 2.35 (t, 2H), 1.95 (d, 2H), 1.8 (t, 2H); LCMS: 392 [M+H].

E22.16. Synthesis of 1'-allylspiro[naphtho[1,2-b][1,4]oxathiine-2,4'-piperidine]-5,6-dione (Compound 131)

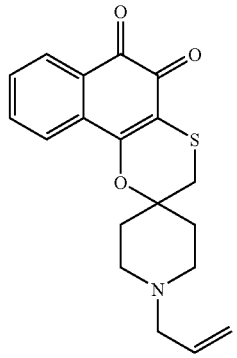

Compound 131 was synthesized using spiro[naphtho[1,2-b][1,4]oxathiine-2,4'-piperidine]-5,6-dione, 3-bromoprop-1-ene and conditions outlined in procedure V. M.p.=166-168° C.; 400 MHz $^1$H NMR (DMSO-d$_6$) δ: 7.9 (d, 1H), 7.75 (s, 2H), 7.55 (s, 1H), 5.8 (m, 1H), 5.2-5.1 (m, 2H), 3.1 (s, 2H), 3.0 (d, 2H), 2.7 (d, 2H), 2.3 (t, 2H), 1.95 (d, 2H), 1.8 (t, 2H); LCMS: 328 [M+H].

E22.17. Synthesis of 1'-(3-methylbutyl)spiro[naphtho[1,2-b][1,4]oxathiine-2,4'-piperidine]-5,6-dione (Compound 132)

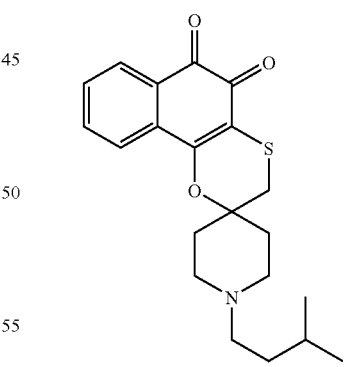

Compound 132 was synthesized using spiro[naphtho[1,2-b][1,4]oxathiine-2,4'-piperidine]-5,6-dione, 3-(bromomethyl)pentane and conditions outlined in procedure V. M.p.=143-146° C.; 400 MHz $^1$H NMR (DMSO-d$_6$) δ: 7.9 (d, 1H), 7.75 (d, 2H), 7.55 (m, 1H), 3.05 (s, 2H), 2.7 (d, 2H), 2.35-2.2 (m, 4H), 1.95 (d, 2H), 1.8-1.7 (d, 2H), 1.6-1.5 (m, 1H), 1.35-1.25 (m, 2H), 0.9-0.8 (m, 6H): LCMS: 372 [M+H].

E22.18. Synthesis of 1'-(3-methylbenzyl)spiro[naphtho[1,2-b][1,4]oxathiine-2,4'-piperidine]-5,6-dione (Compound 133)

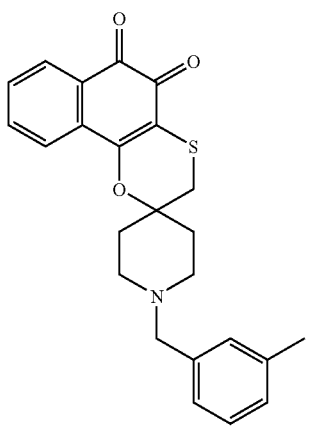

Compound 133 was synthesized using spiro[naphtho[1,2-b][1,4]oxathiine-2,4'-piperidine]-5,6-dione, 1-(bromomethyl)-3-methylbenzene and conditions outlined in procedure V. LCMS: 406 [M+H]; $R_t$=1.02 min.

E22.19. Synthesis of 2-(5,6-dioxo-5,6-dihydro-1'H-spiro[naphtho[1,2-b][1,4]oxathiine-2,4'-piperidin]-1'-yl)-N-phenylpropanamide (Compound 134)

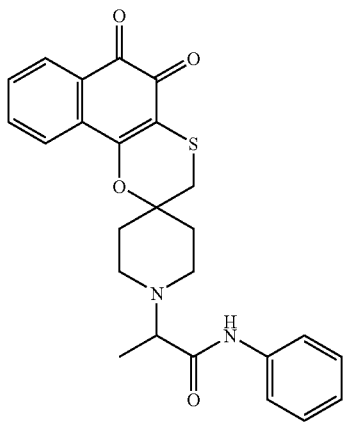

Compound 134 was synthesized using spiro[naphtho[1,2-b][1,4]oxathiine-2,4'-piperidine]-5,6-dione, 2-bromo-N-phenylpropanamide and conditions outlined in procedure V. LCMS: 449 [M+H]; $R_t$=0.98 min.

E22.20. Synthesis of 1'-cyclohex-2-en-1-ylspiro[naphtho[1,2-b][1,4]oxathiine-2,4'-piperidine]-5,6-dione (Compound 135)

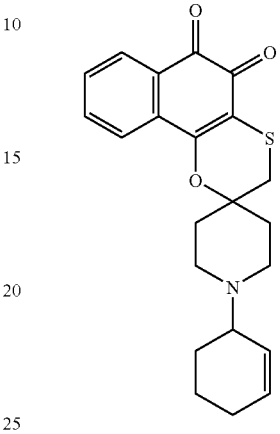

Compound 135 was synthesized using spiro[naphtho[1,2-b][1,4]oxathiine-2,4'-piperidine]-5,6-dione, 3-bromocyclohexene and conditions outlined in procedure V. LCMS: 382 [M+H]; $R_t$=0.94 min.

E22.21. Synthesis of 1'-(cyclohexylmethyl)spiro[naphtho[1,2-b][1,4]oxathiine-2,4'-piperidine]-5,6-dione (Compound 136)

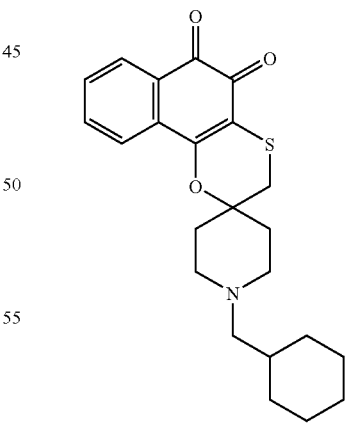

Compound 136 was synthesized using spiro[naphtho[1,2-b][1,4]oxathiine-2,4'-piperidine]-5,6-dione, (bromomethyl)cyclohexane and conditions outlined in procedure V. LCMS: 398 [M+H]; $R_t$=1.03 min.

E22.22. Synthesis of 1'-(1-phenylethyl)spiro[naphtho[12-b][1,4]oxathiine-2,4'-piperidine]-5,6-dione (Compound 137)

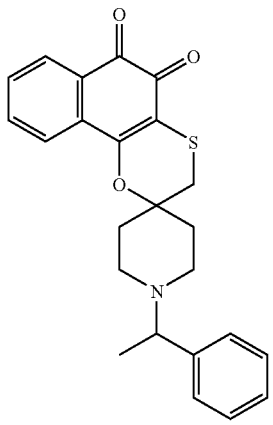

Compound 137 was synthesized using spiro[naphtho[1,2-b][1,4]oxathiine-2,4'-piperidine]-5,6-dione, (1-bromoethyl)benzene and conditions outlined in procedure V. LCMS: 406 [M+H]; $R_t$=0.96 min.

E22.23. Synthesis of 1'-cyclopentylspiro[naphtho[1,2-b][1,4]oxathiine-2,4'-piperidine]-5,6-dione (Compound 138)

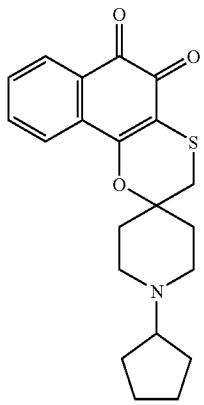

Compound 138 was synthesized using spiro[naphtho[1,2-b][1,4]oxathiine-2,4'-piperidine]-5,6-dione, bromocyclopentane and conditions outlined in procedure V. LCMS: 370 [M+H]; $R_t$=0.90 min.

E22.24. Synthesis of 1'-[(2E)-3-phenylprop-2-en-1-yl]spiro[naphtho[1.2-b][1,4]oxathiine-2,4'-piperidine]-5,6-dione (Compound 139)

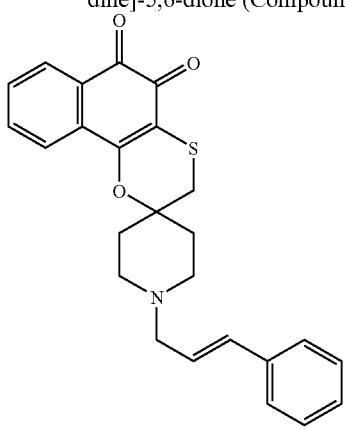

Compound 139 was synthesized using spiro[naphtho[1,2-b][1,4]oxathiine-2,4'-piperidine]-5,6-dione, [(1E)-3-bromoprop-1-en-1-yl]benzene and conditions outlined in procedure V. LCMS: 418 [M+H]; $R_t$=1.05 min.

E22.25. Synthesis of 1'-(2-phenoxyethyl)spiro[naphtho[1,2-b][1,4]oxathiine-2,4'-piperidine]-5,6-dione (Compound 140)

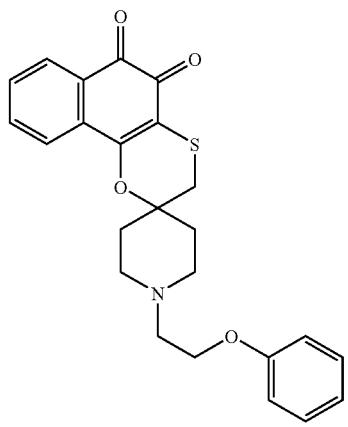

Compound 140 was synthesized using spiro[naphtho[1,2-b][1,4]oxathiine-2,4'-piperidine]-5,6-dione, (2-bromoethoxy)benzene and conditions outlined in procedure V. LCMS: 422 [M+H]; $R_t$=1.01 min.

E22.26. Synthesis of 1'-(4,4,4-trifluorobutyl)spiro[naphtho[1,2-b][1,4]oxathiine-2,4'-piperidine]-5,6-dione (Compound 141)

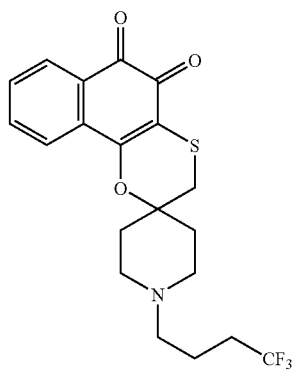

Compound 141 was synthesized using spiro[naphtho[1,2-b][1,4]oxathiine-2,4'-piperidine]-5,6-dione, 4-bromo-1,1,1-trifluorobutane and conditions outlined in procedure V. LCMS: 412 [M+H]; $R_t$=0.96 min.

E22.27. Synthesis of 1'-(3-chloro-4-fluorobenzyl) spiro[naphtho[1,2-b][1,4]oxathiine-2,4'-piperidine]-5,6-dione (Compound 142)

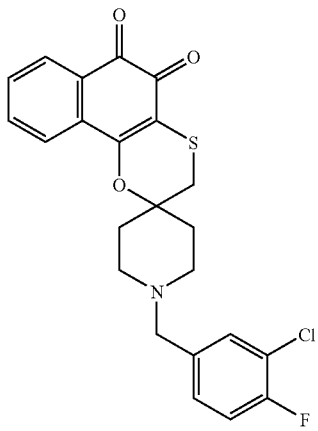

Compound 142 was synthesized using spiro[naphtho[1,2-b][1,4]oxathiine-2,4'-piperidine]-5,6-dione, 4-(bromomethyl)-2-chloro-1-fluorobenzene and conditions outlined in procedure V. LCMS: 444 [M+H]; $R_t$=1.04 min.

E22.28. Synthesis of 1'-but-3-en-1-ylspiro[naphtho[1,2-b][1,4]oxathiine-2,4'-piperidine]-5,6-dione (Compound 143)

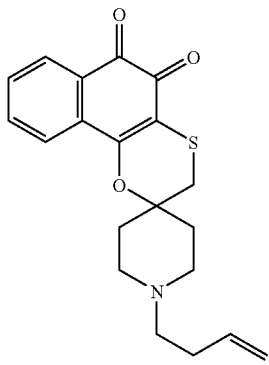

Compound 143 was synthesized using spiro[naphtho[1,2-b][1,4]oxathiine-2,4'-piperidine]-5,6-dione, 4-bromobut-1-ene and conditions outlined in procedure V. LCMS: 356 [M+H]; $R_t$=0.88 min.

E.22.29. Synthesis of 1'-(3-phenoxypropyl)spiro[naphtho[1,2-b][1,4]oxathiine-2,4'-piperidine]-5,6-dione (Compound 144)

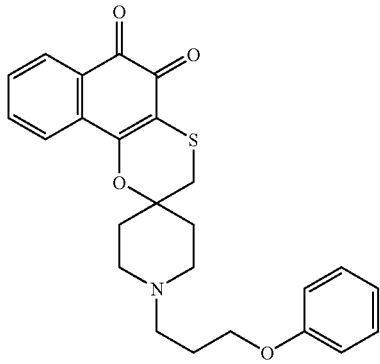

Compound 144 was synthesized using spiro[naphtho[1,2-b][1,4]oxathiine-2,4'-piperidine]-5,6-dione, (3-bromopropoxy)benzene and conditions outlined in procedure V. LCMS: 436 [M+H]; $R_t$=1.05 min.

E22.30. Synthesis of 1'-[2-(4-chlorophenoxy)ethyl]spiro[naphtho[1,2-b][1,4]oxathiine-2,4'-piperidine]-5,6-dione (Compound 145)

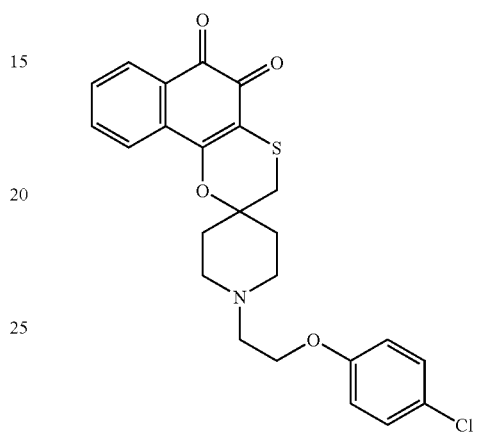

Compound 145 was synthesized using spiro[naphtho[1,2-b][1,4]oxathiine-2,4'-piperidine]-5,6-dione, 1-(2-bromoethoxy)-4-chlorobenzene and conditions outlined in procedure V. LCMS: 456 [M+H]; $R_t$=1.07 min.

E22.31. Synthesis of 1'-(3-fluoro-4-methylbenzyl) spiro[naphtho[1,2-b][1,4]oxathiine-2,4'-piperidine]-5,6-dione (Compound 146)

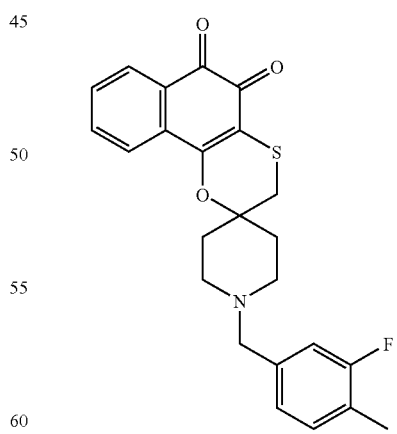

Compound 146 was synthesized using spiro[naphtho[1,2-b][1,4]oxathiine-2,4'-piperidine]-5,6-dione, 4-(bromomethyl)-2-fluoro-1-methylbenzene and conditions outlined in procedure V. LCMS: 424 [M+H]; $R_t$=1.03 min.

E22.32. Synthesis of 1'-(4-fluorobenzyl)-9-methoxyspiro[naphtho[1,2-b][1,4]oxathiine-2,4'-piperidine]-5,6-dione (Compound 147)

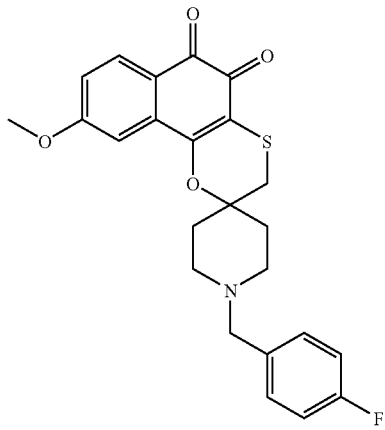

Compound 147 was synthesized using 9-methoxyspiro[naphtho[1,2-b][1,4]oxathiine-2,4'-piperidine]-5,6-dione, 1-(bromomethyl)-4-fluorobenzene and conditions outlined in procedure V. M.p.=196-197° C.; 400 MHz $^1$H NMR (DMSO-d$_6$) δ: 7.86 (d, J=8.4 Hz, 1H), 7.32 (m, 2H), 7.11 (m, 4H), 3.89 (brs, 3H), 3.52 (brs, 2H), 3.04 (s, 2H), 2.68 (brd, J=10.8 Hz, 2H), 2.30 (t, J=11.2 Hz, 2H), 1.97 (m, 2H), 1.77 (m, 2H); LCMS: 440 [M+H].

E22.33. Synthesis of 1'-(4-fluorobenzyl)-9-phenylspiro[naphtho[1,2-b][1,4]oxathiine-2,4'-piperidine]-5,6-dione (Compound 148)

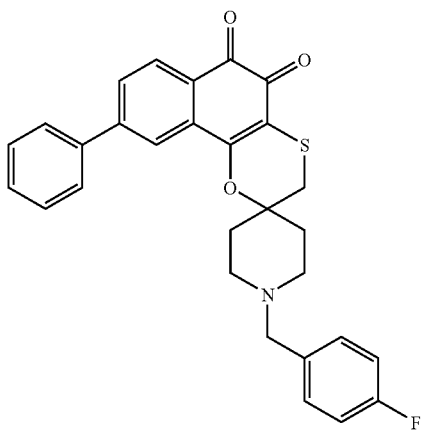

Compound 148 was synthesized using 9-phenylspiro[naphtho[1,2-b][1,4]oxathiine-2,4'-piperidine]-5,6-dione and 1-(bromomethyl)-4-fluorobenzene and conditions outlined in procedure V. M.p.=197-198° C.; 400 MHz $^1$H NMR (DMSO-d$_6$) δ: 7.95 (m, 2H), 7.87 (d, J=7.6 Hz, 1H), 7.74 (d, J=6.8 Hz, 2H), 7.60 (m, 2H), 7.52 (m, 1H), 7.34 (m, 2H), 7.10 (t, J=8 Hz, m, 2H), 3.5 (s, 2H), 3.10 (s, 2H), 2.71 (m, 2H), 2.39 (m, 2H), 2.03 (m, 2H), 1.84 (m, 2H); LCMS: 486 [M+H].

E22.34. Synthesis of 1'-(4-phenylbutyl)spiro[naphtho[1,2-b][1,4]oxathiine-2,4'-piperidine]-5,6-dione (Compound 149)

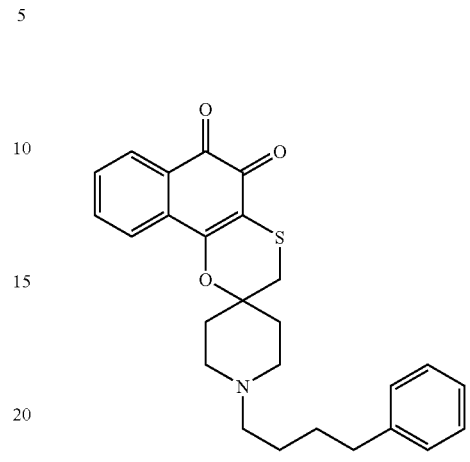

Compound 149 was synthesized using spiro[naphtho[1,2-b][1,4]oxathiine-2,4'-piperidine]-5,6-dione and (4-bromobutyl)benzene and conditions outlined in procedure V. M.p.=145-147° C.; 400 MHz $^1$H NMR (DMSO-d$_6$) δ: 7.93-7.88 (m, 1H), 7.84-7.73 (m, 2H), 7.62-7.52 (m, 1H), 7.35-7.1 (m, 5H), 3.06 (s, 2H), 2.76-2.64 (m, 2H), 2.62-2.54 (m, 2H), 2.4-2.2 (m, 4H), 2.04-1.9 (m, 2H), 1.87-1.7 (m, 2H), 1.68-1.4 (m, 4H); LCMS: 434 [M+H].

E22.35. Synthesis of 1'-[3-(4-chlorophenoxy)propyl]spiro[naphtho[1,2-b][1,4]oxathiine-2,4'-piperidine]-5,6-dione (Compound 150)

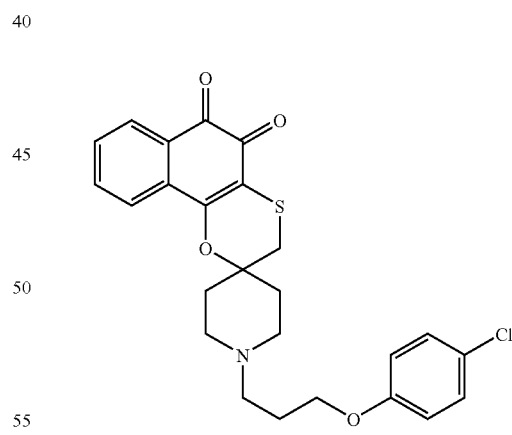

Compound 150 was synthesized using spiro[naphtho[1,2-b][1,4]oxathiine-2,4'-piperidine]-5,6-dione and 1-chloro-4-(3-iodopropoxy)benzene and conditions outlined in procedure V. M.p.=130-132° C.; 400 MHz $^1$H NMR (DMSO-d$_6$) δ: 7.92-7.87 (m, 1H), 7.82-7.74 (m, 2H), 7.6-7.52 (m, 1H), 7.36-7.18 (m, 2H), 7.0-6.92 (m, 2H), 4.1-3.95 (m, 2H), 3.07 (s, 2H), 2.83-2.72 (m, 2H), 2.55-2.48 (m, 2H), 2.4-2.25 (m, 2H), 2.05-1.75 (m, 6H); LCMS: 470 [M+H].

E22.36. Synthesis of 1'-[3-(4-fluorophenoxy)propyl] spiro[naphtho[1,2-b][1,4]oxathiine-2,4'-piperidine]-5,6-dione (Compound 151)

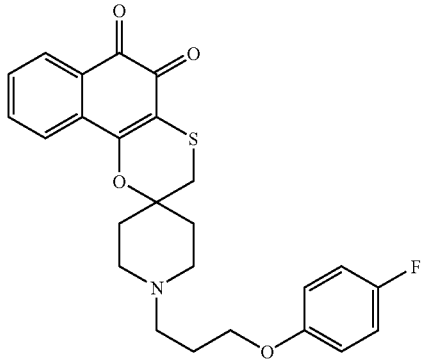

Compound 151 was synthesized using spiro[naphtho[1,2-b][1,4]oxathiine-2,4'-piperidine]-5,6-dione and 1-fluoro-4-(3-iodopropoxy)benzene and conditions outlined in procedure V. M.p.=164-165° C.; 400 MHz $^1$H NMR (DMSO-d$_6$) δ: 7.92-7.87 (m, 1H), 7.82-7.76 (m, 2H), 7.6-7.52 (m, 1H), 7.18-7.06 (m, 2H), 6.97-6.9 (m, 2H), 4.03-3.95 (m, 2H), 3.07 (s, 2H), 2.82-2.72 (m, 2H), 2.55-2.48 (m, 2H), 2.4-2.25 (m, 2H), 2.05-1.75 (m, 6H); LCMS: 454 [M+H].

E22.37. Synthesis of 1'-isopropylspiro[naphtho[1,2-b][1,4]oxathiine-2,4'-piperidine]-5,6-dione (Compound 152)

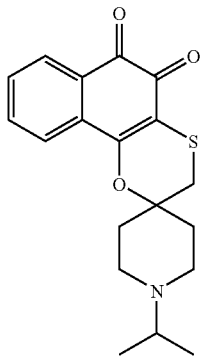

Compound 152 was synthesized using spiro[naphtho[1,2-b][1,4]oxathiine-2,4'-piperidine]-5,6-dione, 2-bromopropane and conditions outlined in procedure V. M.p.=197-198° C.; 400 MHz $^1$H NMR (DMSO-d) δ: 7.92-7.88 (m, 1H), 7.82-7.74 (m, 2H), 7.6-7.52 (m, 1H), 3.06 (s, 2H), 2.8-2.63 (m, 3H), 2.6-2.48 (m, 2H), 2.1-1.94 (m, 2H), 1.85-1.7 (m, 2H), 1.01 (d, J=3.1 Hz, 6H); LCMS: 344 [M+H].

Example 23

Procedure W

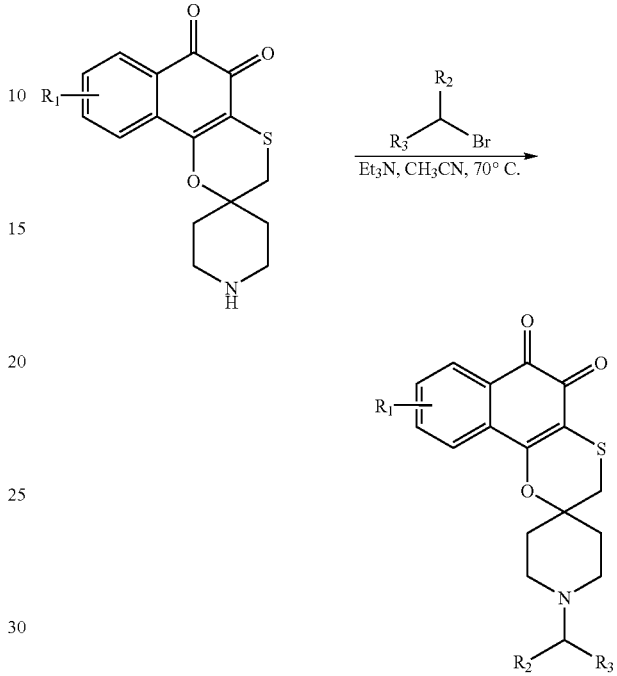

E23.1. Synthesis of 1'-(3-phenylpropyl)spiro[naphtho[1,2-b][1,4]oxathiine-2,4'-piperidine]-5,6-dione (Compound 153)

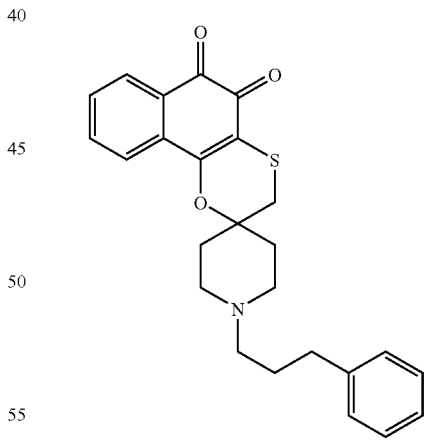

To a solution of spiro[naphtho[1,2-b][1,4]oxathiine-2,4'-piperidine]-5,6-dione (0.566 g, 1.88 mmol) in acetonitrile (30 mL) was added triethylamine (0.80 mL, 5.64 mmol) followed by (3-bromopropyl)benzene (0.747 g, 3.76 mmol). The reaction was stirred at 70° C. for 3 hours. The solvent was then evaporated under reduced pressure. The residue was dissolved in dichloromethane (30 mL) and the organic layer was washed with water (30 mL). The organic extract was dried with Na$_2$SO$_4$ and concentrated under reduced pressure. The crude product was purified by flash column chromatography (SiO₂, 8% CH₃OH in dichloromethane). The product obtained after the chromatography was further purified by crystallization from hexanes and dichloromethane to give the desired product as a purple solid (0.405 g, 51%). M.p.=112-114° C.; 400 MHz ¹H NMR (DMSO-d₆) δ: 7.90 (d, J=7.6 Hz, 1H), 7.78 (d, J=3.2 Hz, 2H), 7.58-7.54 (m, 1H), 7.29-7.22 (m, 2H), 7.21-7.14 (m, 3H), 3.07 (s, 2H), 2.74 (m, 2H), 2.60 (t, J=7.6 Hz 2H), 2.37-2.27 (m, 4H), 2.05-1-97 (m, 2H), 1.85-1.71 (m, 4H); LCMS: 420 [M+H]; Calc. for C₂₅H₂₅NO₃S: C, 71.51, H, 6.005, N, 3.338; Found C, 72.08, H, 5.35, N, 3.43.

E23.2. Synthesis of 1'-(3-phenoxypropyl)spiro[naphtho[1,2-b][1,4]oxathiine-2,4'-piperidine]-5,6-dione (Compound 144)

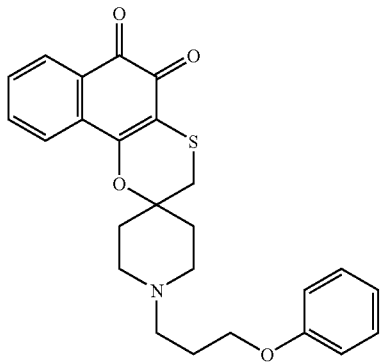

Compound 144 was synthesized using spiro[naphtho[1,2-b][1,4]oxathiine-2,4'-piperidine]-5,6-dione, bromo-3-phenoxypropane and conditions outlined in procedure W. M.p.=127-129° C.:; 400 MHz ¹H NMR (DMSO-d₆): 7.89 (d, J=7.6 Hz, 1H), 7.81-7.78 (m, 2H), 7.57 (dddd, J=2.4, 2.6, 5.2, 5.6 Hz, 2H), 7.28 (dd, J=6.8, 7.6 Hz, 2H), 6.94-6.86 (m, 4H), 4.01 (t, J=6.4 Hz, 2H), 3.08 (s, 2H), 2.77 (d, J=12.0 Hz, 2H), 2.55-2.47 (m, 2H), 2.34 (t, J=10.4 Hz, 2H), 2.00 (d, J=12.6 Hz, 2H), 1.903 (d, J=6.8 Hz, 2H), 1.81 (dt, J=4.0, 12.2 Hz, 2H); LCMS: 436 [M+H].

E23.3. Synthesis of 1'-(4-fluorobenzyl)-8-methoxyspiro[naphtho[1,2-b][1,4]oxathiine-2,4'-piperidine]-5,6-dione (Compound 154)

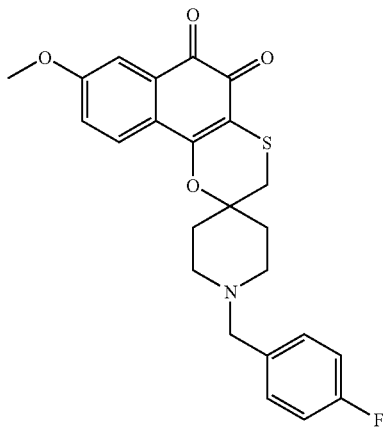

Compound 154 was synthesized using 8-methoxyspiro[naphtho[1,2-b][1,4]oxathiine-2,4'-piperidine]-5,6-dione, 1-(bromomethyl)-4-fluorobenzene ad conditions outlined in procedure W. Mp.=219-221° C.; 400 MHz ¹H NMR (DMSO-d₆) δ: 7.64 (d, J=8.4 Hz, 1H), 7.37-7.27 (m, 4H), 7.15 (dd, J=8.8, 8.8 Hz, 2H), 3.88 (s, 3H), 3.54 (s, 2H), 3.05 (s, 2H), 2.69 (d, J=11.6 Hz, 2H), 2.36 (dd, J=10.4 Hz, 2H), 1.98 (d, J=13.2 Hz, 2H), 1.81 (dd, J=10.4, 10.4 Hz, 2H); LCMS: 440 [M+H].

E23.4. Synthesis of 1'-(2-phenylethyl)spiro[naphtho[1,2-b][1,4]oxathiine-2,4'-piperidine]-5,6-dione (Compound 155)

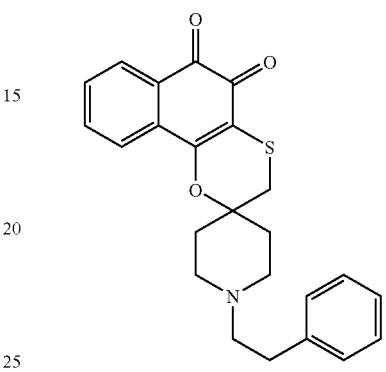

Compound 155 was synthesized using spiro[naphtho[1,2-b][1,4]oxathiine-2,4'-piperidine]-5,6-dione. (2-bromoethyl)benzene and conditions outlined in procedure W. M.p.=117-118° C.; 300 MHz ¹H NMR (CDCl₃) δ: 8.06-8.03 (m, 1H), 7.78-7.75 (m, 1H), 7.68-7.63 (m, 1H), 7.51-7.45 (m, 1H), 7.32-7.26 (m, 2H), 7.23-7.20 (m, 3H), 2.94-2.82 (m, 6H), 2.73-2.67 (m, 2H), 2.18-2.14 (m, 2H), 2.83-2.64 (m, 2H), 1.96-1.86 (m, 2H); LCMS: 406 [M+H].

E23.5. Synthesis of 9-bromo-1'-(4-fluorobenzyl)spiro[naphtho[1,2-b][1,4]oxathiine-2,4'-piperidine]-5,6-dione (Compound 156)

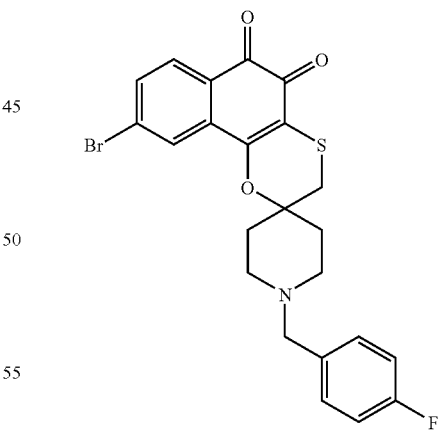

Compound 156 was synthesized using 9-bromospiro[naphtho[1,2-b][1,4]oxathiine-2,4'-piperidine]-5,6-dione, 1-(bromomethyl)-4-fluorobenzene and conditions outlined in general procedure W. M.p.=210-211° C.; 400 MHz ¹H NMR (CDCl₃) δ: 7.91-7.88 (m, 1H), 7.84-7.83 (m, 1H), 7.65-7.62 (m, 1H), 7.30-7.26 (m, 3H), 7.05-7.00 (m, 2H), 3.58 (s, 2H), 2.93 (s, 2H), 2.76-2.72 (m, 2H), 2.50-2.46 (m, 2H), 2.13-2.05 (m, 2H), 1.94-1.83 (m, 2H); LCMS: 488 [M+H].

E23.6. Synthesis of 1'-[2-(4-chlorophenoxy)ethyl]spiro[naphtho[1,2-b][1,4]oxathiine-2,4'-piperidine]-5,6-dione (Compound 145)

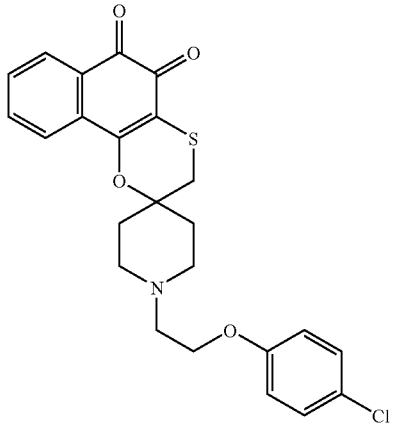

Compound 145 was synthesized Using spiro[naphtho[1,2-b][1,4]oxathiine-2,4-piperidine]-5,6-dione, 1-(2-bromoethoxy)-4-chlorobenzene and conditions outlined in general procedure W. M.p.=131-133° C.; 400 MHz $^1$H NMR (CDCl$_3$) δ: 7.95-7.87 (m, 1H), 7.83-7.67 (iii, 2H), 7.62-7.52 (m, 1H), 7.31 (d, J=6 Hz, 2H), 6.97 (d, J=6 Hz, 2H), 4.18-4.05 (m, 2H), 3.08 (s, 2H), 2.90-2.75 (m, 4H), 2.57-2.48 (m, 2H), 2.08-1.92 (m, 2H), 1.88-1.76 (m, 2H); LCMS: 456 [M+H].

Example 24

Procedure X

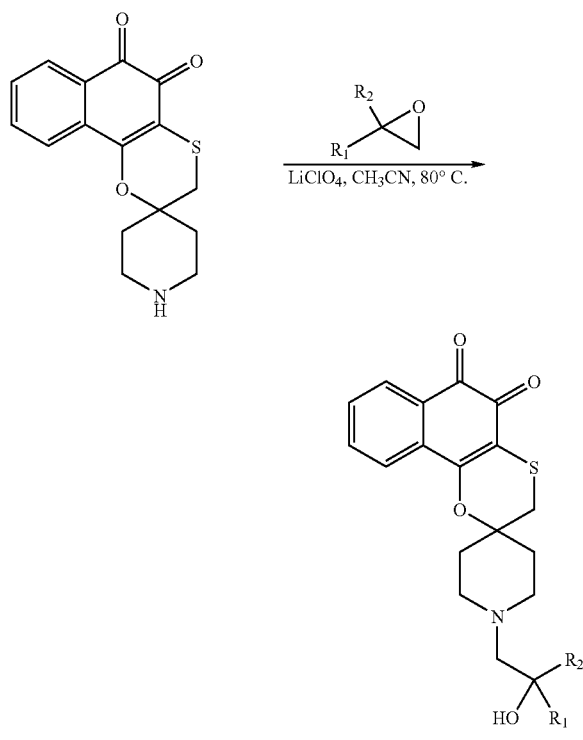

E24.1. Synthesis of 1'-[3-(4-tert-butylphenoxy)-2-hydroxypropyl]spiro[naphtho[1,2-b][1,4]oxathiine-2,4'-piperidine]-5,6-dione (Compound 157)

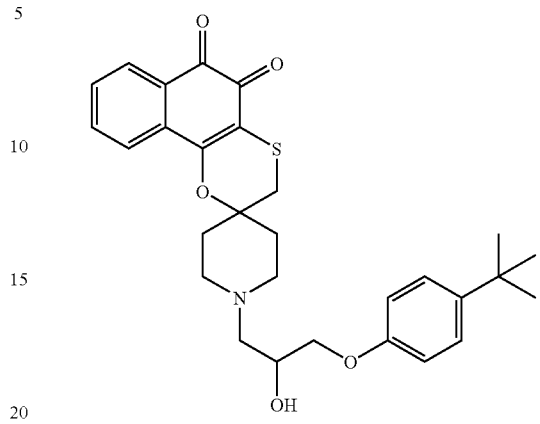

To a mixture of spiro[naphtho[1,2-b][1,4]oxathiine-2,4'-piperidine]-5,6-dione (0.15 g, 0.5 mmol) in acetonitrile (3.0 mL) was added 2-[(4-tert-butylphenoxy)methyl]oxathiine (0.11 g, 0.55 mmol) followed by lithium perchlorate (0.058 g, 0.55 mmol). The reaction mixture was stirred at 80° C. for 16 hours. The solvent was removed under vacuum. The crude product was purified by flash column chromatography (SiO$_2$, 100% EtOAc to 2% methanol in EtOAc) to give the desired product as a purple solid (0.072 g, 29%). M.p.=137-140° C.; 400 MHz $^1$H NMR (CDCl$_3$) δ: 8.05 (d, 1H), 7.75 (d, 1H), 7.65 (t, 1H), 7.5 (t, 1H), 7.35 (d, 2H), 6.9 (d, 2H), 4.15 (m, 1H), 4.0 (d, 2H), 2.95 (m, 3H), 2.8 (m, 2H), 2.65 (m, 2H), 2.55 (t, 2H), 2.15 (d, 2H), 1.9 (m, 2H), 1.3 (s, 9H); LCMS: 508 [M+H].

E24.2. Synthesis of 1'-(2-hydroxy-3-phenoxypropyl)spiro[naphtho[1,2-b][1,4]oxathiine-2,4'-piperidine]-5,6-dione (Compound 158)

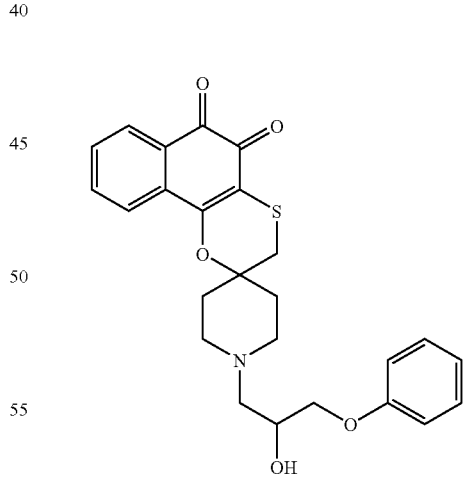

Compound 158 was synthesized using spiro[naphtho[1,2-b][1,4]oxathiine-2,4'-piperidine]-5,6-dione, 2-(phenoxyethyl)oxirane and conditions outlined in procedure X. M.p.=174-176° C.; 400 MHz $^1$H NMR (CDCl$_3$): 8.05 (d, 1H), 7.75 (d, 1H), 7.65 (t, 1H), 7.5 (t, 1H), 7.15 (m, 2H), 6.95 (t, 1H), 6.9 (d, 2H), 4.15 (m, 1H), 4.0 (d, 2H), 2.95 (m, 3H), 2.8 (m, 2H), 2.65 (m, 2H), 2.55 (t, 2H), 2.15 (d, 2H), 1.9 (m, 2H); LCMS: 452 [M+H].

E24.3. Synthesis of 1'-(2-hydroxy-2-methylbut-3-en-1-yl)spiro[naphtho[1,2-b][1,4]oxathiine-2,4'-piperidine]-5,6-dione (Compound 159)

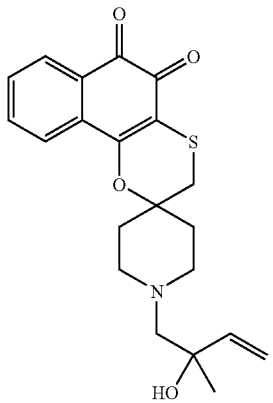

Compound 159 was synthesized using spiro[naphtho[1,2-b][1,4]oxathiine-2,4'-piperidine]-5,6-dione, 2-methyl-2-vinyloxirane and conditions outlined in procedure X. M.p.=74-77° C.; 400 MHz $^1$H NMR (CDCl$_3$) δ: 8.05 (d, 1H), 7.75 (d, 1H), 7.65 (t, 1H), 7.5 (t, 1H), 5.9 (dd, 1H), 5.35 (d, 1H), 5.05 (d, 1H), 3.0-2.7 (m, 4H), 2.6 (m, 4H), 2.45 (d, 1H), 2.1 (t, 2H), 1.9-1.75 (m, 2H), 1.2 (s, 3H); LCMS: 386 [M+H].

E24.4. Synthesis of 1'-(4,4,4-trifluoro-2-hydroxybutyl)spiro[naphtho[1,2-b][1,4]oxathiine-2,4'-piperidine]-5,6-dione (Compound 160)

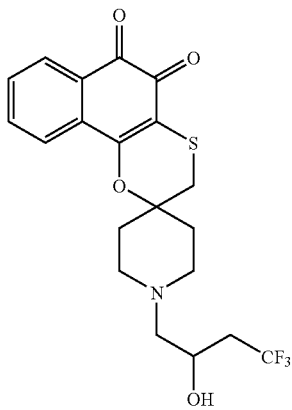

Compound 160 was synthesized using spiro[naphtho[1,2-b][1,4]oxathiine-2,4'-piperidine]-5,6-dione, 2-(2,2,2-trifluoroethyl)oxirane and conditions outlined in procedure X. M.p.=145-148° C. 400 MHz $^1$H NMR (CDCl$_3$) δ: 8.05 (d, 1H), 7.75 (d, 1H), 7.65 (t, 1H), 7.5 (t, 1H), 4.05 (m, 1H), 3.5 (s, 1H), 2.95 (m, 3H), 2.85-2.7 (m, 2H), 2.6-2.3 (m, 4H), 2.2-2.1 (m, 3H), 2.0-1.9 (m, 2H); LCMS: 428 [M+H].

E24.5. Synthesis of 1'-(2-hydroxycyclopentyl)spiro[naphtho[1,2-b][1,4]oxathiine-2,4'-piperidine]-5,6-dione (Compound 161)

Compound 161 was synthesized using spiro[naphtho[1,2-b][1,4]oxathiine-2,4'-piperidine]-5,6-dione, 6-oxabicyclo[3.1.0]hexane and conditions outlined in procedure X. M.p.=110-113° C.; 400 MHz $^1$H NMR (CDCl$_3$) δ: 8.05 (d, 1H), 7.75 (d, 1H), 7.65 (t, 1H), 7.5 (t, 1H), 4.1 (m, 1H), 3.1 (d, 1H), 2.95 (s, 1H), 2.9 (d, 1H), 2.7-2.5 (m, 3H), 2.2-1.85 (m, 8H), 1.8-1.5 (m, 4H); LCMS: 386 [M+H].

E24.6. Synthesis of 1'-(2-hydroxyhexyl)spiro[naphtho[2-b][1,4]oxathiine-2,4'-piperidine]-5,6-dione (Compound 162)

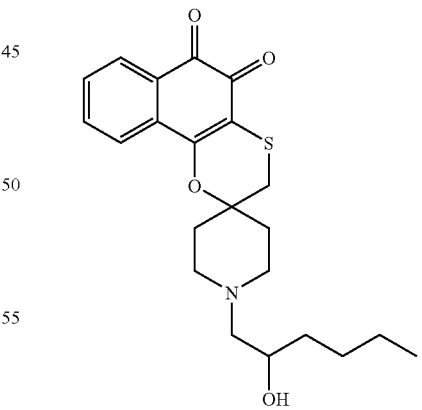

Compound 162 was synthesized using spiro[naphtho[1,2-b][1,4]oxathiine-2,4'-piperidine]-5,6-dione, 2-butyloxirane and conditions outlined in procedure X. M.p.=160-163° C.; 400 MHz $^1$H NMR (CDCl$_3$) δ: 8.05 (d, 1H), 7.75 (d, 1H), 7.65 (t, 1H), 7.5 (t, 1H), 3.7 (m, 1H), 2.95 (m, 3H), 2.8-2.7 (m, 2H), 2.5-2.35 (m, 3H), 2.15 (d, 2H), 1.95-1.8 (m, 2H), 1.5-1.3 (m, 6H), 0.9 (t, 3H); LCMS: 402 [M+H].

E24.7. Synthesis of 1'-(2-hydroxy-3-phenylpropyl)spiro[naphtho[1,2-b][1,4]oxathiine-2,4'-piperidine]-5,6-dione (Compound 163)

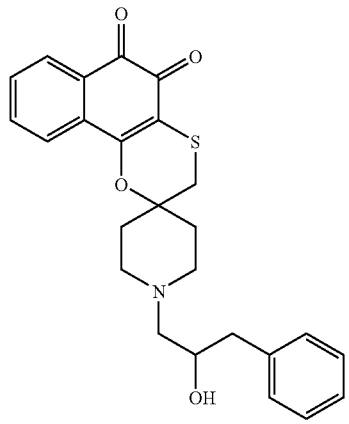

Compound 163 was synthesized using spiro[naphtho[1,2-b][1,4]oxathiine-2,4'-piperidine]-5,6-dione, 2-benzyloxirane and conditions outlined in procedure X. M.p.=70-73° C.; 400 MHz $^1$H NMR (CDCl$_3$) δ: 8.05 (d, 1H), 7.75 (d, 1H), 7.65 (t, 1H), 7.5 (t, 1H), 7.35-7.2 (m, 5H), 3.95 (m, 1H), 2.95-2.8 (m, 5H), 2.75-2.65 (m, 3H), 2.5-2.35 (m, 3H), 2.1 (d, 2H), 1.95-1.75 (m, 2H); LCMS: 436 [M+H].

E24.8. Synthesis of 1'-[3-(4-fluorophenoxy)-2-hydroxypropyl]spiro[naphtho[1,2-b][1,4]oxathiine-2,4'-piperidine]-5,6-dione (Compound 164)

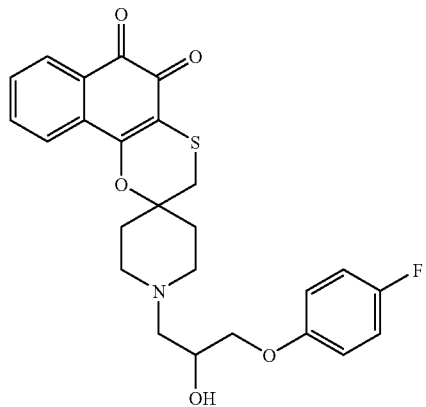

Compound 164 was synthesized using spiro[naphtho[1,2-b][1,4]oxathiine-2,4'-piperidine]-5,6-dione, 2-[(4-fluorophenoxy)methyl]oxathiine and conditions outlined in procedure X. M.p.=163-167° C.; 400 MHz $^1$H NMR (CDCl$_3$) δ: 8.05 (d, 1H), 7.75 (d, 1H), 7.65 (t, 1H), 7.5 (t, 1H), 6.95 (t, 2H), 6.85 (m, 2H), 4.15 (m, 1H), 3.95 (d, 2H), 3.0-2.9 (m, 3H), 2.8 (d, 2H), 2.7-2.6 (m, 2H), 2.55 (t, 2H), 2.15 (d, 2H), 1.95-1.85 (m, 2H); LCMS: 470 [M+H].

E24.9. Synthesis of 1'-[3-(2-furylmethoxy)-2-hydroxypropyl]spiro[naphtho[2-b][1,4]oxathiine-2,4'-piperidine]-5,6-dione (Compound 165)

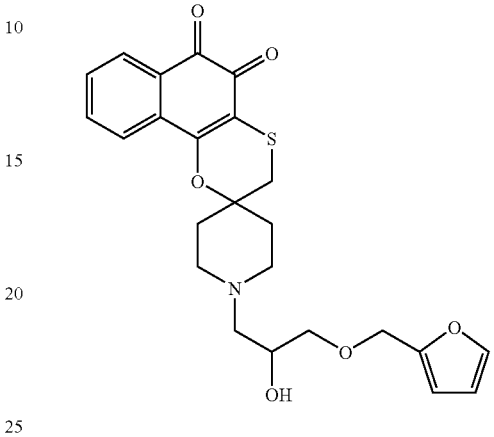

Compound 165 was synthesized using spiro[naphtho[1,2-b][1,4]oxathiine-2,4'-piperidine]-5,6-dione, 2-[(oxiran-2-ylmethoxy)methyl]furan and conditions outlined in procedure X. M.p.=143-145° C.; LCMS: 456 [M+H].

E24.10. Synthesis of 1'-(2-hydroxy-3-morpholin-4-ylpropyl)spiro[naphtho[1,2-b][1,4]oxathiine-2,4'-piperidine]-5,6-dione (Compound 166)

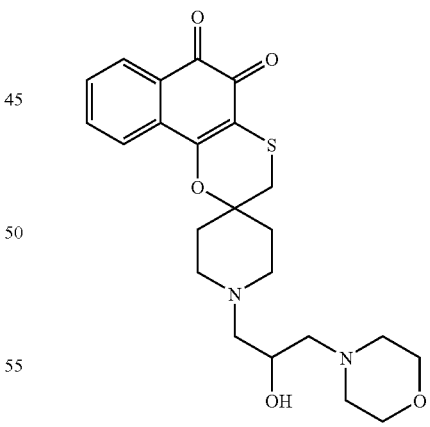

Compound 166 was synthesized using spiro[naphtho[1,2-b][1,4]oxathiine-2,4'-piperidine]-5,6-dione, 4-(oxiran-2-ylmethyl)morpholine and conditions outlined in procedure X. M.p.=75-78° C.; 400 MHz $^1$H NMR (CDCl$_3$) δ: 8.05 (d, 1H), 7.75 (d, 1H), 7.65 (t, 1H), 7.5 (t, 1H), 3.9 (m, 1H), 3.7 (m, 5H), 2.95 (s, 1H), 2.9 (t, 2H), 2.7-2.3 (m, 1H), 2.15 (d, 2H), 1.9 (q, 2H); LCMS: 445 [M+H].

E24.11. Synthesis of 1'-(2-hydroxy-2-phenylethyl)spiro[naphtho[1,2-b][1,4]oxathiine-2,4'-piperidine]-5,6-dione (Compound 167)

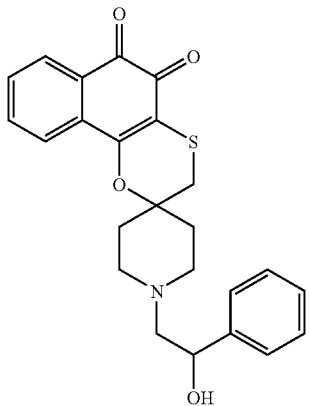

Compound 167 was synthesized using spiro[naphtho[1,2-b][1,4]oxathiine-2,4-piperidine]-5,6-dione, 2-phenyloxirane and conditions outlined in procedure X. M.p.=193-195° C.; 400 MHz $^1$H NMR (DMSO-$d_6$) δ: 8.09-7.75 (m, 3H), 7.6-7.5 (m, 1H), 7.4-7.2 (m, 5H), 5.03 (br. s, 1H), 4.93 (br. s, 1H), 3.07 (s, 2H), 2.9-2.78 (m, 2H), 2.65-2.45 (m, 4H), 2.05-1.7 (m, 4H); LCMS: 422 [M+H].

E24.12. Synthesis of 1'-(2-hydroxybutyl)spiro[naphtho[1,2-b][1,4]oxathiine-2,44'-piperidine]-5,6-dione (Compound 168)

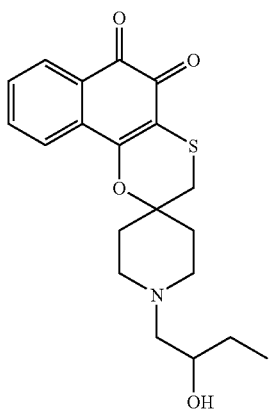

Compound 168 was synthesized using spiro[naphtho[1,2-b][1,4]oxathiine-2,44'-piperidine]-5,6-dione, 2-ethyloxirane and conditions outlined in procedure X. M.p.=180-182° C.; 400 MHz $^1$H NMR (DMSO-$d_6$) δ: 7.9 (m, 1H), 7.75 (m, 2H), 7.55 (m, 1H), 4.2 (s, 1H), 3.5 (br s, 1H), 3.05 (s, 2H), 2.7 (br s, 2H), 2.45-2.25 (m, 4H), 1.9 (m, 2H), 1.8 (m, 2H), 1.5-1.4 (m, 1H), 1.3-1.2 (m, 1H), 0.85 (m, 3H); LCMS: 374 [M+H].

E24.13. Synthesis of 1'-(2-hydroxy-3-isopropoxypropyl)spiro[naphtho[1,2-b][1,4]oxathiine-2,4'-piperidine]-5,6-dione (Compound 169)

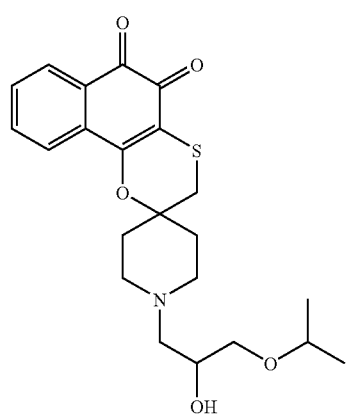

Compound 169 was synthesized using spiro[naphtho[1,2-b][1,4]oxathiine-2,4'-piperidine]-5,6-dione, 2-(isopropoxymethyl)oxathiine and conditions outlined in procedure X. M.p.=97-99° C. 400 MHz $^1$H NMR (DMSO-$d_6$) δ: 7.95-7.9 (m, 1H), 7.94-7.7 (m, 2H), 7.65-7.5 (m, 1H), 4.42 (br. s, 1H), 3.72 (br. s, 1H), 3.6-3.45 (m, 1H), 3.35-3.2 (m, 2H), 3.07 (s, 2H), 2.8 (m, 2H), 2.5-2.2 (m, 4H), 2.05-1.7 (m, 4H), 1.07 (d, J=5.2 Hz, 6H); LCMS: 418 [M+H].

E24.14. Synthesis of 1'-[3-(4-ethylphenoxy)-2-hydroxypropyl]spiro[naphtho[1,2-b][1,4]oxathiine-2,4'-piperidine]-5,6-dione (Compound 170)

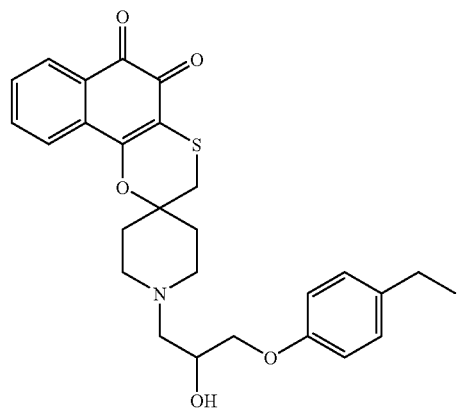

Compound 170 was synthesized using spiro[naphtho[1,2-b][1,4]oxathiine-2,4'-piperidine]-5,6-dione, 2-[(4-ethylphenoxy)methyl]oxirane and conditions outlined in procedure X. LCMS: 480 [M+H]; $R_t$=1.09 min.

E24.15. Synthesis of 1'-[3-(benzyloxy)-2-hydroxypropyl]spiro[naphtho[12-b][1,4]oxathiine-2,4'-piperidine]-5,6-dione (Compound 171)

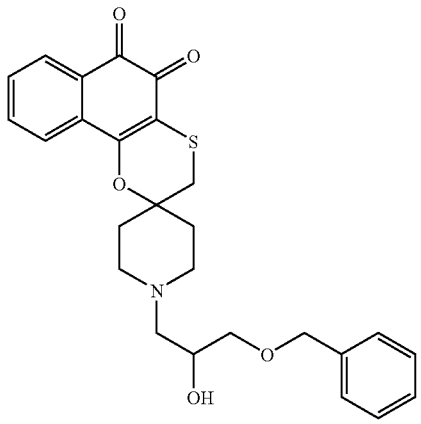

Compound 171 was synthesized using spiro[naphtho[1,2-b][1,4]oxathiine-2,4'-piperidine]-5,6-dione, 2-[(benzyloxy)methyl]oxirane and conditions outlined in procedure X. LCMS: 466 [M+H]; $R_t$=1.01 min.

E24.16. Synthesis of 1'-[3-(2-chlorophenoxy)-2-hydroxypropyl]spiro[naphtho[1,2-b][1,4]oxathiine-2,4'-piperidine]-5,6-dione (Compound 172)

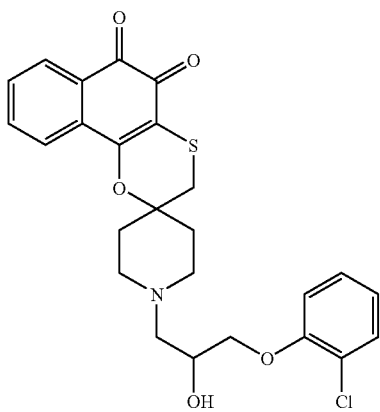

Compound 172 was synthesized using spiro[naphtho[1,2-b][1,4]oxathiine-2,4'-piperidine]-5,6-dione, 2-[(2-chlorophenoxy)methyl]oxirane and conditions outlined in procedure X. LCMS: 486 [M+H]; $R_t$=1.04 min.

E24.17. Synthesis of 1'-[2-hydroxy-3-(2-methylphenoxy)propyl]spiro[naphtho[1,2-b][1,4]oxathiine-2,4'-piperidine]-5,6-dione (Compound 173)

Compound 173 was synthesized using spiro[naphtho[1,2-b][1,4]oxathiine-2,4'-piperidine]-5,6-dione, 2-[(2-methylphenoxy)methyl]oxirane and conditions outlined in procedure X. LCMS: 466 [M+H]; $R_t$=1.05 min.

E24.18. Synthesis of 1'-(2-hydroxy-3-isobutoxypropyl)spiro[naphtho[1,2-b][1,4]oxathiine-2,4'-piperidine]-5,6-dione (Compound 174)

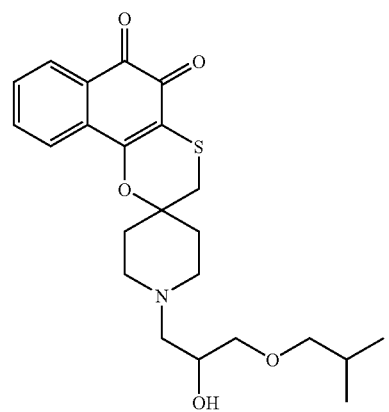

Compound 174 was synthesized using spiro[naphtho[1,2-b][1,4]oxathiine-2,4'-piperidine]-5,6-dione, 2-(isobutoxymethyl)oxirane and conditions outlined in procedure X. LCMS: 432 [M+H]; $R_t$=0.97 min.

E24.19. Synthesis of 1'-[2-hydroxy-3-(4-methoxyphenoxy)propyl]spiro[naphtho[1,2-b][1,4]oxathiine-2,4'-piperidine]-5,6-dione (Compound 175)

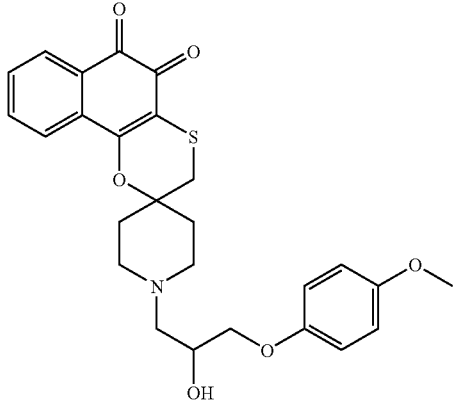

Compound 175 was synthesized using spiro[naphtho[1,2-b][1,4]oxathiine-2,4'-piperidine]-5,6-dione, 2-[(4-methoxyphenoxy)methyl]oxirane and conditions outlined in procedure X. LCMS: 482 [M+H]; $R_t$=0.99 min.

E24.20. Synthesis of 1'-[3-(4-chlorophenoxy)-2-hydroxypropyl]spiro[naphtho[1,2-b][1,4]oxathiine-2,4'-piperidine]-5,6-dione (Compound 176)

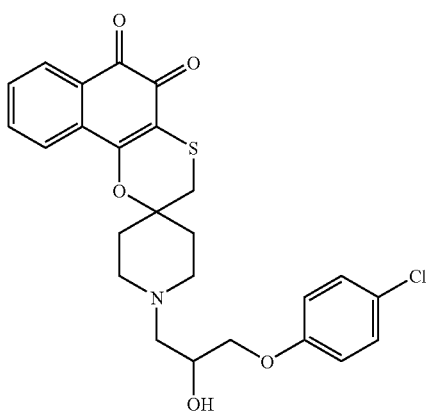

Compound 176 was synthesized using spiro[naphtho[1,2-b][1,4]oxathiine-2,4'-piperidine]-5,6-dione, 2-[(4-chlorophenoxy)methyl]oxathiine and conditions outlined in procedure X. LCMS: 486 [M+H]; $R_t$=1.06 min.

E24.21. Synthesis of 1'-(2-hydroxy-2-phenylpropyl)spiro[naphtho[1,2-b][1,4]oxathiine-2,4'-piperidine]-5,6-dione (Compound 177)

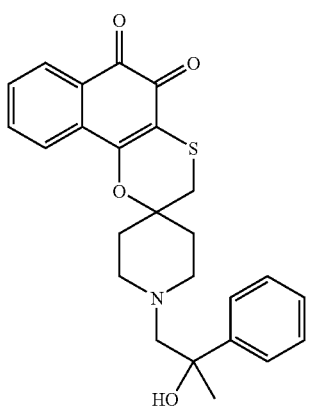

Compound 177 was synthesized using spiro[naphtho[1,2-b][1,4]oxathiine-2,4'-piperidine]-5,6-dione, 2-methyl-2-phenyloxirane and conditions outlined in general procedure X. M.p.=117° C. (dec); 400 MHz $^1$H NMR (DMSO-$d_6$) δ: 7.88 (d, J=8 Hz, 1H), 7.77 (d, J=4 Hz, 2H), 7.56 (d, J=4 Hz, 1H), 7.49 (d, J=7.2 Hz, 2H), 7.30 (t, J=7.2 Hz, 2H), 7.19 (t, J=7.2 Hz, 1H), 4.84 (bs, 1H), 3.05 (s, 2H), 2.72-2.34 (m, 2H), 1.96-1.83 (m, 4H), 1.80-1.57 (m, 4H), 1.47 (s, 3H). LCMS: 436 [M+H].

E24.22. Synthesis of 1'-[3-(4-chlorophenyl)-2-hydroxypropyl]spiro[naphtho[1,2-b][1,4]oxathiine-2,4'-piperidine]-5,6-dione (Compound 178)

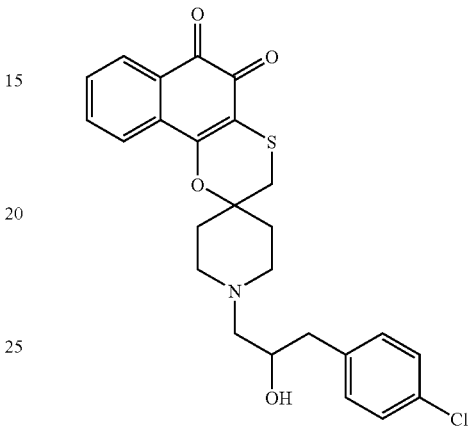

Compound 178 was synthesized using spiro[naphtho[1,2-b][1,4]oxathiine-2,4'-piperidine]-5,6-dione, 2-(4-chlorobenzyl)oxirane and conditions outlined in procedure X. M.p.=195-196° C.; 300 MHz $^1$H NMR (CDCl$_3$) δ: 8.05-8.02 (m, 1H), 7.75-7.72 (m, 1H), 7.67-7.62 (m, 1H), 7.50-7.45 (m, 1H), 7.28-7.26 (m, 2H), 7.18-7.16 (m, 2H), 3.95-3.90 (m, 1H), 2.93 (s, 1H), 2.89-2.82 (m, 2H), 2.83-2.64 (m, 4H), 2.47-2.39 (m, 4H), 2.13 (d, J=13.8 Hz, 2H), 1.90-1.82 (m, 2H); LCMS: 470 [M+H].

E24.23. Synthesis of 1'-(2-hydroxy-2-methyl-3-phenylpropyl)spiro[naphtho[1,2-b][1,4]oxathiine-2,4'-piperidine]-5,6-dione (Compound 179)

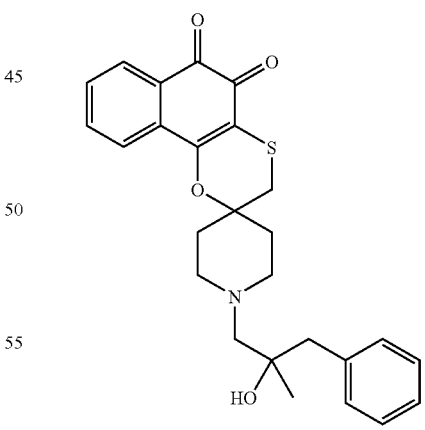

Compound 179 was synthesized using spiro[naphtho[1,2-b][1,4]oxathiine-2,4'-piperidine]-5,6-dione, 2-benzyl-2-methyloxirane and conditions outlined in procedure X. M.p.=186-187° C.; 400 MHz $^1$H NMR (DMSO-$d_6$) δ: 7.89 (d, J=7.8 Hz, 1H), 7.82-7.76 (m, 2H), 7.64-7.54 (m, 1H), 7.28-7.16 (m, 5H), 4.22 (s, 1H), 4.11 (q, J=5.1 Hz, 1H), 3.38 (d, J=1.1 Hz, 1H), 3.17 (d, J=5.5 Hz, 3H), 3.08 (s, 2H), 2.94-2.76 (m, 2H), 2.63-2.72 (m, 2H), 2.41-2.20 (m, 2H), 2.02-1.94 (m, 2H), 1.92-1.80 (m, 2H). LCMS: 450 [M+H].

Example 25

Procedure Y

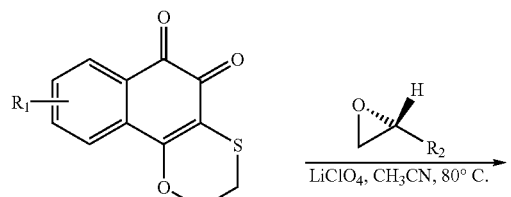

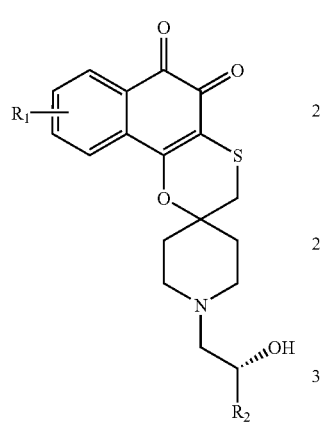

The chiral benzyloxiranes were synthesized using the procedure outlined in Schaus et. al J. Am. Chem. Soc. 124 (7) 2002, 1307-1315. The chiral phenoxymethyloxiranes were synthesized using chiral glycidol (Sigma Aldrich), DIAD, triphenylphosphine and the corresponding phenols and procedure outline in Steffan et. al. Bioorg. Med. Chem. Lett. 2002, 12, 2957-2961.

E25.1. Synthesis of 1'-[(2S)-3-(4-fluorophenoxy)-2-hydroxypropyl]spiro[naphtho[1,2-b][1,4]oxathiine-2,4'-piperidine]-5,6-dione (Compound 180)

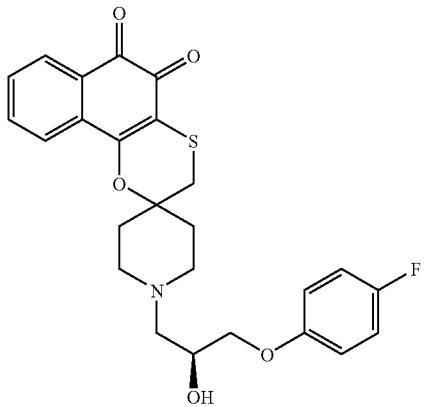

To a mixture of spiro[naphtho[1,2-b][1,4]oxathiine-2,4'-piperidine]-5,6-dione (1.0 g 3.32 mmol) in acetonitrile (12.0 mL) was added (2S)-2-[(4-fluorophenoxy)methyl]oxirane (0.614 g, 3.65 mmol) followed by lithium perchlorate (0.388 g, 3.65 mmol). The reaction mixture was stirred at 80° C. for 2 hours. The reaction was cooled to room temperature and dichloromethane (100 mL) added to it. The reaction was then washed with water (100 mL). The organic layer was separated, washed with water, dried with sodium sulfate and concentrated under vacuum. The crude product vas purified by flash column chromatography (SiO$_2$, 80% EtOAc in dichloromethane to 100% EtOAc) to give the desired product as a purple solid (0.73 g, 45%). M.p.=174-175° C.; 400 MHz $^1$H NMR (CDCl$_3$) δ: 8.06 (dd, J=1.6, 7.6 Hz, 1H), 7.79-7.75 (m, 1H), 7.66 (dt, J=1.6, 7.6 Hz, 1H), 7.5 (dt, J=1.6, 7.6 Hz, 1H), 7.05-6.94 (m, 2H), 6.9-6.84 (m, 2H), 4.18-4.1 (m, 1H), 4.0-3.94 (m, 2H), 3.02-2.92 (m, 1H), 2.96 (s, 2H), 2.86-2.76 (m, 2H), 2.72-2.62 (m, 2H), 2.6-2.5 (m, 2H), 2.2-2.12 (m, 2H), 1.98-1.82 (m, 2H); LCMS: 470 [M+H]; enantiomeric excess determined from chiral HPLC: 98%; Chiral HPLC R$_t$=30.54

E25.2. Synthesis of 1'-[(2R)-3-(4-fluorophenoxy)-2-hydroxypropyl]spiro[naphtho[1,2-b][1,4]oxathiine-2,4'-piperidine]-5,6-dione (Compound 181)

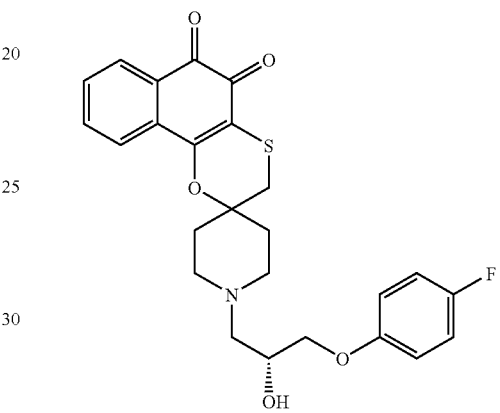

Compound 181 was synthesized using spiro[naphtho[2,1-b][1,4]oxathiine-2,4'-piperidine]-5,6-dione, (2R)-2-[(4-fluorophenoxy)methyl]oxirane and conditions outlined in procedure Y. M.p.=176-177° C.; 400 MHz $^1$H NMR (DMSO-d$_6$) δ: 7.90 (d, J=7.6 Hz, 1H), 7.82-7.76 (m, 2H), 7.60-7.50 (m, 1H), 7.14-7.08 (m, 2H), 6.98-6.93 (m, 2H), 4.88 (d, J=4.8 Hz, 1H), 4.00-3.94 (m, 2H), 3.88-3.82 (m, 1H), 3.07 (s, 2H), 2.87-2.74 (m, 2H), 2.55-2.40 (m, 4H), 2.03-1.95 (m, 2H), 1.86-1.76 (m, 2H); LCMS: 470 [M+H]; enantiomeric excess determined from chiral HPLC: 98%; Chiral HPLC R$_t$=62.58 min.

E25.3. Synthesis of 1'-[(2S)-3-(4-chlorophenoxy)-2-hydroxypropyl]spiro[naphtho[2-b][1,4]oxathiine-2,4'-piperidine]-5,6-dione (Compound 182)

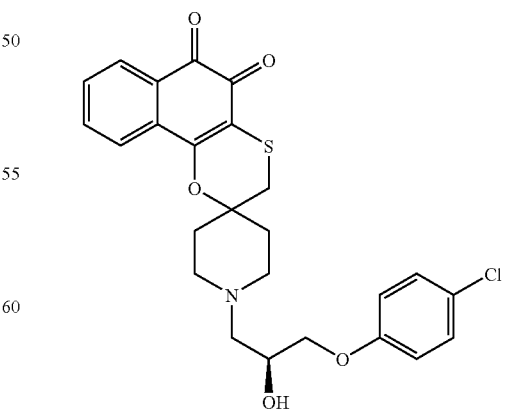

Compound 182 was synthesized using spiro[naphtho[1,2-b][1,4]oxathiine-2,4'-piperidine]-5,6-dione, (2S)-2-[(4-chlorophenoxy)methyl]oxathiine and conditions outlined in procedure Y. M.p.=138-140° C.; 400 MHz $^1$H NMR (CDCl$_3$) δ: 8.06 (dd, J=7.7, 1.5 Hz, 1H), 7.77 (d, J=7.7 Hz, 1H), 7.67 (td, J=7.7, 1.1 Hz, 1H), 7.49 (td, J=7.5, 1.1 Hz, 1H), 7.28-7.21 (m, 2H), 6.88-6.82 (m, 2H), 4.17-4.08 (m, 1H), 4.02-3.94 (m, 2H), 3.02-2.92 (m, 1H), 2.95 (s, 2H), 2.84-2.76 (m, 2H), 2.71-2.61 (m, 2H), 2.54 (td, J=11.5, 2.4 Hz, 1H), 2.17 (br. d, J=13.9 Hz, 2H), 1.98-1.82 (m, 2H); LCMS: 486 [M+H]; enantiomeric excess determined from chiral HPLC: 98%; Chiral HPLC R$_t$=62.95 min.

E25.4. Synthesis of 1'-[(2R)-3-(4-chlorophenoxy)-2-hydroxypropyl]spiro[naphtho[1,2-b][1,4]oxathiine-2,4'-piperidine]-5,6-dione (Compound 183)

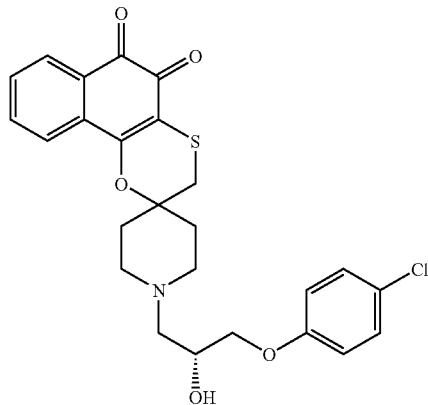

Compound 183 was synthesized using spiro[naphtho[1,2-b][1,4]oxathiine-2,4'-piperidine]-5,6-dione, (2R)-2-[(4-chlorophenoxy)methyl]oxirane and conditions outlined in procedure Y. M.p.=155-157° C.; 400 MHz $^1$H NMR (CDCl$_3$) δ: 8.05 (dd, J=6.4, 7.6 Hz, 1H), 7.76 (d, J=7.7 Hz, 1H), 7.68-7.64 (m, 1H), 7.51-7.47 (m, 1H), 7.25-7.22 (m, 2H), 6.86-6.84 (m, 2H), 4.14-4.11 (m, 1H), 3.98-3.96 (m, 2H), 2.94 (brs, 3H), 2.80-2.77 (m, 2H), 2.70-2.62 (m, 2H), 2.56-2.50 (m, 1H), 2.17 (d, J=13.6 Hz, 2H), 1.96-1.84 (m, 2H); LCMS: 486 [M+H]; enantiomeric excess determined from chiral HPLC: 98%; Chiral HPLC R$_t$=33.67 min.

E25.5. Synthesis of 1'-[(2S)-3-(4-tert-butylphenoxy)-2-hydroxypropyl]spiro[naphtho[1,2-b][1,4]oxathiine-2,4'-piperidine]-5,6-dione (Compound 184)

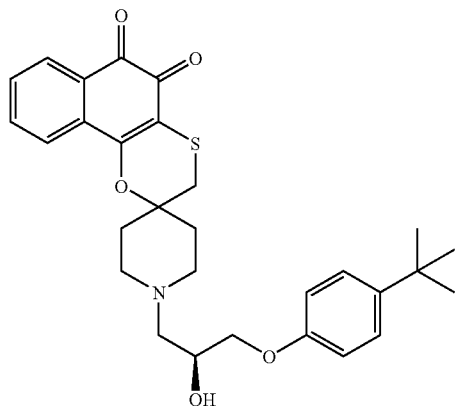

Compound 184 was synthesized using spiro[naphtho[1,2-b][1,4]oxathiine-2,4-piperidine]-5,6-dione, (2S)-2-[(4-tert-butylphenoxy)methyl]oxirane and conditions outlined in procedure Y. M.p.=155-157° C.; 400 MHz $^1$H NMR (CDCl$_3$) δ: 8.06 (dd, J=1.2 and 8 Hz, 1H), 7.77 (dd, J=1.2 and 8 Hz, 1H), 7.67 (dt, J=1.2 and 8 Hz, 1H), 7.49 (dt, J=1.2 and 8 Hz, 1H), 7.31 (d, J=9.2 Hz, 2H), 6.86 (d, J=8.8 Hz, 2H), 4.10-4.17 (m, 1H), 4.00 (dd, J=1.2 and 4.8 Hz, 2H), 2.99-2.95 (s, 3H), 2.74-2.86 (m, 2H), 2.64-2.7 (m, 2H), 2.51-2.6 (m, 1H), 2.13-2.2 (m, 2H), 1.84-1.98 (m, 2H), 1.3 (s, 9H); LCMS: 508 [M+H]; enantiomeric excess determined from chiral HPLC: 98%; Chiral HPLC R$_t$=50.98 min.

E25.6. Synthesis of 1'-[(2R)-3-(4-tert-butylphenoxy)-2-hydroxypropyl]spiro[naphtho[2-b][1,4]oxathiine-2,4'-piperidine]-5,6-dione (Compound 185)

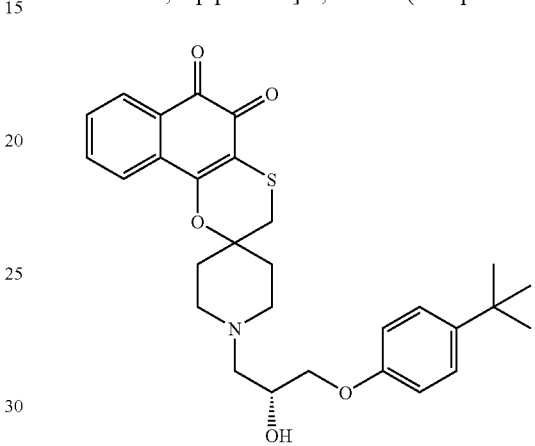

Compound 185 was synthesized using spiro[naphtho[1,2-b][1,4]oxathiine-2,4'-piperidine]-5,6-dione, (2R)-2-[(4-tert-butylphenoxy)methyl]oxirane and conditions outlined in procedure Y. M.p.=150-152° C.; 400 MHz $^1$H NMR (DMSO-d$_6$) δ: 7.89 (d, J=7.2 Hz, 1H), 7.79 (m, 2H), 7.56 (m, 1H), 7.28 (d, J=8 Hz, 2H), 6.85 (d, J=8 Hz, 2H), 4.84 (s, 1H), 3.94 (m, 2H), 3.85 (m, 1H), 3.07 (s, 2H), 2.80 (m, 2H), 2.45 (m, 4H), 1.99 (m, 2H), 1.82 (m, 2H); LCMS: 508 [M+H]; enantiomeric excess determined from chiral HPLC: 98%; Chiral HPLC R$_t$=35.55 min.

E25.7. Synthesis of 1'-[(2R)-2-hydroxy-3-phenylpropyl]spiro[naphtho[1,2-b][1,4]oxathiine-2,4'-piperidine]-5,6-dione (Compound 186)

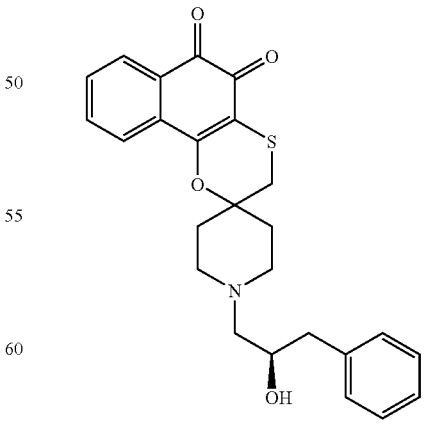

Compound 186 was synthesized using spiro[naphtho[1,2-b][1,4]oxathiine-2,4'-piperidine]-5,6-dione, (2R)-2-benzyloxirane and conditions outlined in procedure Y. M.p.=82-84° C.; 400 MHz $^1$H NMR (DMSO) δ: 7.92-7.88 (m, 1H), 7.8-

7.74 (m, 2H), 7.6-7.52 (m, 1H), 7.3-7.14 (m, 5H), 4.44 (brd, J=4.4 Hz, 1H), 3.9-3.8 (m, 1H), 3.07 (s, 2H), 2.82-2.7 (m, 3H), 2.64-2.56 (m, 1H), 2.46-2.28 (m, 4H), 2.04-1.94 (m, 2H), 1.88-1.76 (m, 2H); LCMS: 436 [M+H]; enantiomeric excess determined from chiral HPLC: >99%; Chiral HPLC $R_t$=50.74 min.

E25.8. Synthesis of 1'-[(2S)-2-hydroxy-3-phenylpropyl]spiro[naphtho[1,2-b][1,4]oxathiine-2,4'-piperidine]-5,6-dione (Compound 187)

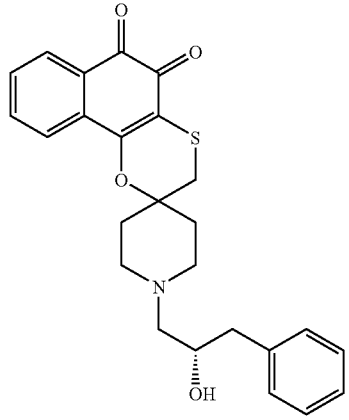

Compound 187 was synthesized using spiro[naphtho[1,2-b][1,4]oxathiine-2,4'-piperidine]-5,6-dione, (2S)-2-benzyloxirane and conditions outlined in procedure Y. M.p.=149-150° C.; 400 MHz $^1$H NMR (CDCl$_3$) δ: 8.04 (dd, J=7.8, 1.2 Hz, 1H), 7.73 (dd, J=7.8, 0.8 Hz, 1H), 7.64 (td, J=7.6, 1.2 Hz, 1H), 7.48 (td, J=7.4, 1.2 Hz, 1H), 7.34-7.20 (m, 5H), 4.02-3.94 (m, 1H), 2.93 (s, 2H), 2.87 (dd, J=13.3, 6.8 Hz, 2H), 2.78-2.66 (m, 3H), 2.50-2.38 (m, 3H), 2.18-2.08 (m, 2H), 1.94-1.78 (m, 2H); LCMS: 436 [M+H]; enantiomeric excess determined by chiral HPLC: >99%; Chiral HPLC $R_t$=63.08 min.

E25.9. Synthesis of 9-bromo-1'-[(2S)-2-hydroxy-3-phenylpropyl]spiro[naphtho[1,2-b][1,4]oxathiine-2,4'-piperidine]-5,6-dione (Compound 188)

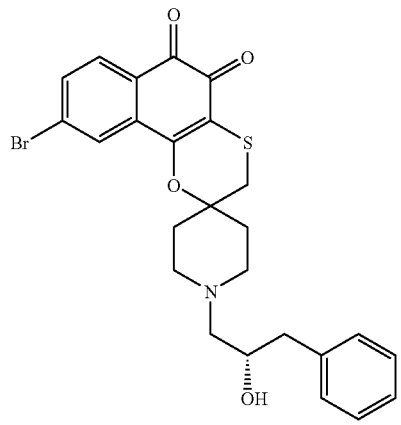

Compound 188 was synthesized using 9-bromospiro[naphtho[1,2-b][1,4]oxathiine-2,4'-piperidine]-5,6-dione, (2S)-2-benzyloxirane and conditions outlined in procedure Y. M.p.=82-83° C.; 400 MHz $^1$H NMR (DMSO-d$_6$) δ: 7.82-7.76 (m, 3H), 7.29-7.21 (m, 4H), 7.19-7.14 (m, 1H), 4.47-4.44 (m, 1H), 3.89-3.82 (m, 1H), 3.08 (s, 2H), 2.82-2.69 (m, 3H), 2.63-2.54 (m, 1H), 2.42-2.27 (m, 4H), 2.20-1.94 (m, 2H), 1.86-1.77 (m, 2H); LCMS: 514 [M+H].

E25.10. Synthesis of 9-bromo-1'-[(2S)-3-(4-tert-butylphenoxy)-2-hydroxypropyl]spiro[naphtho[1,2-b][1,4]oxathiine-2,4'-piperidine]-5,6-dione (Compound 189)

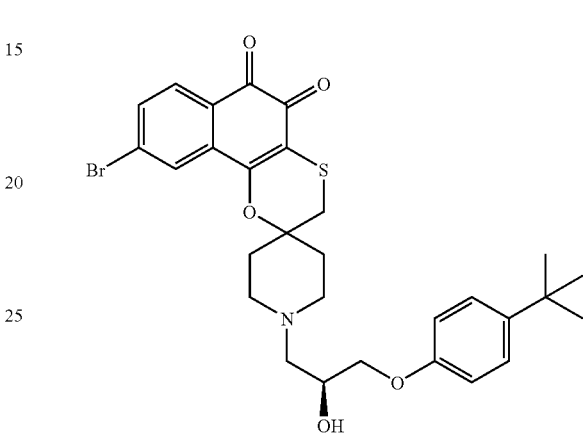

Compound 189 was synthesized using 9-bromospiro[naphtho[1,2-b][1,4]oxathiine-2,4'-piperidine]-5,6-dione, (2S)-2-[(4-tert-butylphenoxy)methyl]oxathiine and conditions outlined in procedure Y. M.p.=150-152° C.; 400 MHz $^1$H NMR (CDCl$_3$) δ: 7.92-7.89 (m, 1H), 7.87-7.85 (m, 1H), 7.65-7.62 (m, 1H), 7.33-7.29 (m, 2H), 6.89-6.85 (m, 2H), 4.20-4.10 (m, 1H), 4.03-3.98 (m, 2H), 2.96 (s, 2H), 2.83-2.73 (m, 2H), 2.73-2.62 (m, 2H), 2.62-2.50 (m, 1H), 2.20-2.12 (m, 2H), 2.00-1.85 (m, 2H), 1.29 (s, 9H); LCMS: 586 [M+H].

E25.11. Synthesis of 9-bromo-1'-[(2S)-3-(4-chlorophenoxy)-2-hydroxypropyl]spiro[naphtho[1,2-b][1,4]oxathiine-2,4'-piperidine]-5,6-dione (Compound 190)

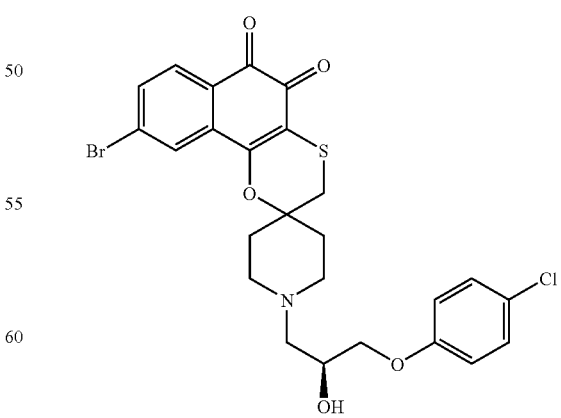

Compound 190 vas synthesized using 9-bromospiro[naphtho[1,2-b][1,4]oxathiine-2,4'-piperidine]-5,6-dione, (2S)-2-[(4-chlorophenoxy)methyl]oxathiine and conditions outlined in procedure Y. M.p.=150-152° C.; 400 MHz $^1$H NMR (CDCl$_3$) δ: 7.92-7.89 (m, 1H), 7.87-7.85 (m, 1H), 7.65-7.62 (m, 1H), 7.27-7.22 (m, 2H), 6.88-6.84 (m, 2H), 4.20-4.08 (m, 1H), 4.03-3.95 (m, 2H), 2.96 (s, 3H), 2.85-2.74 (m, 2H), 2.74-2.60 (m, 2H), 2.60-2.50 (m, 1H), 2.21-2.12 (m, 2H), 2.00-1.85 (m, 2H); LCMS: 564 [M+H].

E25.12. Synthesis of 1'-[(2S)-3-(4-tert-butylphenoxy)-2-hydroxypropyl]-9-fluorospiro[naphtho[1,2-b][1,4]oxathiine-2,4'-piperidine]-5,6-dione (Compound 191)

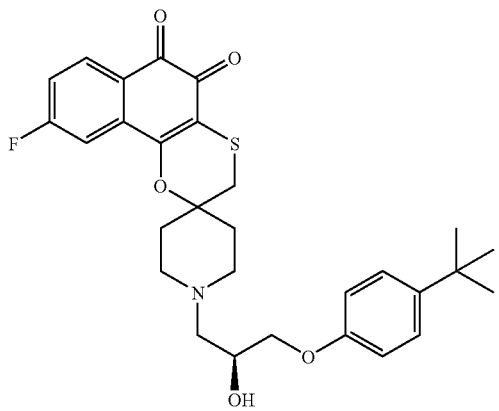

Compound 191 was synthesized using 9-fluorospiro[naphtho[1,2-b][1,4]oxathiine-2,4'-piperidine]-5,6-dione, (2S)-2-[(4-tert-butylphenoxy)methyl]oxathiine and conditions outlined in procedure Y. M.p.=114-116° C., 400 MHz $^1$H NMR (DMSO-d$_6$) δ: 7.99-7.95 (m, 1H), 7.46-7.37 (m, 2H), 7.29-7.27 (d, J=8.60 Hz, 2H), 6.86-6.84 (d, J=8.99 Hz, 2H), 4.85 (br s, 1H), 3.96-3.4 (m, 2H), 3.86-3.84 (m, 1H), 3.34 (s, 2H), 2.79-2.74 (m, 3H), 2.50-2.44 (m, 3H), 1.99-1.96 (m, 2H), 1.83-1.81 (m, 2H), 1.24 (s, 9H); LCMS: 526 [M+H]

E25.13. Synthesis of 1'-[(2S)-3-(4-tert-butylphenoxy)-2-hydroxypropyl]-9-chlorospiro[naphtho[1,2-b][1,4]oxathiine-2,4'-piperidine]-5,6-dione (Compound 192)

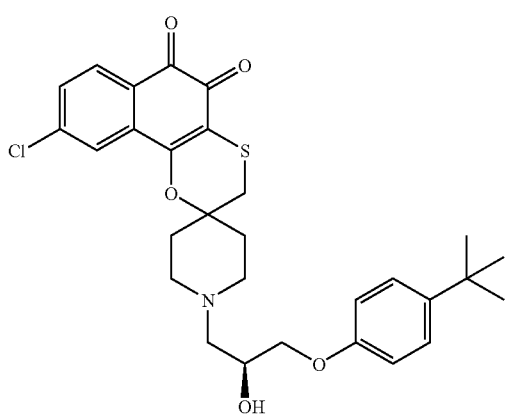

Compound 192 was synthesized using 9-chlorospiro[naphtho[1,2-b][1,4]oxathiine-2,4'-piperidine]-5,6-dione, (2S)-2-[(4-tert-butylphenoxy)methyl]oxathiine and conditions outlined in procedure Y. M.p.=94-97° C.; 400 MHz $^1$H NMR (DMSO-d$_6$) δ: 7.89 (d, J=8.4 Hz, 1H), 7.67-7.62 (m, 2H), 7.28 (d, J=8.8 Hz, 2H), 6.85 (d, J=8.8 Hz, 2H), 4.86 (d, J=4.4 Hz, 1H), 4.0-3.92 (m, 2H), 3.87-3.83 (m, 1H), 3.08 (s, 2H), 2.84-2.75 (m, 2H), 2.48-2.41 (m, 4H), 2.02-1.94 (m, 2H), 1.86-1.76 (m, 2H), 1.25 (s, 9H); LCMS: 542 [M+H].

E25.14. Synthesis of 9-chloro-1'-[(2S)-2-hydroxy-3-phenylpropyl]spiro[naphtho[1,2-b][1,4]oxathiine-2,4'-piperidine]-5,6-dione (Compound 193)

Compound 193 was synthesized using 9-chlorospiro[naphtho[1,2-b][1,4]oxathiine-2,4'-piperidine]-5,6-dione, (2S)-2-benzyloxirane and conditions outlined in procedure Y. M.p.=92-96° C., 400 MHz $^1$H NMR (CDCl$_3$) δ: 7.99-7.97 (d, J=8.21 Hz, 1H), 7.667-7.662 (d, J=1.95 Hz, 1H), 7.46-7.43 (dd, J=1.56, 7.82 Hz, 1H), 7.33-7.23 (m, 5H), 4.01-3.94 (m, 1H), 3.33 (br s, 1H), 2.93-2.82 (m, 4H), 2.74-2.70 (m, 3H), 2.51-2.41 (m, 3H), 2.14-2.10 (d, J=13.7 Hz, 2H), 1.94-1.80 (m, 2H); LCMS: 470 [M+H].

E25.15. Synthesis of 9-chloro-1'-[(2R)-2-hydroxy-3-phenylpropyl]spiro[naphtho[1,2-b][1,4]oxathiine-2,4'-piperidine]-5,6-dione (Compound 194)

Compound 194 was synthesized using 9-chlorospiro[naphtho[1,2-b][1,4]oxathiine-2,4'-piperidine]-5,6-dione, (2R)-2-benzyloxirane and conditions outlined in procedure Y.

M.p.=92-93° C., 400 MHz $^1$H NMR (CDCl$_3$) δ: 8.00-7.97 (d, J=8.21 Hz, 1H), 7.668-7.663 (d, J=1.95 Hz, 1H), 7.46-7.43 (dd, J=1.95, 8.21 Hz, 1H), 7.33-7.23 (m, 5H), 4.09-3.94 (m, 1H), 3.33 (br s, 1H), 2.88-2.82 (m, 4H), 2.75-2.70 (m, 3H), 2.52-2.41 (m, 3H), 2.14-2.11 (d, J=12.9 Hz, 2H), 1.94-1.80 (m, 2H); LCMS: 470 [M+H].

E25.16. Synthesis of 1'-[(2R)-2-hydroxy-3-phenyl-propyl]spiro[naphtho[1,2-b][1,4]oxathiine-2,3'-piperidine]-5,6-dione (Compound 195)

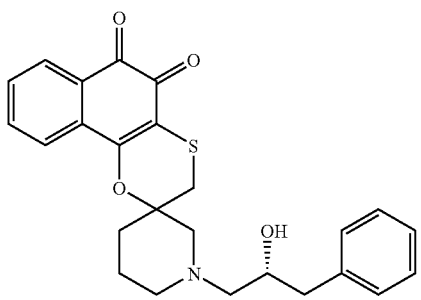

Compound 195 was synthesized using spiro[naphtho[1,2-b][1,4]oxathiine-2,3'-piperidine]-5,6-dione, (2R)-2-benzyloxirane and conditions outlined in procedure Y. M.p.=65-67° C., 400 MHz $^1$H NMR (CDCl$_3$) δ: 8.04-8.03 (br d, J=7.82 Hz, 1H), 7.73-7.60 (m, 2H), 7.49-7.44 (m, 1H), 7.31-7.18 (m, 5H), 3.95-3.91 (m, 1H), 3.18-2.91 (m, 3H), 2.78-2.53 (m, 5H), 2.45-2.33 (m, 2H), 2.03-1.70 (m, 4H); LCMS: 436 [M+H].

E25.17. Synthesis of 1'-[(2S)-2-hydroxy-3-phenyl-propyl]spiro[naphtho[1,2-b][1,4]oxathiine-2,3'-piperidine]-5,6-dione (Compound 196)

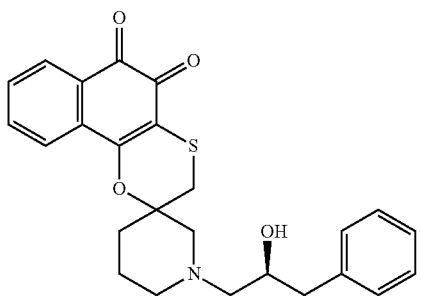

Compound 196 was synthesized using spiro[naphtho[1,2-b][1,4]oxathiine-2,3'-piperidine]-5,6-dione, (2S)-2-benzyloxirane and conditions outlined in procedure Y. M.p.=59-60° C., 400 MHz $^1$H NMR (CDCl$_3$) δ: 8.05-8.03 (br d, J=7.43 Hz, 1H), 7.73-7.70 (m, 1H), 7.65-7.60 (m, 1H), 7.52-7.44 (m, 1H), 7.31-7.18 (m, 5H), 3.95-3.91 (m, 1H), 3.18-2.91 (m, 3H), 2.78-2.53 (m, 5H), 2.45-2.33 (m, 2H), 2.03-1.71 (m, 4H); LCMS: 436 [M+H].

E25.18. Synthesis of 1'-[(2S)-3-(4-tert-butylphenoxy)-2-hydroxypropyl]spiro[naphtho[1,2-b][1,4]oxathiine-2,3'-piperidine]-5,6-dione (Compound 197)

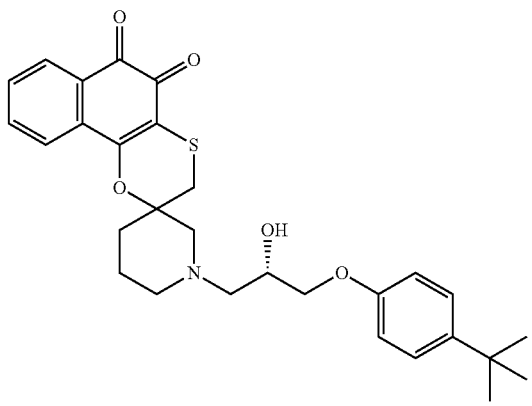

Compound 197 was synthesized using spiro[naphtho[1,2-b][1,4]oxathiine-2,3'-piperidine]-5,6-dione, (2S)-2-[(4-tert-butylphenoxy)methyl]oxathiine and conditions outlined in procedure Y. M.p.=90-92° C., 400 MHz $^1$H NMR (CDCl$_3$) δ: 8.04-8.02 (d, J=7.43 Hz, 1H), 7.75-7.73 (d, J=7.82 Hz, 1H), 7.63-7.58 (m, 1H), 7.48-7.44 (m, 1H), 7.31-7.21 (m, 2H), 6.83-6.80 (m, 1H), 4.13-4.07 (m, 1H), 3.15-2.96 (m, 3H), 2.82 (s, 1H), 2.65-2.50 (m, 5H), 2.04-1.73 (m, 4H), 1.29 (s, 9H); LCMS: 508 [M+H].

E25.19. Synthesis of 1'-{1-[(2S)-3-(4-tert-butylphenoxy)-2-hydroxypropyl]piperidine-4-yl}spiro[naphtho[1,2-b][1,4]oxathiine-2,4'-piperidine]-5,6-dione (Compound 198)

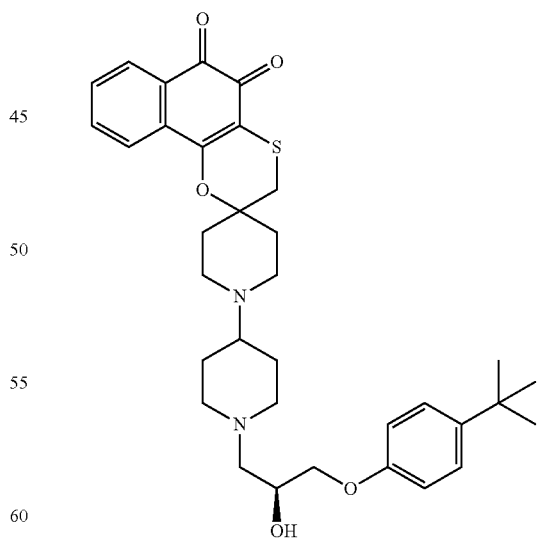

Compound 198 was synthesized using 1'-piperidin-4-yl-spiro[naphtho[1,2-b][1,4]oxathiine-2,4'-piperidine]-5,6-dione bis-hydrochloride, (2S)-2-[(4-tert-butyl phenoxy)methyl]oxirane, hunig's base and conditions outlined in procedure Y. M.p.=190-193° C.; 400 MHz $^1$H NMR (CDCl$_3$)

δ: 8.04-8.02 (m, 1H), 7.74-7.67 (m, 2H), 7.51-7.47 (m, 1H), 7.30-7.28 (m, 2H), 6.85-6.83 (m, 2H), 4.30 (t, 1H), 4.02-3.94 (m, 2H), 3.46-3.1 (m, 3H), 2.95-2.92 (m, 4H), 2.82 (d, 2H), 2.72 (t, 2H), 2.65 (bs, 2H), 2.45 (t, 1H), 2.19 (d, 2H), 1.98-1.93 (m, 6H), 1.29 (s, 9H); LCMS: 591 [M+H].

E25.20. Synthesis of 1'-[(2R)-3-(4-tert-butylphenoxy)-2-hydroxypropyl]-9-phenylspiro[naphtho[1,2-b][1,4]oxathiine-2,4'-piperidine]-5,6-dione (Compound 199)

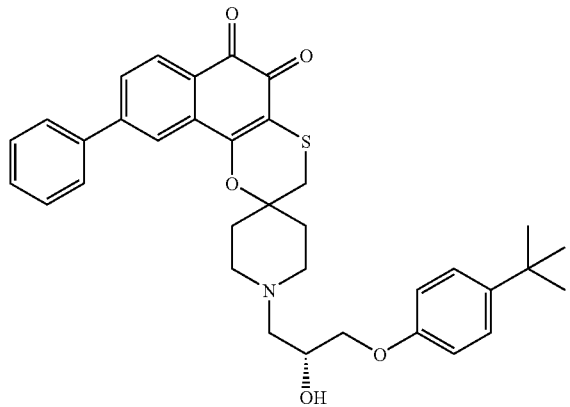

Compound 199 was synthesized using 9-phenyl-5,6-dihydro-1'H-spiro[naphtho[1,2-b][1,4]oxathiine-2,4'-piperidine]-5,6-dione, (2R)-2-[(4-tert-butylphenoxy)methyl]oxirane, hunig's base and conditions outlined in procedure Y. M.p.=94-97° C.; 400 MHz $^1$H NMR (DMSO-$d_6$) δ: 8.01 (d, J=1.6 Hz, 1H), 7.97 (d, J=8.0 Hz, 1H), 7.88-7.85 (dd, 1H), 7.76 (d, J=7.6 Hz, 2H), 7.58-7.49 (m, 3H), 7.28-7.26 (m, 2H), 6.84 (d, J=8.8 Hz, 2H), 4.85 (s, 1H), 3.96-3.92 (m, 2H), 3.86-3.84 (m, 1H), 3.10 (s, 2H), 2.82 (t, 2H), 2.46 (d, 4H), 2.04 (d, 2H), 1.84 (t, 2H), 1.20 (s, 9H); LCMS: 584 [M+H].

E25.21. Synthesis of 1'-[(2S)-2-hydroxy-3-(2-methylphenoxy)propyl]spiro[naphtho[1,2-b][1,4]oxathiine-2,4'-piperidine]-5,6-dione (Compound 200)

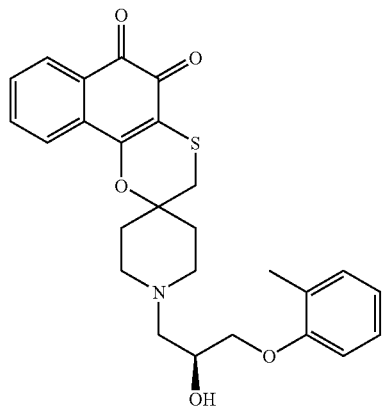

Compound 200 was synthesized using spiro[naphtha[1,2-b][1,4]oxathiine-2,4'-piperidine]-5,6-dione, (2S)-2-[(2-methylphenoxy)methyl]oxirane and conditions outlined in procedure Y. M.p.=197-199° C.; 400 MHz $^1$H NMR (CDCl$_3$) δ: 8.05 (dd, J=1.2 and 7.6 Hz, 1H), 7.77 (dd, J=0.8 and 7.6 Hz, 1H), 7.67 (dt, J=1.6 and 8.0 Hz, 1H), 7.48 (dt, J=1.2 and 7.6 Hz, 1H), 7.17-7.13 (m, 2H), 6.90-6.82 (m, 2H), 4.20-4.14 (m, 1H), 4.06-3.98 (m, 2H), 3.00-2.95 (m, 4H), 2.84-2.75 (m, 2H), 2.73-2.66 (m, 2H), 2.55 (dt, J=2.4 and 11.2 Hz, 1H), 2.24 (s, 3H), 2.20-2.12 (m, 2H), 1.97-1.84 (m, 2H); LCMS: 466 [M+H].

E25.22. Synthesis of 1'-[(2R)-3-(4-tert-butylphenoxy)-2-hydroxypropyl]-8-methoxyspiro[naphtho[1,2-b][1,4]oxathiine-2,4'-piperidine]-5,6-dione (Compound 201)

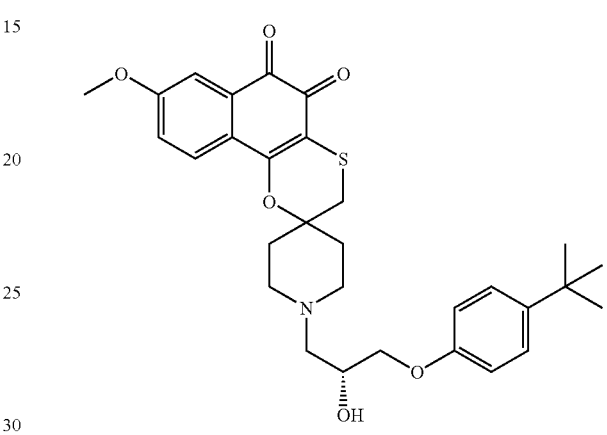

Compound 201 was synthesized using 8-methoxyspiro[naphtho[1,2-b][1,4]oxathiine-2,4'-piperidine]-5,6-dione, (2R)-2-[(4-tert-butylphenoxy)methyl]oxirane and conditions outlined in procedure Y. M.p.=188-190° C.; 400 MHz $^1$H NMR (DMSO-$d_6$) δ: 7.73 (d, J=8.6 Hz, 1H), 7.38 (d, J=7.6 Hz, 1H), 7.34 (d, J=2.8 Hz, 1H), 7.31 (d, J=3.0 Hz, 1H), 7.28 (d, J=8.0 Hz, 2H), 6.85 (d, J=9.0 Hz, 1H), 4.86 (d, J=4.7 Hz, 1H), 4.00-3.81 (m, 1H), 3.87 (s, 3H), 3.05 (s, 2H), 2.86-2.73 (m, 2H), 2.54-2.38 (m, 2H), 2.02-1.95 (m, 2H), 1.86-1.74 (m, 2H), 1.25 (s, 9H). LCMS: 538 [M+H].

E25.23. Synthesis of 1'-[(2S)-3-(4-tert-butylphenoxy)-2-hydroxypropyl]-8-methoxyspiro[naphtho[1,2-b][1,4]oxathiine-2,4'-piperidine]-5,6-dione (Compound 202)

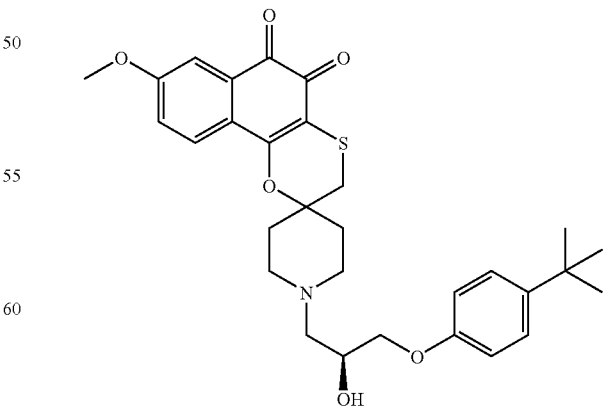

Compound 202 was synthesized using 8-methoxyspiro[naphtho[1,2-b][1,4]oxathiine-2,4'-piperidine]-5,6-dione, (2S)-2-[(4-tert-butylphenoxy)methyl]oxirane and conditions outlined in procedure Y. M.p.=188-190° C.; 400 MHz $^1$H NMR (DMSO-d$_6$) δ: 7.73 (d, J=8.6 Hz, 1H), 7.38 (d, J=7.6 Hz, 1H), 7.34 (d, J=2.8 Hz, 1H), 7.31 (d, J=3.0 Hz, 1H), 7.28 (d, J=8.0 Hz, 2H), 6.85 (d, J=9.0 Hz, 1H), 4.86 (d, J=4.7 Hz, 1H), 4.00-3.81 (m, 1H), 3.87 (s, 3H), 3.05 (s, 2H), 2.86-2.73 (m, 2H), 2.54-2.38 (m, 2H), 2.02-1.95 (m, 2H), 1.86-1.74 (m, 2H), 1.25 (s, 9H). LCMS: 538 [M+H].

E25.24. Synthesis of 1'-[(2S)-2-hydroxy-3-phenylpropyl]-8-methoxyspiro[naphtho[1,2-b][1,4]oxathiine-2,4'-piperidine]-5,6-dione (Compound 203)

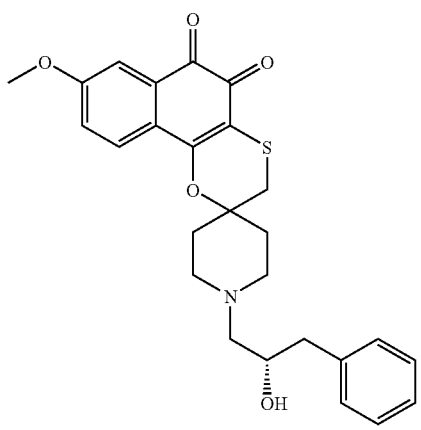

Compound 203 was synthesized using 8-methoxyspiro[naphtho[1,2-b][1,4]oxathiine-2,4'-piperidine]-5,6-dione, (2S)-2-benzyloxirane and conditions outlined in procedure Y. M.p.=146-147° C.; 400 MHz $^1$H NMR (DMSO-d$_6$) δ: 7.73 (d, J=8.6 Hz, 1H), 7.38 (d, J=7.6 Hz, 1H), 7.34 (d, J=2.8 Hz, 1H), 7.31 (d, J=3.0 Hz, 1H), 7.28-7.12 (m, 4H), 4.43 (d, J=4.7 Hz, 1H), 3.84 (s, 3H), 3.03 (s, 2H), 2.80-2.68 (m, 2H), 2.58 (dd, J=7.4, 14.0 Hz, 1H), 2.47-2.26 (m, 3H), 1.99-1.90 (m, 2H), 1.87-1.72 (m, 2H). LCMS: 466 [M+H].

E25.25. Synthesis of 1'-[(2R)-2-hydroxy-3-phenylpropyl]-8-methoxyspiro[naphtho[1,2-b][1,4]oxathiine-2,4'-piperidine]-5,6-dione (Compound 204)

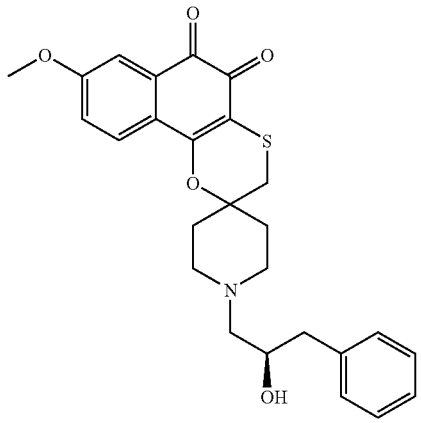

Compound 204 was synthesized using 8-methoxyspiro[naphtho[1,2-b][1,4]oxathiine-2,4'-piperidine]-5,6-dione, (2R)-2-benzyloxirane and conditions outlined in procedure Y. M.p.=145-147° C.; 400 MHz $^1$H NMR (DMSO-d$_6$) δ: 7.73 (d, J=8.6 Hz, 1H), 7.38 (d, J=7.6 Hz, 1H), 7.34 (d, J=2.8 Hz, 1H), 7.31 (d, J=3.0 Hz, 1H), 7.28-7.12 (m, 4H), 4.43 (d, J=4.7 Hz, 1H), 3.84 (s, 3H), 3.03 (s, 2H), 2.80-2.68 (m, 2H), 2.58 (dd, J=7.4, 14.0 Hz, 1H), 2.47-2.26 (m, 3H), 1.99-1.90 (m, 2H), 1.87-1.72 (m, 2H). LCMS: 466 [M+H].

E25.26. Synthesis of 1'-[(2S)-3-(4-chlorophenoxy)-2-hydroxypropyl]-8-methoxyspiro[naphtho[1,2-b][1,4]oxathiine-2,4'-piperidine]-5,6-dione (Compound 205)

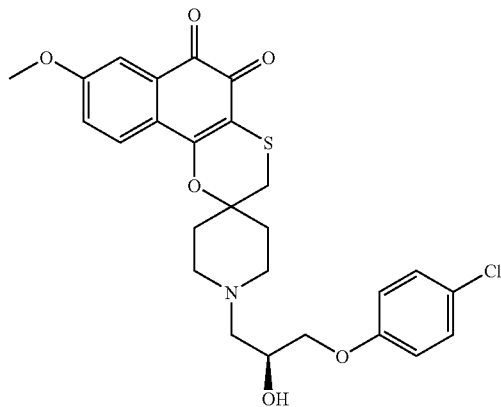

Compound 205 was synthesized using 8-methoxyspiro[naphtho[1,2-b][1,4]oxathiine-2,4'-piperidine]-5,6-dione, (2S)-2-[(4-chlorophenoxy)methyl]oxirane and conditions outlined in procedure Y. M.p.=189-191° C.; 400 MHz $^1$H NMR (DMSO-d$_6$) δ: 7.73 (d, J=8.6 Hz, 1H), 7.38 (d, J=7.6 Hz, 1H), 7.34 (d, J=2.8 Hz, 1H), 7.31 (dd, J=1.5, 6.8 Hz, 3H), 6.98 (d, J=3.5 Hz, 1H), 4.90 (d, J=4.7 Hz, 1H), 4.05-3.92 (m, 2H), 3.87 (s, 3H), 3.05 (s, 2H), 2.86-2.74 (m, 2H), 2.55-2.38 (m, 4H), 2.01-1.93 (m, 2H), 1.86-1.73 (m, 2H). LCMS: 516 [M+H].

E25.27. Synthesis of 1'-[(2S)-3-(4-fluorophenoxy)-2-hydroxypropyl]-8-methoxyspiro[naphtho[1,2-b][1,4]oxathiine-2,4'-piperidine]-5,6-dione (Compound 206)

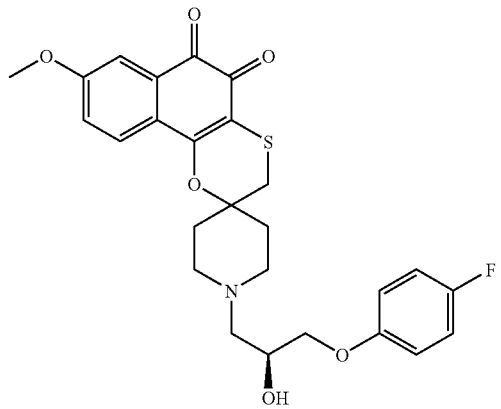

Compound 206 was synthesized using 8-methoxyspiro[naphtho[1,2-b][1,4]oxathiine-2,4'-piperidine]-5,6-dione, (2S)-2-[(4-fluorophenoxy)methyl]oxirane and conditions outlined in procedure Y. M.p.=189-191° C.; 400 MHz $^1$H NMR (DMSO-d$_6$) δ: 7.73 (d, J=8.6 Hz, 1H), 7.38 (d, J=7.6 Hz, 1H), 7.34 (d, J=2.8 Hz, 1H), 7.31 (dd, J=1.5, 6.8 Hz, 3H), 6.98 (d, J=3.5 Hz, 1H), 4.90 (d, J=4.7 Hz, 1H), 4.05-3.92 (m, 2H), 3.87 (s, 3H), 3.06 (s, 2H), 2.87-2.72 (m, 2H), 2.57-2.32 (m, 4H), 2.01-1.90 (m, 2H), 1.86-1.73 (m, 2H). LCMS: 500 [M+H].

E25.28. Synthesis of 1'-[(2S)-3-(4-ethylphenoxy)-2-hydroxypropyl]spiro[naphtho[1,2-b][1,4]oxathiine-2,4'-piperidine]-5,6-dione (Compound 207)

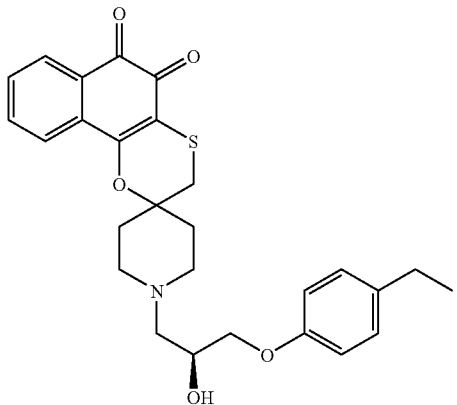

Compound 207 was synthesized using spiro[naphtho[1,2-b][1,4]oxathiine-2,4'-piperidine]-5,6-dione, (2S)-2-[(4-ethylphenoxy)methyl]oxirane and conditions outlined in procedure Y. M.p.=137-138° C.; 400 MHz $^1$H NMR (DMSO-d$_6$) δ: 7.90 (d, 1H, J=7.8 Hz), 7.82-7.78 (m, 2H), 7.57 (dt, 1H, J=2.0, 6.8 Hz), 7.10 (d, 2H, J=5.6 Hz), 6.85 (d, 2H, J=8.2 Hz), 4.86 (bs, 1H), 4.03-3.80 (m, 3H), 3.07 (s, 2H), 2.88-2.74 (m, 2H), 2.58-2.41 (m, 2H), 2.02-1.94 (m, 2H), 1.88-1.78 (m, 2H), 1.14 (t, J=7.9 Hz, 3H). LCMS: 480 [M+H].

E25.29. Synthesis of 1'-[(2R)-2-hydroxy-3-phenylpropyl]-9-methoxyspiro[naphtho[1,2-b][1,4]oxathiine-2,4'-piperidine]-5,6-dione (Compound 208)

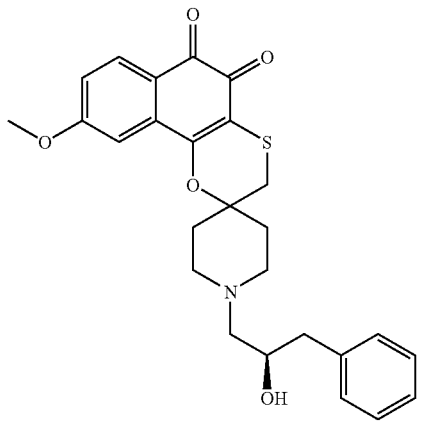

Compound 208 was synthesized using 9-methoxyspiro[naphtho[1,2-b][1,4]oxathiine-2,4'-piperidine]-5,6-dione, (2R)-2-benzyloxirane using conditions outlined in procedure Y. M.p.=106° C.; 400 MHz $^1$H NMR (DMSO-d$_6$) δ: 7.88 (d, J=8.8 Hz, 1H), 7.08-7.28 (m, 7H), 4.50 (brs, 1H), 3.93 (brs, 4H), 3.07 (s, 2H), 2.76 (M, 4H), 2.60 (m, 2H), 2.33 (m, 2H), 1.95 (m, 2H), 1.83 (m, 2H); LCMS: 466 [M+H];

E25.30. Synthesis of 1'-[(2S)-2-hydroxy-3-phenylpropyl]-9-methoxyspiro[naphtho[1,2-b][1,4]oxathiine-2,4'-piperidine]-5,6-dione (Compound 209)

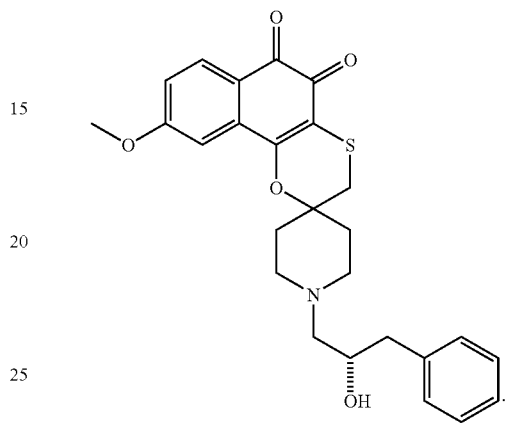

Compound 209 was synthesized using 9-methoxyspiro[naphtho[1,2-b][1,4]oxathiine-2,4'-piperidine]-5,6-dione (2S)-2-benzyloxirane following conditions outlined in procedure Y. M.p.=110° C.; 400 MHz $^1$H NMR (DMSO-d$_6$) δ: 7.92 (d, J=8.8 Hz, 1H), 7.21-7.31 (m, 6H), 7.11 (m, 1H), 4.10 (m, 1H), 3.92 (s, 3H), 3.15 (s, 2H), 3.10 (s, 2H), 2.76 (m, 4H), 2.60 (m, 2H), 2.22 (m, 2H), 1.95 (m, 2H); LCMS: 466 [M+H].

E25.31. Synthesis of 1'-[(2S)-3-(4-chlorophenoxy)-2-hydroxypropyl]-9-methoxyspiro[naphtho[1,2-b][1,4]oxathiine-2,4'-piperidine]-5,6-dione (Compound 210)

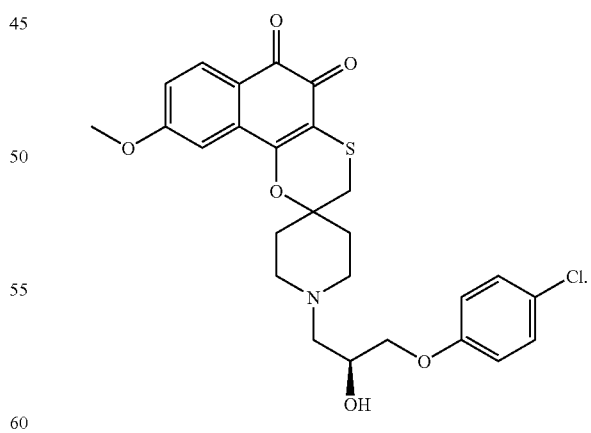

Compound 210 was synthesized using 9-methoxyspiro[naphtho[1,2-b][1,4]oxathiine-2,4'-piperidine]-5,6-dione, (2S)-2-[(4-chlorophenoxy)methyl]oxirane and conditions outlined in procedure Y. M.p.=109-110° C.; 400 MHz $^1$H NMR (DMSO-d$_6$) δ: 7.88 (d, J=8.8 Hz, 1H), 7.32 (d, J=8.8 Hz, 2H), 7.21 (brs, 1H), 7.10 (dd, 1H), 6.97 (d, J=9.2 Hz, 2H), 4.84 (s, 1H), 3.98 (brm, 6H), 3.07 (s, 2H), 2.80 (m, 2H), 2.41 (m, 4H), 1.99 (m, 2H), 1.82 (m, 2H); LCMS: 516 [M+H].

E25.32. Synthesis of 1'-[(2S)-3-(4-fluorophenoxy)-2-hydroxypropyl]-9-methoxyspiro[naphtho[1,2-b][1,4]oxathiine-2,4'-piperidine]-5,6-dione (Compound 211)

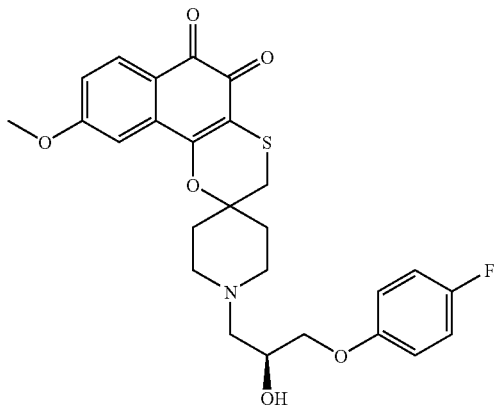

Compound 211 vas synthesized using 9-methoxyspiro[naphtho[1,2-b][1,4]oxathiine-2,4'-piperidine]-5,6-dione, (2S)-2-[(4-fluorophenoxy)methyl]oxirane and conditions outlined in procedure Y. M.p.=80-81° C.; 400 MHz $^1$H NMR (DMSO-$d_6$) δ: 7.88 (d, J=8.8 Hz, 1H), 7.32 (d, J=8.8 Hz, 1H), 7.09 (m, 3H), 6.95 (m, 2H), 4.85 (s, 1H), 3.98 (brm, 6H), 3.07 (s, 2H), 2.80 (m, 2H), 2.41 (m, 4H), 1.99 (m, 2H), 1.80 (m, 2H); LCMS: 500 [M+H].

E25.33. Synthesis of 1'-[(2S)-3-(4-tert-butylphenoxy)-2-hydroxypropyl]-9-phenylspiro[naphtho[1,2-b][1,4]oxathiine-2,4'-piperidine]-5,6-dione (Compound 212)

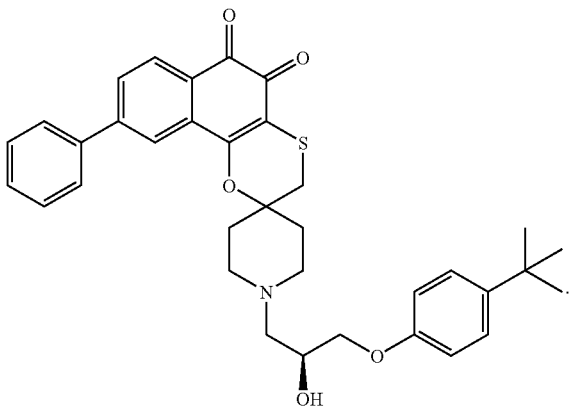

Compound 212 was synthesized using 9-phenylspiro[naphtho[1,2-b][1,4]oxathiine-2,4'-piperidine]-5,6-dione, (2S)-2-[(4-tert-butylphenoxy)methyl]oxirane and conditions outlined in procedure Y. M.p.=151-152° C.; 400 MHz $^1$H NMR (DMSO $d_6$) δ: 7.98 (m, 2H), 7.86 (d, J=7.6 Hz, 1H), 7.76 (d, J=8.0 Hz, 2H), 7.53 (m, 3H), 7.28 (m, 2H), 6.85 (m, 2H), 4.85 (brs, 1H), 3.98 (brm, 3H), 3.10 (s, 2H), 2.82 (m, 2H), 2.44 (m, 4H), 2.0 (m, 2H), 1.80 (m, 2H), 1.20 (s, 9H); LCMS: 584 [M+H].

E25.34. Synthesis of 1'-[(2R)-3-(4-chlorophenoxy)-2-hydroxypropyl]-9-phenylspiro[naphtho[1,2-b][1,4]oxathiine-2,4'-piperidine]-5,6-dione (Compound 213)

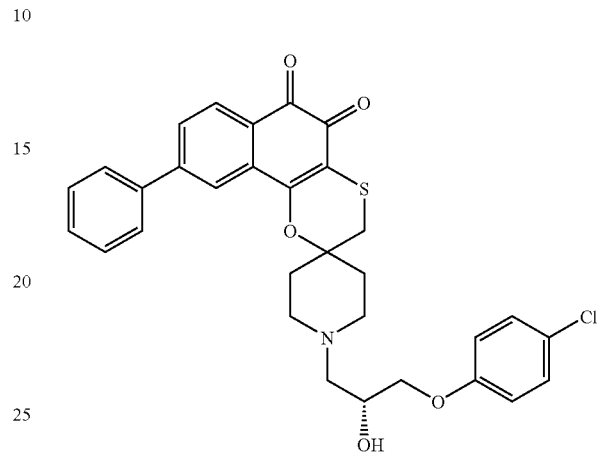

Compound 213 was synthesized using 9-phenylspiro[naphtho[1,2-b][1,4]oxathiine-2,4'-piperidine]-5,6-dione and (2R)-2-[(4-chlorophenoxy)methyl]oxirane using conditions outlined in procedure Y. M.p.=111-112° C.; 400 MHz $^1$H NMR (DMSO-$d_6$) δ: 7.96 (brs, 2H), 7.83 (d, J=8.0 Hz, 1H), 7.73 (d, J=8 Hz, 2H), 7.53 (t, J=7.2 Hz, 2H), 7.47 (m 1H), 7.28 (m, 2H), 6.92 (m, 2H), 4.88 (brs, 1H), 3.95 (brm, 2H), 3.84 (t, 8.8 Hz, 1H), 3.07 (s, 2H), 2.80 (m, 2H), 2.41 (m, 4H), 1.98 (m, 2H), 1.80 (m, 2H); LCMS: 562 [M+H].

E25.35. Synthesis of 1'-[(2S)-3-(4-tert-butylphenoxy)-2-hydroxypropyl]-9-morpholin-4-ylspiro[naphtho[1,2-b][1,4]oxathiine-2,4'-piperidine]-5,6-dione (Compound 214)

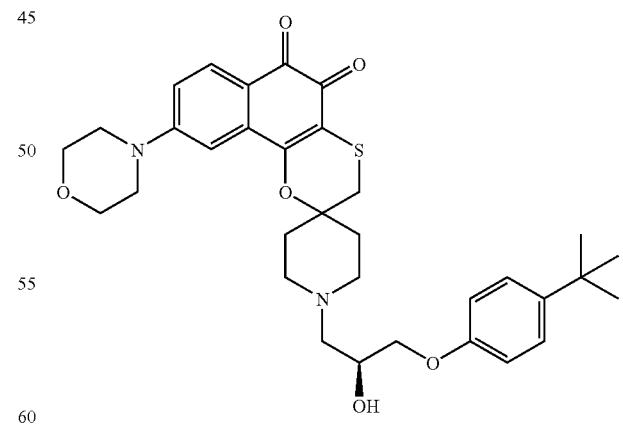

Compound 214 was synthesized using 9-morpholin-4-ylspiro[naphtho[1,2-b][1,4]oxathiine-2,4'-piperidine]-5,6-dione, (2S)-2-[(4-tert-butylphenoxy)methyl]oxirane and conditions outlined in procedure Y. M.p.=107-109° C.; 400 MHz $^1$H NMR (DMSO $d_6$) δ: 7.74 (d, J=8.0 Hz, 1H), 7.25 (d, J=8.8 Hz, 2H), 7.18 (brs, 1H), 7.0 (d, J=8.8 Hz, 1H), 6.83 (d, J=8.4

Hz, 2H), 4.85 (brs, 1H), 3.91 (m, 2H), 3.82 (m, 1H), 3.74 (m, 4H), 3.43 (m, 4H), 3.05 (s, 2H), 2.76 (m, 2H), 2.43 (m, 4H), 1.97 (m, 2H), 1.78 (m, 2H), 1.22 (s, 9H); LCMS: 593 [M+H].

E25.36. Synthesis of methyl (4-{[(2R)-3-(5,6-dioxo-5,6-dihydro-1'H-spiro[naphtho[1,2-b][1,4]oxathiine-2,4'-piperidine]-1'-yl)-2-hydroxypropyl]oxy}phenyl)acetate (Compound 215)

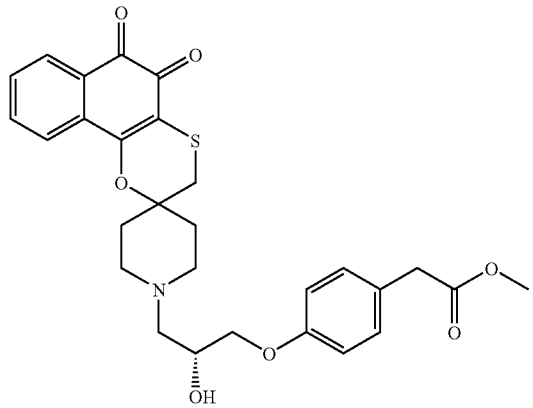

Compound 215 was synthesized using spiro[naphtho[1,2-b][1,4]oxathiine-2,4'-piperidine]-5,6-dione, methyl {4-[(2R)-oxiran-2-ylmethoxy]phenyl}acetate and conditions outlined in procedure Y. M.p.=122-124° C.; 400 MHz $^1$H NMR (CDCl$_3$) δ: 8.06 (dd, J=8.1, 0.7 Hz, 1H), 7.70 (d, J=7.7 Hz, 1H), 7.67 (td, J=7.7, 0.7 Hz, 1H), 7.50 (t, J=7.5 Hz, 1H), 7.20 (d, J=8.4 Hz, 2H), 6.89 (d, J=8.4 Hz, 2H), 4.2-4.1 (m, 1H), 4.0 (d, J=4.8 Hz, 2H), 3.69 (s, 2H), 3.57 (s, 2H), 3.0-2.9 (m, 1H), 2.95 (s, 3H), 2.84-2.74 (m, 2H), 2.69-2.62 (m, 2H), 2.54 (td, J=10.4, 1.8 Hz, 1H), 2.2-2.12 (m, 2H), 1.98-1.84 (m, 2H); LCMS: 524 [M+H].

E25.37. Synthesis of 1'-{(2S)-3-[(6-bromo-2-naphthyl)oxy]-2-hydroxypropyl}spiro[naphtho[1,2-b][1,4]oxathiine-2,4'-piperidine]-5,6-dione (Compound 216)

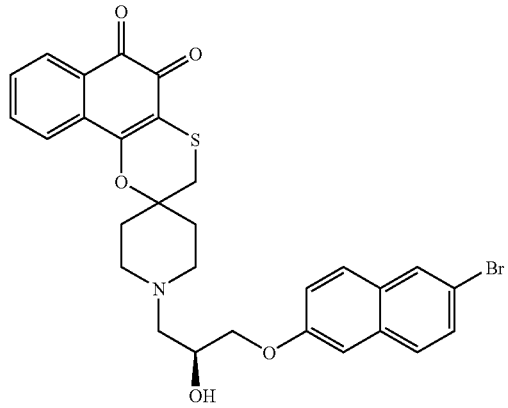

Compound 216 was synthesized using spiro[naphtho[1,2-b][1,4]oxathiine-2,4'-piperidine]-5,6-dione, (2S)-2-{[(6-bromo-2-naphthyl)oxy]methyl}oxirane and conditions outlined in procedure Y. M.p.=183-184° C.; 400 MHz $^1$H NMR (CDCl$_3$) δ: 8.06 (dd, J=7.7, 0.7 Hz, 1H), 7.92 (d, J=1.2 Hz, 1H), 7.77 (d, J=8.4 Hz, 1H), 7.69-7.64 (m, 2H), 7.60 (d J=8.8 Hz, 1H), 7.52-7.47 (m, 2H), 7.20 (dd, J=9.2, 2.6 Hz, 1H), 7.12 (d, J=2.6 Hz, 1H), 4.25-4.18 (m, 1H), 4.12 (d, J=4.8 Hz, 2H), 3.04-2.92 (m, 1H), 2.96 (s, 2H), 2.90-2.80 (m, 2H), 2.78-2.68 (m, 2H), 2.57 (t, J=10.4 Hz, 1H), 2.25-2.12 (m, 2H), 1.98-1.84 (m, 2H); LCMS: 580 [M+H].

E25.38. Synthesis of 9-bromo-1'-{(2S)-3-[(6-bromo-2-naphthyl)oxy]-2-hydroxypropyl}spiro[naphtho[1,2-b][1,4]oxathiine-2,4'-piperidine]-5,6-dione (Compound 217)

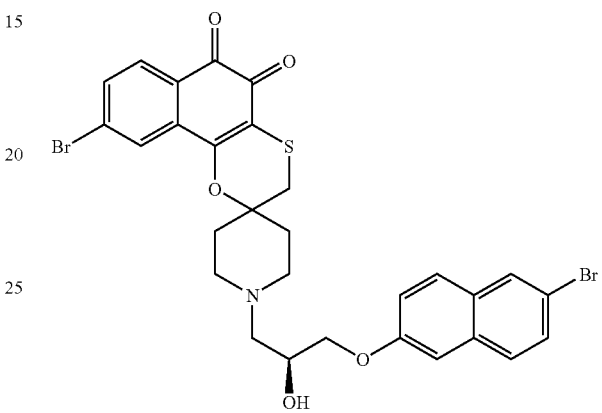

Compound 217 was synthesized using 9-bromospiro[naphtho[1,2-b][1,4]oxathiine-2,4'-piperidine]-5,6-dione, (2S)-2-{[(6-bromo-2-naphthyl)oxy]methyl}oxirane and conditions outlined in procedure Y. M.p.=104-105° C.: 400 MHz $^1$H NMR (CDCl$_3$) δ: 7.94-7.85 (m, 3H), 7.70-7.56 (m, 3H), 7.54-7.47 (m, 1H), 7.23-7.17 (m, 1H), 7.12 (d, J=2.6 Hz, 1H), 4.26-4.18 (m, 1H), 4.17-4.08 (m, 2H), 3.04-2.94 (m, 1H), 2.96 (s, 2H), 2.90-2.78 (m, 2H), 2.76-2.66 (m, 2H), 2.56 (t, J=11.4 Hz, 1H), 2.24-2.12 (m, 2H), 2.00-1.85 (m, 2H); LCMS: 660 [M+H].

E25.39. Synthesis of benzyl 4-{[(2S)-3-(5,6-dioxo-5,6-dihydro-1'H-spiro[naphtho[1,2-b][1,4]oxathiine-2,4'-piperidine]-1'-yl)-2-hydroxypropyl]oxy}benzoate (Compound 218)

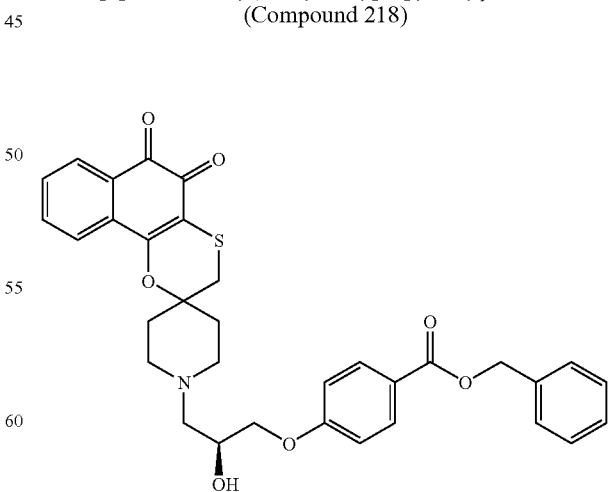

Compound 218 was synthesized using spiro[naphtho[1,2-b][1,4]oxathiine-2,4'-piperidine]-5,6-dione, benzyl 4-[(2S)-oxiran-2-ylmethoxy]benzoate and conditions outlined in procedure Y. M.p.=83-84° C.; 400 MHz $^1$H NMR (CDCl$_3$) δ:

8.08-8.00 (m, 3H), 7.76 (dd, J=7.8, 0.8 Hz, 1H), 7.66 (td, J=7.6, 1.2 Hz, 1H), 7.49 (td, J=7.6, 1.2 Hz, 1H), 7.46-7.32 (m, 5H), 6.97-6.92 (m, 2H), 5.34 (s, 2H), 4.20-4.12 (m, 1H), 4.06 (d, J=5.6 Hz, 2H), 3.02-2.92 (m, 1H), 2.95 (s, 2H), 2.84-2.76 (m, 2H), 2.72-2.62 (m, 2H), 2.55 (t, J=10.4 Hz, 1H), 2.22-2.12 (m, 2H), 1.98-1.82, (m, 2H); LCMS: 586 [M+H].

E25.40. Synthesis of 9-fluoro-1'-[(2R)-2-hydroxy-3-phenylpropyl]spiro[naphtho[1,2-b][1,4]oxathiine-2,4'-piperidine]-5,6-dione (Compound 219)

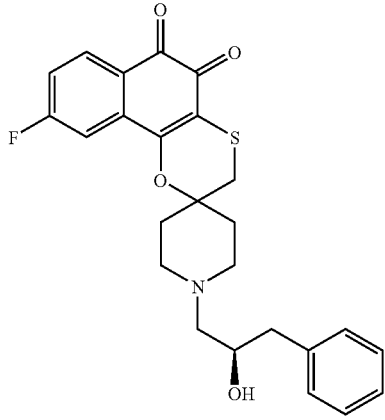

Compound 219 was synthesized using 9-fluorospiro[naphtho[1,2-b][1,4]oxathiine-2,4'-piperidin]-5,6-dione, (2R)-2-benzyloxirane and conditions outlined in procedure Y. M.p.=76-77° C.; 400 MHz $^1$H NMR (CDCl$_3$) δ: 8.08 (dd, J=8.6, 5.9 Hz, 1H), 7.37 (dd, J=9.4, 2.7 Hz, 1H), 7.34-7.28 (m, 2H), 7.27-7.21 (m, 3H), 7.14 (td, J=8.2, 2.7 Hz, 1H), 4.04-3.95 (m, 1H), 2.98-2.82 (m, 2H), 2.93 (s, 2H), 2.79-2.66 (m, 3H), 2.54-2.37 (111, 3H), 2.16-2.08 (11, 2H), 1.97-1.80 (m, 2H); LCMS: 454 [M+H].

E25.41. Synthesis of 9-fluoro-1'-[(2S)-2-hydroxy-3-phenylpropyl]spiro[naphtho[1,2-b][1,4]oxathiine-2,4'-piperidine]-5,6-dione (Compound 220)

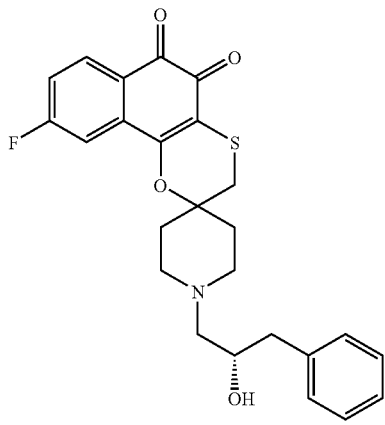

Compound 220 was synthesized using 9-fluorospiro[naphtho[1,2-b][1,4]oxathiine-2,4'-piperidine]-5,6-dione, (2S)-2-benzyloxirane and conditions outlined in procedure Y. M.p.=77-79° C.; 400 MHz $^1$H NMR (CDCl$_3$) δ: 8.08 (dd, J=8.6, 5.9 Hz, 1H), 7.37 (dd, J=9.4, 2.7 Hz, 1H), 7.34-7.28 (m, 2H), 7.27-7.21 (m, 3H), 7.14 (td, J=8.2, 2.7 Hz, 1H), 4.04-3.95 (m, 1H), 2.98-2.82 (m, 2H), 2.93 (s, 2H), 2.79-2.66 (m, 3H), 2.54-2.37 (m, 3H), 2.16-2.08 (m, 2H), 1.97-1.80 (m, 2H); LCMS: 454 [M+H].

E25.42. Synthesis of 1'-[(2S)-2-hydroxy-3-(2-naphthyloxy)propyl]spiro[naphtho[1,2-b][1,4]oxathiine-2,4'-piperidine]-5,6-dione (Compound 221)

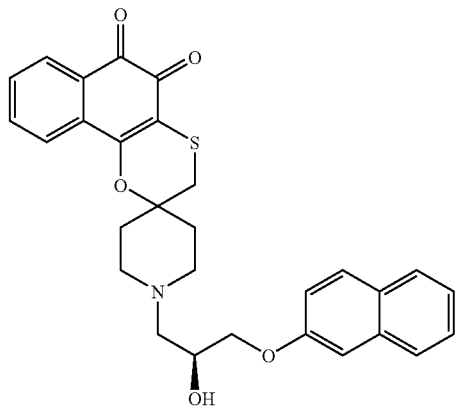

Compound 221 was synthesized using spiro[naphtho[1,2-b][1,4]oxathiine-2,4'-piperidine]-5,6-dione, (2S)-2-[(2-naphthyloxy)methyl]oxathiine and conditions outlined in procedure Y. M.p.=164-167° C., (DMSO-d$_6$) δ: 7.91-7.87 (m, 1H), 7.84-7.78 (m, 5H), 7.6-7.52 (m, 1H), 7.48-7.4 (m, 1H), 7.38-7.3 (m, 2H), 7.2-7.14 (m, 1H), 5.0-4.93 (m, 1H), 4.2-3.97 (m, 3H), 3.07 (s, 2H), 2.93-2.76 (m, 2H), 2.63-2.4 (m, 4H), 2.06-1.93 (m, 2H), 1.9-1.78 (m, 2H); LCMS=502 [M+H].

E25.43. Synthesis of 9-bromo-1'-[(2R)-2-hydroxy-3-phenylpropyl]spiro[naphtho[1,2-b][1,4]oxathiine-2,4'-piperidine]-5,6-dione (Compound 222)

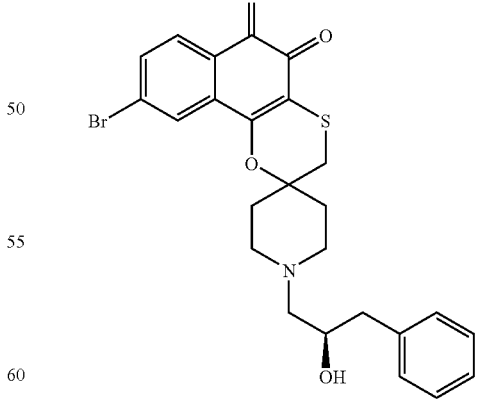

Compound 222 was synthesized using 9-bromospiro[naphtho[1,2-b][1,4]oxathiine-2,4'-piperidine]-5,6-dione, (2R)-2-benzyloxirane and conditions outlined in procedure Y. M.p.=82-84° C., (DMSO-d$_6$) δ: 7.88-7.72 (m, 3H), 7.3-7.1 (m, 5H), 4.46-4.4 (m, 1H), 3.9-3.8 (m, 1H), 3.08 (s, 2H), 2.82-2.67 (m, 3H), 2.63-2.55 (m, 1H), 2.4-2.25 (m, 4H), 2.06-1.93 (m, 2H), 1.9-1.78 (m, 2H); LCMS=514 [M+H].

E25.44. Synthesis of 9-bromo-1'-[(2R)-3-(4-tert-butylphenoxy)-2-hydroxypropyl]spiro[naphtho[1,2-b][1,4]oxathiine-2,4'-piperidine]-5,6-dione (Compound 223)

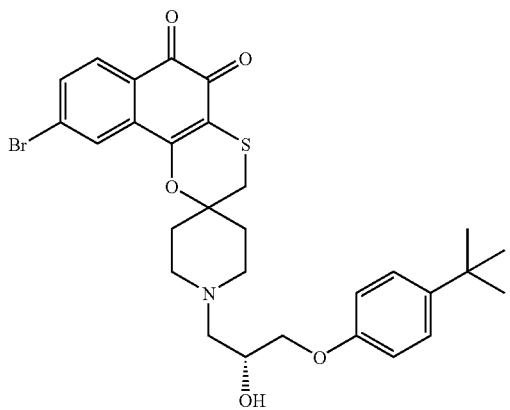

Compound 223 was synthesized using 9-bromospiro[naphtho[1,2-b][1,4]oxathiine-2,4-piperidine]-5,6-dione, (2R)-2-[(4-tert-butylphenoxy)methyl]oxathiine and conditions outlined in procedure Y. 400 MHz $^1$H NMR (DMSO) δ: 7.83 (s, 1H), 7.79 (m, 2H), 7.29 (d, 2H), 6.86 (d, 2H), 4.86 (br s, 1H), 3.99-3.94 (m, 2H), 3.89-3.86 (m, 1H), 3.19 (s, 2H), 2.87-2.72 (m, 2H), 2.56-2.50 (m, 2H), 2.47-2.35 (m, 2H), 2.04-1.96 (m, 2H), 1.87-1.78 (m, 2H), 1.25 (s, 9H); LCMS: 587 [M+H].

E25.45. Synthesis of 1'-[(2R)-2-hydroxy-3-(2-methylphenoxy)propyl]spiro[naphtho[1,2-b][1,4]oxathiine-2,4'-piperidine]-5,6-dione (Compound 224)

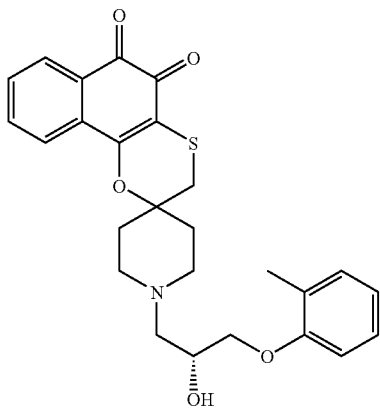

Compound 224 was synthesized using spiro[naphtha[1,2-b][1,4]oxathiine-2,4'-piperidine]-5,6-dione, (2R)-2-[(2-methylphenoxy)methyl]oxirane and conditions outlined in procedure Y. M.p.=191-193° C.; 400 MHz $^1$H NMR (CDCl$_3$) δ: 8.06 (d, J=8.0 Hz, 1H), 7.77 (d, J=8.0 Hz, 1H), 7.67 (m, 1H), 7.49 (t, 1H), 7.17-7.13 (m, 2H), 6.89-6.82 (m, 2H), 4.18-4.15 (m, 1H), 4.05-3.98 (m, 2H), 2.95 (s, 3H), 2.80-2.75 (m, 2H), 2.70-2.66 (m, 2H), 2.57-2.51 (m, 1H), 2.24 (s, 2H), 2.18-2.15 (m, 2H), 1.96-1.84 (m, 2H); LCMS: 466 [M+H].

Example 26

Procedure Z

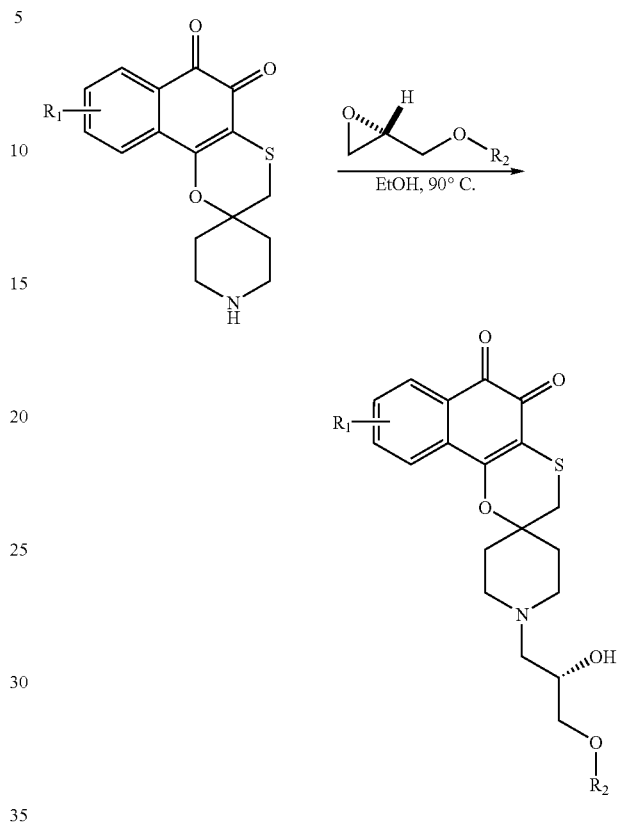

E26.1. Synthesis of 1'-[(2S)-3-(4-tert-butylphenoxy)-2-hydroxypropyl]spiro[naphtho[1,2-b][1,4]oxathiine-2,4'-piperidine]-5,6-dione (Compound 184)

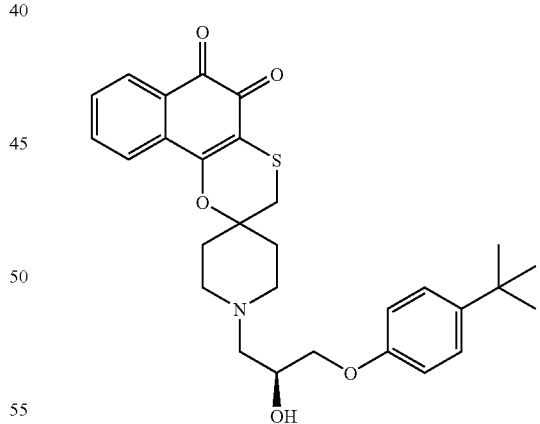

To a mixture of spiro[naphtho[1,2-b][1,4]oxathiine-2,4'-piperidine]-5,6-dione (10.0 g, 33.18 mmol) in absolute ethanol (100 mL) was added (2S)-2-[(4-tert-butylphenoxy)methyl]oxirane (8.9 g, 43.14 mmol). The reaction mixture was stirred at 90° C. for 15 h (sometimes the reaction is complete within 2-3 hours). The reaction mixture was cooled to room temperature the solvent was removed under reduced pressure. The crude product was purified by flash column chromatography (SiO$_2$, 10% EtOAc in dichloromethane to 50% EtOAc in dichloromethane) to give the desired product as a purple solid (8.1 g, 49%). M.p.=155-157° C.; 400 MHz $^1$H NMR (CDCl$_3$) δ: 8.1-8.03 (m, 1H), 7.8-7.74 (m, 1H), 7.7-7.6 (m, 1H), 7.55-7.45 (m, 1H), 7.35-7.28 (m, 2H), 6.9-6.8 (m, 2H), 4.10-4.17 (m, 1H), 4.0-3.93 (m, 2H), 2.99-2.95 (s, 3H), 2.86-2.74 (m, 2H), 2.7-2.64 (m, 2H), 2.6-2.51 (m, 1H), 2.22-2.13 (m, 2H), 1.98-1.84 (m, 2H), 1.3 (s, 9H); LCMS: 508 [M+H]; enantiomeric excess determined from chiral HPLC: 98%; Chiral HPLC R$_t$=50.98 min E26.2. Synthesis of 1'-[(2S)-3-(4-fluorophenoxy)-2-hydroxypropyl]-9-phenylspiro[naphtho[1,2-b][1,4]oxathiine-2,4'-piperidine]-5,6-dione (Compound 225)

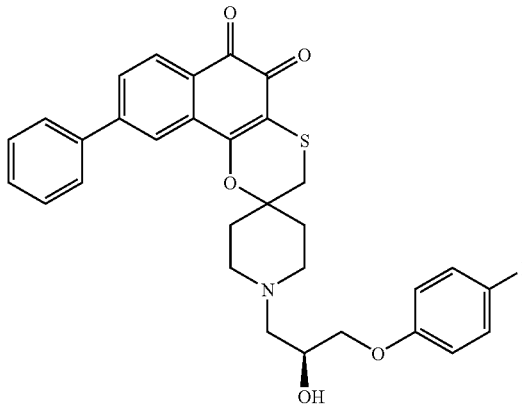

Compound 225 was synthesized using 9-phenylspiro[naphtho[1,2-b][1,4]oxathiine-2,4'-piperidine]-5,6-dione, (2S)-2-[(4-fluorophenoxy)methyl]oxirane and conditions outlined in procedure Z. M.p.=173-175° C.; 400 MHz $^1$H NMR (DMSO-d$_6$) δ: 8.01 (d, J=1.2 Hz, 1H), 7.98 (d, J=8.8 Hz, 1H), 7.87 (dd, J=1.6, 7.6 Hz, 1H), 7.76 (d, J=7.6 Hz, 2H), 7.57 (dd, J=7.6, 7.6 Hz, 2H), 7.52-7.47 (m, 1H), 7.10 (dd, J=8.8, 8.8 Hz, 2H), 6.94 (dd, J=4.4, 8.8 Hz, 2H), 4.88 (d, J=4.8 Hz, 1H), 3.97-3.95 (m, 2H), 3.87-3.82 (m, 1H), 3.11 (s, 2H), 2.87-2.78 (m, 2H), 2.54-2.39 (m, 4H), 2.03 (d, J=14.4 Hz, 2H), 1.87-1.81 (m, 2H); LCMS: 546 [M+H].

E26.3. Synthesis of 1'-[(2S)-3-(4-chlorophenoxy)-2-hydroxypropyl]-9-phenylspiro[naphtho[1,2-b][1,4]oxathiine-2,4'-piperidine]-5,6-dione (Compound 226)

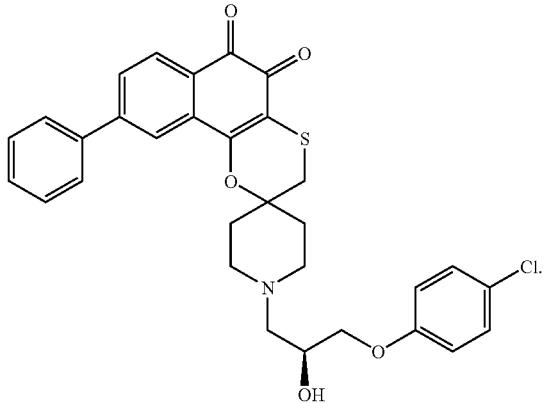

Compound 226 was synthesized using 9-phenylspiro[naphtho[1,2-b][1,4]oxathiine-2,4'-piperidine]-5,6-dione, (2S)-2-[(4-chlorophenoxy)methyl]oxirane and conditions outlined in procedure Z. M.p.=93-98° C.; 400 MHz $^1$H NMR (DMSO-d$_6$) δ: 8.01-7.97 (m, 2H), 7.87 (dd, J=1.6, 7.6 Hz, 1H), 7.77 (d, J=7.2 Hz, 2H), 7.59-7.47 (m, 3H), 7.31 (d, J=9.2 Hz, 2H), 6.96 (d, J=9.2 Hz, 2H), 4.90 (d, J=4.0 Hz, 1H), 4.04-3.90 (m, 2H), 3.90-3.84 (m, 1H), 3.11 (s, 2H), 2.88-2.72 (m, 2H), 2.52-2.38 (m, 4H), 2.03 (d, J=14.0 Hz, 2H), 1.88-1.80 (m, 2H); LCMS: 562 [M+H].

E26.4. Synthesis of 1'-[(2S)-3-(4-tert-butylphenoxy)-2-hydroxypropyl]-9-methoxyspiro[naphtho[1,2-b][1,4]oxathiine-2,4'-piperidine]-5,6-dione (Compound 227)

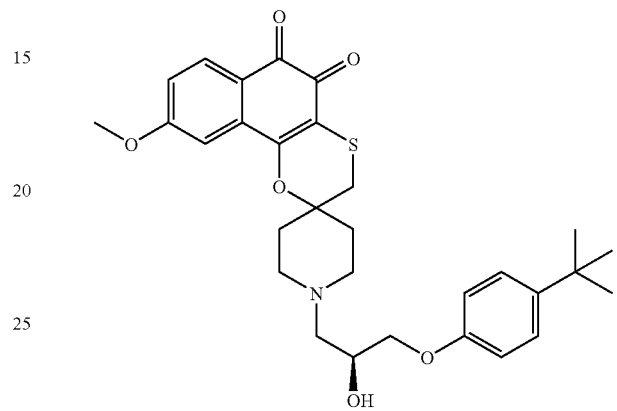

Compound 227 was synthesized using 9-methoxyspiro[naphtho[1,2-b][1,4]oxathiine-2,4'-piperidine]-5,6-dione, (2S)-2-[(4-tert-butylphenoxy)methyl]oxathiine and conditions outlined in procedure Z. Mp.=153-156° C.; 400 MHz $^1$H NMR (DMSO-d$_6$) δ: 7.90 (d, J=8.8 Hz, 1H), 7.28 (d, J=8.8 Hz, 2H), 7.22 (d, J=2.4 Hz, 1H), 7.11 (dd, J=2.4, 8.8 Hz, 1H), 6.85 (d, J=8.8 Hz, 2H), 4.85 (d, J=4.8 Hz, 1H), 3.96-3.92 (m, 2H), 3.92 (s, 3H), 3.86-3.81 (m, 1H), 3.07 (s, 2H), 2.81 (dd, J=10.8, 22 Hz, 2H), 2.54 (m, 1H), 2.45-2.39 (m, 3H), 1.98 (d, J=14.0 Hz, 2H), 1.84-1.76 (m, 2H), 1.25 (s, 9H); LCMS: 538 [M+H].

E26.5. Synthesis of 1'-[(2R)-3-(4-ethylphenoxy)-2-hydroxypropyl]spiro[naphtho[1,2-b][1,4]oxathiine-2,4'-piperidine]-5,6-dione (Compound 228)

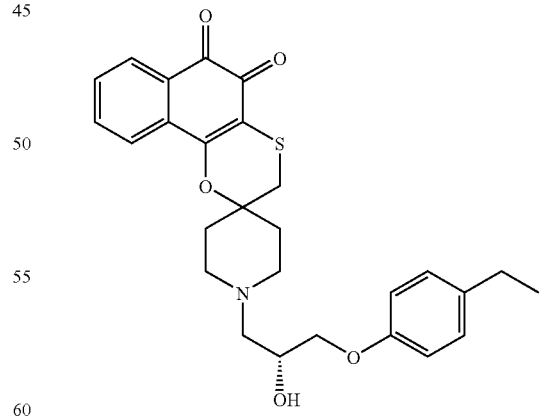

Compound 228 was synthesized using spiro[naphtho[1,2-b][1,4]oxathiine-2,4'-piperidine]-5,6-dione, (2R)-2-[(4-ethylphenoxy)methyl]oxirane and conditions outlined in procedure Z. M.p.=145-147° C.; 400 MHz $^1$H NMR (DMSO-d$_6$) δ: 7.90 (d, J=7.6 Hz, 1H), 7.81-7.76 (m, 2H), 7.59-7.54 (m, 1H), 7.10 (d, J=8.4 Hz, 2H), 6.87-6.82 (m, 2H), 4.85 (d, J=4.8 Hz, 1H), 3.99-3.92 (m, 2H), 3.86-3.81 (m, 1H), 3.07 (s, 2H), 2.85-2.75 (m, 2H), 2.55-2.41 (m, 6H), 1.98 (d, J=14.4 Hz, 2H), 1.85-1.77 (m, 2H), 1.14 (t, J=8.0 Hz, 3H); LCMS: 480 [M+H].

Example 27

Procedure AA

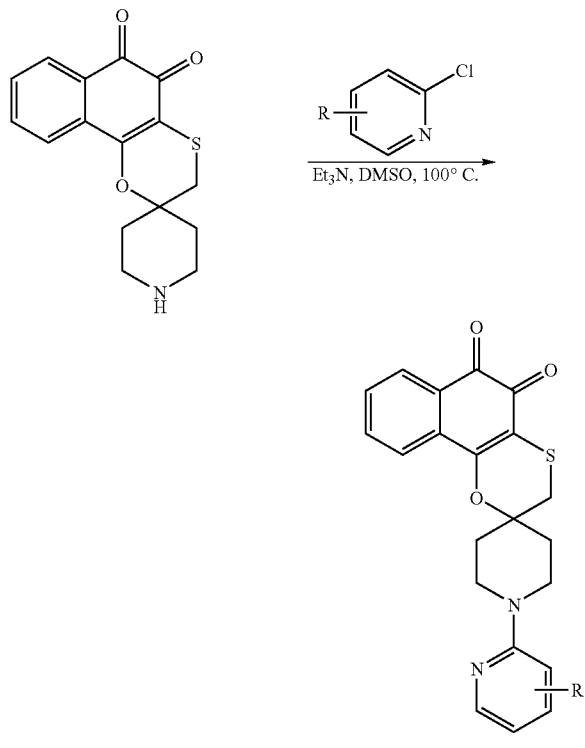

E27.1. Synthesis of 1'-pyrazin-2-ylspiro[naphtho[1,2-b][1,4]oxathiine-2,4'-piperidine]-5,6-dione (Compound 229)

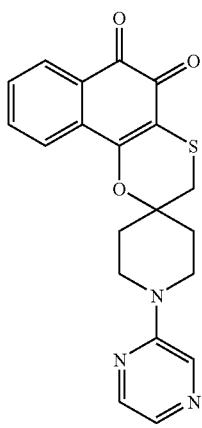

A mixture of spiro[naphtho[1,2-b][1,4]oxathiine-2,4'-piperidine]-5,6-dione (0.150 g, 0.50 mmol), 2-chloropyrazine (0.57 g, 1.67 mmol), triethylamine (0.1 mil, 0.72 mmol), and DMSO (50 ml) was stirred for three hours at 100° C. The crude reaction mixture was purified directly by reverse phase HPLC to give the product as a purple solid (0.014 g, 0.7%) MP=255-256° C.; 400 MHz $^1$H NMR (DMSO-$d_6$) δ: 8.41 (s, 1H), 8.10-8.07 (m, 1H), 7.91-7.81 (m, 3H), 7.76-7.70 (m, 1H), 7.58-7.52 (m, 1H), 4.28-4.22 (m, 2H), 3.39-3.28 (m, 2H), 3.12 (s, 2H), 2.11-2.04 (m, 2H), 1.88-1.79 (m, 2H); LCMS: 380 [M+H].

E27.2. Synthesis of 1'-(6-chloropyrimidin-4-yl)spiro[naphtho[2-b][1,4]oxathiine-2,4'-piperidine]-5,6-dione (Compound 230)

Compound 230 was synthesized using spiro[naphtho[1,2-b][1,4]oxathiine-2,4'-piperidine]-5,6-dione, 4,6-dichloropyrimidine and conditions outlined in procedure AA. M.p.=172-174° C.; 400 MHz $^1$H NMR (DMSO-$d_6$) δ: 8.25 (s, 1H), 7.91-7.86 (m, 2H), 7.76-7.70 (m, 1H), 7.58-7.53 (m, 1H), 7.08 (s, 1H), 3.42-3.33 (m, 4H), 3.10 (s, 2H), 2.09-2.04 (m, 2H), 1.85-1.76 (m, 2H); LCMS: 414 [M+H].

Example 28

Procedure AB

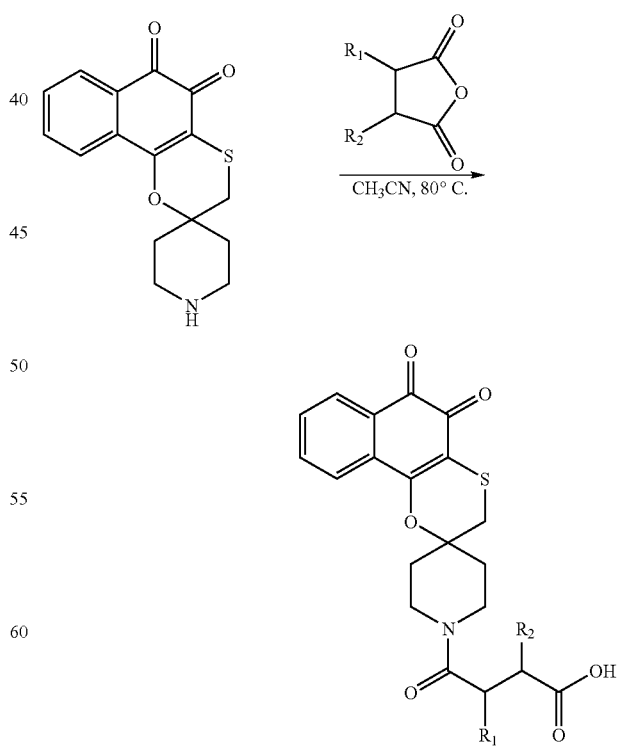

E28.1. Synthesis of 2-[(5,6-dioxo-5,6-dihydro-1'H-spiro[naphtho[1,2-b][1,4]oxathiine-2,4'-piperidin]-1'-yl)carbonyl]cyclohexanecarboxylic acid (Compound 231)

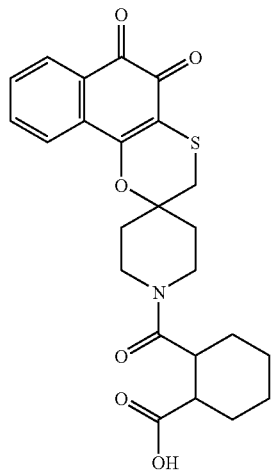

A mixture of spiro[naphtho[1,2-b][1,4]oxathiine-2,4'-piperidine]-5,6-dione (0.5 g, 1.66 mmol), hexahydro-2-benzofuran-1,3-dione (0.256 g, 1.66 mmol), and anhydrous acetonitrile (10 ml) was stirred for three hours at 80° C. The solvents were removed under vacuum and the crude product was purified by flash column chromatography (SiO$_2$, 20% EtOAc in DCM to 20% EtOAC and 2% MeOH in DCM) to afford the product as a purple solid (0.246 g, 33%). M.p.=214-220° C.; 400 MHz $^1$H NMR (DMSO-d$_6$) δ: 11.87 (s, 1H), 7.90-7.78 (m, 2H), 7.77-7.71 (m, 1H), 7.58-7.52 (m, 1H), 4.25-4.10 (m, 1H), 3.90-3.75 (m, 1H), 3.50-3.37 (m, 1H), 3.37-3.23 (m, 1H), 3.15-2.90 (m, 3H), 2.45-2.36 (m, 1H), 2.18-1.95 (m, 2H), 1.9-1.6 (m, 4H), 1.60-1.47 (m, 2H), 1.47-1.35 (m, 2H), 1.35-1.17 (m, 2H); LCMS: 456 [M+H].

Example 29

Procedure AC

E29.1. Synthesis of 1'-acetylspiro[naphtho[1,2-b][1,4]oxathiine-2,4'-piperidine]-5,6-dione (Compound 232)

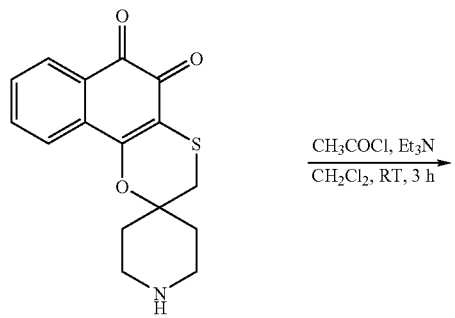

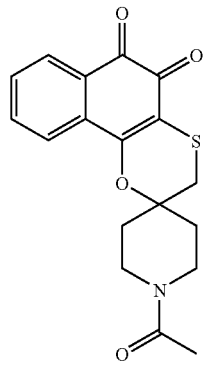

A mixture of spiro[naphtho[1,2-b][1,4]oxathiine-2,4'-piperidine]-5,6-dione (0.5 g, 1.66 mmol), acetyl chloride (0.118 ml, 1.67 mmol), triethylamine (1.2 ml, 8.61 mmol), and dichloromethane (50 ml) was stirred for three hours at room temperature. The reaction mixture was washed with 50 ml water. The organic extract was dried with Na$_2$SO$_4$ and concentrated under reduced pressure. The crude product was purified by flash column chromatography (SiO$_2$, 5% EtOAc in dichloromethane) to afford the product as a purple solid (0.327 g, 57%). M.p.=252-255° C.; 400 MHz $^1$H NMR (CDCl$_3$) δ: 8.09-8.06 (m, 1H), 7.75-7.72 (m, 1H), 7.69-7.64 (m, 1H), 7.54-7.48 (m, 1H), 4.59-4.52 (m, 1H), 3.82-3.68 (m, 1H), 3.55-3.46 (m, 1H), 3.22-3.12 (m, 1H), 3.0-2.91 (m, 2H), 2.26-2.18 (m, 2H), 2.18 (s, 3H), 1.82-1.72 (m, 2H); LCMS: 344 [M+H].

E29.2. Synthesis of 1'-isonicotinoylspiro[naphtho[1,2-b][1,4]oxathiine-2,4'-piperidine]-5,6-dione (Compound 57)

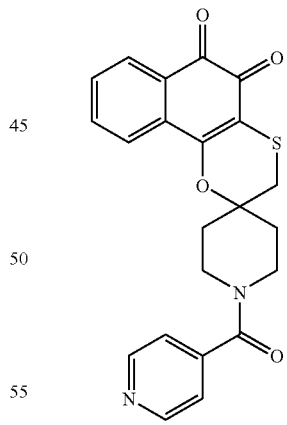

Compound 57 was synthesized using spiro[naphtho[1,2-b][1,4]oxathiine-2,4'-piperidine]-5,6-dione, isonicotinoyl chloride and conditions outlined in procedure AC. M.p.=267-269° C.; 400 MHz $^1$H NMR (CDCl$_3$) δ: 8.74-8.70 (m, 2H), 8.06-8.10 (m, 1H), 7.73-7.76 (m, 1H), 7.66-7.70 (m, 1H), 7.49-7.55 (m, 1H), 7.30-7.33 (m, 2H), 4.65-4.71 (m, 1H), 3.62-3.69 (m, 1H), 3.45-3.56 (m, 1H), 3.34-3.45 (m, 1H), 2.96-3.04 (m, 2H), 2.26-2.32 (m, 1H), 2.12-2.18 (m, 1H), 1.85-1.97 (m, 1H), 1.68-1.78 (m, 1H); LCMS: 407 [M+H].

Example 30

Procedure AD

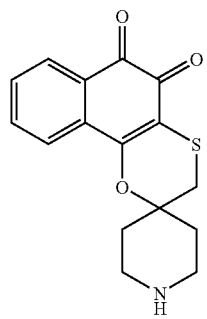 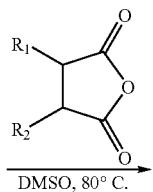

DMSO, 80° C.

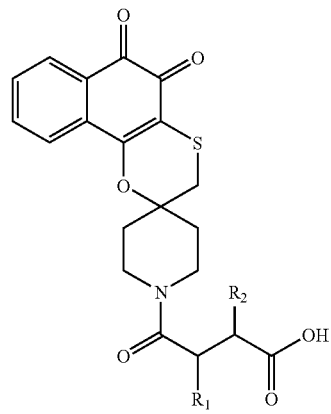

E30.1. Synthesis of 4-(5,6-dioxo-5,6-dihydro-1'H-spiro[naphtho[1,2-b][1,4]oxathiine-2,4'-piperidin]-1'-yl)-4-oxobutanoic acid (Compound 233)

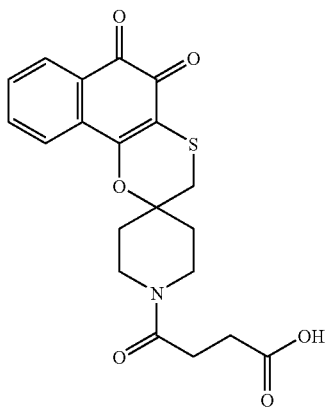

A mixture of spiro[naphtho[1,2-b][1,4]oxathiine-2,4'-piperidine]-5,6-dione (0.5 g, 1.66 mmol) and dihydrofuran-2,5-dione (0.167 ml, 1.67 mmol) and anhydrous DMSO (8 ml) was stirred for three hours at 80° C. To the reaction mixture was then added water (50 mL) and extracted with dichloromethane (2×50 mL). The organic extract was dried with sodium sulfate and concentrated under reduced pressure. The crude product was purified by flash column chromatography (SiO$_2$, 70% EtOAc in hexanes) to afford the product as a purple solid (0.057 g, 8.6%). M.p.=215-217° C.; 400 MHz $^1$H NMR (DMSO-d$_6$) δ: 12.02 (s, 1H), 7.90-7.87 (m, 1H), 7.85-7.82 (m, 1H), 7.76-7.71 (m, 1H), 7.58-7.53 (m, 1H), 4.25-4.20 (m, 1H), 3.87-3.81 (m, 1H), 3.44-3.36 (m, 1H), 3.10-3.00 (m, 3H), 2.60-2.55 (m, 2H), 2.45-2.41 (m, 2H), 2.07-1.96 (m, 2H), 1.84-1.77 (m, 1H), 1.70-1.61 (m, 1H); LCMS: 402 [M+H].

E30.2. Synthesis of {[2-(5,6-dioxo-5,6-dihydro-1'H-spiro[naphtho[1,2-b][1,4]oxathiine-2,4'-piperidine]-1'-yl)-2-oxoethyl]thio}acetic acid (Compound 234)

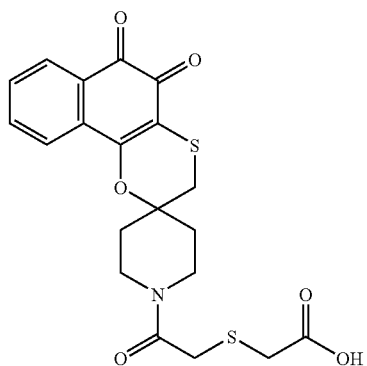

Compound 234 was synthesized using spiro[naphtho[1,2-b][1,4]oxathiine-2,4'-piperidine]-5,6-dione, 1,4-oxathiane-2,6-dione and conditions outlined in procedure AD. LCMS: 434 [M+H]; R$_t$=0.98 min.

E30.3. Synthesis of 2-[(5,6-dioxo-5,6-dihydro-1'H-spiro[naphtho[1,2-b][1,4]oxathiine-2,4'-piperidin]-1'-yl)carbonyl]cyclobutanecarboxylic acid (Compound 235)

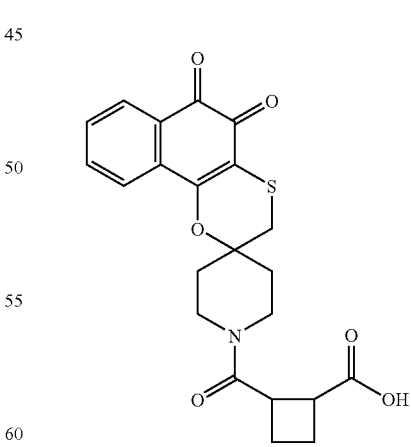

Compound 235 was synthesized using spiro[naphtho[1,2-b][1,4]oxathiine-2,4'-piperidine]-5,6-dione, 3-oxabicyclo[3.2.0]heptane-2,4-dione and conditions outlined in procedure AD. LCMS: 428 [M+H]; R$_t$=0.97 min.

E30.4. Synthesis of 3-[(5,6-dioxo-5,6-dihydro-1'H-spiro[naphtho[1,2-b][1,4]oxathiine-2,4'-piperidin]-1'-yl)carbonyl]pyrazine-2-carboxylic acid (Compound 236)

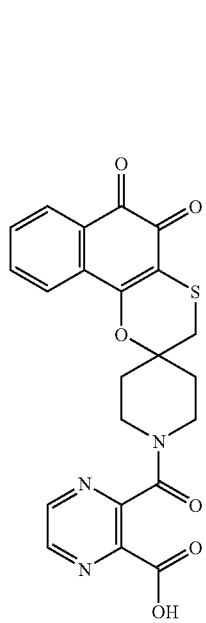

Compound 236 was synthesized using spiro[naphtho[1,2-b][1,4]oxathiine-2,4'-piperidine]-5,6-dione, furo[3,4-b]pyrazine-5,7-dione and conditions outlined in procedure AD. LCMS: 452 [M+H]; $R_t$=0.90 min.

E30.5. Synthesis of 3-[(5,6-dioxo-5,6-dihydro-1'H-spiro[naphtho[1,2-b][1,4]oxathiine-2,4'-piperidin]-1'-yl)carbonyl]isonicotinic acid (Compound 237)

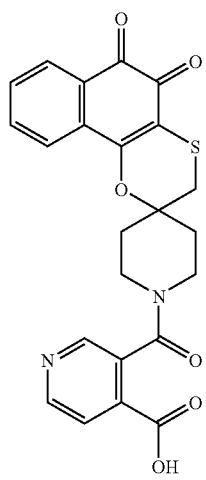

Compound 237 was synthesized using spiro[naphtho[1,2-b][1,4]oxathiine-2,4'-piperidine]-5,6-dione, furo[3,4-c]pyridine-1,3-dione and conditions outlined in procedure AD. LCMS: 451 [M+H]; $R_t$=0.89 min.

Example 31

General Procedure AE

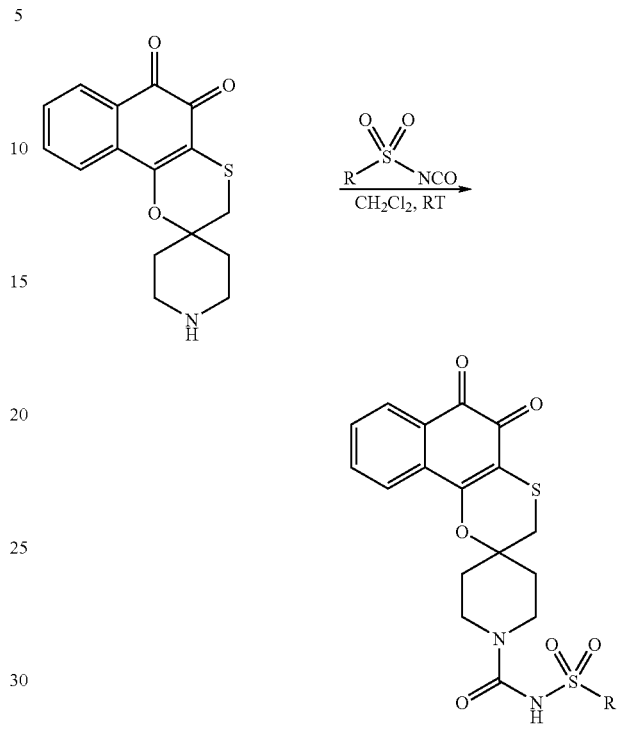

E31.1. Synthesis of N-[(4-chlorophenyl)sulfonyl]-5,6-dioxo-5,6-dihydro-1'H-spiro[naphtho[1,2-b][1,4]oxathiine-2,4'-piperidine]-1'-carboxamide (Compound 238)

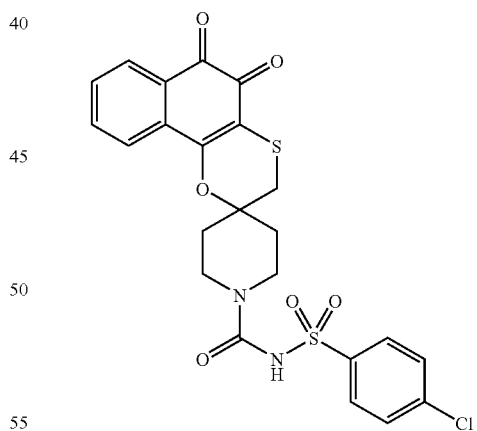

To a solution of spiro[naphtho[1,2-b][1,4]oxathiine-2,4'-piperidine]-5,6-dione (0.3 g, 1.0 mmol) in dichloromethane (5 mL) was added 4-chlorobenzenesulfonyl isocyanate (0.217 g, 1.0 mmol). The reaction mixture was allowed to stir at room temperature for 2 hours. The reaction was quenched by adding water (5 mL), the organic layer was separated, dried with sodium sulfate and concentrated under reduced pressure. Flash column chromatography (SiO$_2$, 80% EtOAc in hexanes to 100% EtOAc) gave the desired product (0.081 g, 16%) as purple solid. M.p.=173-180° C.; (DMSO-d$_6$) δ 11.19 (s, 1H), 7.93-7.87 (m, 3H), 7.85-7.8 (m, 1H), 7.79-7.63

(m, 3H), 7.6-7.53 (m, 1H), 3.95-3.8 (m, 2H), 3.25-3.1 (m, 2H), 3.09 (s, 2H), 2.05-1.93 (m, 2H), 1.8-1.63 (m, 2H); LCMS=519 [M+H].

E31.2. Synthesis of N-[(4-fluorophenyl)sulfonyl]-5,6-dioxo-5,6-dihydro-1'H-spiro[naphtho[1,2-b][1,4]oxathiine-2,4'-piperidine]-1'-carboxamide (Compound 239)

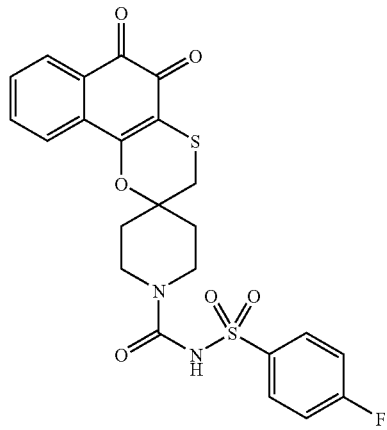

Compound 239 was synthesized using spiro[naphtho[1,2-b)][1,4]oxathiine-2,4'-piperidine]-5,6-dione, 4-fluorobenzenesulfonyl isocyanate and conditions outlined in procedure AE. M.p.=173-180° C.; (DMSO-d) δ 11.13 (s, 1H), 8.03-7.94 (m, 2H), 7.92-7.87 (m, 1H), 7.85-7.8 (m, 1H), 7.77-7.7 (m, 1H), 7.6-7.52 (m, 1H), 7.48-7.4 (m, 2H), 3.93-3.8 (m, 2H), 3.3-3.1 (m, 2H), 3.09 (s, 2H), 2.1-1.95 (m, 2H), 1.8-1.63 (m, 2H); LCMS=503 [M+H].

E31.3: Synthesis of 5,6-dioxo-N-(phenylsulfonyl)-5,6-dihydro-1'H-spiro[naphtho[1,2-b][1,4]oxathiine-2,4'-piperidine]-1'-carboxamide (Compound 240)

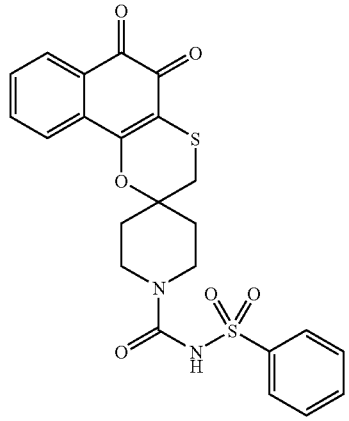

Compound 240 was synthesized using spiro[naphtho[1,2-b][1,4]oxathiine-2,4'-piperidine]-5,6-dione, benzenesulfonyl isocyanate and conditions outlined in procedure AE. M.p.=155-165° C., (DMSO-d$_6$) δ 11.09 (s, 1H), 7.93-7.88 (m, 2H), 7.85-7.81 (m, 1H), 7.76-7.71 (m, 1H), 7.7-7.53 (m, 5H), 3.93-3.8 (m, 2H), 3.3-3.1 (m, 2H), 3.09 (s 2H), 2.1-1.97 (m, 2H), 1.8-1.63 (m, 2H); LCMS=485 [M+H].

E31.4. Synthesis of N-[(4-methylphenyl)sulfonyl]-5,6-dioxo-5,6-dihydro-1'H-spiro[naphtho[1,2-b][1,4]oxathiine-2,4'-piperidine]-1'-carboxamide (Compound 241)

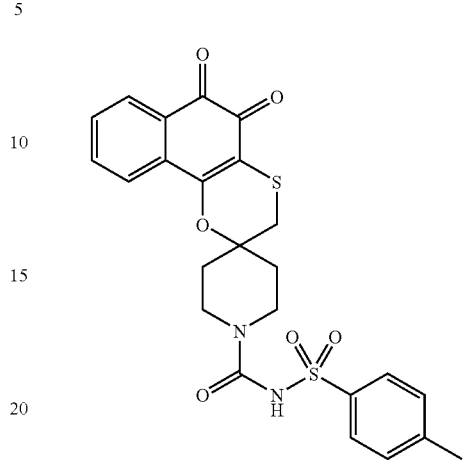

Compound 241 was synthesized using spiro[naphtho[1,2-b][1,4]oxathiine-2,4'-piperidine]-5,6-dione, 4-methylbenzenesulfonyl isocyanate and conditions outlined in procedure AE. M.p.=153-158° C., (DMSO-d$_6$) δ 10.99 (s, 1H), 7.92-7.87 (m, 1H), 7.84-7.7 (m, 4H), 7.59-7.54 (m, 1H), 7.42-7.36 (m, 2H), 3.93-3.8 (m, 2H), 3.3-3.1 (m, 2H), 3.09 (s, 2H), 2.39 (s, 3H), 2.05-1.97 (m, 2H), 1.8-1.63 (m, 2H); LCMS=499 [M+H].

Example 32

General Procedure AF

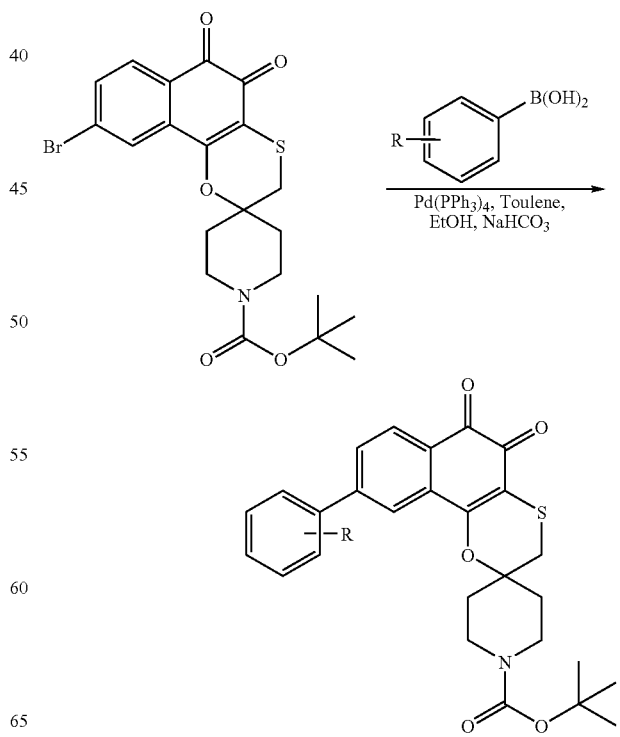

E32.1. Synthesis of tert-butyl 5,6-dioxo-9-phenyl-5,6-dihydro-1'H-spiro[naphtho[1,2-b][1,4]oxathiine-2,4'-piperidine]-1'-carboxylate (Compound 242)

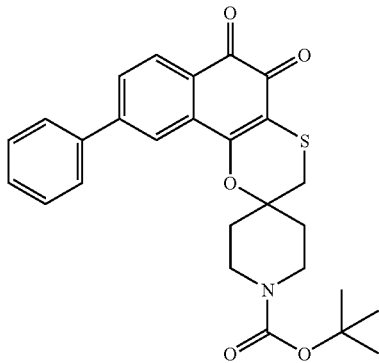

To a solution of tert-butyl 9-bromo-5,6-dioxo-5,6-dihydro-1'H-spiro[naphtho[1,2-b][1,4]oxathiine-2,4'-piperidine]-1'-carboxylate (0.05 g, 0.104 mmol) and phenylboronic acid (2 eq.) in toluene (2.0 mL) and ethanol (2.0 mL) was added saturated sodium bicarbonate solution (2.0 mL) followed by of $Pd(PPh_3)_4$ (0.012 g, 0.01 mmol) under $N_2$. The reaction mixture was stirred at 90° C. for 3 h under an atmosphere of nitrogen. The reaction was then allowed to cool to room temperature. It was then extracted with ethyl acetate (3×50 mL). The combined organic extracts were dried over $Na_2SO_4$ and concentrated under reduced pressure. The crude product was purified by flash column chromatography ($SiO_2$, 10% ethyl acetate in hexanes to 40% ethyl acetate in hexanes) to afford the product as purple solid (0.047 g, 94%). M.p.=102-106° C.; 400 MHz $^1$H NMR (DMSO-$d_6$) δ: 8.03-7.97 (m, 2H), 7.86 (dd, J=2.0, 7.6 Hz, 1H), 7.79-7.77 (m, 2H), 7.58-7.47 (m, 3H), 3.83 (d, J=13.6 Hz, 2H), 3.22 (br, 2H), 3.14 (s, 2H), 2.04 (d, J=13.6 Hz, 2H), 1.76 (ddd, J=2.8, 12.8, 12.8 Hz, 2H), 1.41 (s, 9H); LCMS: 478 [M+H].

E32.2. Synthesis of tert-butyl 5,6-dioxo-9-[4-(trifluoromethyl)phenyl]-5,6-dihydro-1'H-spiro[naphtho[1,2-b][1,4]oxathiine-2,4'-piperidine]-1'-carboxylate (Compound 243)

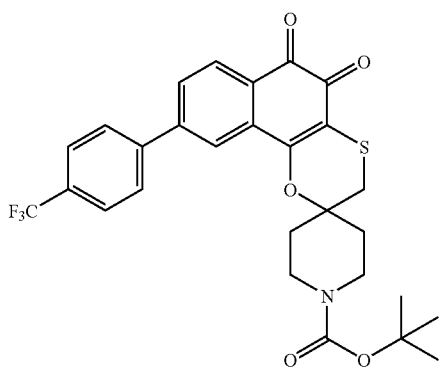

Compound 243 was synthesized by using tert-butyl 9-bromo-5,6-dioxo-5,6-dihydro-1'H-spiro[naphtho[1,2-b][1,4]oxathiine-2,4'-piperidine]-1'-carboxylate, [4-(trifluoromethyl)phenyl]boronic acid and conditions as described in general procedure AF. M.p.=238-240° C.; 400 MHz $^1$H NMR (DMSO-$d_6$) δ: 8.01-7.97 (m, 4H), 7.92-7.88 (m, 3H), 3.80 (d, J=13.6 Hz, 2H), 3.23 (br, 2H), 3.12 (s, 2H), 2.01 (d, J=14.0 Hz, 2H), 1.78-1.70 (m, 2H), 1.39 (s, 9H); LCMS: 546 [M+H].

E32.3. Synthesis of tert-butyl 5,6-dioxo-9-[3-(trifluoromethyl)phenyl]-5,6-dihydro-1'H-spiro[naphtho[1,2-b][1,4]oxathiine-2,4'-piperidine]-1'-carboxylate (Compound 244)

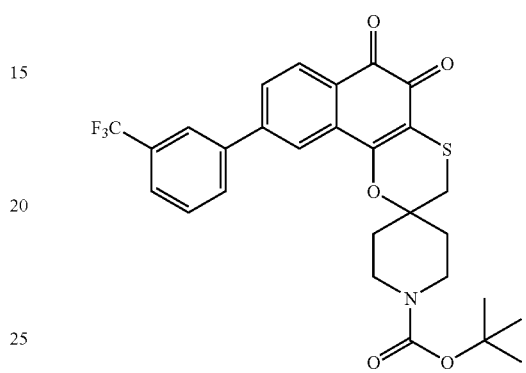

Compound 244 was synthesized by using tert-butyl 9-bromo-5,6-dioxo-5,6-dihydro-1'H-spiro[naphtho[1,2-b][1,4]oxathiine-2,4'-piperidine]-1'-carboxylate, [3-(trifluoromethyl)phenyl]boronic acid and conditions as described in general procedure AF. M.p.=231-233° C.; 400 MHz $^1$H NMR (DMSO-$d_6$): 8.10-7.92 (m, 5H), 7.86-7.76 (m, 2H), 3.80 (d, J=14.0 Hz, 2H), 3.22 (br, 2H), 3.12 (s, 2H), 2.02 (d, J=14.0 Hz, 2H), 1.74 (m, 2H), 1.39 (s, 9H); LCMS: 546 [M+H].

E32.4. Synthesis of tert-butyl 5,6-dioxo-9-[2-(trifluoromethyl)phenyl]-5,6-dihydro-1H-spiro[naphtho[1,2-b][1,4]oxathiine-2,4'-piperidine]-1'-carboxylate (Compound 245)

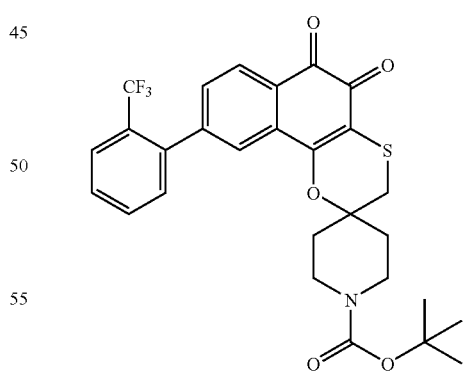

Compound 245 was synthesized by using tert-butyl 9-bromo-5,6-dioxo-5,6-dihydro-1'H-spiro[naphtho[1,2-b][1,4]oxathiine-2,4'-piperidine]-1'-carboxylate, [2-(trifluoromethyl)phenyl]boronic acid and conditions as described in general procedure AF. M.p.=223-225° C.; 400 MHz $^1$H NMR (DMSO-$d_6$) δ: 7.99 (d, J=7.6 Hz, 1H), 7.91 (d, J=7.2 Hz, 1H), 7.83-7.77 (t, J=7.6 Hz, 1H), 7.73-7.68 (m, 2H), 7.54 (dd, J=1.6, 8.0 Hz, 1H), 7.50 (d, J=8.0 Hz, 1H), 3.82 (d, J=12.4 Hz, 2H), 3.11 (s, 2H), 3.04 (br, 2H), 1.97 (d, J=13.2 Hz, 2H), 1.70 (ddd, J=4.8, 13.6 Hz, 2H), 1.39 (s, 9H); LCMS: 546 [M+H].

E32.5. Synthesis of tert-butyl 5,6-dioxo-9-pyridin-3-yl-5,6-dihydro-1'H-spiro[naphtho[1,2-b][1,4]oxathiine-2,4'-piperidine]-1'-carboxylate (Compound 246)

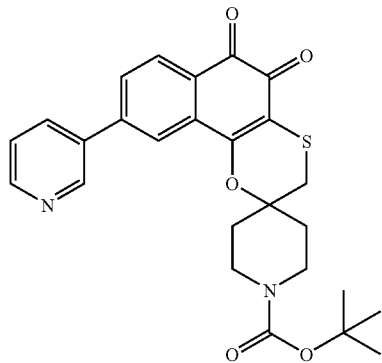

Compound 246 was synthesized by using tert-butyl 9-bromo-5,6-dioxo-5,6-dihydro-1'H-spiro[naphtho[1,2-b][1,4]oxathiine-2,4'-piperidine]-1'-carboxylate, pyridin-3-yl-boronic acid and conditions as described in general procedure AF. M.p.=217-219° C.; 400 MHz $^1$H NMR (CDCl$_3$) δ: 8.90 (d, J=2.0 Hz, 1H), 8.72 (dd, J=1.6, 4.8 Hz, 1H), 8.17 (d, J=7.6 Hz, 1H), 7.95-7.91 (m, 2H), 7.70 (dd, J=2.0, 8.0 Hz, 1H), 7.47 (ddd, J=0.8, 5.2, 7.6 Hz, 1H), 4.01 (br, 2H), 3.25 (dd, J=12.0, 12.0 Hz, 2H), 2.97 (s, 2H), 2.14 (d, J=13.2 Hz, 2H), 1.79 (m, 2H), 1.48 (s, 9H); LCMS: 479 [M+H].

E32.6. Synthesis of tert-butyl 5,6-dioxo-9-pyridin-4-yl-5,6-dihydro-1'H-spiro[naphtho[1,2-b][1,4]oxathiine-2,4'-piperidine]-1'-carboxylate (Compound 247)

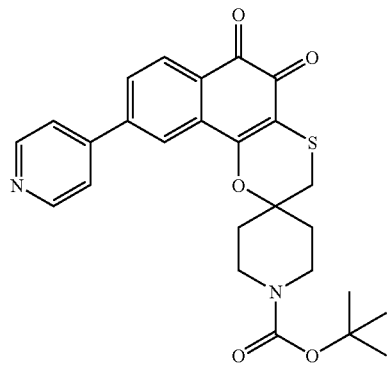

Compound 247 was synthesized by using tert-butyl 9-bromo-5,6-dioxo-5,6-dihydro-1'H-spiro[naphtho[1,2-b][1,4]oxathiine-2,4'-piperidine]-1'-carboxylate, pyridin-4-yl-boronic acid and conditions as described in general procedure AF. M.p.=225-227° C.; 400 MHz $^1$H NMR (CDCl$_3$) δ: 8.79-8.77 (m, 2H), 8.17 (d, J=7.6 Hz, 1H), 7.95 (d, J=1.6 Hz, 1H), 7.73 (dd, J=1.6, 7.6 Hz, 1H), 7.54-7.52 (m, 2H), 4.02 (br, 2H), 3.27 (ddd, J=2.8, 11.2, 12.4 Hz, 2H), 2.98 (s, 2H), 2.15 (d, J=12.8 Hz, 2H), 1.80 (m, 2H), 1.48 (s, 9H); LCMS: 479 [M+H].

Example 33

General Procedure AG

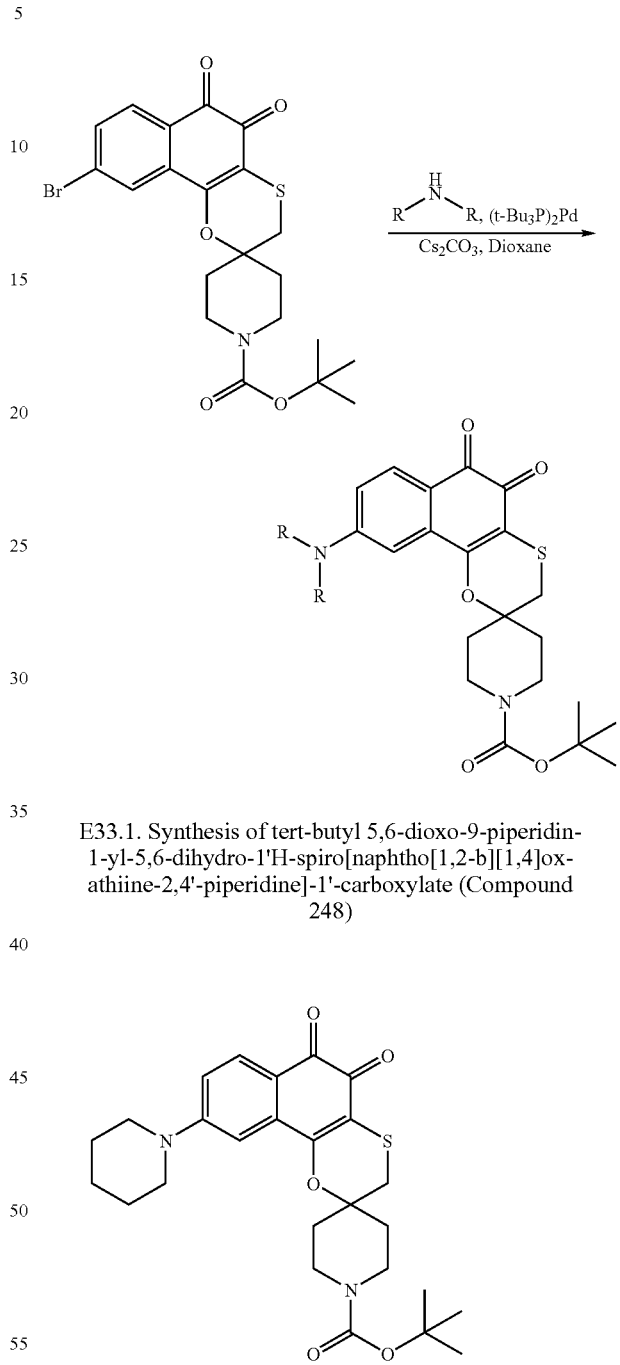

E33.1. Synthesis of tert-butyl 5,6-dioxo-9-piperidin-1-yl-5,6-dihydro-1'H-spiro[naphtho[1,2-b][1,4]oxathiine-2,4'-piperidine]-1'-carboxylate (Compound 248)

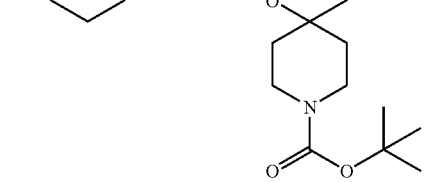

To a solution of tert-butyl 9-bromo-5,6-dioxo-5,6-dihydro-1'H-spiro[naphtho[1,2-b][1,4]oxathiine-2,4'-piperidine]-1'-carboxylate (0.045 g, 0.09 mmol) in dioxane (2 mL) was added piperidine (0.011 g, 0.15 mmol), cesium carbonate (0.045 g, 0.135 mmol, 1.5 eq) and bis(tri-tert-butyl phosphine)palladium(0) (0.010 g). The reaction mixture was stirred and heated at 115° C. for 3.5 hours. The solvent was then removed under reduced pressure and the residue was dissolved in dichloromethane and filtered. The filtrate was concentrated under reduced pressure and the crude product purified by flash column chromatography (SiO$_2$, 70% EtOAc in hexanes) to afford the product (0.020 g, 45%). as a purple solid. M.p.=243-244° C.; 400 MHz $^1$H NMR (DMSO-d$_6$) δ: 7.71 (d, J=8 Hz, 1H), 7.12 (brs, 1H), 6.94 (dd, J=2.4 and 8.8 Hz, 1H), 3.78 (brd, 2H), 3.50 (s, 2H), 3.12 (brm, 4H), 3.08 (s, 2H), 2.0 (d, J=8.8 Hz, 2H), 1.56-1.73 (m, 8H), 1.39 (s, 9H); LCMS: 485 [M+H].

E33.2. Synthesis of tert-butyl 9-morpholin-4-yl-5,6-dioxo-5,6-dihydro-1'H-spiro[naphtho[1,2-b][1,4]oxathiine-2,4'-piperidine]-1'-carboxylate (Compound 249)

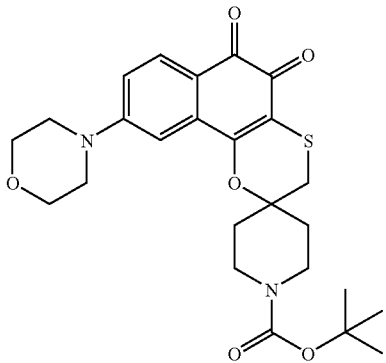

Compound 249 was synthesized using tert-butyl 9-bromo-5,6-dioxo-5,6-dihydro-1'H-spiro[naphtho[1,2-b][1,4]oxathiine-2,4'-piperidine]-1'-carboxylate, morpholine and conditions outlined in general procedure AG. M.p.=243-244° C.; 400 MHz $^1$H NMR (DMSO-d$_6$) δ: 7.7 (d, J=8.8 Hz, 1H), 7.13 (s, 1H), 6.98 (d, J=8.4 Hz, 1H), 3.73 (br, 8H), 3.40 (s, 2H), 3.12 (brm, 2H), 3.08 (s, 2H), 2.0 (d, J=11.2 Hz, 2H), 1.70 (t, J=10 Hz, 2H), 1.39 (s, 9H); LCMS: 487 [M+H].

Example 34

Procedure AH

E34.1. Synthesis of 4-{[(2S)-3-(5,6-dioxo-5,6-dihydro-1'H-spiro[naphtho[1,2-b][1,4]oxathiine-2,4'-piperidine]-1'-yl)-2-hydroxypropyl]oxy}benzoic acid (Compound 250)

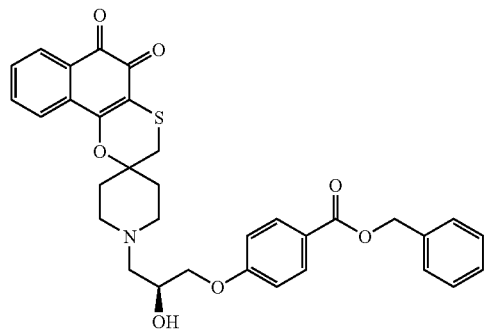

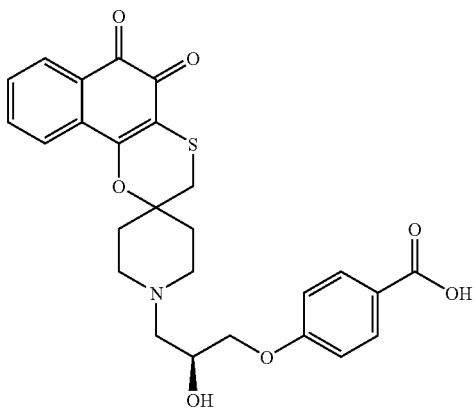

To a solution of benzyl 4-{[(2S)-3-(5,6-dioxo-5,6-dihydro-1'H-spiro-[naphtho[1,2-b][1,4]oxathiine-2,4'-piperidine]-1'-yl)-2-hydroxypropyl]oxy}benzoate (0.1 g, 0.17 mmole) in EtOAc (10 mL) was added the 10% Pd on carbon (0.020 g). The reaction mixture was subjected to an atmospheric pressure of hydrogen for three days. The mixture was filtered over Celite and concentrated under reduced pressure affording the title compound as a deep purple solid. M.p.=173-175° C.; 400 MHz $^1$H NMR (DMSO-d$_6$) δ: 7.92-7.86 (m, 3H), 7.83-7.76 (m, 2H), 7.60-7.54 (m, 1H), 7.03 (d, J=8.6 Hz, 2H), 4.12-3.92 (m, 4H), 3.08 (s, 2H), 2.90-2.74 (m, 2H), 2.60-2.40 (m, 3H), 2.35-1.94 (m, 2H), 1.88-1.76 (m, 2H); LCMS: 496 [M+H].

Example 35

Procedure AI

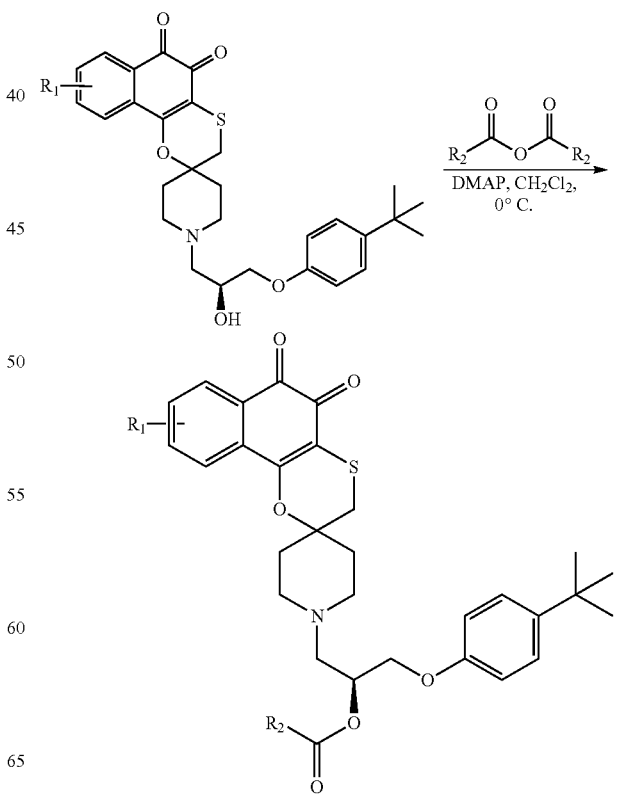

E35.1. Synthesis (1S)-2-(4-tert-butylphenoxy)-1-[(5,6-dioxo-5,6-dihydro-1'H-spiro[naphtho[1,2-b][1,4]oxathiine-2,4'-piperidin]-1'-yl)methyl]ethyl acetate (Compound 251)

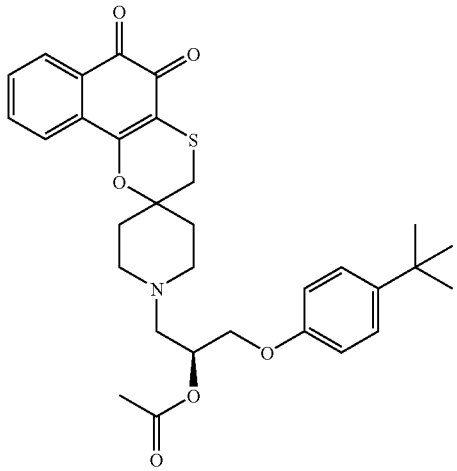

To a solution of 1'-[(2S)-3-(4-tert-butylphenoxy)-2-hydroxypropyl]spiro[naphtho[1,2-b][1,4]oxathiine-2,4'-piperidine]-5,6-dione (0.5 g, 0.99 mmol) in dichloromethane (10 mL), which had been cooled to 0° C. was added dimethylaminopyridine (0.012 g, 0.099 mmol) followed by acetic anhydride (0.19 mL, 1.97 mmol). The reaction was stirred at 0° C. for 8 hours. The reaction mixture was washed with saturated NaHCO$_3$ (20 mL), dried with sodium sulfate and concentrated under reduced pressure. The crude product was purified by flash column chromatography (SiO$_2$, 30% EtOAc in hexanes) to afford the product (0.53 g, 97%) as a purple solid. M.p.=64-66° C.; 400 MHz $^1$H NMR (CDCl$_3$) δ 8.05-7.95 (m, 1H), 7.78-7.7 (m, 1H), 7.68-7.6 (m, 1H), 7.5-7.4 (m, 1H), 7.3-7.22 (m, 2H), 6.87-6.8 (m, 2H), 5.38-5.25 (m, 1H), 4.18-4.03 (m, 3H), 2.89 (s, 2H), 2.9-2.8 (m, 2H), 2.78-2.7 (m, 2H), 2.65-2.52 (m, 2H), 2.06 (s, 3H), 2.15-2.02 (m, 2H), 1.86-1.75 (m, 2H), 1.28 (s, 9H); LCMS: 550 [M+H].

Example 36

Procedure AJ

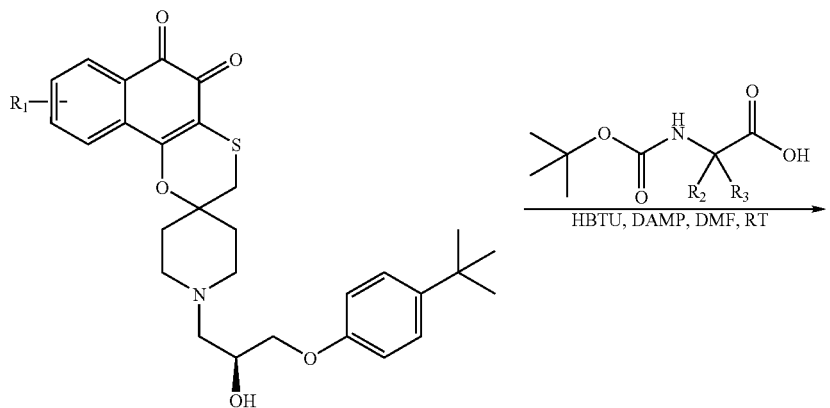

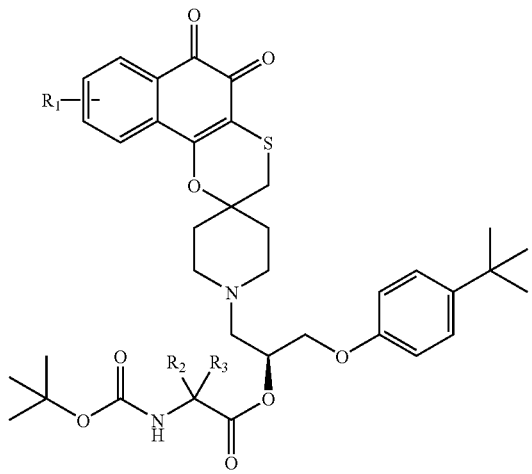

195

E36.1. Synthesis of (1S)-2-(4-tert-butylphenoxy)-1-[(5,6-dioxo-5,6-dihydro-1'H-spiro[naphtho[1,2-b][1,4]oxathiine-2,4'-piperidine]-1'-yl)methyl]ethyl N-(tert-butoxycarbonyl)glycinate (Compound 252)

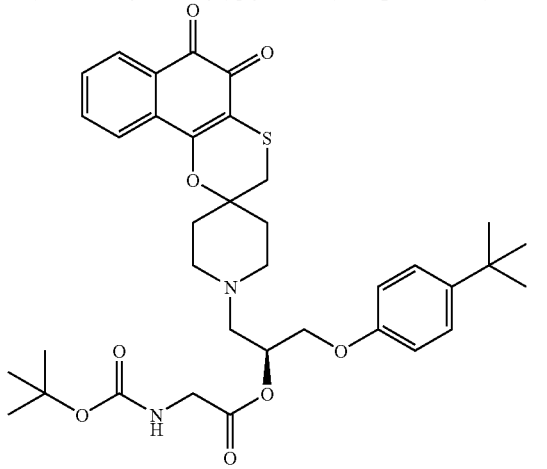

To a solution of 1'-[(2S)-3-(4-tert-butylphenoxy)-2-hydroxypropyl]spiro[naphtho[1,2-b][1,4]oxathiine-2,4'-piperidine]-5,6-dione hydrochloride (1.0 g, 1.84 mmol) in dimethylformamide (10 mL) was added N-(tert-butoxycarbonyl) glycine (0.415 g, 2.39 mmol) and triethylamine (0.52 mL, 3.86 mmol) followed by HBTU (0.782 mmol, 2.39 mmol). The reaction mixture was stirred at room temperature for 16 hours. The reaction was then diluted with EtOAc (100 mL) and washed with saturated NaHCO$_3$ (2×50 mL), brine (3×50 mL), dried with sodium sulfate and concentrated under reduced pressure. The crude product was purified by flash column chromatography (SiO$_2$, 30% EtOAc in hexanes to 50% EtOAc in hexanes) to afford the product (0.53 g, 97%) as a purple solid. M.p.=85-95° C.; 400 MHz $^1$H NMR (CDCl$_3$) δ 8.05-7.95 (m, 1H), 7.78-7.7 (m, 1H), 7.68-7.6 (m, 1H), 7.5-7.4 (m, 1H), 7.3-7.22 (m, 2H), 6.87-6.8 (m, 2H), 5.5-5.4 (m, 1H), 5.08-5.0 (m, 1H), 4.2-4.1 (m, 1H), 4.0-3.78 (m, 2H), 3.0-2.86 (m, 3H), 2.85-2.8 (m, 2H), 2.79 (s, 2H), 2.76-2.58 (m, 2H), 2.15-2.02 (m, 2H), 1.94-1.80 (m, 2H), 1.44 (s, 9H), 1.28 (s, 9H); LCMS: 665 [M+H].

Example 37

Procedure AK

E37.1. Synthesis of (1S)-2-(4-tert-butylphenoxy)-1-[(5,6-dioxo-5,6-dihydro-1'H-spiro[naphtho[1,2-b][1,4]oxathiine-2,4'-piperidine]-1'-yl)methyl]ethyl glycinate hydrochloride (Compound 253)

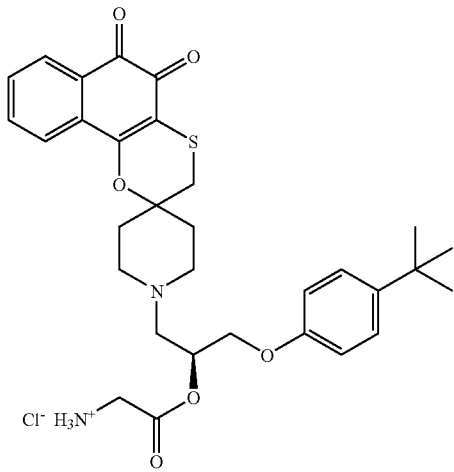

196

To a solution of (1S)-2-(4-tert-butylphenoxy)-1-[(5,6-dioxo-5,6-dihydro-1'H-spiro[naphtho[1,2-b][1,4]oxathiine-2,4'-piperidine]-1'-yl)methyl]ethyl N-(tert-butoxycarbonyl) glycinate (0.2 g, 0.3 mmol) in isopropyl acetate (50 mL) was added 12.1N HCl (3.4 mL). The reaction was stirred vigorously for 16 hours after which a purple solid separated out. The solid was filtered and washed with isopropyl acetate (50 mL). The solid was then dried under high vacuum to afford the product (0.143 g, 62%) as a purple solid. M.p.=193-195° C.; 400 MHz $^1$H NMR (DMSO-d$_6$) δ 11.45-11.25 (br m, 1H), 8.47 (brs, 3H), 7.98-7.9 (m, 2H), 7.8-7.7 (m, 1H), 7.63-7.55 (m, 1H), 7.45-7.28 (m, 2H), 6.94-6.87 (m, 2H), 5.8-5.7 (brs, 1H), 4.3-4.15 (m, 3H), 4.0-3.2 (m, 7H), 3.1 (s, 2H), 2.45-2.2 (m, 4H), 1.25 (s, 9H); LCMS: 565 [M+H]

Example 38

Procedure AL

E38.1. Synthesis of 5,6-dioxo-5,6-dihydro-1'H-spiro[naphtho[1,2-b][1,4]oxathiine-2,4'-piperidine]-1'-carboximidamidinium chloride (Compound 254)

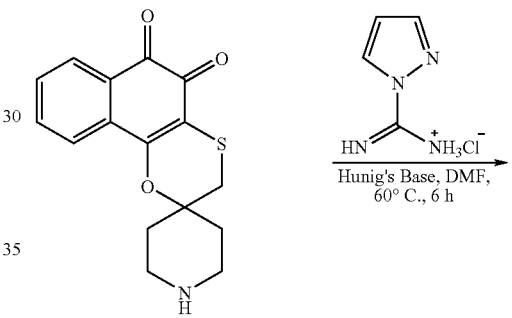

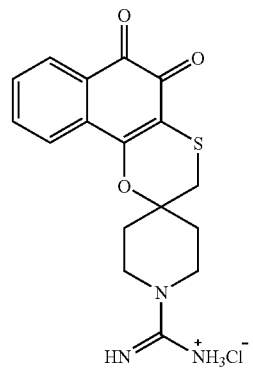

To a solution of spiro[naphtha[1,2-b][1,4]oxathiine-2,4'-piperidine]-5,6-dione (0.500 g, 1.66 mmol) in dimethylformamide (10 mL) was treated with pyrazole carboxamide hydrochloride (0.243 g, 1.66 mmol) and diisopropylethylamine (0.289 mL, 1.66 mmol). The reaction was heated at 60° C. for 6 hours, then cooled to room temperature. The reaction mixture was diluted with ether (100 mL) and vigorously stirred for one hour. The supernatant was decanted, more ether was added. This process was repeated until a solid was formed. The solid was collected, washed with ether, and dried under high vacuum to give a purple solid (0.503 g, 88%). M.p.=262-264° C.; 400 MHz $^1$H NMR (DMSO-d$_6$) δ: 7.87 (m, 2H), 7.73 (t, J=7.6 Hz, 1H), 7.67 (br. s, 3H), 7.56 (t, 1H), 3.87 (d, J=13.6 Hz, 2H), 3.38 (m, 2H), 3.34 (s, 2H), 2.06 (d, J=13.6 Hz, 2H), 1.85 (m, 2H); LCMS: 344 [M+H].

Example 39

Procedure AM

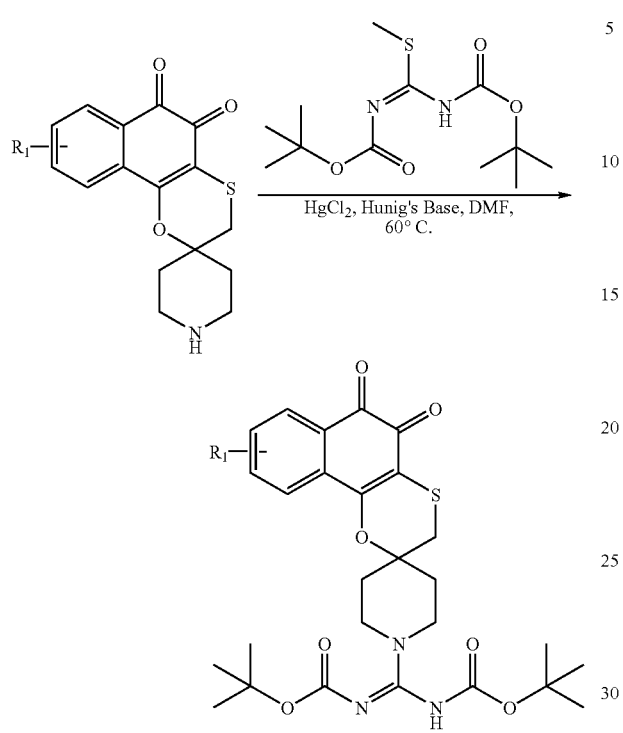

E39.1. Synthesis of di-tert-butyl [(E)-(5,6-dioxo-5,6-dihydro-1'H-spiro[naphtho[1,2-b][1,4]oxathiine-2,4'-piperidine]-1'-yl)methylylidene]biscarbamate (Compound 255)

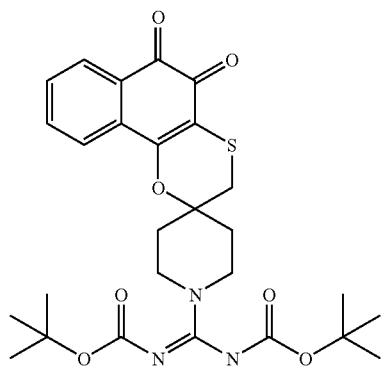

To a solution of spiro[naphtha[1,2-b][1,4]oxathiine-2,4'-piperidine]-5,6-dione (2.60 g, 8.63 mmol), $N^1,N^2$-bis(tert-butoxycarbonyl)-S-methylisothiourea (2.76 g, 9.49 mmol), and triethylamine (3.60 mL, 25.88 mmol) in anhydrous dimethylformamide was added mercury (II) chloride (2.58 g, 9.49 mmol). The suspension was stirred at room temperature for 4 hours and then concentrated under reduced pressure. The crude reaction mixture was suspended in diethylether (200 mL) and filtered. The filtrate was washed with saturated aqueous ammonium chloride (50 mL), water (50 mL), brine (50 mL), dried over sodium sulfate and concentrated under reduced pressure. The crude product was purified by flash column chromatography (SiO$_2$, 10% Methanol in dichloromethane) to afford the product as a purple solid (4.10 g, 87%). M.p.=272-274° C.; 400 MHz $^1$H NMR (CDCl$_3$) δ: 10.30 (br. s, 1H), 8.06 (m, 1H), 7.73 (m, 1H), 7.64 (m, 1H), 7.50 (m, 1H), 4.11 (m, 2H), 3.39-3.44 (m, 2H), 2.96 9 (s, 2H), 2.18 (d, J=12.8 Hz, 2H), 2.00-1.95 (m, 2H), 1.50 (br. s, 18H); LCMS: 544 [M+H].

Example 40

Procedure AN

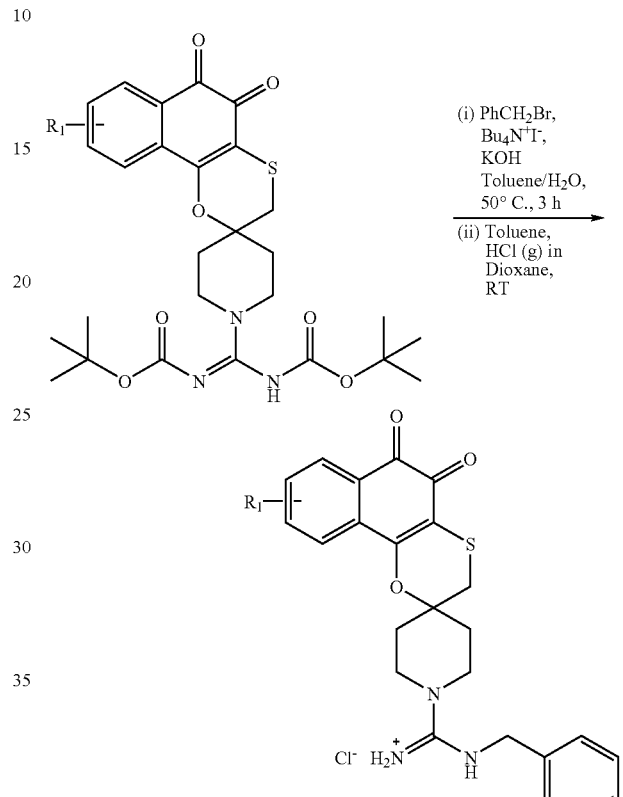

E40.1. Synthesis of N-benzyl-5,6-dioxo-5,6-dihydro-1'H-spiro[naphtho[1,2-b][1,4]oxathiine-2,4'-piperidine]-1'-carboximidamidinium chloride (Compound 256)

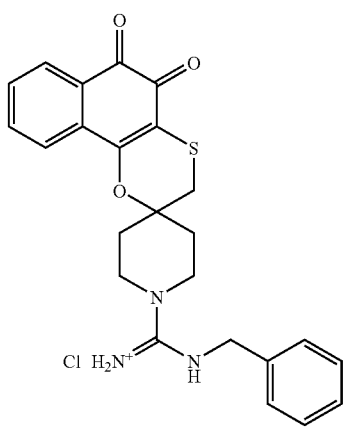

Step (i): To a solution of di-tert-butyl [(E)-(5,6-dioxo-5,6-dihydro-1'H-spiro[naphtho[1,2-b][1,4]oxathiine-2,4'-piperidin]-1'-yl)methylylidene]biscarbamate (0.090 g, 0.166 mmol), in toluene (2 mL) was added tetrabutylammonium iodide (0.006 g, 0.033 mmol), potassium hydroxide (0.019 mg, 0.332 mmol) and water (2 mL) followed by benzyl bromide (0.039 mL, 0.332 mmol). The reaction mixture was stirred at 50° C. for 3 hours, then poured into water (20 mL) and extracted with dichloromethane (3×50 mL). The combined organic extracts were washed with brine (30 mL), dried over sodium sulfate, and concentrated under reduced pressure to afford the desired intermediate, which was used in step (ii) without any further purification.

Step (ii): To a solution of the crude intermediate from step (i) in toluene was added a solution of 4.0 M HCl (g) in dioxane (0.166 mL, 0.664 mmol). The reaction mixture was allowed to stir at room temperature for 3 hours, and then concentrated to dryness under reduced pressure. The crude product was washed with ether and dried under high vacuum to afford the product as a purple solid (0.039 g, 54%). M.p.=190-195° C.; 400 MHz $^1$H NMR (DMSO-d$_6$) δ: 8.42-8.30 (m, 1H), 7.90-7.83 (m, 3H), 7:74 (t, J=7.2 Hz, 1H)), 7.56 (t, J=7.6 Hz, 1H)), 7.39-7.27 (m, 5H), 4.48-4.46 (m, 2H), 3.90 (d, J=14 Hz, 2H), 3.40-3.37 (m, 4H), 2.06 (d, J=14 Hz, 2H), 1.90-1.86 (m, 2H); LCMS: 434 [M+H].

Example 41

Procedure AO

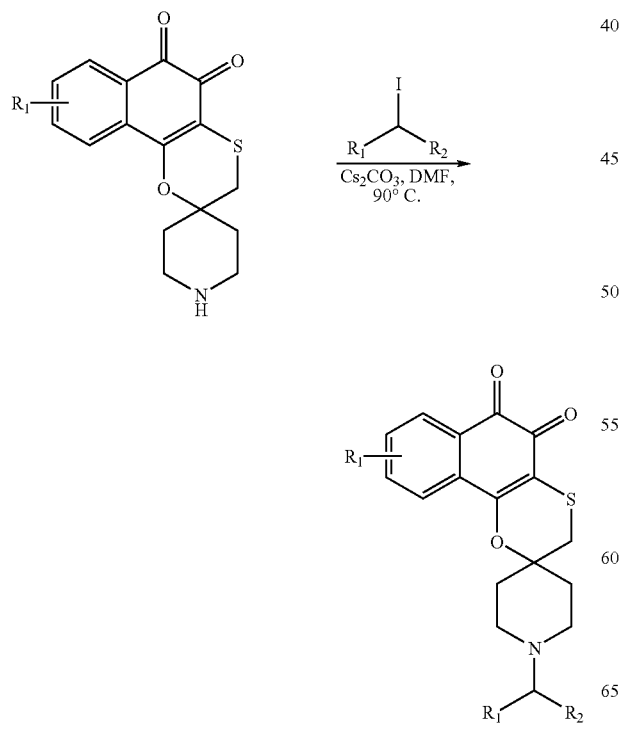

E41.1. Synthesis of tert-butyl 4-(5,6-dioxo-5,6-dihydro-1'H-spiro[naphtho[1,2-b][1,4]oxathiine-2,4'-piperidine]-1'-yl)piperidine-1-carboxylate (Compound 257)

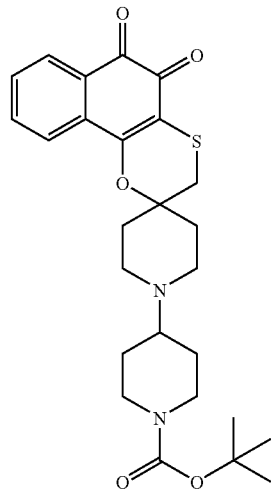

To a solution of spiro[naphtho[12-b][1,4]oxathiine-2,4'-piperidine]-5,6-dione (5.0 g, 16.61 mmol), tert-butyl 4-bromopiperidine-1-carboxylate (20.7 g, 80 mmol) and cesium carbonate (10.8 g, 33.2 mmol) in dimethylformamide (50 mL) was heated at 90° C. for 30 hours. The resulting mixture was diluted with dichloromethane (200 mL), washed with water (3×50 mL), dried over sodium sulfate and concentrated under reduced pressure. The crude product was purified by column chromatography (SiO$_2$, 5% CH$_3$OH in CH$_2$Cl$_2$) to afford the product as a purple solid (1.1 g, 14%). M.p.=87-91° C.; 400 MHz $^1$H NMR (CDCl$_3$) δ: 8.03 (d, J=7.2 Hz, 1H), 7.72 (d, J=7.6 Hz, 1H), 7:65 (t, J=8.0 Hz, 1H), 7.47 (t, J=8.0 Hz, 1H), 4.17 (brs, 2H), 2.91 (s, 2H), 2.85 (m, 2H), 2.63-2.69 (m, 4H), 2.52 (m, 1H), 2.15 (d, J=13.2 Hz, 2H), 1.88-1.80 (m, 6H), 1.47 (s, 9H); LCMS: 484 [M+H].

E41.2. Synthesis of 1'-cyclohexylspiro[naphtho[1,2-b][1,4]oxathiine-2,4'-piperidine]-5,6-dione (Compound 258)

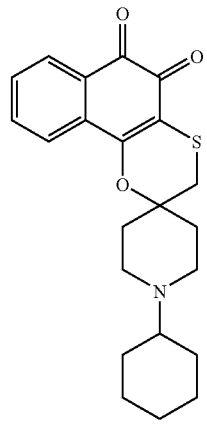

Compound 258 was synthesized using spiro[naphtho[1,2-b][1,4]oxathiine-2,4'-piperidine]-5,6-dione, iodocyclohexane, and conditions outlined in procedure AO. M.p.=195-196° C.; 300 MHz $^1$H NMR (DMSO-d) δ: 7.89 (d, J=7.2 Hz, 1H), 7.77-7.75 (m, 2H), 7.58-7.52 (m, 1H), 2.77-2.72 (m, 2H), 2.64-2.58 (m, 2H), 2.34 (br. s, 1H), 2.01 (d, J=17.6 Hz, 2H), 1.83-1.75 (m, 6H), 1.57 (d, J=14.8 Hz, 2H), 1.30-1.15 (m, 6H); LSMS: 384 [M+H].

Example 42

Procedure AP

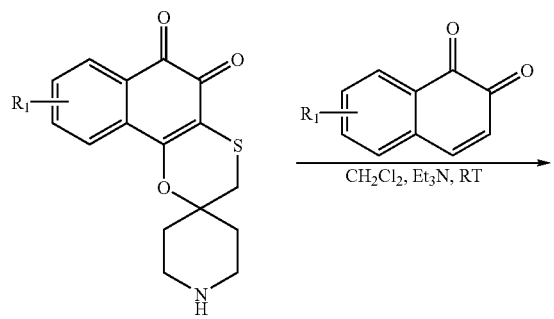

E42.1. Synthesis of 1'-(3,4-dioxo-3,4-dihydronaphthalen-1-yl)spiro[naphtho[1,2-b][1,4]oxathiine-2,4'-piperidine]-5,6-dione (Compound 259)

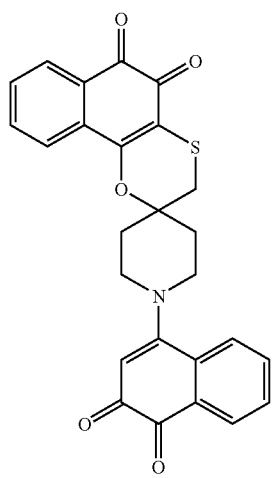

To a solution of spiro[naphtho[1,2-b][1,4]oxathiine-2,4'-piperidine]-5,6-dione (2.3 g, 7.64 mmol) in dichloromethane (200 mL) was added naphthalene-1,2-dione (1.2 g, 7.64 mmol) followed by triethylamine (1.05 mL, 8.4 mmol). The reaction mixture was stirred at room temperature for 2 hours. The mixture was then concentrated under reduced pressure. The residue was dissolved in minimal tetrahydrofuran and then precipitated with EtOAc. The precipitate was collected by vacuum filtration. The filtrate was then suspended in tetrahydrofuran:EtOAc (1:1, 100 mL). The suspension was stirred, sonicated, and the solid collected by vacuum filtration. The tituration was once more repeated and the resulting reddish brown powder was recrystallized from dichloromethane/methanol (1:1) to afford the product (0.5 g) as the pure reddish brown solid. M.p.=250-260° C.; 400 MHz $^1$H NMR (DMSO-$d_6$) δ: 7.89-7.93 (m, 3H), 7.71-7.81 (m. 3H), 7.55-7.65 (m, 2H), 6.10 (s, 1H), 3.67-3.75 (m, 2H), 3.45-3.53 (m, 2H), 3.19 (s, 2H), 2.20 (m, 2H), 1.25 (m, 1H), 1.01 (m, 1H). LCMS: 458 [M+H].

Example 43

Procedure AQ

E43.1. Synthesis of 4-hydroxyspiro[cyclohexane-1,2'-naphtho[1,2-b][1,4]oxathiine]-5',6'-dione (Compound 260)

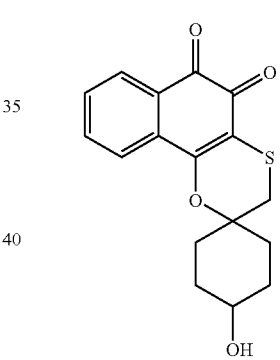

To a solution of 4H-spiro[cyclohexane-1,2'-naphtho[1,2-b][1,4]oxathiine]-4,5',6'-trione (0.180 g, 0.57 mmol) in anhydrous methanol (25 ml) was added sodium borohydride (0.085 mg, 2.25 mmol). On addition the reaction mixture turned pale yellow, which after 30 minutes turned back to purple. The reaction mixture was stirred at room temperature for 16 hours after which the solvent was removed under reduced pressure. The residue was dissolved in dichloromethane (50 ml) and water (50 ml) was added to it. The organic layer was removed and the aqueous layer was extracted with dichloromethane (3×50 ml). The combined organic extracts were dried over sodium sulfate, filtered and concentrated under reduced pressure. The crude product was purified by C-18 reverse phase preparative liquid chromatography to afford the product (0.018 g) as a purple solid. M.p.=166-168° C., 400 MHz $^1$H NMR (acetone-$d_6$) δ: 7.97 (dd, 1H), 7.90 (dd, 1H), 7.80 (dt, 1H), 7.59 (dt, 1H), 3.74 (m, 1H), 3.06 (s, 2H), 2.21 (m, 2H), 1.89 (m, 2H), 1.74 (m, 4H); LCMS: 317 [M+H].

Example 44

E44.1. Synthesis of spiro[cyclohexane-1,2'-naphtho[1,2-b][1,4]oxathiine]-5',6'-dione (Compound 261)

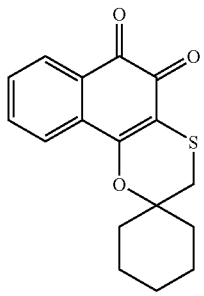

Step (i): 1-(mercaptomethyl)cyclohexanol was synthesized using 1-oxaspiro[2.5]octane as outlined in procedure C.

Step (ii): The crude 1-(mercaptomethyl)cyclohexanol was then reacted with naphthalene-1,2-dione as outlined in procedure F [both step (i) and (ii)] to afford crude spiro[cyclohexane-1,2'-naphtho[1,2-b][1,4]oxathiine]-5',6'-dione. The crude spiro[cyclohexane-1,2'-naphtho[1,2-b][1,4]oxathiine]-5',6'-dione was purified by flash column chromatography (SiO$_2$, 100% dichloromethane) to afford the product (0.183 g) as a purple solid. M.p.=194-195° C., 400 MHz $^1$H NMR CDCl$_3$ δ 8.05-8.0 (m, 1H), 7.8-7.72 (m, 1H), 7.68-7.6 (m, 1H), 7.5-7.4 (m, 1H), 2.91 (s, 2H), 2.15-2.0 (m, 2H), 1.8-1.53 (m, 7H), 1.5-1.35 (m, 1H); LCMS=301 [M+H].

E44.2. Synthesis of 2',3',5',6'-tetrahydrospiro[naphtho[1,2-b][1,4]oxathiine-2,4'-pyran]-5,6-dione (Compound 262)

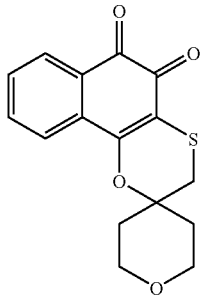

Step (i): 1,6-dioxaspiro[2.5]octane was synthesized using tetrahydro-4H-pyran-4-one as outlined in procedure A.

Step (ii): The crude 1,6-dioxaspiro[2.5]octane was then used to synthesize 4-(mercaptomethyl)tetrahydro-2H-pyran-4-ol as outlined in procedure B.

Step (iii): The crude 4-(mercaptomethyl)tetrahydro-2H-pyran-4-ol was then reacted with naphthalene-1,2-dione as outlined in procedure F [both step (i) and (ii)] to afford crude 2',3',5',6'-tetrahydrospiro[naphtho[1,2-b][1,4]oxathiine-2,4'-pyran]-5,6-dione. The crude 2',3',5',6'-tetrahydrospiro[naphtho[1,2-b][1,4]oxathiine-2,4'-pyran]-5,6-dione was purified by flash column chromatography (SiO$_2$, 100% dichloromethane) to afford the product as a purple solid. M.p.=195-197° C.; 400 MHz $^1$H NMR (CDCl$_3$) δ: 8.06 (dd, J=7.6 1.0 Hz, 1H), 7.79 (dd, J=7.6 0.8 Hz, 1H), 7.67 (td, J=8.0 1.6 Hz 1H), 7.50 (td, J=8.0 1.2 Hz, 1H), 3.96-3.83 (m, 4H), 2.97 (s, 2H), 2.10-2.05 (m, 2H), 1.95-1.87 (m, 2H); LCMS: 303 [M+H].

E44.3. Synthesis of 2',3',5',6'-tetrahydrospiro[naphtho[1,2-b][1,4]oxathiine-2,4'-thiopyran]-5,6-dione (Compound 263)

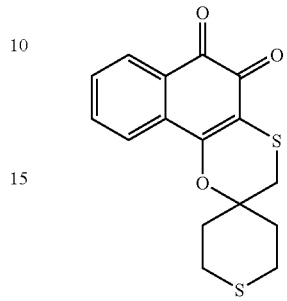

Step (i): 1-oxa-6-thiaspiro[2.5]octane was synthesized using tetrahydro-4H-thiopyran-4-one as outlined in procedure A.

Step (ii): The crude 1-oxa-6-thiaspiro[2.5]octane was then used to synthesize 4-(mercaptomethyl)tetrahydro-2H-thiopyran-4-ol as outlined in procedure B.

Step (iii): The crude 4-(mercaptomethyl)tetrahydro-2H-thiopyran-4-ol was then reacted with naphthalene-1,2-dione as outlined in procedure F [both step (i) and (ii)] to afford crude 2',3',5',6'-tetrahydrospiro[naphtho[1,2-b][1,4]oxathiine-2,4'-thiopyran]-5,6-dione. The crude 2',3',5',6'-tetrahydrospiro[naphtho[1,2-b][1,4]oxathiine-2,4'-thiopyran]-5,6-dione was purified by flash column chromatography (SiO$_2$, 25% EtOAc in hexanes) to afford the product as a purple solid. M.p.=221-223° C., 400 MHz $^1$H NMR (CDCl$_3$) δ 8.05 (dd, d, J=7.4 Hz, 1.1 Hz, 1H), 7.78 (d, J=8.6 Hz, 1H), 7.67 (dt, J=6.2 Hz, 1.1 Hz, 1H), 7.50 (dt, J=6.2 Hz, 1.1 Hz, 1H), 3.10-3.03 (m, 1H), 2.64-2.60 (m2, 2H), 2.47-2.43 (m, 2H), 1.99-1.92 (m, 2H); LCMS: 319 [M+H].

E44.4. Synthesis of 4-phenylspiro[cyclohexane-1,2'-naphtho[1,2-b][1,4]oxathiine]-5',6'-dione (Compound 264)

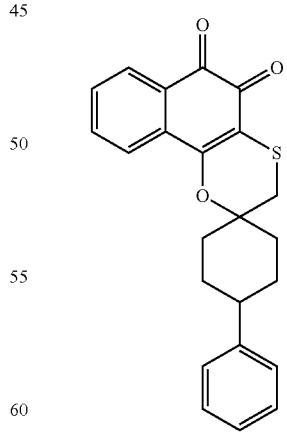

Step (i): 6-phenyl-1-oxaspiro[2.5]octane was synthesized using 4-phenylcyclohexanone as outlined in procedure A.

Step (ii): The crude 6-phenyl-1-oxaspiro[2.5]octane was then used to synthesize 1-(mercaptomethyl)-4-phenylcyclohexanol as outlined in procedure C.

Step (iii): The crude 1-(mercaptomethyl)-4-phenylcyclohexanol was then reacted with naphthalene-1,2-dione as outlined in procedure F [both step (i) and (ii)] to afford crude 4-phenylspiro[cyclohexane-1,2'-naphtho[1,2-b][1,4]oxathiine]-5',6'-dione. The crude 4-phenylspiro[cyclohexane-1,2'-naphtho[1,2-b][1,4]oxathiine]-5',6'-dione was purified by flash column chromatography (SiO$_2$, 100% dichloromethane) to afford the product as a purple solid. M.p.=183-187° C.; 400 MHz $^1$H NMR (DMSO) δ: 7.92-7.78 (m, 3H), 7.60-7.56 (td, 1H), 7.34-7.18 (m, 5H), 3.09 (s, 2H), 2.71-2.66 (m, 1H), 2.20 (d, 2H), 1.90-1.72 (m, 6H); LCMS: 377 [M+H].

E44.5. Synthesis of dispiro[1,3-dioxolane-2,1'-cyclohexane-4',2''-naphtho[1,2-b][1,4]oxathiine]-5'',6''-dione (Compound 265) and 4H-spiro[cyclohexane-1,2'-naphtho[1,2-b][1,4]oxathiine]-4,5',6'-trione (Compound 266)

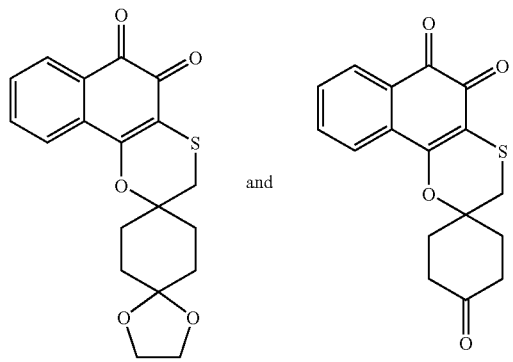

and

Step (i): 1,7,10-trioxadispiro[2.2.4.2]dodecane was synthesized using 1,4-dioxaspiro[4.5]decan-8-one as outlined in procedure A.

Step (ii): The crude 1,7,10-trioxadispiro[2.2.4.2]dodecane was then used to synthesize 8-(mercaptomethyl)-1,4-dioxaspiro[4.5]decan-8-ol as outlined in procedure B.

Step (iii): The crude 8-(mercaptomethyl)-1,4-dioxaspiro[4.5]decan-8-ol was then reacted with naphthalene-1,2-dione as outlined in procedure F [both step (i) and (ii)] to afford crude dispiro[1,3-dioxolane-2,1'-cyclohexane-4',2''-naphtho[1,2-b][1,4]oxathiine]-5'',6''-dione and 4H-spiro[cyclohexane-1,2'-naphtho[1,2-b][1,4]oxathiine]-4,5',6'-trione. The crude dispiro[1,3-dioxolane-2,1'-cyclohexane-4',2''-naphtho[1,2-b][1,4]oxathiine]-5'',6''-dione and 4H-spiro[cyclohexane-1,2'-naphtho[1,2-b][1,4]oxathiine]-4,5',6'-trione was purified by flash column chromatography (SiO$_2$, gradient from 1% EtOAc in hexanes to 50% EtOAc in hexanes) to afford both the products as a purple solid. Compound 265: M.p.=251-252° C., 400 MHz $^1$H NMR (DMSO-d$_6$) δ: 7.87 (dd, 1H), 7.74 (m, 2H), 7.54 (dt, 1H), 3.89 (s, 4H), 3.08 (s, 2H), 2.05 (m, 2H), 1.80 (m, 4H), 1.67 (m, 2H); LCMS: 359 [M+H]. Compound 266: M.p.=117-118° C., 400 MHz $^1$H NMR (DMSO-d$_6$) δ: 7.88 (dd, 1H), 7.84 (d, 1H), 7.71 (dt, 1H), 7.54 (dt, 1H), 3.16 (s, 2H), 2.63 (m, 2H), 2.31 (m, 4H), 2.10 (m, 2H); LCMS: 315 [M+H].

E44.6. Synthesis of tert-butyl (5',6'-dioxo-5',6'-dihydrospiro[cyclohexane-1,2'-naphtho[1,2-b][1,4]oxathiin]-4-yl)carbamate (Compound 267)

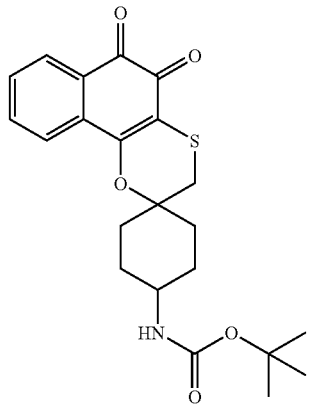

Step (i): tert-butyl 1-oxaspiro[2.5]oct-6-ylcarbamate was synthesized using tert-butyl (4-oxocyclohexyl)carbamate as outlined in procedure A.

Step (ii): The crude tert-butyl 1-oxaspiro[2.5]oct-6-ylcarbamate was then used to synthesize tert-butyl [4-hydroxy-4-(mercaptomethyl)cyclohexyl]carbamate as outlined in procedure C.

Step (iii): The crude tert-butyl [4-hydroxy-4-(mercaptomethyl)cyclohexyl]carbamate was reacted with naphthalene-1,2-dione as outlined in procedure G [both step (i) (ii) and (iii)] to afford crude tert-butyl (5',6'-dioxo-5',6'-dihydrospiro[cyclohexane-1,2'-naphtho[1,2-b][1,4]oxathiin]-4-yl)carbamate. The crude product was purified by flash column chromatography (SiO$_2$, 100% dichloromethane) to afford the product as a purple solid. M.p.=224-225° C.; 400 MHz $^1$H NMR (DMSO-d$_6$) δ: 7.90 (dd, J=7.6 Hz, 0.8 Hz, 1H), 7.83 (d, J=6.8 Hz, 1H), 7.75 (td, J=7.6 Hz, 1.2 Hz, 1H), 6.92 (d, J=8.4 Hz, 1H), 3.34 (br, 1H), 3.02 (s, 2H), 2.05 (d, J=10.8 Hz, 2H), 1.76-1.53 (m, 6H), 1.39 (s, 9H); LCMS: 416 [M+H].

Example 45

Antiproliferative Activity

Compounds of the present invention have demonstrated potent antiproliferative activity against a variety of cancer cell lines, including DLD-1 and HT-29 human colon carcinoma cells; A549 human lung carcinoma cells; DU-145 human prostate carcinoma cells; K-562 human leukemia cells; and PACA-2 human pancreatic carcinoma cells. Since β-lapachone induces cell death only in cancer cell lines and not in normal cells (Li et al., (2003) *Proc Natl Acad Sci USA.* 100 (5): 2674-8), the present compounds were also tested in a panel of normal cell lines from a variety of tissues including NCM-460 normal colon epithelial cells.

Table 1 shows the concentrations of the compounds required to inhibit 50% of cell growth (IC$_{50}$). (In Table 1, "N/A"="data not available") As shown in Table 1. IC$_{50}$ values in the low micromolar range and below were obtained for several of these compounds in all cancer cell lines tested.

Another effect of the compounds of the present invention is the induction or elevation of activity (e.g. elevation of the level) of one or more checkpoint molecules (i.e., a member of the E2F family of transcription factors). Studies have shown that β-lapachone induces activation of E2F1 checkpoint pathway in nuclei of cancer cells but not in normal cells, resulting in the arrest of cancer cells in G1 and/or S phase. Several compounds of the present invention were effective in activating the E2F1 checkpoint pathway (e.g. elevation of E2F1 levels), thus causing G1 and/or S phase arrest. Furthermore, the compounds of the present invention have no significant toxic effects on normal cells (See. Table 1).

Cell viability was determined by measuring the activity of dehydrogenase enzymes in metabolically active cells using a tetrazolium compound, MTS. The assay was performed as described in Promega Technical Bulletin No. 169 (CellTiter 96 Aqueous Non-Radioactive Cell Proliferation Assay): All cells lines were grown in DMEM media (4.5 g/L glucose) supplemented with 15% heat-inactivated FBS, 10 mM L-glutamine, and 10 mM HEPES. Briefly, cells were seeded in 96-well plates and incubated for 16-24 hours; test compounds were serially diluted in DMSO, further diluted in cell culture media, then added to cells (final DMSO concentration of 0.33% v/v); cells were incubated in the presence of compound for 4 hours; MTS was added to the cells and incubated for four hours; SDS was added to a final concentration of 1.4% v/v and absorbance at 490 nM was measured within two hours using a plate reader. The amount of 490 nM absorbance was directly proportional to the number of living cells in the culture. The $IC_{50}$ was defined as the concentration of compound that results in a 50% reduction in the number of viable cells as compared to control wells treated with DMSO only (0.33% v/v) and 1.4% v/v SDS, and was calculated using non-linear regression analysis within Activity base software suite.

The assays of the present invention as shown in Table 1 and methods of measuring induction of E2F1 activity and elevation of E2F1 levels can be carried out following the descriptions found in Li et al., (2003) *Proc Natl Acad Sci USA.* 100(5): 2674-8 and U.S. Patent Application Publication No. 2002/0169135, both incorporated herein by reference.

The antiproliferative activity of the present spiro-oxathiine naphthoquinone derivative compounds indicate that the compounds of the present invention may show wide anticancer activity. For example, the compounds of the invention are effective for treating cancers such as colon, lung, prostate, leukemia, and pancreas. These treatments are accomplished utilizing the present spiro-oxathiine naphthoquinone derivative compounds (Formula I), alone or can be utilized in combination with, other chemotherapy agents or zenith radiation therapy. For example, the compounds of the present invention are used for the prevention or treatment of a hyperproliferative disorder and cancer (e.g. as a preventative drug) by preventing hyperproliferative or cancer cell formation. The results of experiments with β-lapachone and similar chemical compounds have shown that the compounds of the present invention have a cell death effect on a variety of human cancer cells and that they can inhibit growth of other human cancer cells.

Example 45

Colon Cancer Xenograft Model

Treatment with several compounds of the present invention reduced the mean tumor volume of human colon cancer xenograft by 41.7~70.2% compared to vehicle treated control.

E45.1

Athymic female nude mice (CR-L:NU/NU-nuBR) were injected subcutaneously in the flank with HT29 human colon cancer cells ($5 \times 10^6$ cells/mouse). Tumors were allowed to grow to approximately 70 mm$^3$ in size. Animals were randomized into two groups of eight animals per group. At day four post injection, mice with established tumors were treated intraperitoneally with either Compound 184 (32 mg/kg) or vehicle control. Drug or vehicle was administered every Monday, Wednesday and Friday for a total of nine doses (qMWFx3). Tumor size was evaluated periodically during the study. For each subject, tumor volume was calculated using the formula (L×W$^2$)/2 where L and W were the length and width of the tumor, respectively. The arithmetic mean tumor volume was calculated for each treatment group +/− standard error of the mean (SEM).

Treatment with Compound 184 at 32 mg/kg qMWF reduced the mean tumor volume of human colon cancer xenograft by 70.2% (% T/C 29.8, p=0.02) compared to vehicle treated control. See, e.g., FIG. 1A.

E45.2

Athymic female nude mice (CRL:NU/NU-nuBR) were injected subcutaneously in the flank with HT29 human colon cancer cells ($5 \times 10^6$ cells/mouse). Tumors were allowed to grow to approximately 90 mm$^3$ in size. Animals were randomized into three groups of eight animals per group. At day six post injection, mice with established tumors were treated intraperitoneally with either Compound 186 (32 mg/kg) or Compound 187 (48 mg/kg) and vehicle control. Drug or vehicle was administered every Monday, Wednesday and Friday for a total of nine doses (qMWFx3). Tumor size was evaluated periodically during the study. For each subject, tumor volume was calculated using the formula (L×W$^2$)/2 where L and W were the length and width of the tumor, respectively. The arithmetic mean tumor volume was calculated for each treatment group +/− standard error of the mean (SEM).

Figure 1B:
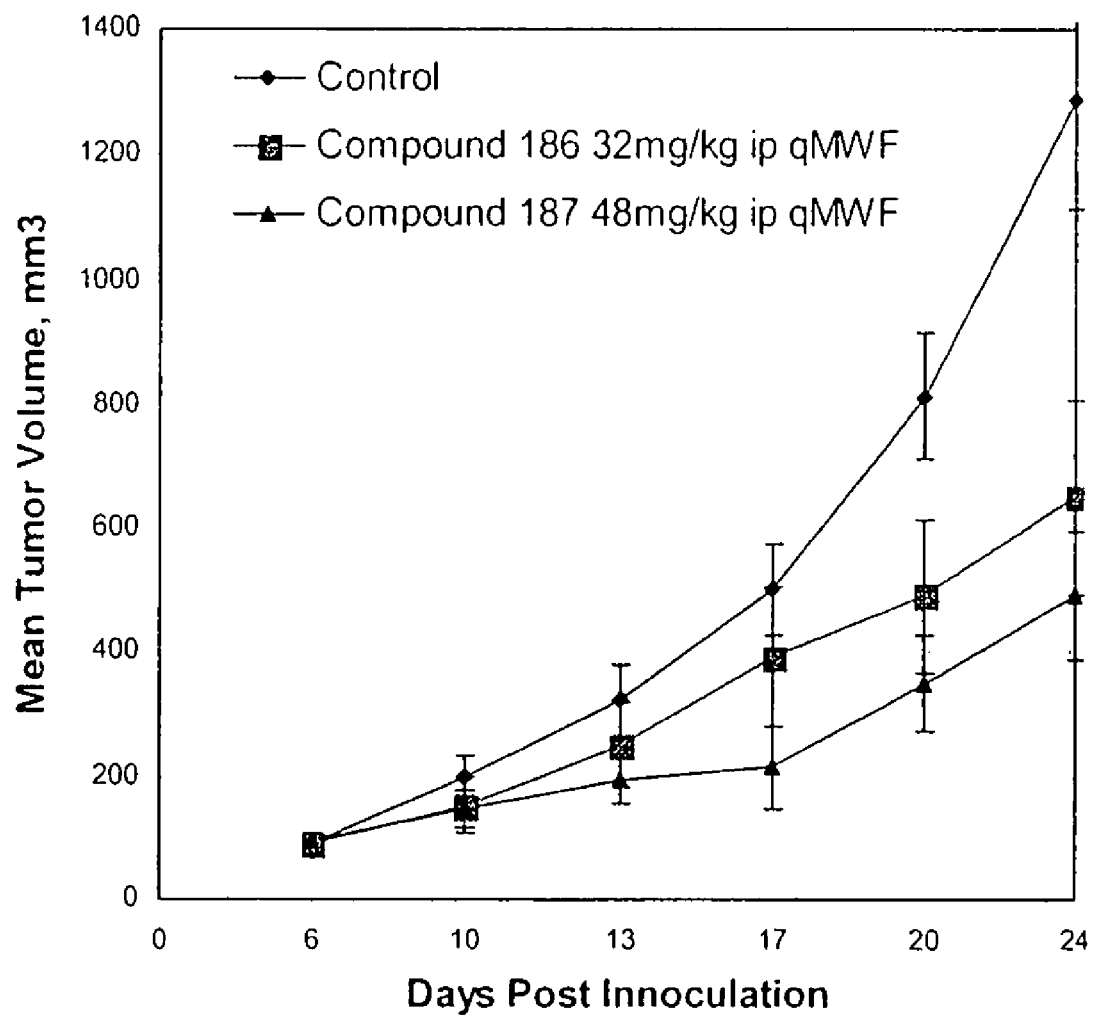
FIG. 1B shows the treatments with Compound 186 and Compound 187

Treatment with Compound 186 (32 mg/kg qMWF) and Compound 187 (48 mg/kg qMWF) reduced the mean tumor volume of human colon cancer xenograft by 50% (Opt. % T/C=50% p=0.02) and 62% (Opt. % T/C=38% p=0.00006) respectively compared to vehicle treated control. See, e.g., FIG. 1B.

E45.3

Athymic female nude mice (CRL:NU/NU-nuBR) were injected subcutaneously in the flank with HT29 human colon cancer cells ($5 \times 10^6$ cells/mouse). Tumors were allowed to grow to approximately 60 mm$^3$ in size. Animals were randomized into two groups of eight animals per group. At day five post injection, mice with established tumors were treated intraperitoneally with either Compound 182 (40 mg/kg) or vehicle control. Drug or vehicle was administered every Monday, Wednesday and Friday for a total of nine doses (qMWFx3). Tumor size was evaluated periodically during the study. For each subject, tumor volume was calculated using the formula (L×W$^2$)/2 where L and W were the length and width of the tumor, respectively. The arithmetic mean tumor volume was calculated for each treatment group +/− standard error of the mean (SEM).

Figure 1C:
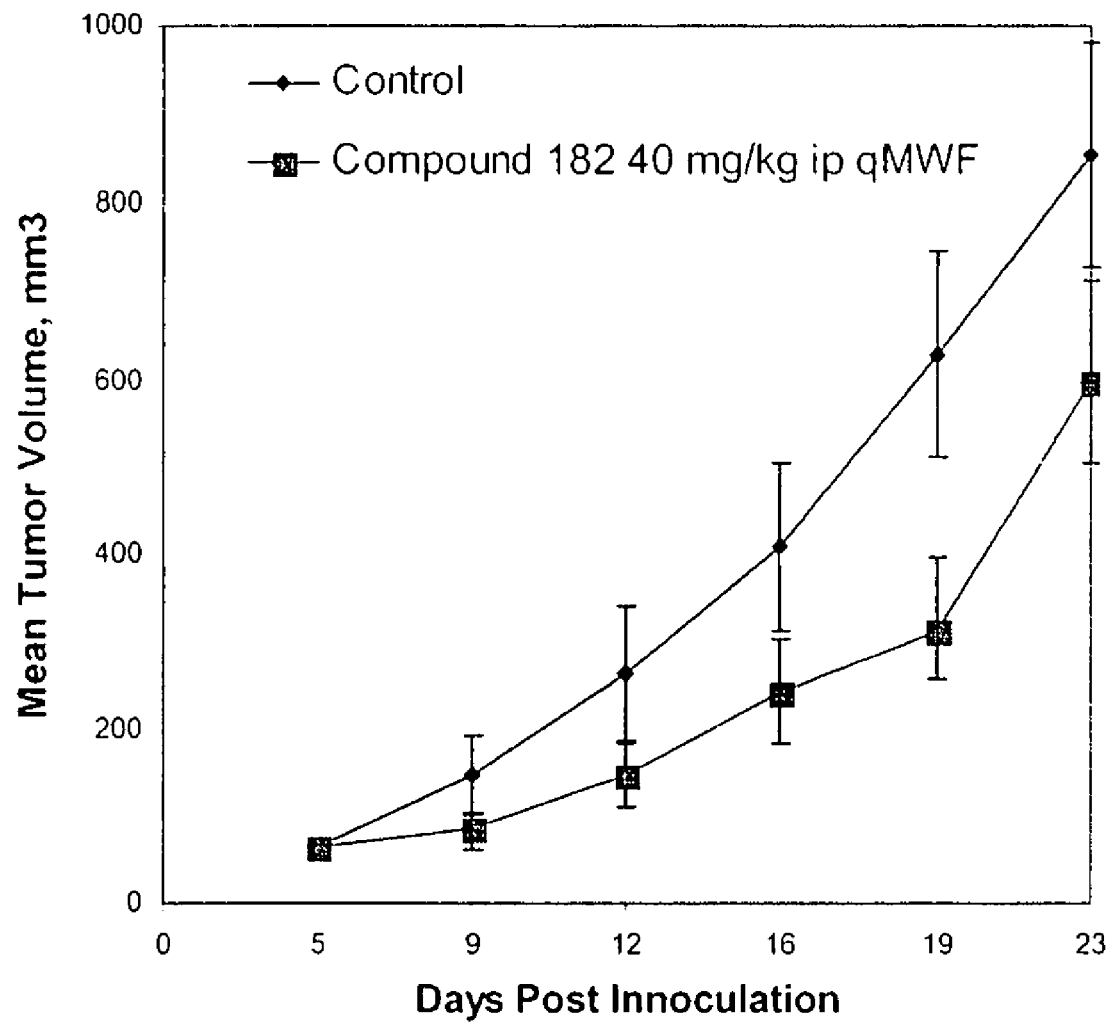
FIG. 1C shows the treatment with Compound 182

Treatment with Compound 182 at 40 mg/kg qMWF reduced the mean tumor volume of human colon cancer xenograft by 55.2% (% T/C=44.8% p=0.02) compared to vehicle treated control. See, e.g., FIG. 1C.

E45.4

Athymic female nude nmice (CRL:NU/NU-nuBR) were injected subcutaneously in the flank with HT29 human colon cancer cells (5×10⁶ cells/mouse). Tumors were allowed to grow to approximately 50 mm³ in size. Animals were randomized into three groups of five animals per group. At day eight post injection, mice with established tumors were treated intraperitoneally with either Compound 180 (40 mg/kg) or Compound 125 (40 mg/kg) and vehicle control. Drug or vehicle was administered every Monday, Wednesday and Friday for a total of twelve doses (qMWFx4). Tumor size was evaluated periodically during the study. For each subject, tumor volume was calculated using the formula $(L \times W^2)/2$ where L and W were the length and width of the tumor, respectively. The arithmetic mean tumor volume was calculated for each treatment group +/−standard error of the mean (SEM).

Figure 1D:
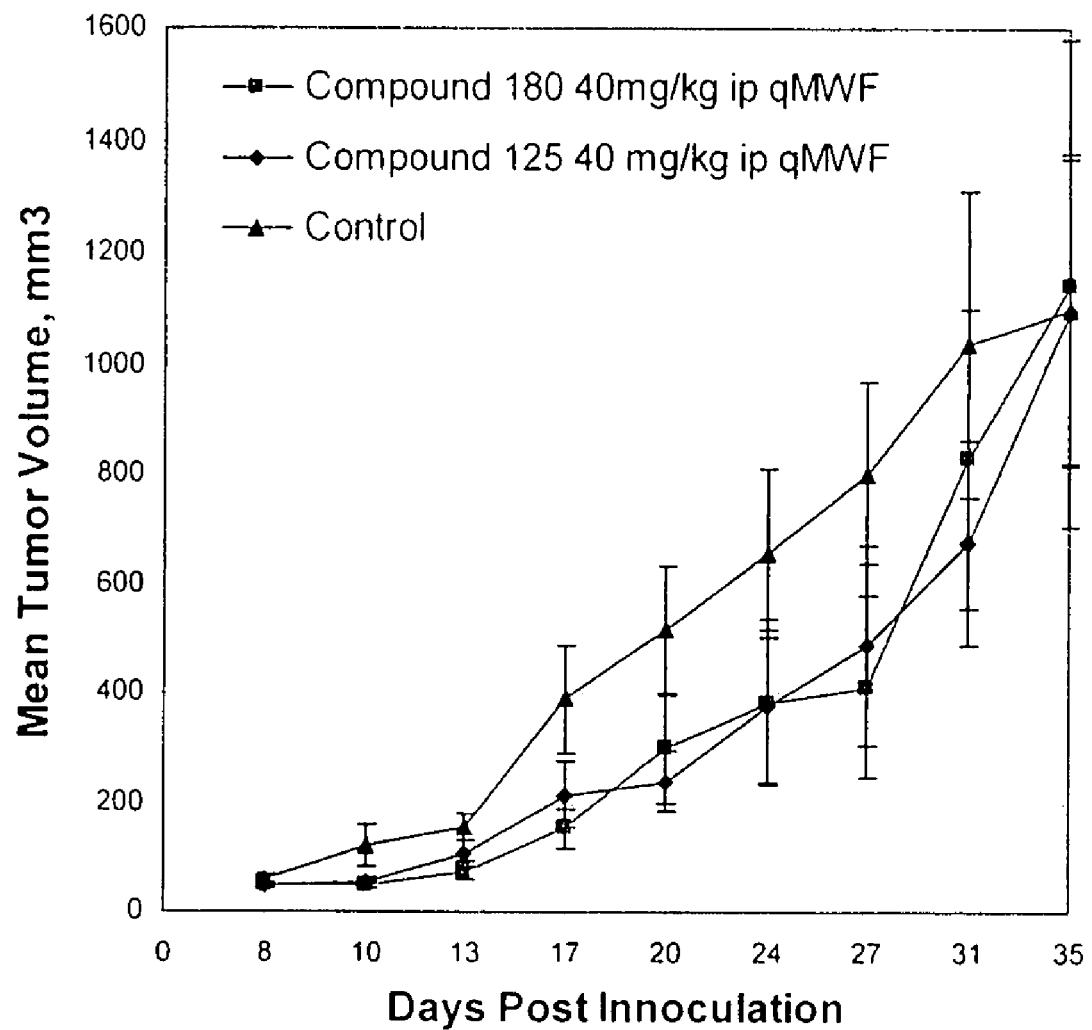
FIG. 1D shows the treatments with Compound 180 and Compound 125

Treatment with Compound 180 and Compound 125 at 40 mg/kg qMWF reduced the mean tumor volume of human colon cancer xenograft by 41.7% (% T/C 58.3) and 57.8% (% T/C 46.2) respectively compared to vehicle treated control. See, e.g., FIG. 1D.

TABLE 1

$IC_{50}$ Values (μM)

| Compound No. | Cancerous Cells | | | | | | Normal Cells | Fold Selectivity (NCM-460/DLD1) | E2F-1 Induction (HT-29) |
| | Lung A549 | Colon DLD-1 | Prostate DU-145 | Leukemia K-562 | Colon HT-29 | Pancreas PACA-2 | Colon NCM-460 | | |
| --- | --- | --- | --- | --- | --- | --- | --- | --- | --- |
| 13 | 3.78 | 1.46 | 1.54 | 1.35 | N/A | 0.856 | 3.25 | 2.2 | N/A |
| 20 | >100 | 49.5 | 60.5 | 48 | N/A | 27.5 | 61.7 | 1.2 | N/A |
| 39 | 7.69 | 1.45 | 3.86 | 1.87 | N/A | 1.52 | 6.35 | 4.4 | N/A |
| 40 | 15.5 | 4.09 | 14.4 | 3.92 | N/A | 8.39 | 10.2 | 2.5 | N/A |
| 41 | 4.84 | 1.58 | 3.1 | 1.44 | N/A | 1.47 | 5.8 | 3.7 | N/A |
| 42 | 43 | 8.95 | 12.7 | 5.64 | N/A | 5.12 | 12.6 | 1.4 | N/A |
| 43 | 9.96 | 2.26 | 4.12 | 2.77 | N/A | 2.14 | 9.44 | 4.2 | N/A |
| 45 | 19.7 | 4 | 4.3 | 3.95 | N/A | 4.49 | 9.84 | 2.5 | N/A |
| 46 | >100 | 5.26 | 5.03 | 9.61 | N/A | 4.24 | 28.6 | 5.4 | N/A |
| 48 | 11.8 | 1.55 | 4.12 | 1.5 | N/A | 2.37 | 5.7 | 3.7 | N/A |
| 49 | 5.58 | 2.87 | 4.11 | 1.8 | N/A | 2.39 | 7.72 | 2.7 | N/A |
| 50 | 5.41 | 1.54 | 3.55 | 1.44 | N/A | 1.42 | 7.14 | 4.6 | N/A |
| 51 | >100 | 11.6 | 5.52 | 10.3 | N/A | 4.28 | 33 | 2.8 | N/A |
| 52 | 14.4 | 4.15 | 4.49 | 2.71 | N/A | 3.92 | 10.1 | 2.4 | N/A |
| 53 | 3.83 | 1.42 | 1.37 | 1.44 | 2.21 | 1.06 | 8.52 | 6.0 | YES |
| 54 | 7.57 | 1.49 | 1.91 | 1.74 | N/A | 1.33 | 11 | 7.4 | N/A |
| 55 | 4.57 | 2.1 | 3.85 | 3.93 | 5.74 | 3.36 | 11.2 | 5.3 | Yes |
| 57 | 24.8 | 4.29 | 12.2 | 4.37 | N/A | 5.36 | 9.91 | 2.3 | N/A |
| 58 | 42.2 | 13.7 | 12.2 | 14.2 | N/A | 11 | 79.9 | 5.8 | N/A |
| 59 | 16.8 | 4.1 | 10.4 | 4.24 | N/A | 4.24 | 10.7 | 2.6 | N/A |
| 60 | 8.59 | 2.21 | 4.16 | 3.38 | N/A | 2.39 | 10.5 | 4.8 | N/A |
| 75 | 19.4 | 4.45 | 7.82 | 2.93 | N/A | 4.02 | 9.56 | 2.1 | N/A |
| 76 | >100 | 27.1 | 28 | >33.3 | N/A | 14.3 | 100 | 3.7 | N/A |
| 77 | >100 | 20.6 | 49.2 | 22.9 | N/A | 16.1 | 76.4 | 3.7 | N/A |
| 78 | 46.7 | 11.1 | 12.7 | 14.7 | N/A | 11.1 | 30 | 2.7 | N/A |
| 79 | 23.5 | 8.26 | 11.9 | 5.92 | N/A | 7.26 | 20.5 | 2.5 | N/A |
| 80 | 18.3 | 3.53 | 4.25 | 3.81 | N/A | 3.35 | 12.9 | 3.7 | N/A |
| 81 | >100 | 12.3 | 13.7 | 12.3 | N/A | 12.1 | 30.2 | 2.5 | N/A |
| 82 | 15.3 | 8.88 | 7.88 | 10 | N/A | 4.59 | 21.1 | 2.4 | N/A |
| 84 | 16.9 | 4.69 | 10.3 | 6.83 | N/A | 6.38 | 19.1 | 4.1 | N/A |
| 85 | 6.38 | 1.29 | 1.88 | 1.32 | N/A | 1.14 | 3.31 | 2.6 | N/A |
| 86 | 3.84 | 1.48 | 1.03 | 2.17 | N/A | 1.33 | 10.1 | 6.8 | N/A |
| 87 | 3.31 | 3.04 | 0.888 | 3.11 | N/A | 1.34 | 30.5 | 10.0 | N/A |
| 88 | 13.3 | 1.49 | 4.33 | 2.14 | N/A | 1.85 | 6.08 | 4.1 | N/A |
| 90 | 21 | 1.84 | 4.18 | 1.8 | N/A | 1.59 | 10.1 | 5.5 | N/A |
| 91 | 10.2 | 1.6 | 2.87 | 1.45 | N/A | 1.35 | 9 | 5.6 | N/A |
| 92 | 31 | 4.01 | 9.11 | 4.54 | N/A | 4.29 | 13.1 | 3.3 | N/A |
| 93 | 4.87 | 1.68 | 4.25 | 2.46 | N/A | 3.55 | 10.8 | 6.4 | N/A |
| 94 | 8.52 | 2.41 | 3.69 | 2.49 | N/A | 2.81 | 9.48 | 3.9 | N/A |
| 95 | 51.4 | 10.9 | 5.13 | 12.3 | N/A | 4.72 | 37.7 | 3.5 | N/A |
| 96 | >100 | 31.7 | 20 | 36.3 | 20.5 | 26.7 | 100 | 3.2 | Yes |
| 97 | 26 | 4.39 | 6.59 | 4.28 | 12.6 | 4.93 | 13.3 | 3.0 | YES |
| 98 | 7.3 | 3.11 | 3.98 | 1.43 | N/A | 1.61 | 4.78 | 1.5 | N/A |
| 100 | 8 | 1.13 | 1.39 | 1.37 | N/A | 1.32 | 5.67 | 5.0 | N/A |
| 110 | 7.52 | 1.62 | 4.04 | 3.15 | N/A | 2.48 | 7.25 | 4.5 | N/A |
| 111 | 4.63 | 1.52 | 4.1 | 2.01 | N/A | 1.7 | 4.78 | 3.1 | N/A |
| 112 | 11.2 | 1.54 | 3.99 | 2.97 | N/A | 1.83 | 6.3 | 4.1 | N/A |
| 118 | 10.1 | 2.42 | 5.02 | 3.85 | N/A | 2.27 | 8.3 | 3.4 | N/A |
| 120 | 9.04 | 4.23 | 9.27 | 5.47 | N/A | 4.35 | 10.4 | 2.5 | N/A |
| 121 | 9.42 | 3.98 | 5.48 | 4.03 | N/A | 3.71 | 11 | 2.8 | N/A |
| 122 | 6.02 | 1.66 | 2.02 | 1.45 | N/A | 1.31 | 3.37 | 2.0 | N/A |
| 123 | 36.8 | 4.37 | 4.32 | 4.09 | N/A | 4.18 | 9.96 | 2.3 | N/A |
| 125 | 9.57 | 1.71 | 5.06 | 3.74 | 4.95 | 2.5 | 9.75 | 5.7 | Yes |
| 126 | 5 | 3.12 | 4.05 | 1.63 | N/A | 1.44 | 5.26 | 1.7 | N/A |
| 128 | 42.8 | 16.9 | 7.41 | 21 | N/A | 9.22 | 40.8 | 2.4 | N/A |
| 129 | 66.9 | 3.98 | 6.75 | 4.44 | 7.05 | 4.12 | 16.5 | 4.1 | Yes |
| 130 | 7.4 | 1.57 | 4.58 | 3.84 | N/A | 2.74 | 10.2 | 6.5 | N/A |
| 131 | 6.9 | 1.46 | 2.7 | 1.39 | N/A | 1.44 | 2.95 | 2.0 | N/A |
| 132 | 6.62 | 1.53 | 4.05 | 2.86 | N/A | 1.94 | 9.74 | 6.4 | N/A |

TABLE 1-continued

| | IC$_{50}$ Values (μM) | | | | | | | | |
|---|---|---|---|---|---|---|---|---|---|
| | Cancerous Cells | | | | | | Normal Cells | Fold | E2F-1 |
| Compound No. | Lung A549 | Colon DLD-1 | Prostate DU-145 | Leukemia K-562 | Colon HT-29 | Pancreas PACA-2 | Colon NCM-460 | Selectivity (NCM-460/DLD1) | Induction (HT-29) |
|---|---|---|---|---|---|---|---|---|---|
| 133 | 73 | 13.1 | 12.9 | 15 | N/A | 12.5 | 29.6 | 2.3 | N/A |
| 134 | 23.3 | 3.94 | 6.87 | 7.22 | N/A | 4.43 | 15.6 | 4.0 | N/A |
| 135 | 19.2 | 4.89 | 5.07 | 4.02 | N/A | 7.42 | 8.35 | 1.7 | N/A |
| 136 | 9.6 | 2.95 | 4.32 | 4.34 | N/A | 4.13 | 8.7 | 2.9 | N/A |
| 137 | 8.27 | 4.08 | 4.32 | 4.25 | N/A | 4.12 | 10 | 2.5 | N/A |
| 138 | 7.8 | 1.43 | 2.52 | 1.43 | N/A | 1.48 | 3.55 | 2.5 | N/A |
| 139 | 27.8 | 4.32 | 4.42 | 4.8 | N/A | 4.17 | 19.5 | 4.5 | N/A |
| 140 | 21.5 | 3.37 | 4.2 | 4.26 | N/A | 3.93 | 12.2 | 3.6 | N/A |
| 141 | 5.01 | 1.95 | 4.01 | 2.39 | N/A | 2.44 | 8.13 | 4.2 | N/A |
| 142 | 44.2 | 4.25 | 6.93 | 8.72 | N/A | 10.5 | 15.1 | 3.6 | N/A |
| 143 | 7.39 | 2.14 | 4.26 | 3.29 | N/A | 2.5 | 6.39 | 3.0 | N/A |
| 144 | 8.19 | 2.17 | 4.91 | 4.32 | N/A | 2.82 | 9.9 | 4.6 | N/A |
| 145 | 5.55 | 3.8 | 4.03 | 7.87 | N/A | 2.74 | 21 | 5.5 | N/A |
| 146 | 38.2 | 4.53 | 5.77 | 12.1 | N/A | 4.1 | 26.4 | 5.8 | N/A |
| 157 | 8.03 | 3.63 | 2.26 | 7.6 | N/A | 2.08 | 28.2 | 7.8 | N/A |
| 158 | 5.6 | 1.48 | 1.71 | 1.44 | N/A | 1.32 | 4.91 | 3.3 | N/A |
| 159 | 14.3 | 4.47 | 5.03 | 4.13 | N/A | 4.03 | 10.2 | 2.3 | N/A |
| 160 | 6.72 | 1.69 | 3.92 | 1.53 | N/A | 1.55 | 5.56 | 3.3 | N/A |
| 162 | 6.95 | 1.36 | 2.77 | 1.5 | N/A | 1.45 | 2.8 | 2.1 | N/A |
| 163 | 4.31 | 0.714 | 1.38 | 1 | 4.48 | 0.764 | 2.84 | 4.0 | Yes |
| 164 | 9.02 | 1.52 | 2.88 | 3.12 | N/A | 1.42 | 9.74 | 6.4 | N/A |
| 165 | 6.73 | 1.92 | 3.08 | 2.31 | N/A | 1.44 | 4.71 | 2.5 | N/A |
| 166 | 13.6 | 3.7 | 4.16 | 2.26 | N/A | 1.47 | 8.69 | 2.3 | N/A |
| 167 | 7.56 | 1.35 | 2.76 | 1.53 | N/A | 1.26 | 3.68 | 2.7 | N/A |
| 170 | 4.69 | 1.49 | 1.42 | 5.31 | N/A | 1.37 | 14 | 9.4 | N/A |
| 171 | 6.55 | 1.34 | 3.22 | 3.6 | N/A | 1.46 | 9.69 | 7.2 | N/A |
| 172 | 6.16 | 1.36 | 1.55 | 1.48 | N/A | 1.09 | 5.53 | 4.1 | N/A |
| 173 | 7 | 1.49 | 2.92 | 4.1 | N/A | 1.42 | 10.3 | 6.9 | N/A |
| 174 | 6.29 | 1.3 | 1.55 | 1.61 | N/A | 1.25 | 3.2 | 2.5 | N/A |
| 175 | 7.29 | 1.42 | 1.59 | 3.27 | N/A | 1.39 | 6.12 | 4.3 | N/A |
| 176 | 5.14 | 2.4 | 2.43 | 4.76 | N/A | 3 | 11 | 4.6 | N/A |
| 177 | 14.9 | 6.22 | 4.55 | 8.99 | N/A | 4.18 | 20.5 | 3.3 | N/A |
| 180 | 3.53 | 0.708 | 1.48 | 1.46 | 2.2 | 0.958 | 3.57 | 5.0 | Yes |
| 181 | 4.93 | 0.734 | 1.52 | 1.32 | 3.11 | 0.909 | 4.53 | 6.2 | Yes |
| 182 | 6.45 | 1.3 | 1.28 | 3.25 | 2.07 | 1.33 | 11.2 | 8.6 | Yes |
| 183 | 3.1 | 1.04 | 0.796 | 2.42 | 3.88 | 0.7 | 10.2 | 9.8 | Yes |
| 184 | 5.85 | 2.58 | 1.65 | 5.34 | 3.67 | 1.71 | 27.8 | 10.8 | Yes |
| 185 | 7.42 | 3.38 | 1.01 | 4.46 | 2.47 | 1.37 | 13.7 | 4.1 | YES |
| 186 | 5.5 | 1.5 | 2.1 | 2.3 | 6.5 | 1.5 | 6.8 | 4.7 | YES |
| 187 | 5.1 | 2.1 | 3 | 2.7 | 5.5 | 1.9 | 8.1 | 8.1 | YES |
| 229 | 22.6 | 4.27 | 4.63 | 4.14 | N/A | 4.33 | 12.8 | 3.0 | N/A |
| 231 | 27.9 | 9.27 | 12 | 10.6 | N/A | 4.84 | 12.3 | 1.3 | N/A |
| 232 | 13.7 | 4.13 | 9.26 | 2.58 | N/A | 4.14 | 9.13 | 2.2 | N/A |
| 233 | >100 | 64.3 | 40.4 | 62.8 | N/A | 56.3 | 48.8 | 0.8 | N/A |
| 234 | >100 | >100 | >100 | >100 | N/A | 55.6 | >100 | n/a | N/A |
| 235 | >100 | 69.6 | 54.4 | 52.4 | N/A | 48.5 | 85.8 | 1.2 | N/A |
| 237 | >100 | 66.1 | 61.3 | 49.3 | N/A | 48 | 94.2 | 1.4 | N/A |
| 258 | 5.42 | 1.49 | 3.9 | 1.49 | N/A | 1.99 | 5.91 | 4.0 | N/A |

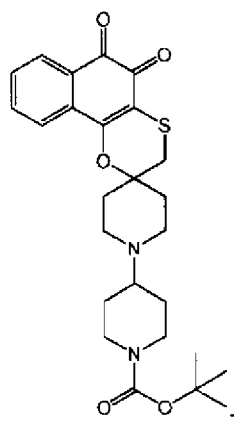

What is claimed is:

1. A compound of Formula I:

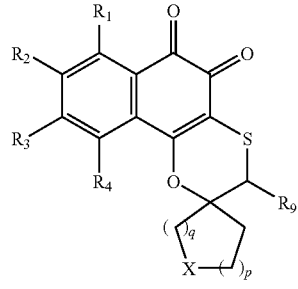

(I)

or a pharmaceutically acceptable salt and/or an individual diastereomer thereof, wherein:

$X=N-J_1$, $$C\begin{matrix}J_2\\ \\J_3\end{matrix}$$

O, or S;

p=1 or 2;

q=p or p+1;

$R_1$, $R_2$, $R_3$, and $R_4$ are each, independently, H, OH, F, Cl, Br, I, $CH_3$, $CF_3$, $C_2$-$C_6$ straight chain alkyl, substituted $C_1$-$C_6$ straight chain alkyl, $C_3$-$C_6$ branched alkyl, $C_3$-$C_8$ cycloalkyl, allyl, $C_2$-$C_6$ straight chain alkenyl, substituted $C_2$-$C_6$ straight chain alkenyl, $C_3$-$C_6$ branched alkenyl, $C_5$-$C_8$ cycloalkenyl, $C_2$-$C_6$ alkynyl, $NO_2$, CN, $NH_2$, alkylamine, substituted alkylamine, dialkylamine, arylamine, $C(O)NHR_{14}$, $NHC(O)R_{15}$, carbamoyl, aminesulfoxide, sulfonamide, sulfamoyl, sulfonic acid, phenyl, $C_5$-$C_8$ aryl, heteroaryl, heterocyclyl, $OCH_3$, $OCF_3$, $C_2$-$C_6$ alkoxy, alkoxycarbonyl, carboxyacid, carbonylalkoxy, SH, thioalkyl, thioaryl, alkylthioaryl, or $C_1$-$C_6$ hydroxyl alkyl;

$J_1$ is -$(CR_5R_6)_n$-$(CR_7R_8)_m$—Y, —$S(O)_O$—Z, amidine, substituted amidine, heterocyclyl, substituted heterocyclyl, 3,4-dioxo-3,4-dihydronaphthalenyl, heteroaryl, substituted heteroaryl, or

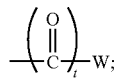

m=0, 1, 2, 3, 4, or 5;
n=0, 1, 2, 3, 4, or 5;
o=1 or 2;
t=1 or 2;

$R_5$ and $R_6$ are each, independently, H, OH, $CH_3$, $CF_3$, $C_2$-$C_6$ straight chain alkyl, $C_3$-$C_6$ branched alkyl, $C_3$-$C_8$ cycloalkyl, allyl, $C_2$-$C_6$ straight chain alkenyl, $C_3$-$C_6$ branched alkenyl, $C_5$-$C_8$ cycloalkenyl, $C_2$-$C_6$ alkynyl, phenyl, $C_5$-$C_8$ aryl, heteroaryl, heterocyclyl, carboxylate, or carbonylalkoxy; when $R_5$=$R_6$, $R_5$ is not OH;

$R_7$ and $R_8$ are each, independently, H, F, Cl, Br, I, OH, $CH_3$, $C_2$-$C_6$ straight chain alkyl, $CF_3$, $C_3$-$C_6$ branched alkyl, $C_3$-$C_8$ cycloalkyl, $C_2$-$C_6$ alkoxy, allyl, $C_2$-$C_6$ straight chain alkenyl, $C_3$-$C_6$ branched alkenyl, $C_5$-$C_8$ cycloalkenyl, $C_2$-$C_6$ alkynyl, $NO_2$, CN, amine, alkylamine, dialkylamine, arylamine, carbamoyl, aminesulfoxide, sulfonamide, sulfonic acid, phenyl, $C_5$-$C_8$ aryl, heteroaryl, heterocyclyl, $OCH_3$, $OCF_3$, alkoxycarbonyl, carboxyacid, carbonylalkoxy, SH, thioalkyl, thioaryl, or alkylthioaryl; when $R_7$=$R_8$, $R_7$ is not OH, $NH_2$, SH, or $NO_2$;

Y is H, F, Cl, Br, I, $CR_{10}$=$CHR_{11}$, $CF_3$, $CH_3$, $C_2$-$C_6$ straight chain alkyl, substituted $C_2$-$C_6$ straight chain alkyl, $C_3$-$C_6$ branched alkyl, $CH_2OR_{16}$, phenyl, substituted phenyl, $C_5$-$C_8$ aryl, substituted $C_5$-$C_8$ aryl, $C_3$-$C_8$ cycloalkyl, substituted $C_3$-$C_8$ cycloalkyl, $CH_2$-heterocycle, $C_5$-$C_8$ cycloalkenyl, aryloxy, substituted aryloxy, heteroaryl, substituted heteroaryl, heterocyclyl, substituted heterocyclyl, benzyl, alkylamine, substituted alkylamine, benzylamine, OH, $OCR_{12}$=$CHR_{13}$, $C_2$-$C_6$ alkynyl, amine, dialkylamine, arylamine, amide, carbamoyl, aminesulfoxide, sulfamide, sulfamoyl, sulfonic acid, heteroaryloxy, $OCH_3$, $OCF_3$, $C_2$-$C_6$ alkoxy, alkenoxy, phenoxy, benzyloxy, alkoxycarbonyl, carboxyacid, carboxyalkoxy, carbonylalkyl, thio, alkylthio, thioalkyl, arylthio, thioaryl, alkylthioaryl, or

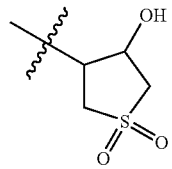

provided that, when n=0 and m=0, Y is H, heterocyclyl, heteroaryl, $C_3$-$C_8$ cycloalkyl, $C_5$-$C_8$ cycloalkenyl, aryl, or

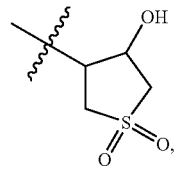

each of which may be substituted;

W is $C_2$-$C_6$ straight chain alkyl, substituted $C_1$-$C_6$ straight chain alkyl, $OCH_3$, $C_2$-$C_6$ alkoxy, alkylthioalkyl, substituted alkylthioalkyl, $C_3$-$C_8$ cycloalkyl, substituted $C_3$-$C_8$ cycloalkyl, $C_5$-$C_8$ aryl, substituted aryl, phenyl, substituted phenyl, $CR_{10}$=$CHR_{11}$, alkylthio, benzyl, substituted benzyl, heterocyclyl, substituted heterocyclyl, phenoxy, aryloxy, substituted aryloxy, $OCR_{12}$=$CHR_{13}$, benzyloxy, heteroaryloxy, substituted heteroaryloxy, amine, substituted amine, arylamine, substituted arylamine, phenylamine, substituted phenylamine, $CH_3$, $CF_3$, $C_3$-$C_6$ branched alkyl, $C_5$-$C_8$ cycloalkenyl, $C_2$-$C_6$ alkynyl, alkylamine, dialkylamine, heteroaryl, $CH_2$-heterocyclyl, $CH_2$-substituted heterocyclyl, $OCF_3$, alkenoxy, $CH_2OR_{16}$, thioalkyl, arylthio, thioaryl, alkylthioaryl, alkylcarboxy, phenyl sulfonylamide, substituted aryl sulfonylamide, or chlorophenylacetyl;

Z is $CH_3$, $CF_3$, $C_2$-$C_6$ straight chain alkyl, heteroaryl, substituted heteroaryl, phenyl, substituted phenyl, $C_5$-$C_8$ aryl, substituted $C_5$-$C_8$ aryl, $C_3$-$C_6$ branched alkyl, $C_3$-$C_8$ cycloalkyl, $C_5$-$C_8$ cycloalkenyl, $C_2$-$C_6$ alkynyl, amine, alkylamine, dialkylamine, arylamine, benzyl, heteroaryloxy, heterocyclyl, $CH_2$-heterocycle, $OCH_3$, $OCF_3$, $C_2$-$C_6$ alkoxy, alkenoxy, phenoxy, aryloxy or benzyloxy;

$R_9$ is H, $CH_3$, $C_2$-$C_6$ straight chain alkyl, or $C_3$-$C_6$ branched alkyl;

$R_{10}$, $R_{11}$, $R_{12}$, and $R_{13}$ are each, independently, H, phenyl, $C_5$-$C_8$ aryl, $CH_3$, $CF_3$, $C_2$-$C_6$ straight chain alkyl, $C_3$-$C_8$ cycloalkyl, heteroaryl, or heterocyclyl;

$R_{14}$ and $R_{15}$ are each, independently H, $C_2$-$C_6$ straight alkyl, $C_3$-$C_6$ branched alkyl, $C_3$-$C_8$ cycloalkyl, allyl, $C_2$-$C_6$ straight alkenyl, branched alkenyl, $C_5$-$C_8$ cycloalkenyl, phenyl, $C_5$-$C_8$ aryl, benzyl, $CH_2C(OCH_3)_2$, heteroaryl, or heterocyclyl;

$R_{16}$ is $C_3$-$C_6$ branched alkyl, $C_5$-$C_8$ aryl, substituted $C_5$-$C_8$ aryl, heteroaryl, phenyl, substituted phenyl, $CH_2$-aryl, benzyl, H, $CH_3$, $CF_3$, $C_2$-$C_6$ straight chain alkyl, $C_3$-$C_8$ cycloalkyl, heterocyclyl, or $CH_2$-heteroaryl, $J_2$ and $J_3$ are each, independently, H, F, Cl, Br, I, $CR_{17}$=$CHR_{18}$, $CF_3$, $CH_3$, $C_2$-$C_6$ straight chain alkyl, substituted $C_1$-$C_6$ straight chain alkyl, $C_3$-$C_6$ branched alkyl, $CH_2OR_{21}$, phenyl, $C_5$-$C_8$ aryl, substituted $C_5$-$C_8$ aryl, $C_3$-$C_8$ cycloalkyl, substituted $C_3$-$C_8$ cycloalkyl, $CH_2$-heterocycle, $C_5$-$C_8$ cycloalkenyl, aryloxy, substituted aryloxy, heteroaryl, substituted heteroaryl, heterocyclyl, substituted heterocyclyl, benzyl, alkylamine, substituted alkylamine, benzylamine, OH, $OCR_{19}$=$CHR_{20}$, $C_2$-$C_6$ alkynyl, amine, dialkylamine, arylamine, amide, carbamoyl, aminesulfoxide, sulfamide, sulfamoyl, sulfonic acid, heteroaryloxy, $OCH_3$, $OCF_3$, $C_2$-$C_6$ alkoxy, alkenoxy, phenoxy, benzyloxy, alkoxycarbonyl, carboxyacid, carboxyalkoxy, carbonylalkyl, thio, alkylthio, thioalkyl, arylthio, thioaryl, alkylthioaryl, or

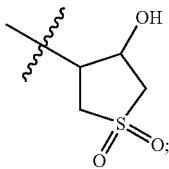

when $J_2 = J_3$, $J_2$ is not OH, $NH_2$, or SH; or $J_2$ and $J_3$ can form a 4, 5, 6, 7, or 8 membered spiro ring containing 0, 1, or 2 heteroatoms selected from O, N, and S;

$R_{17}$, $R_{18}$, $R_{19}$, and $R_{20}$ are each, independently, H, phenyl, $C_5$-$C_8$ aryl, $CH_3$, $CF_3$, $C_2$-$C_6$ straight chain alkyl, $C_3$-$C_8$ cycloalkyl, heteroaryl, or heterocyclyl; and $R_{21}$ is H, $C_2$-$C_6$ straight alkyl, $C_3$-$C_6$ branched alkyl, $C_3$-$C_8$ cycloalkyl, allyl, $C_2$-$C_6$ straight alkenyl, branched alkenyl, $C_5$-$C_8$ cycloalkenyl, phenyl, $C_5$-$C_8$ aryl, benzyl, $CH_2C(OCH_3)_2$, heteroaryl, or heterocyclyl.

2. The compound of claim 1, wherein p=1 and q=1.
3. The compound of claim 1, wherein p=1 and q=2.
4. The compound of claim 1, wherein p=2 and q=2.
5. The compound of claim 1, wherein p=2 and q=3.
6. The compound of claim 1, wherein $R_1$, $R_2$, $R_3$, and $R_4$ are each, independently, H, OH, F, Cl, Br, I, $CH_3$, $CF_3$, $OCH_3$, $C_2$-$C_6$ alkoxy, $C_2$-$C_6$ straight chain alkyl, substituted $C_2$-$C_6$ straight chain alkyl, phenyl, $C_5$-$C_8$ aryl, $NO_2$, CN, $C(O)NHR_{14}$ or $NHC(O)R_{15}$.
7. The compound of claim 6, wherein $R_1$, $R_2$, $R_3$, and $R_4$ are each, independently, H, OH, F, Cl, Br, I, $CH_3$, $CF_3$, $OCH_3$, or $C_2$-$C_6$ alkoxy.
8. The compound of claim 7, wherein $R_1$, $R_2$, $R_3$, and $R_4$ are each, independently, H or $OCH_3$.
9. The compound of claim 8, wherein $R_1$, $R_2$ and $R_4$ are each H and $R_3$ is $OCH_3$.
10. The compound of claim 1, wherein X=O or S.
11. The compound of claim 1, wherein X=

12. The compound of claim 1, wherein X=N-$J_1$.
13. The compound of claim 12, wherein $J_1$ is —$(CR_5R_6)_n$—$(CR_7R_8)_m$—Y.
14. The compound of claim 13, wherein n=0 and m=0.
15. The compound of claim 13, wherein n=1 and m=0.
16. The compound of claim 13, wherein n=1 and m=1.
17. The compound of claim 13, wherein n=1 and m=2.
18. The compound of claim 13, wherein n=5 and m=5.
19. The compound of claim 13, wherein $R_5$ and $R_6$ are each, independently, H or $CH_3$.
20. The compound of claim 13, wherein $R_7$ and $R_8$ are each, independently, H, F, Cl, Br, I, OH, $CH_3$, $C_2$-$C_6$ straight chain alkyl, $CF_3$, $C_3$-$C_6$ branched alkyl, $C_3$-$C_8$ cycloalkyl, or $C_2$-$C_6$ alkoxy.
21. The compound of claim 20, wherein $R_7$ and $R_8$ are each, independently, H or OH.
22. The compound of claim 13, wherein Y is $CH_2OR_{16}$, phenyl, substituted $C_5$-$C_8$ aryl or benzyl.

23. The compound of claim 15, wherein $R_5$ and $R_6$ are each H.
24. The compound of claim 23, wherein Y is substituted or unsubstituted $C_5$-$C_8$ aryl.
25. The compound of claim 24, wherein the substituted $C_5$-$C_8$ aryl is substituted with from 1 to 5 substituents, each of which is independently CN, Cl or F.
26. The compound of claim 16, wherein $R_5$ and $R_6$ are each H and $R_7$ and $R_8$ are each, independently, H or OH.
27. The compound of claim 26, wherein Y is $CH_2OR_{16}$.
28. The compound of claim 27, wherein $R_{16}$ is substituted or unsubstituted $C_5$-$C_8$ aryl.
29. The compound of claim 28, wherein the substituted $C_5$-$C_8$ aryl is substituted with from 1 to 5 substituents, each of which is independently $C_3$-$C_6$ branched alkyl, Cl, or F.
30. The compound of claim 12, wherein $J_1$ is —$S(O)_o$—Z.
31. The compound of claim 30, wherein o=1.
32. The compound of claim 30, wherein o=2.
33. The compound of claim 30, wherein Z is $CH_3$, $CF_3$, $C_2$-$C_6$ straight chain alkyl, heteroaryl, substituted heteroaryl, phenyl, substituted phenyl, $C_5$-$C_8$ aryl, or substituted $C_5$-$C_8$ aryl.
34. The compound of claim 12, wherein $J_1$ is

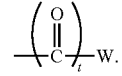

35. The compound of claim 34, wherein t=1.
36. The compound of claim 34, wherein t=2.
37. The compound of claim 35, wherein W is substituted aryl, phenyl, phenoxy, aryloxy or substituted aryloxy.
38. The compound of claim 37, wherein the aryl and aryloxy is substituted with from 1 to 5 substituents, each of which is independently $CF_3$ or F.
39. The compound of claim 34, wherein t=2 and W is $C_2$-$C_6$ alkoxy.
40. The compound of claim 12, wherein $R_9$ is H.
41. The compound of claim 12, wherein $R_{10}$ and $R_{11}$ are both H.
42. The compound of claim 12, wherein $R_{12}$ and $R_{13}$ are both H.
43. The compound of claim 12, wherein $R_{12}$ is H and $R_{13}$ is phenyl.
44. The compound of claim 12, wherein $R_{16}$ is $C_3$-$C_6$ branched alkyl, $C_5$-$C_8$ aryl, substituted $C_5$-$C_8$ aryl, heteroaryl, phenyl, substituted phenyl, $CH_2$-aryl, or benzyl.
45. The compound of claim 1, which is selected from the following compounds, or a pharmaceutically acceptable salt and/or an individual diastereomer thereof:
  1'-(3-chlorobenzoyl) spiro [naphtho [1,2-b][1,4]oxathiine-2,4'-piperidine]-5,6-dione;
  1'-(3,4-dichlorobenzoyl)spiro[naphtho [1,2-b][1,4]oxathiine-2,4'-piperidine]-5,6-dione;
  4-[(5,6-dioxo-5,6-dihydro-1'H-spiro[naphtho[1,2-b][1,4]oxathiine-2,4'-piperidin]-1'-yl)methyl]benzonitrile;
  1'-(2-phenylethyl)spiro[naphtho[1,2-b][1,4]oxathiine-2,4'-piperidine]-5,6-dione;
  1'-(4-fluorobenzyl)spiro [naphtho [1,2-b][1,4]oxathiine-2,4'-piperidine]-5,6-dione;
  1'-[3-(4-tert-butylphenoxy)-2-hydroxypropyl]spiro[naphtho[1,2-b][1,4]oxathiine-2,4'-piperidine]-5,6-dione;
  1'-(2-hydroxy-3-phenylpropyl)spiro[naphtho[1,2-b][1,4]oxathiine-2,4'-piperidine]-5,6-dione;

3-(trifluoromethyl)phenyl 5,6-dioxo-5,6-dihydro-1'H-Spiro [naphtho [1,2-b][1,4]oxathiine -2,4'-piperidine]-1'-carboxylate;
4-fluorophenyl-5,6-dioxo-5,6-dihydro-1'H-Spiro[naphtho [1,2-b][2,4]oxathiine-2,4'-piperidine]-1'-carboxylate;
1'-(2-chloro-6-fluorobenzyl)spiro[naphtho[1,2-b][1,4]oxathiine-2,4'-piperidine]-5,6-dione;
1'-(3-chloro-4-fluorobenzyl)spiro[naphtho[1,2-b][1,4]oxathiine-2,4'-piperidine]-5,6-dione;
1'-(3-phenoxypropyl)spiro [naphtho [1,2-b][1,4]oxathiine-2,4'-piperidine]-5,6-dione;
1'-[2-(4-chlorophenoxy)ethyl]Spiro[naphtho[1,2-b][1,4]oxathiine-2,4'-piperidine]-5,6-dione;
1'-[(2S)-3-(4-fluorophenoxy)-2-hydroxypropyl]Spiro [naphtho [1,2-b][1,4]oxathiine-2,4'-piperidine]-5,6-dione;
1'-[(2S)-3-(4-tert-butylphenoxy)-2-hydroxypropyl]spiro [naphtho [1,2-b][1,4]oxathiine -2,4' -piperidine]-5,6-dione;
1'-[(2R)-3-(4-tert-butylphenoxy)-2-hydroxypropyl]spiro [naphtho [1,2-b][1,4]oxathiine -2,4'-piperidine]-5,6-dione;
1'-[(2R)-3-(4-fluorophenoxy)-2-hydroxypropyl]spiro [naphtho[1,2-b][1,4]oxathiine-2,4'-piperidine]-5,6-dione;
1'-[(2S)-3-(4-chlorophenoxy)-2-hydroxypropyl]Spiro [naphtho [1,2-b][1,4]oxathiine-2,4'-piperidine]-5,6-dione;
1'-[(2R)-3-(4-chlorophenoxy)-2-hydroxypropyl]spiro [naphtho[1,2-b][1,4]oxathiine-2,4'-piperidine]-5,6-dione;
1'-[(2R)-2-hydroxy-3-phenylpropyl]spiro[naphtho[1,2-b][1,4]oxathiine-2,4'-piperidine]-5,6-dione;
1'-[(2S)-2-hydroxy-3-phenylpropyl]spiro[naphtho[1,2-b][1,4]oxathiine-2,4'-piperidine]-5,6-dione;
1'-[(2S)-2-hydroxy-3-(2-methylphenoxy)propyl]spiro [naphtho[1,2-b][1,4]oxathiine-2,4'-piperidine]-5,6-dione;
1'-isopropylspiro[naphtho[1,2-b][1,4]oxathiine-2,4'-piperidine]-5,6-dione;
1'-[(2S)-3-(4-ethylphenoxy)-2-hydroxypropyl]spiro [naphtho[1,2-b][1,4]oxathiine-2,4'-piperidine]-5,6-dione;
1'-[(2R)-3-(4-ethylphenoxy)-2-hydroxypropyl]spiro [naphtho[1,2-b][1,4]oxathiine-2,4'-piperidine]-5,6-dione; and
1'-[(2R)-2-hydroxy-3-(2-methylphenoxy)propyl]spiro [naphtho[1,2-b][1,4]oxathiine-2,4'-piperidine]-5,6-dione.

46. A pharmaceutical composition comprising a compound of claim 1 in combination with a pharmaceutically acceptable carrier or excipient.

47. The pharmaceutical composition of claim 46 further comprising a second chemotherapeutic agent.

48. The pharmaceutical composition of 47, wherein said second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

49. The compound of claim 1, selected from the group consisting of:

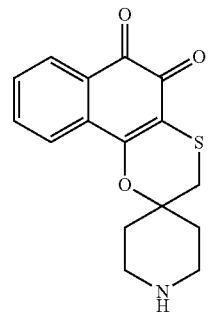

16

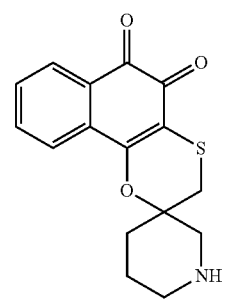

17

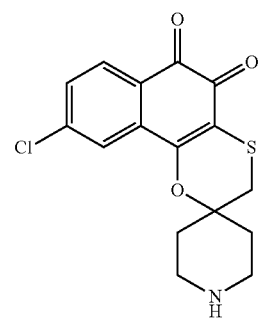

18

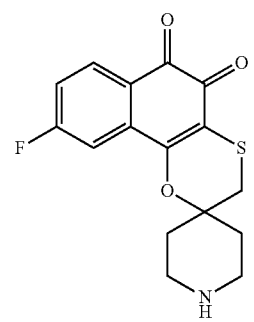

19

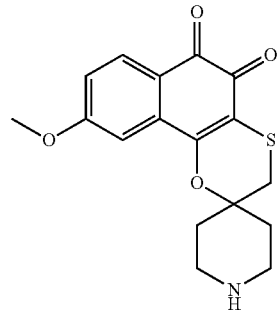

20

21
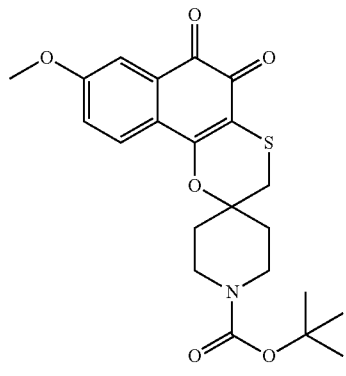
22
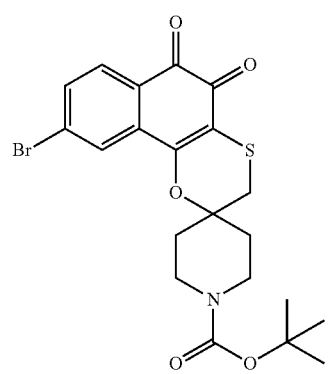
23
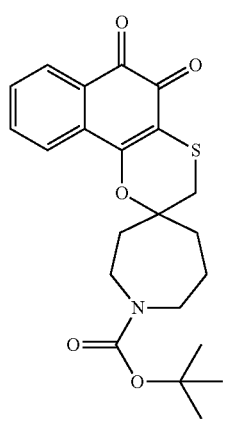
24
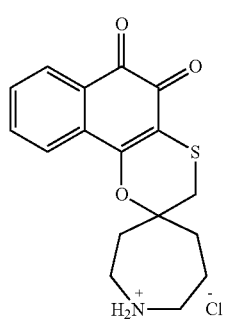
25
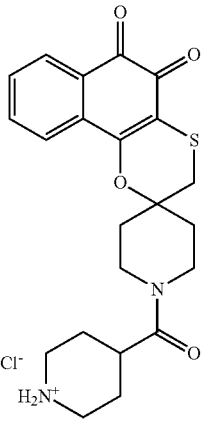
26
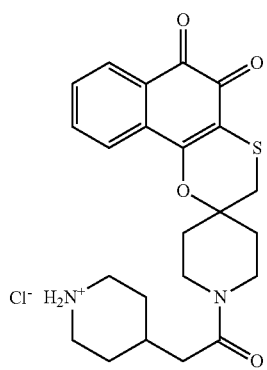
27
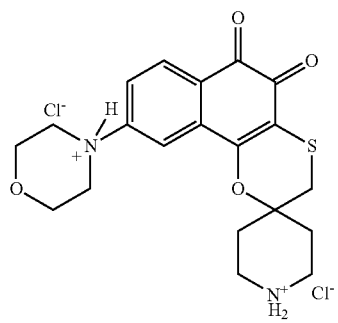
28
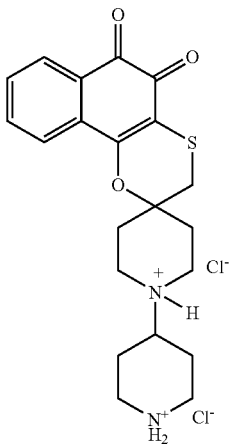

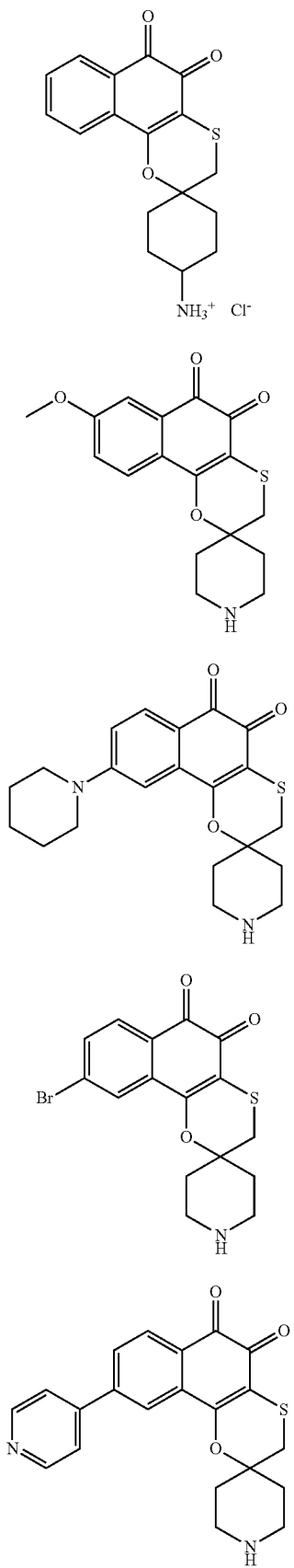
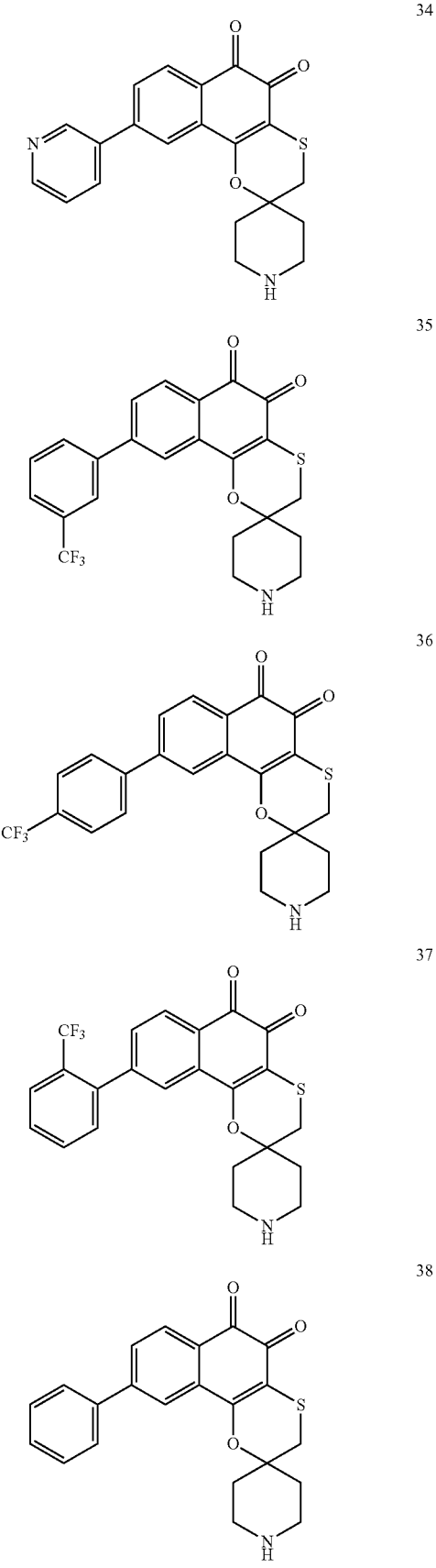

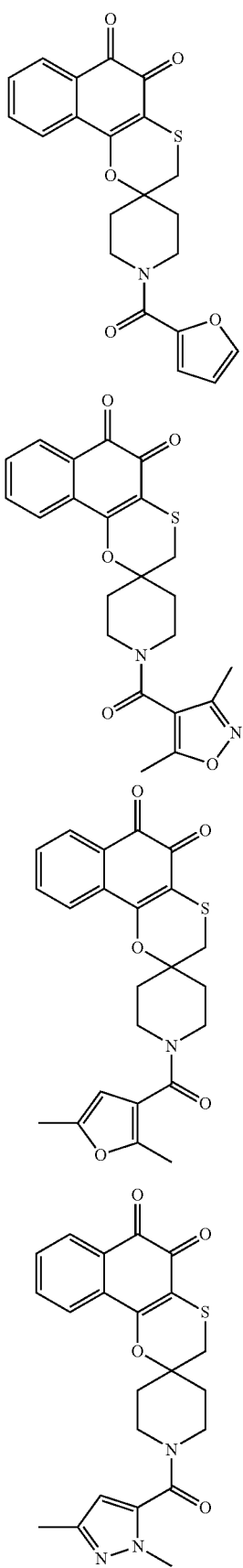
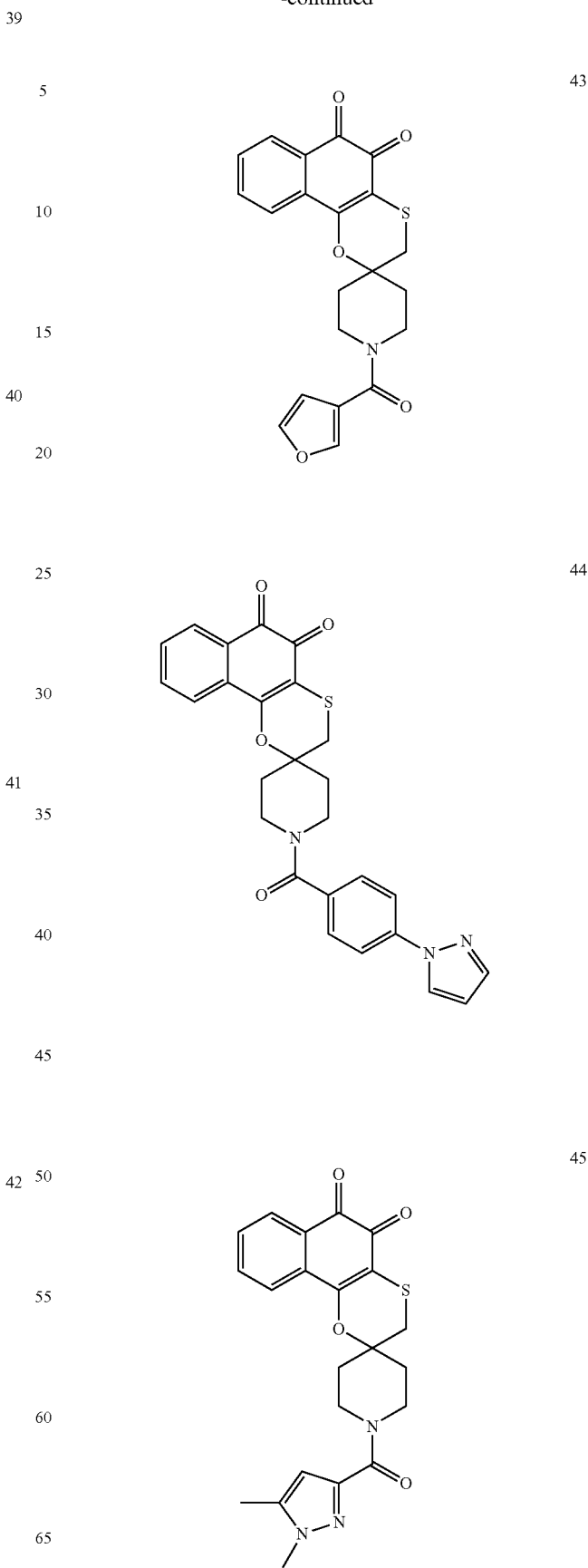

| 46 | | 50 |
|---|---|---|
| 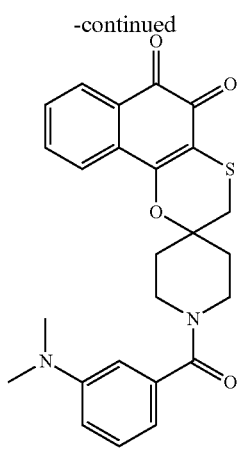 | | 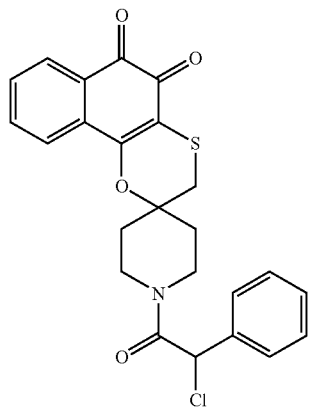 |
| 47 | | |
| 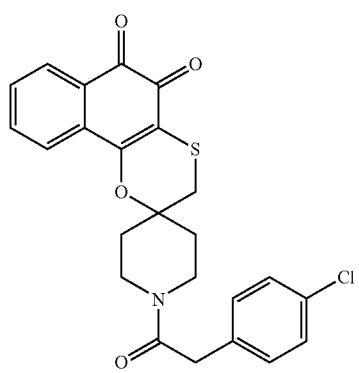 | | |
| 48 | | 51 |
| 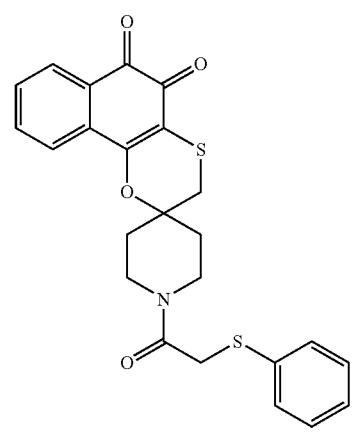 | | 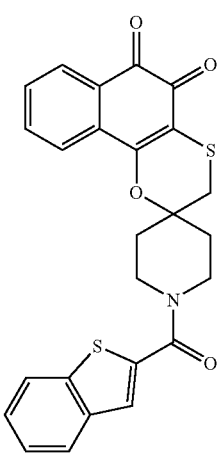 |
| 49 | | 52 |
| 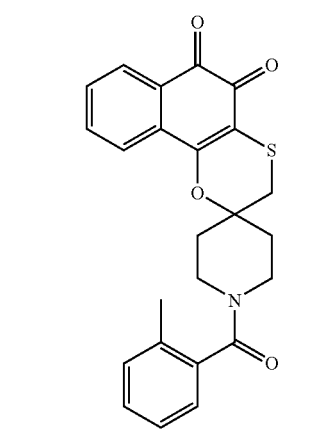 | | 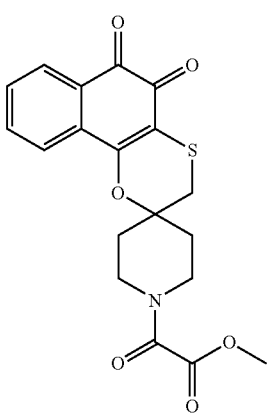 |

53 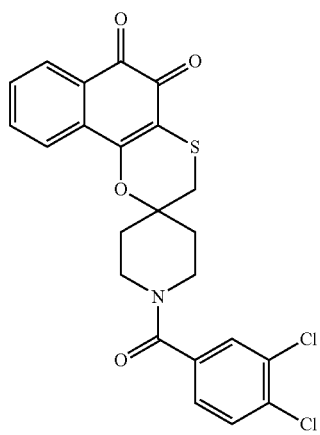
54 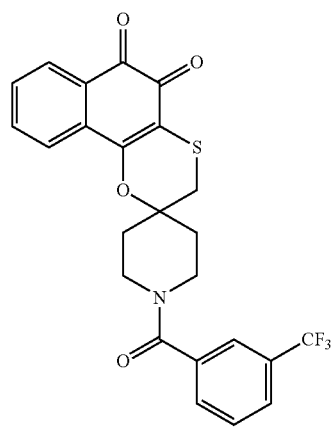
55 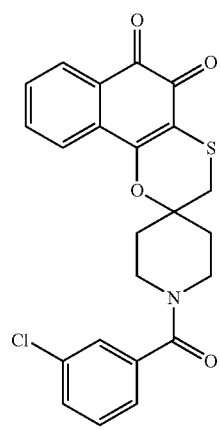
56 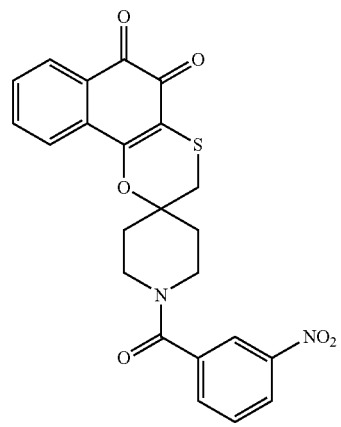
57 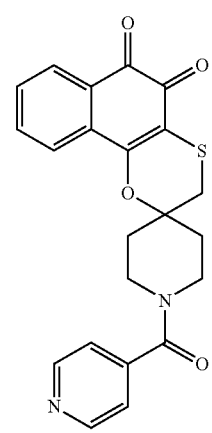
58 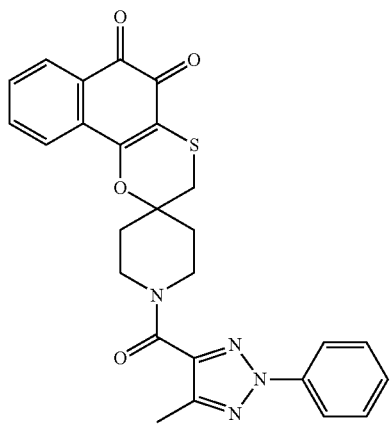

| 59 | 62 |
|---|---|
| 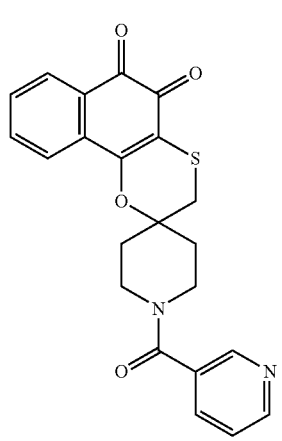 | 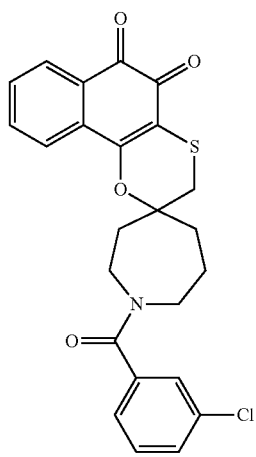 |
| 60 | 63 |
| 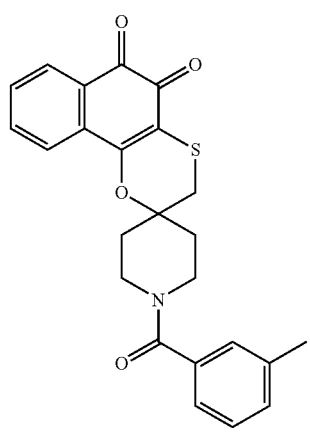 | 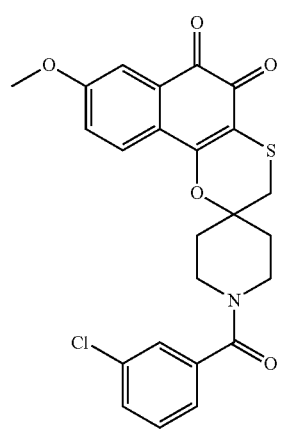 |
| 61 | 64 |
| 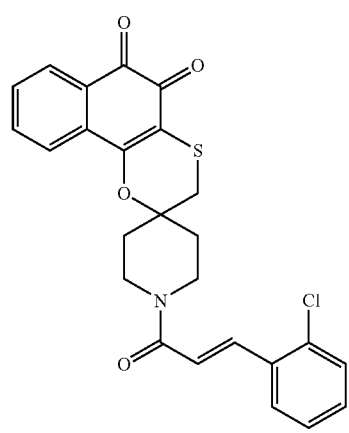 | 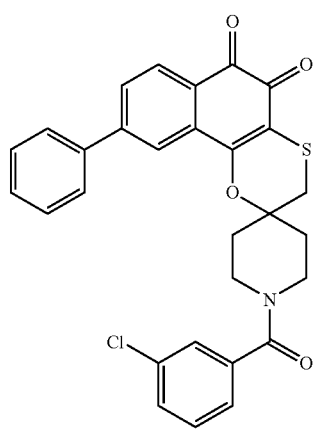 |

231
-continued
65
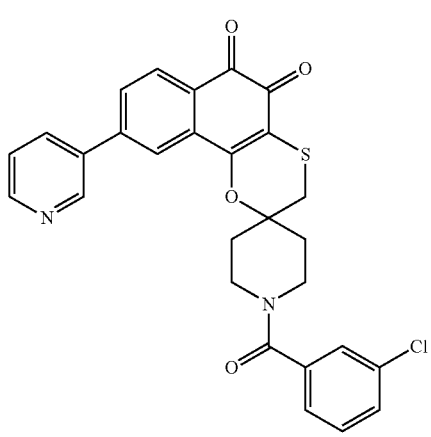
66
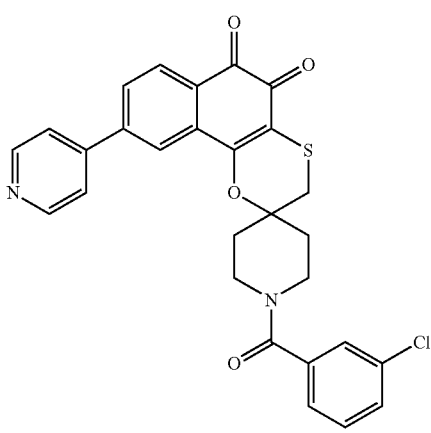
67
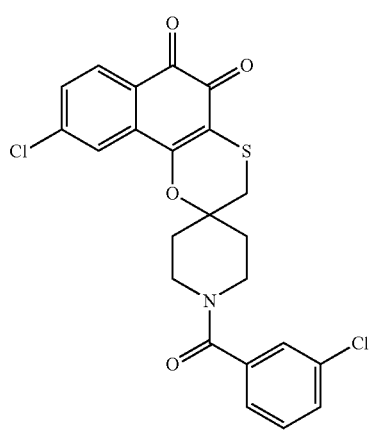
232
-continued
68
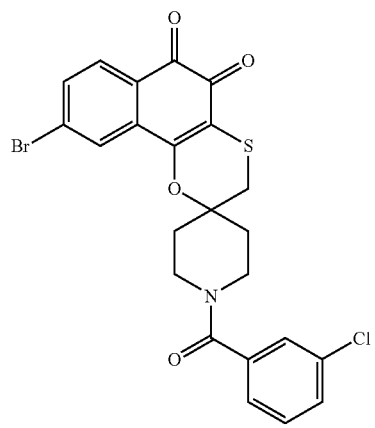
69
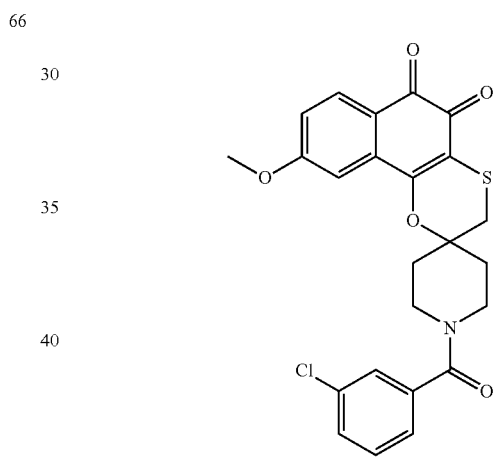
70
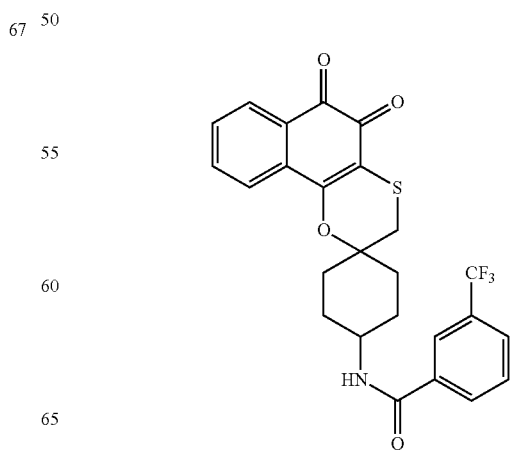

| 71 | 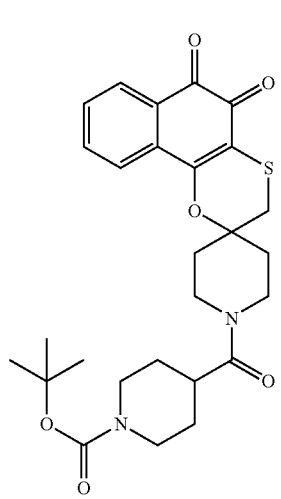 | 74 | 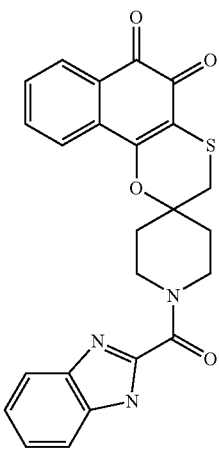 |
| 72 | 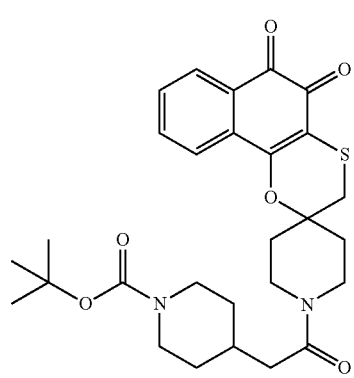 | 75 | 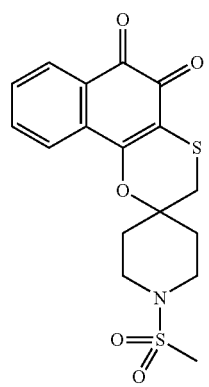 |
| 73 | 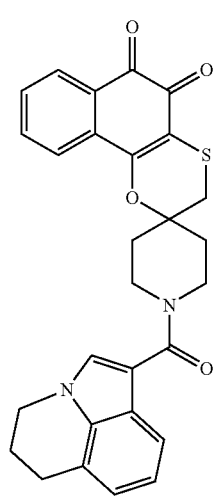 | 76 | 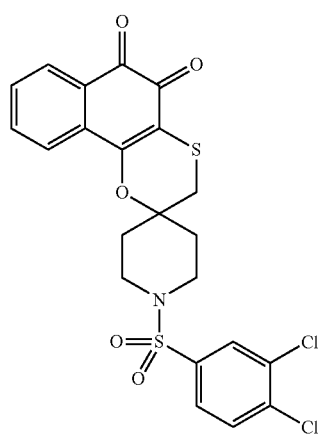 |

-continued
| 77 | 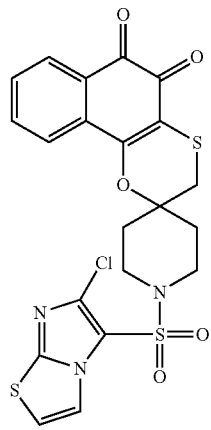 |
| 78 | 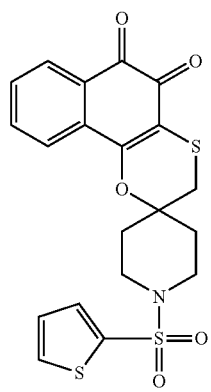 |
| 79 | 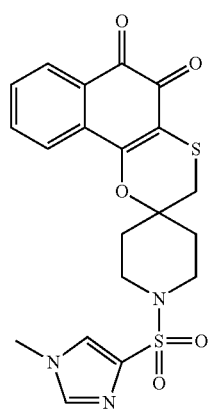 |
| 80 | 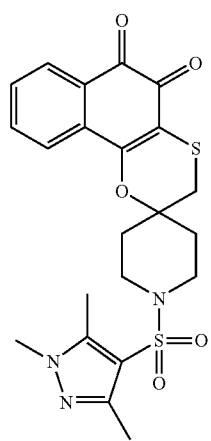 |
-continued
| 81 | 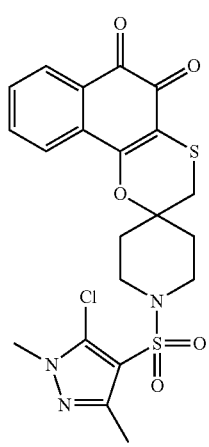 |
| 82 | 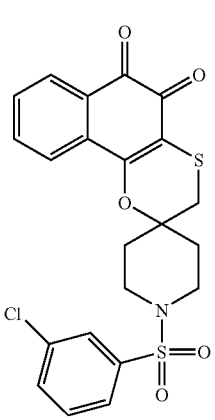 |
| 83 | 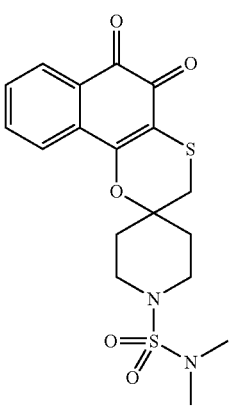 |
| 84 | 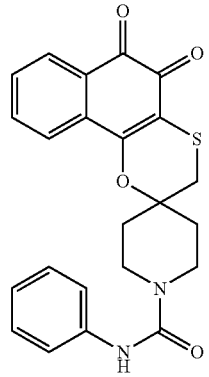 |

85 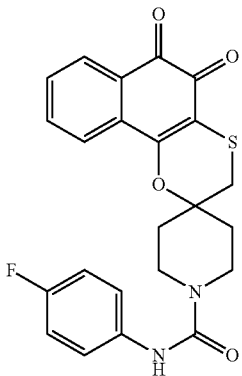
86 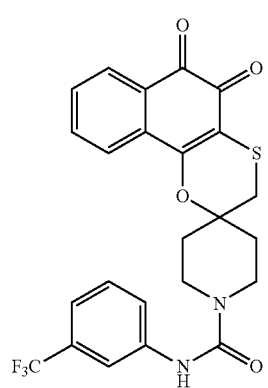
87 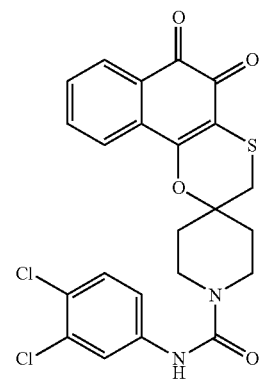
88 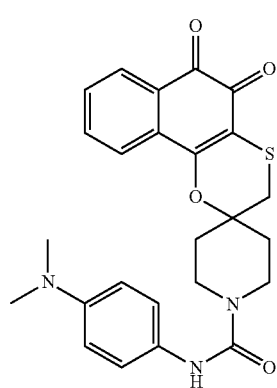
89 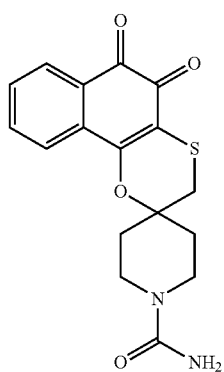
90 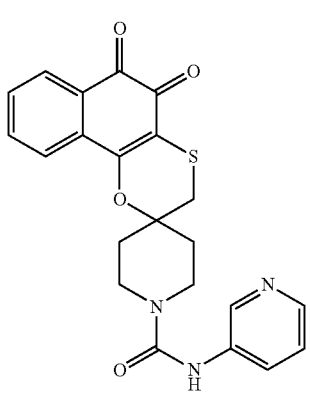
91 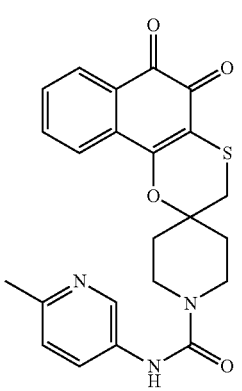
92 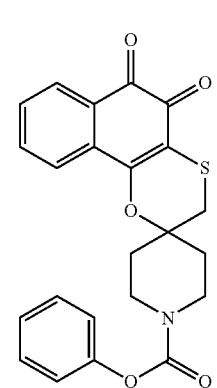

239
-continued
93
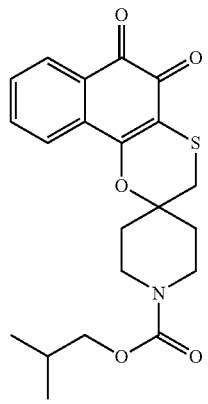
94
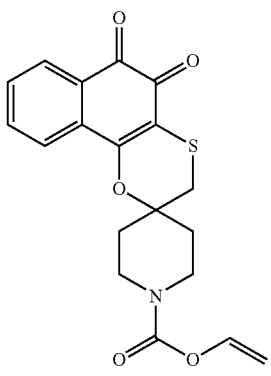
96
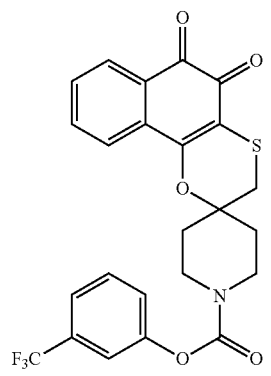
97
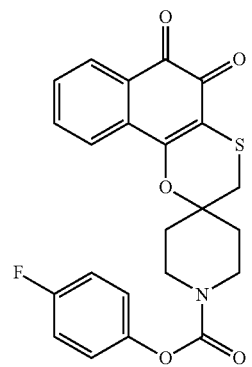
240
-continued
98
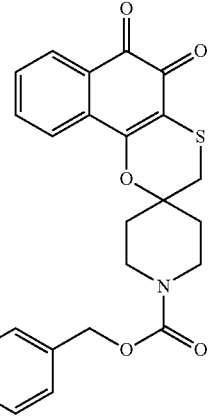
99
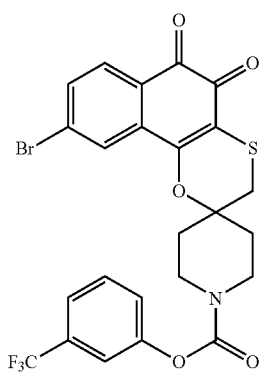
100
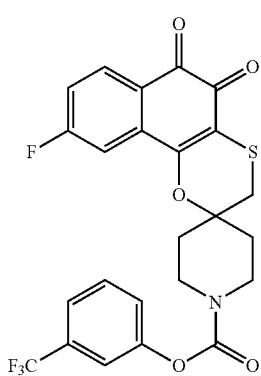
101
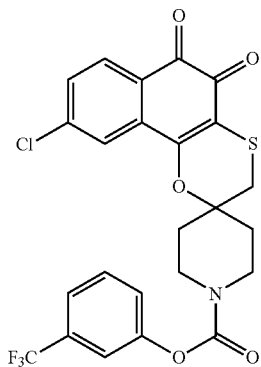

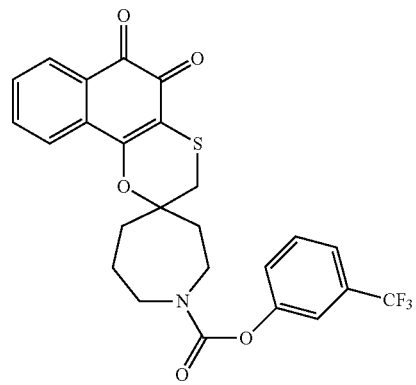
102
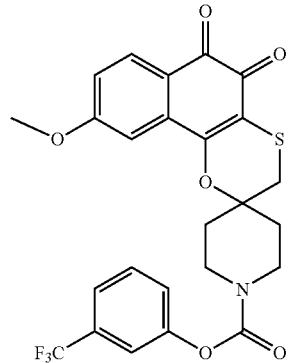
106
103
107
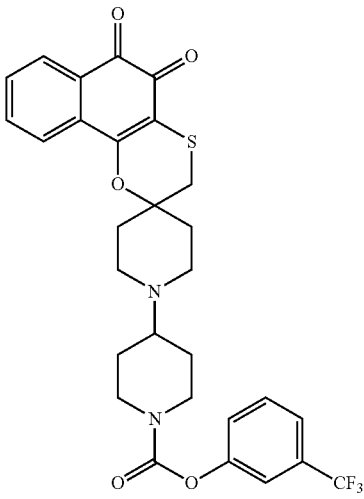
104
108
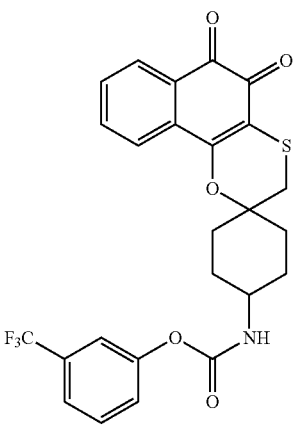
105
109
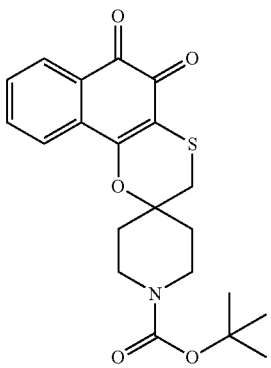

-continued
110 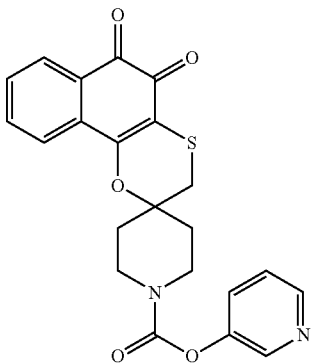
111 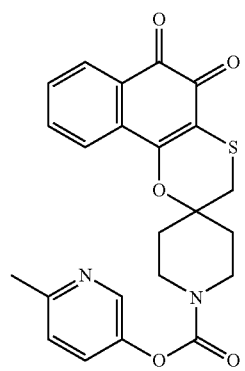
112 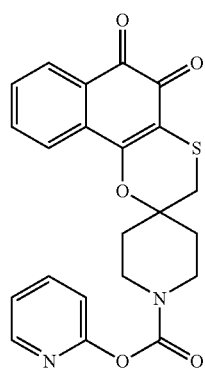
114 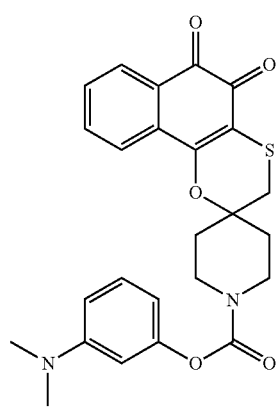
-continued
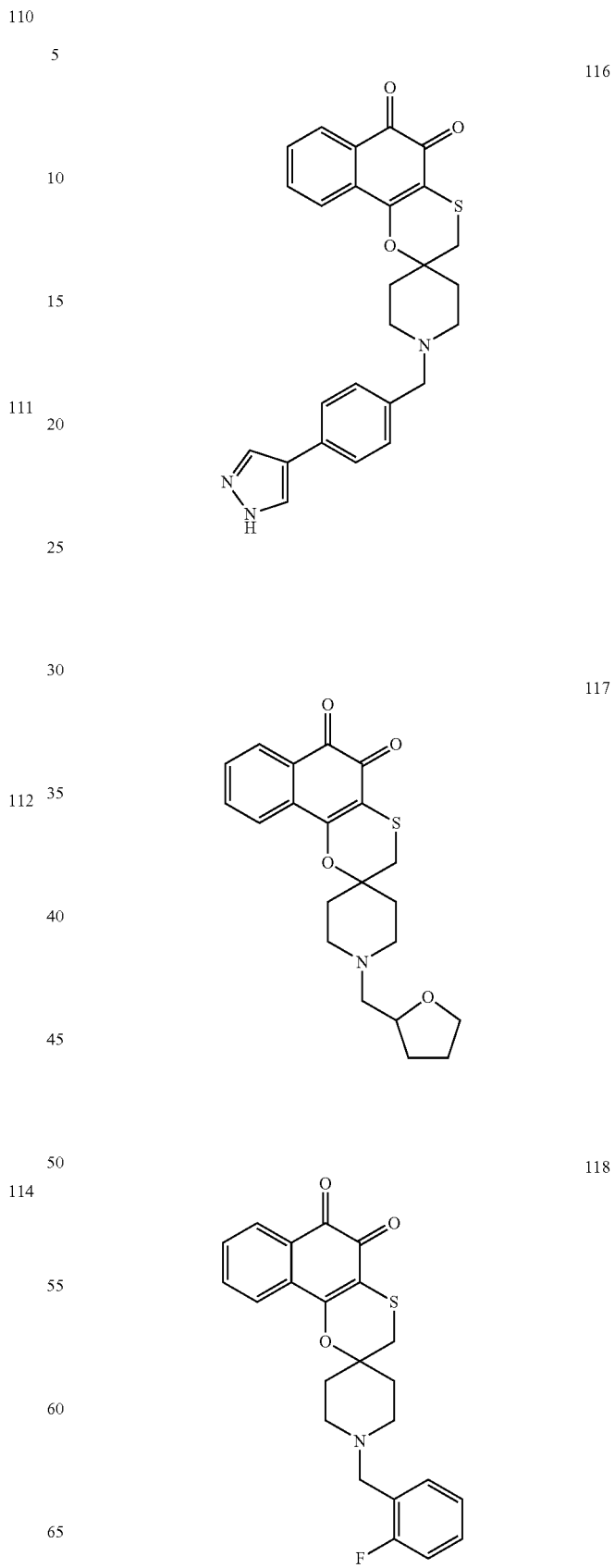

| 119 | 122 |
|---|---|
| 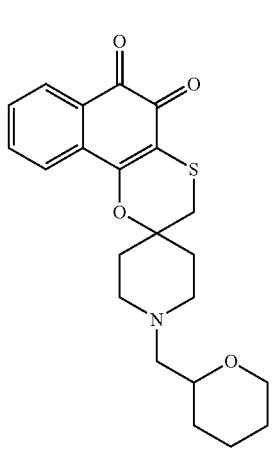 | 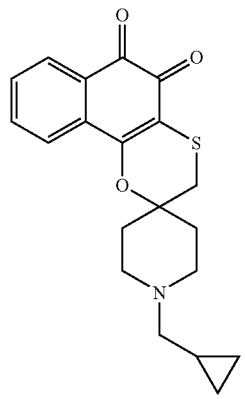 |
| 120 | 123 |
|---|---|
| 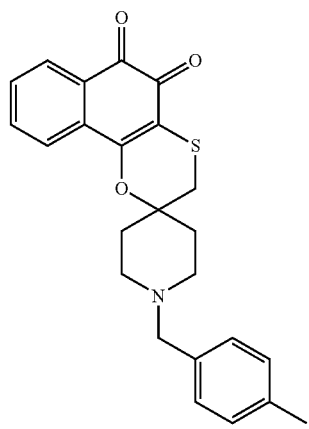 | 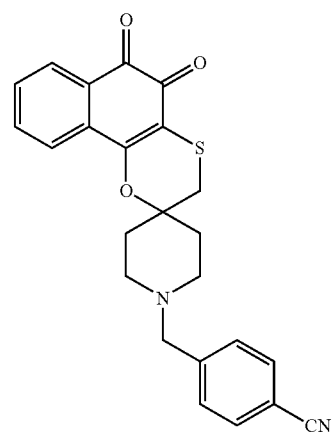 |
| 121 | 124 |
|---|---|
| 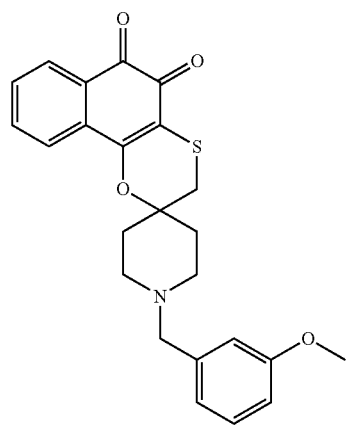 | 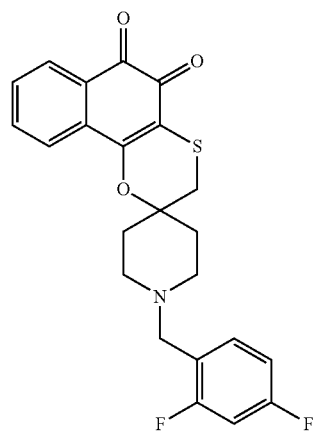 |

125 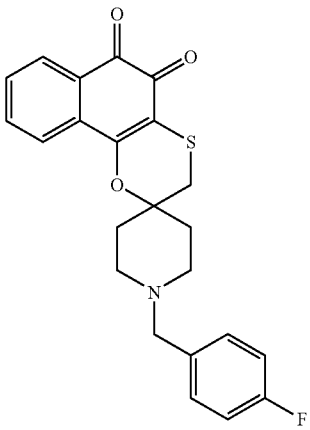
126 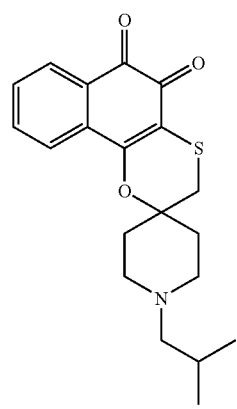
128 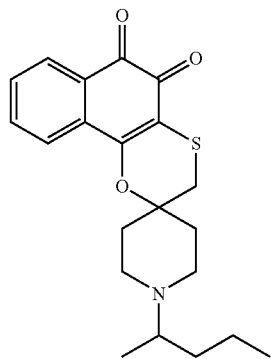
128 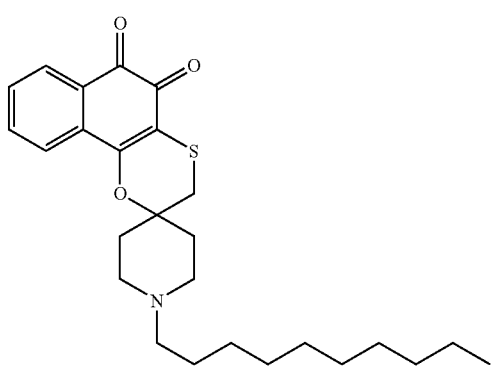
130 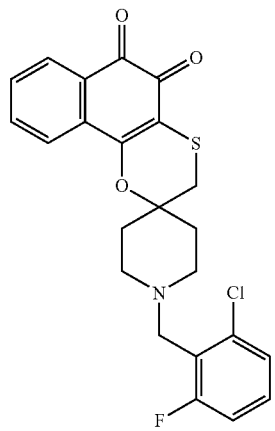
130 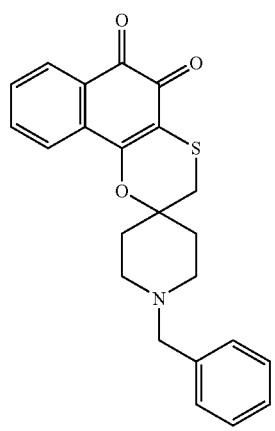
131 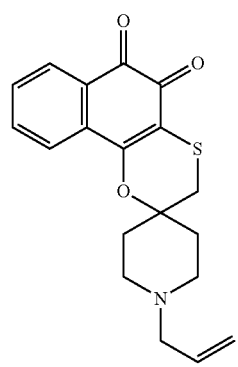
132 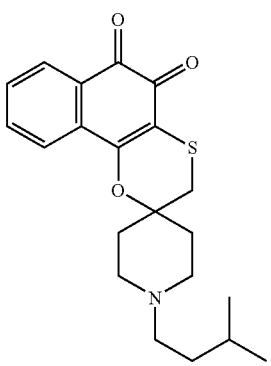

133 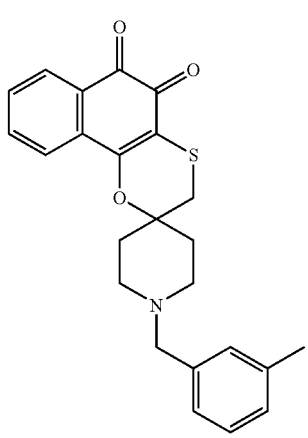
134 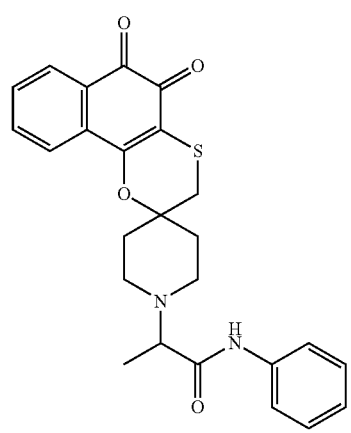
135 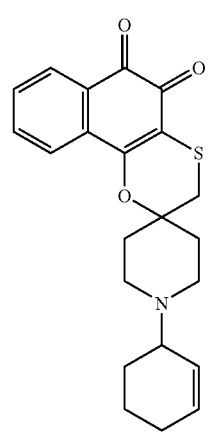
136 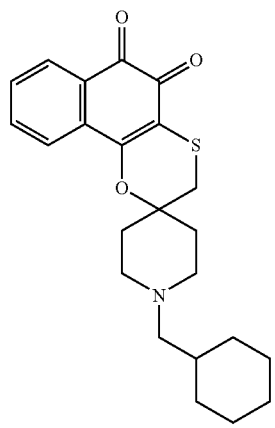
137 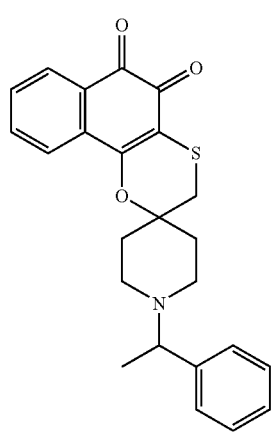
138 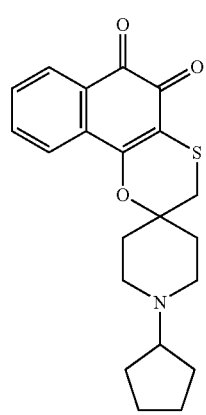

251
-continued
139
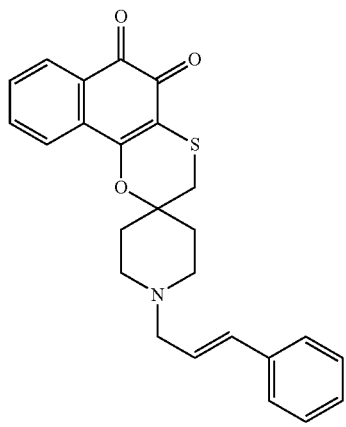
140
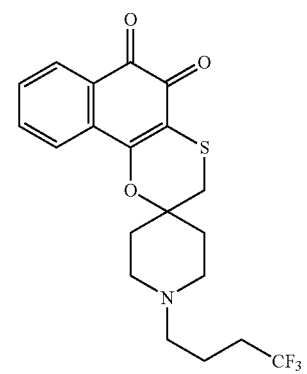
141
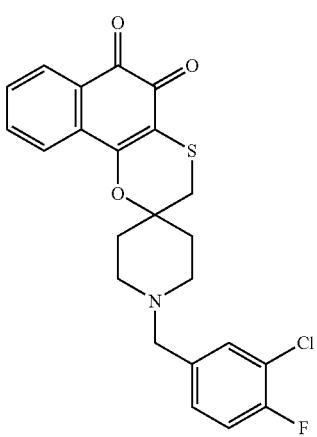
252
-continued
143
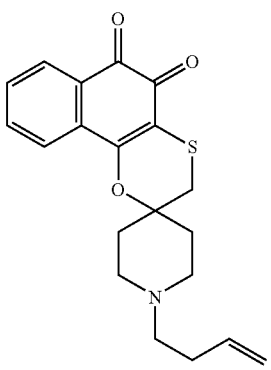
144
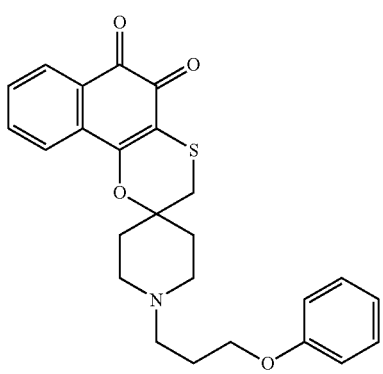
145
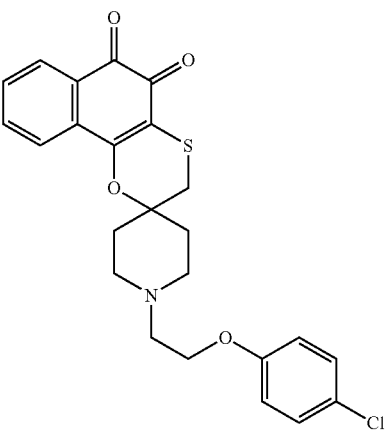
146
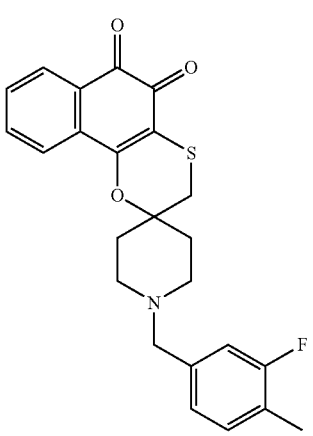

253
-continued
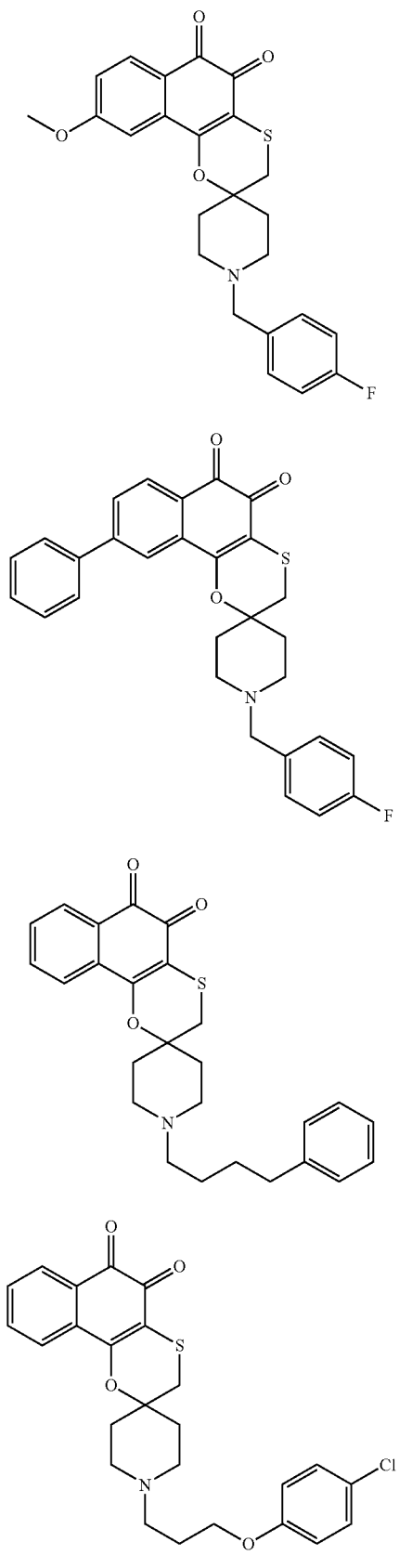
254
-continued
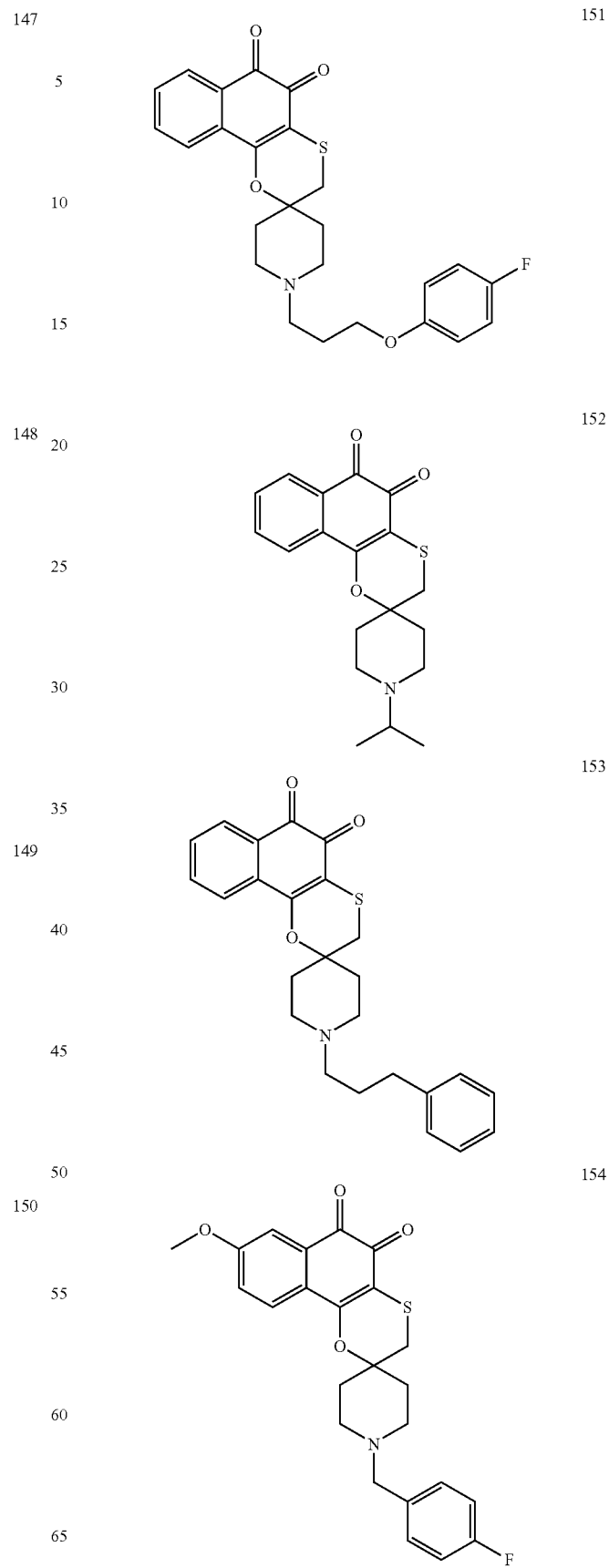

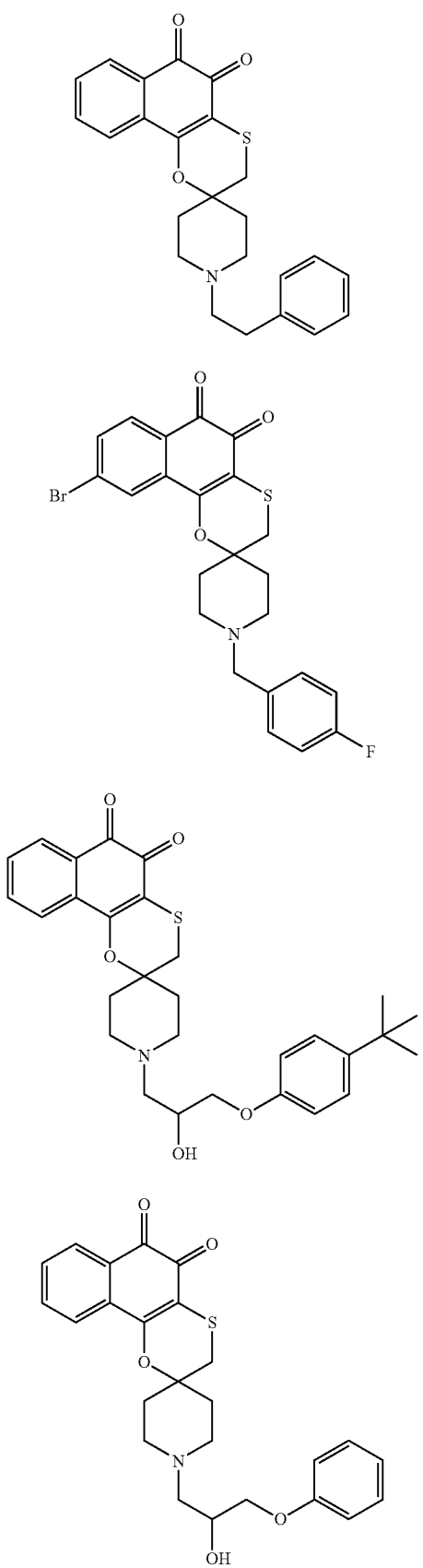

163 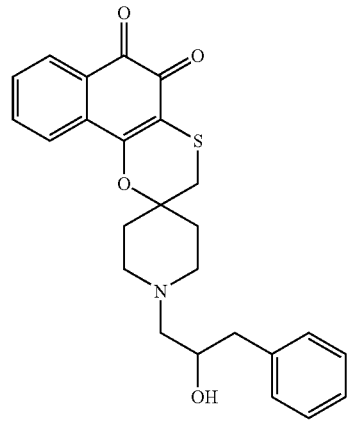
164 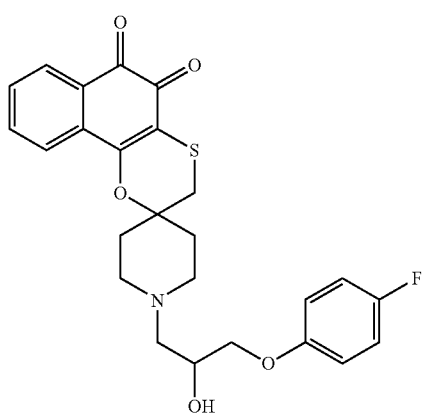
165 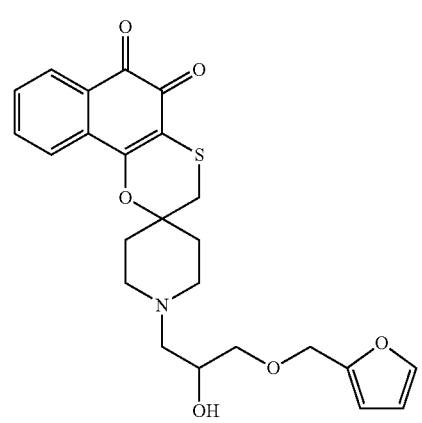
166 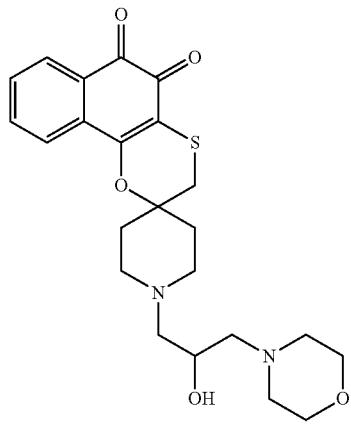
167 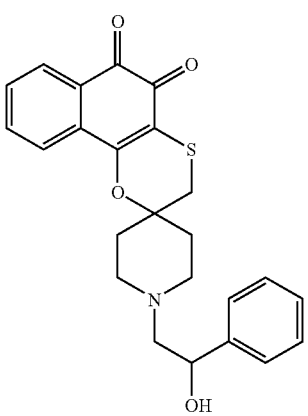
168 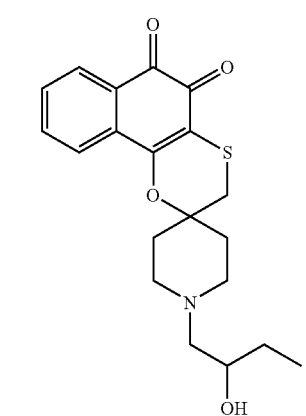
169 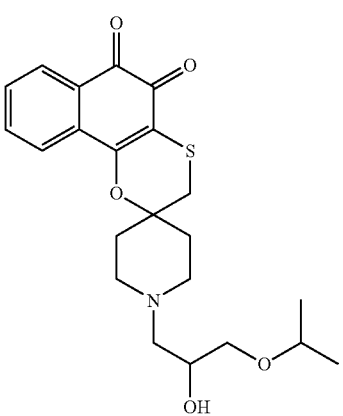

170
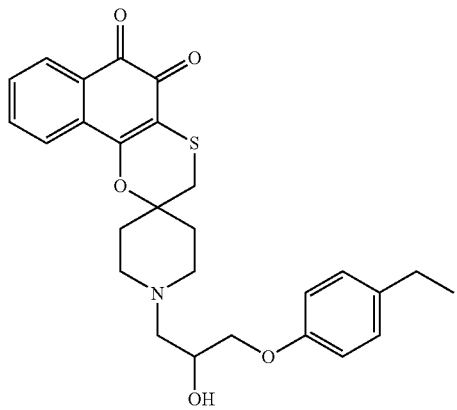
171
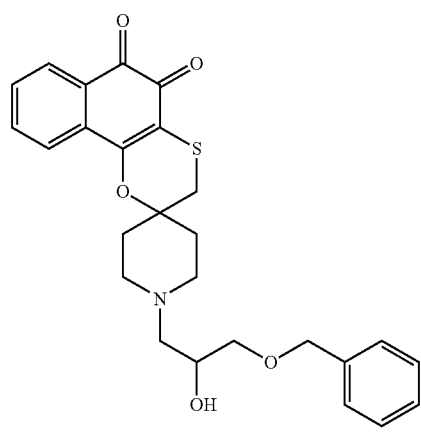
172
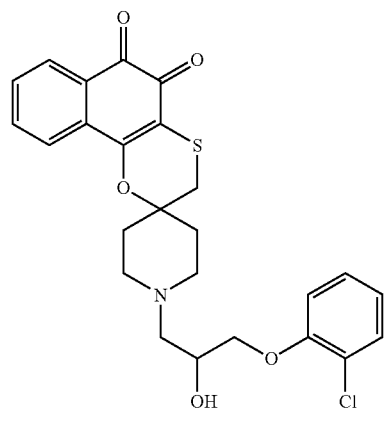
173
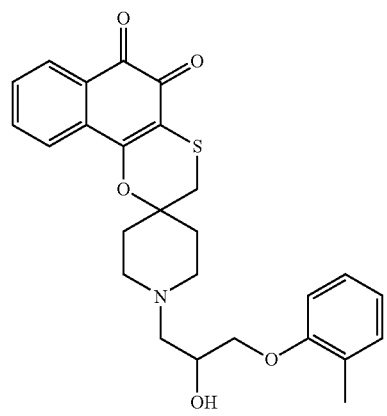
174
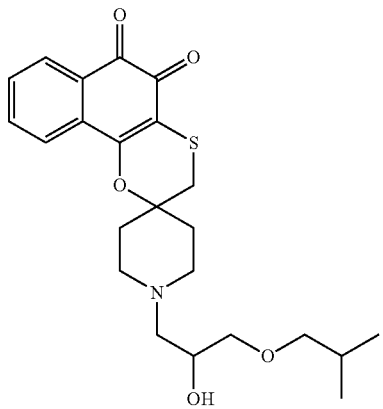
175
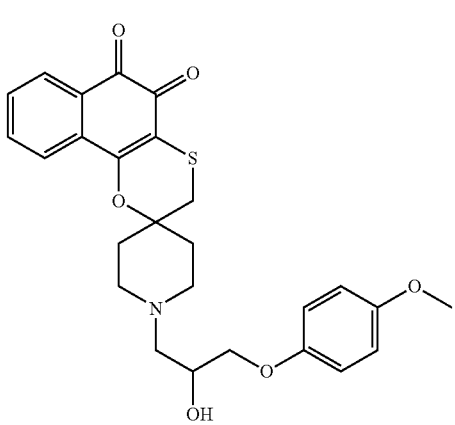
176
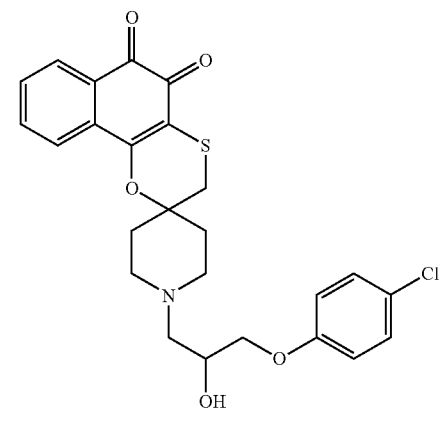
177
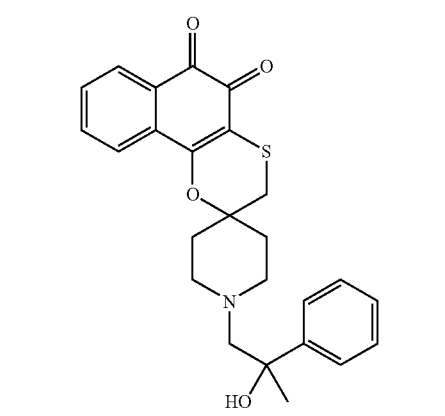

178
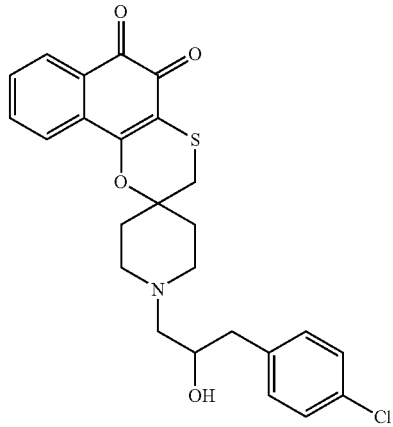
179
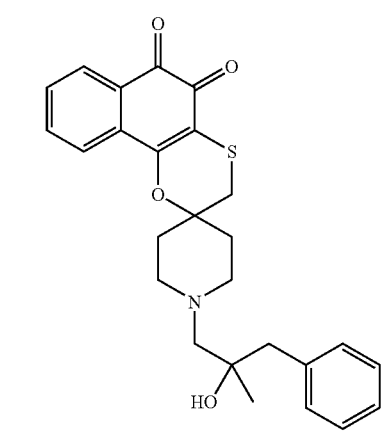
180
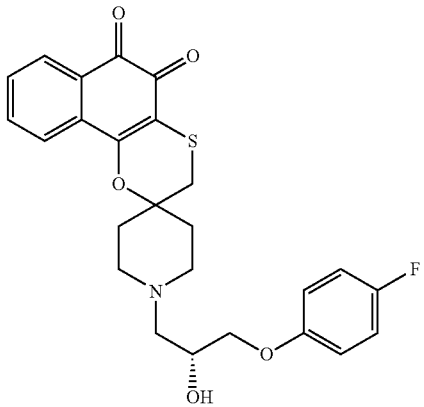
181
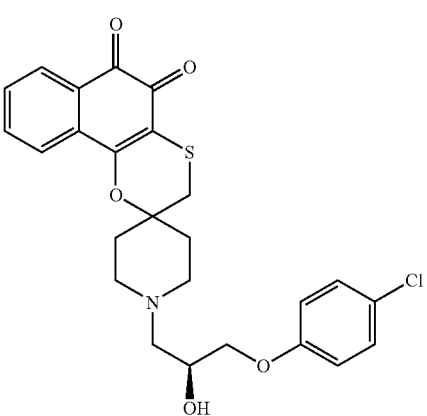
182
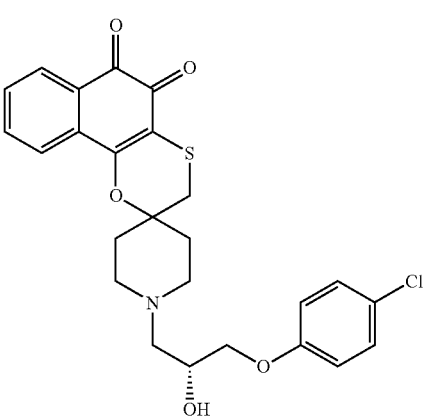
183
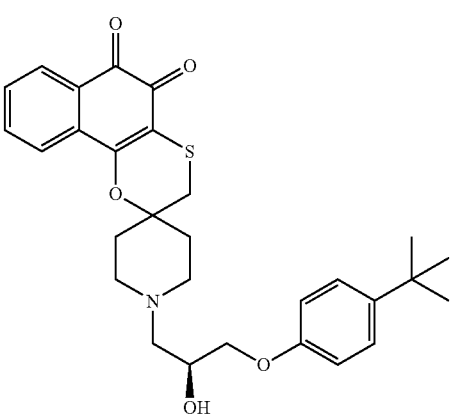
184

185
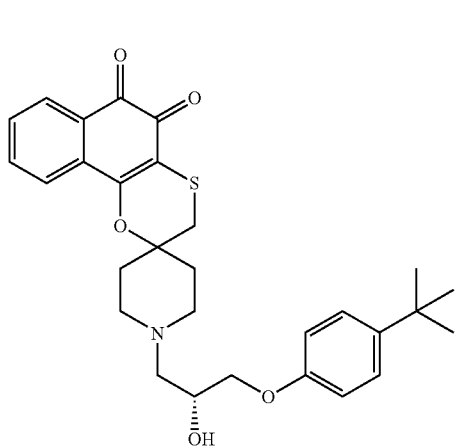
186
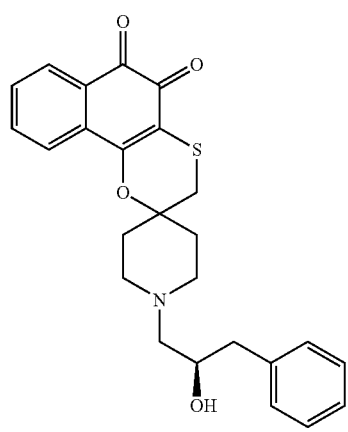
187
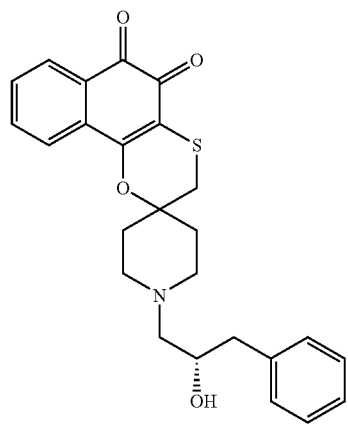
188
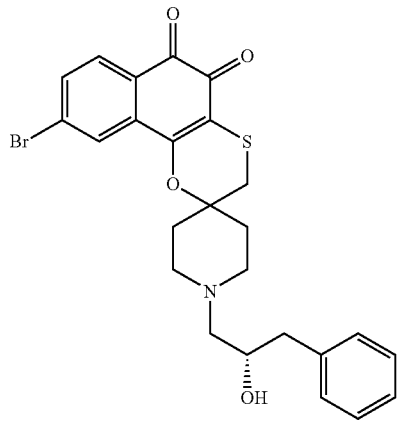
189
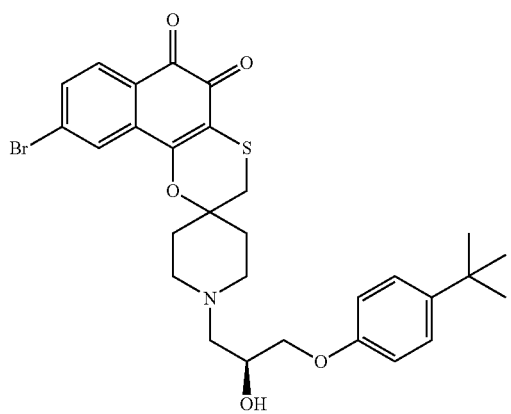
190
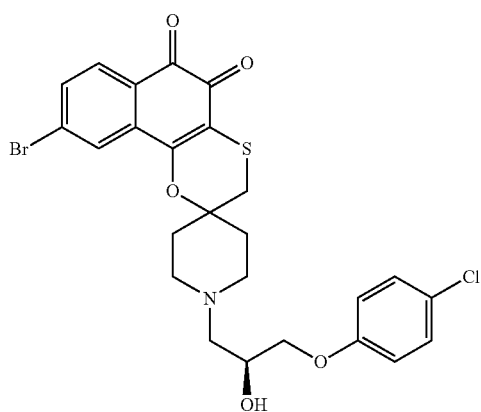

265
-continued
191
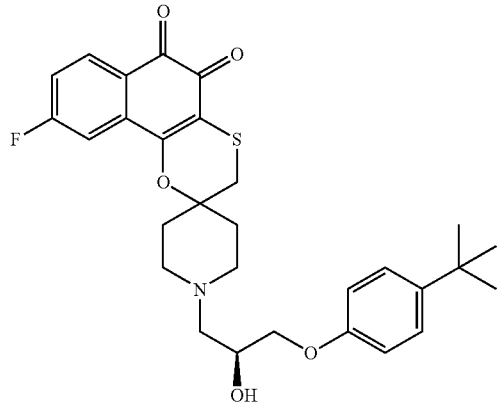
192
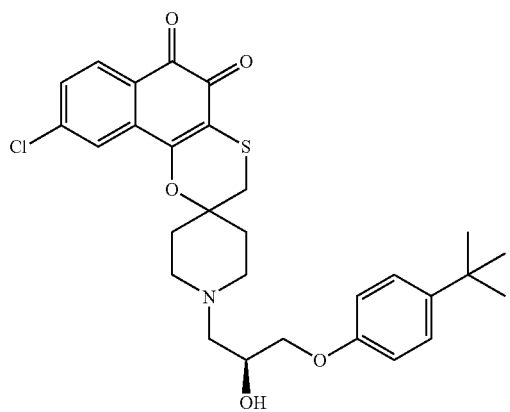
193
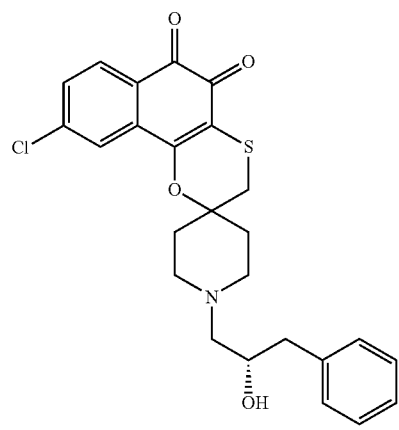
266
-continued
194
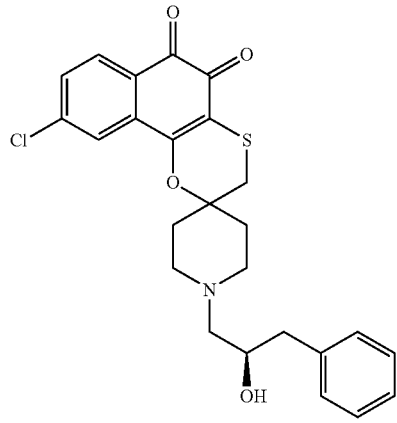
195
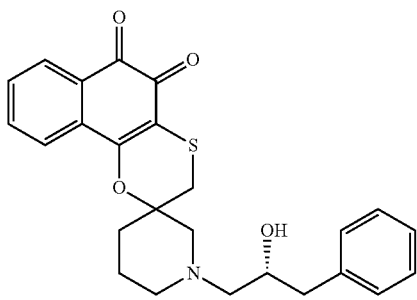
196
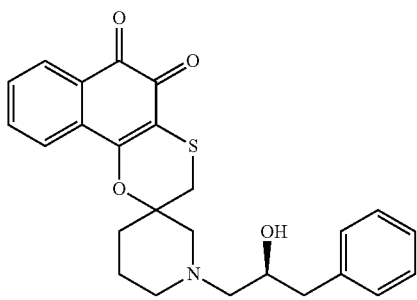
197
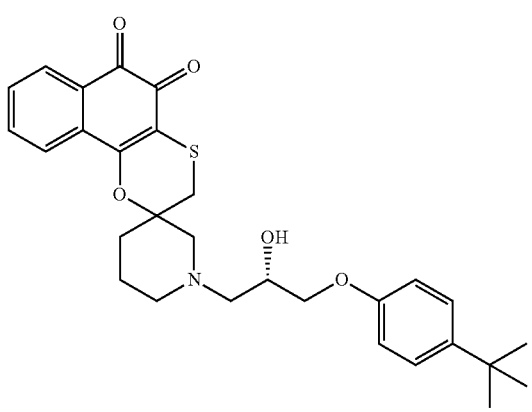

198 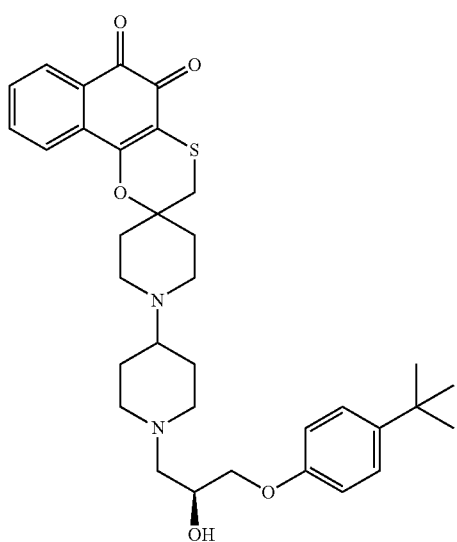
199 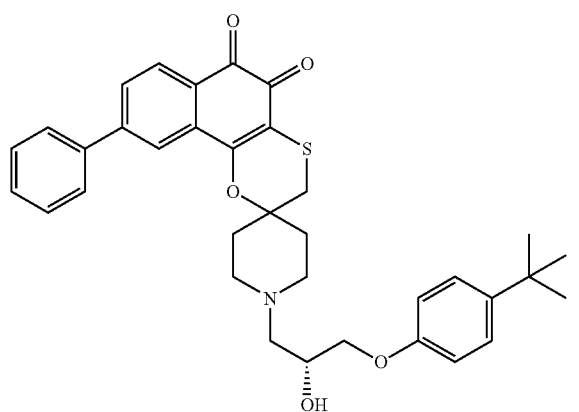
200 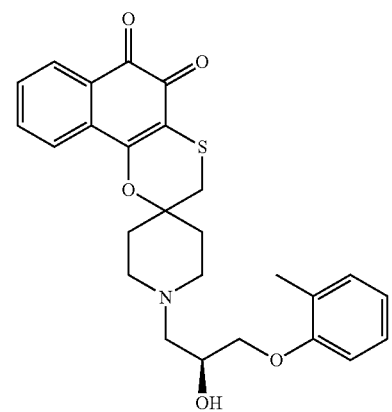
201 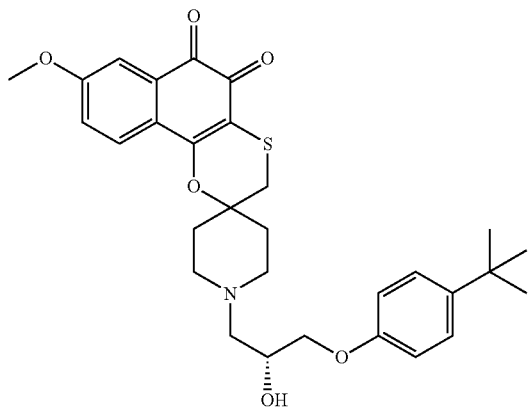
202 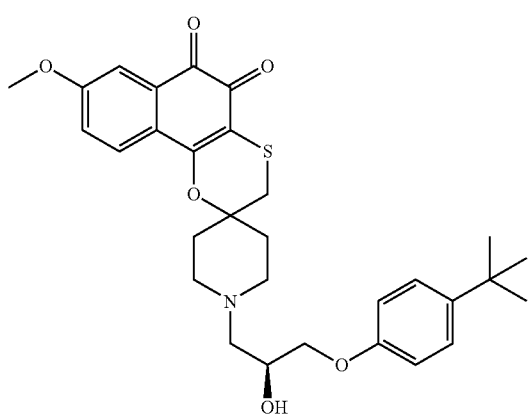
203 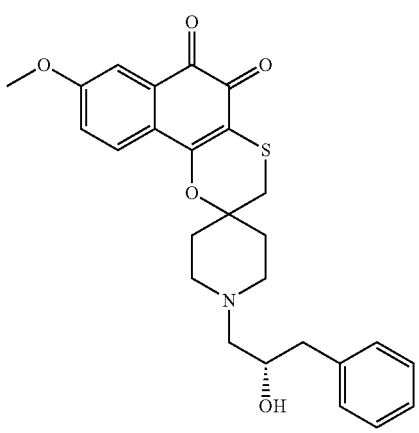

269
-continued
270
-continued
204
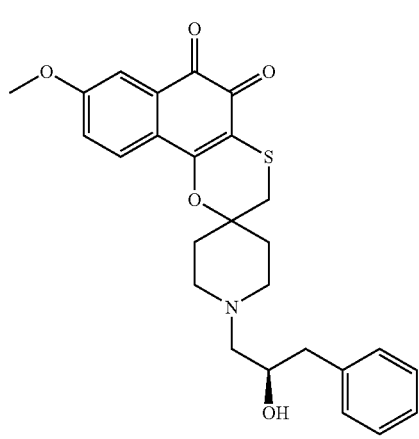
205
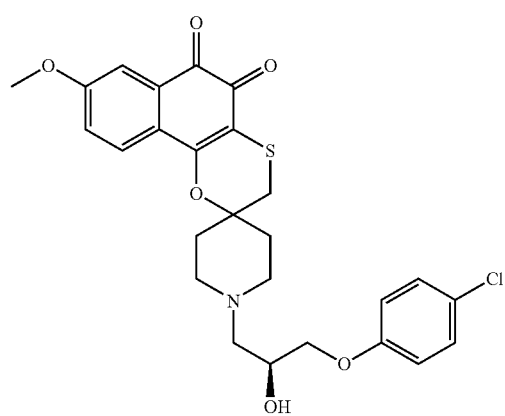
206
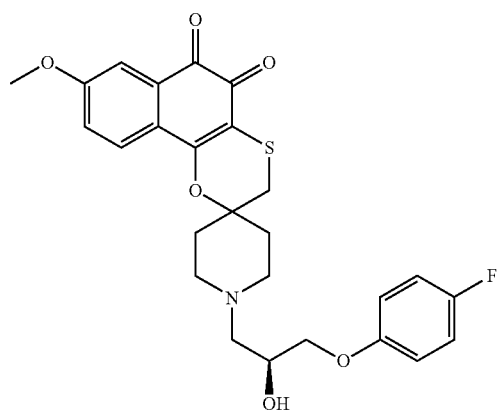
207
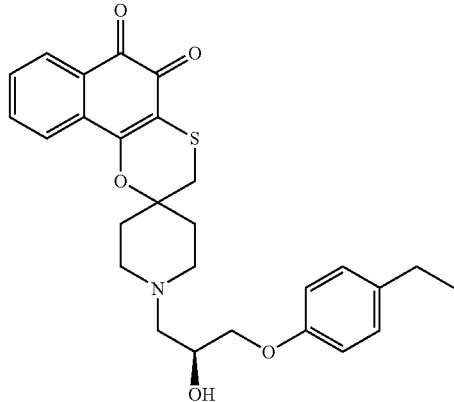
208
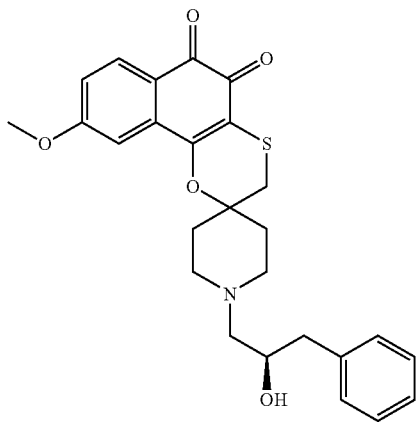
209
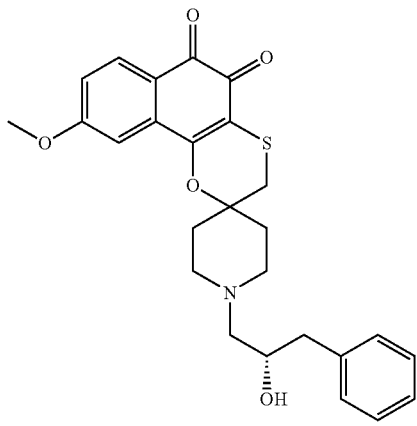

271
-continued
272
-continued
210
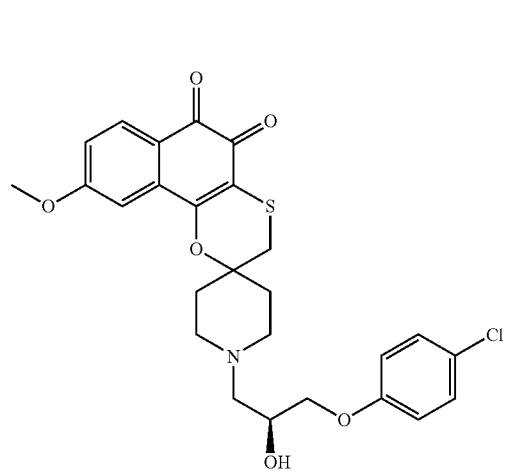
211
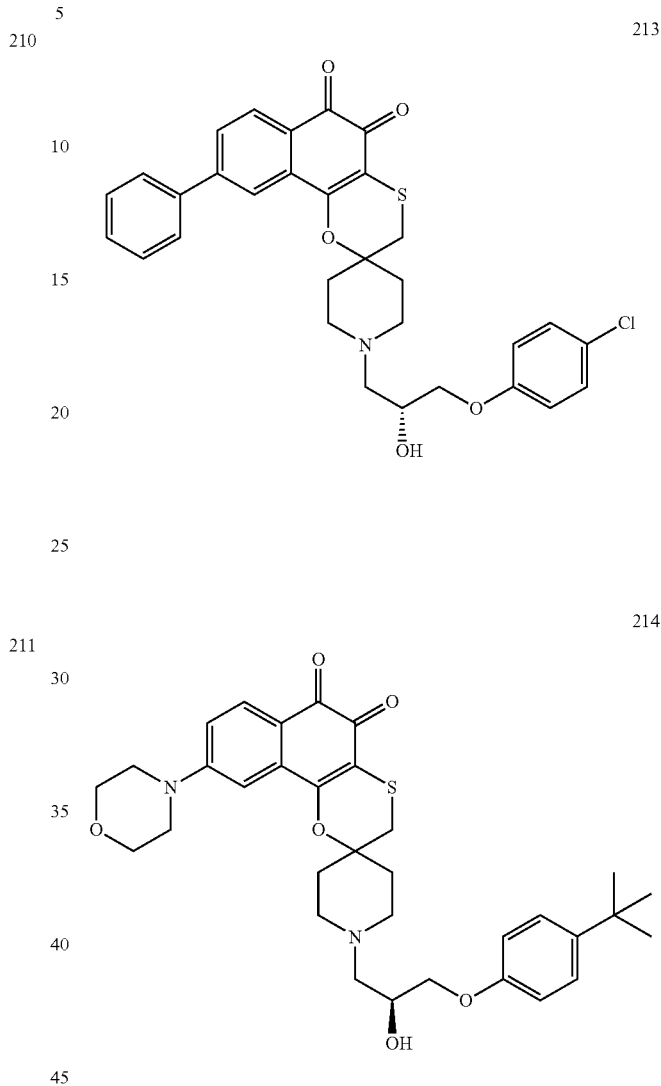
213
214
212
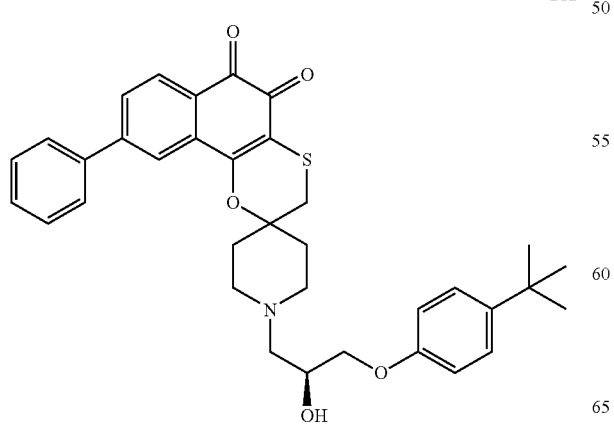
215
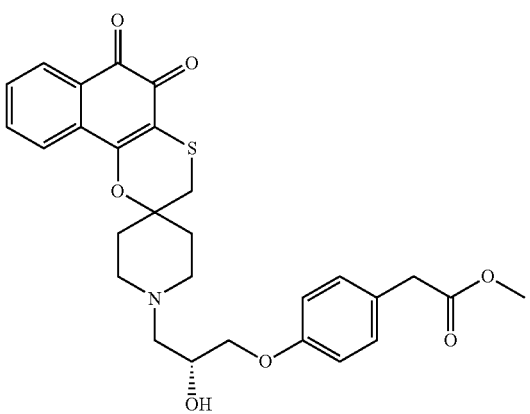

-continued
218
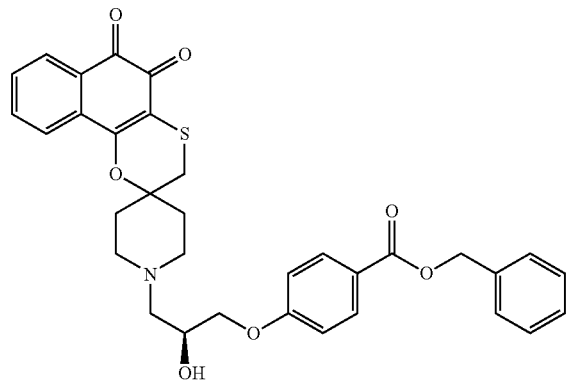
219
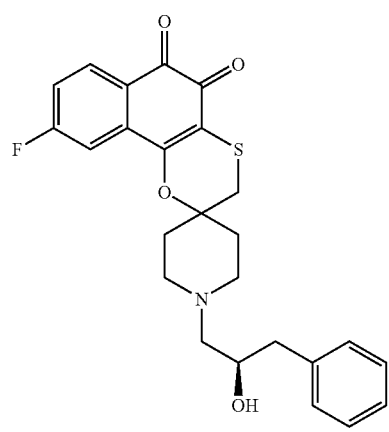
220
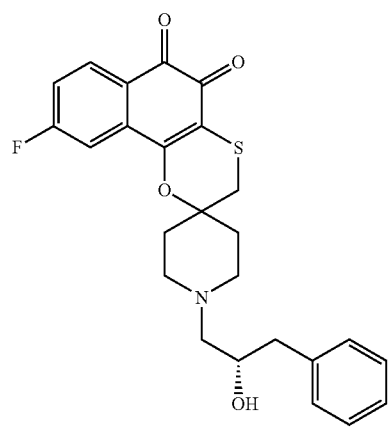
-continued
222
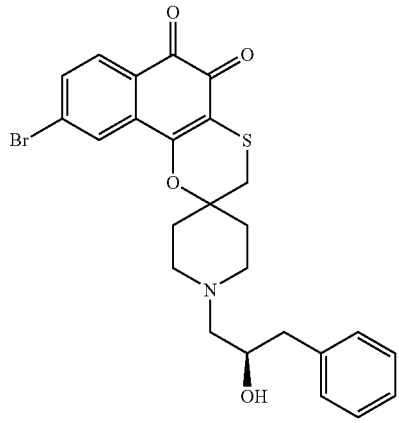
223
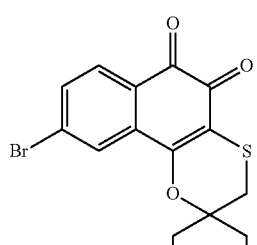
224
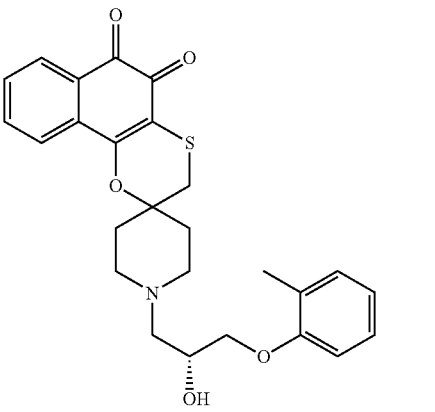
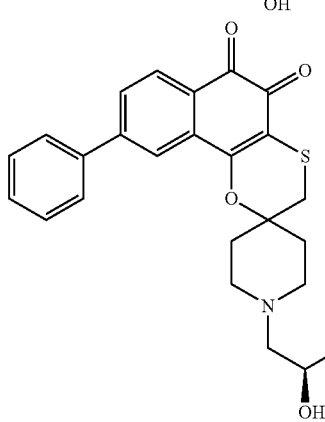

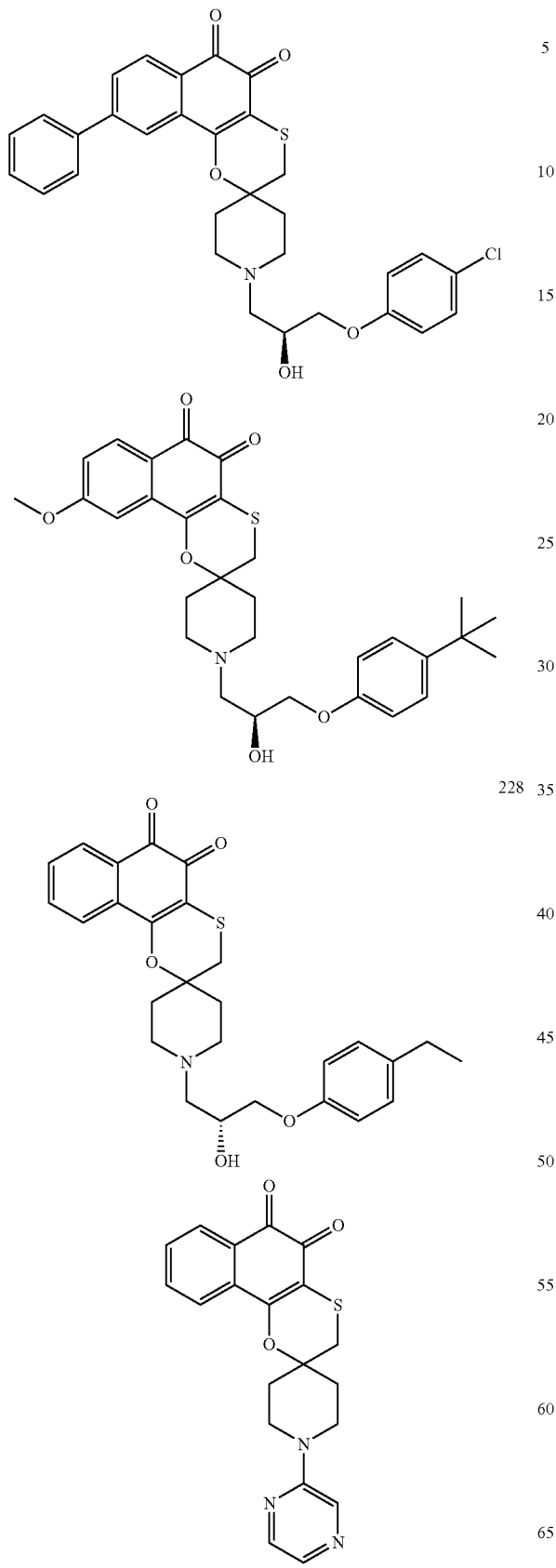

233
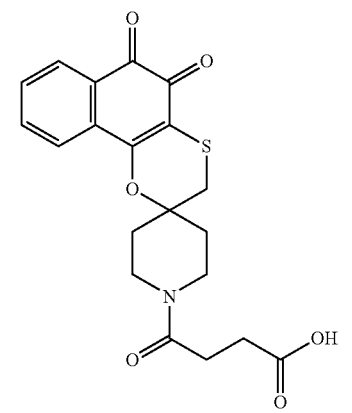
234
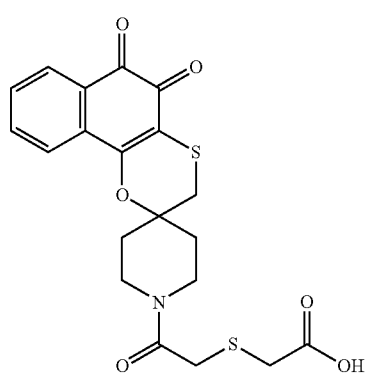
235
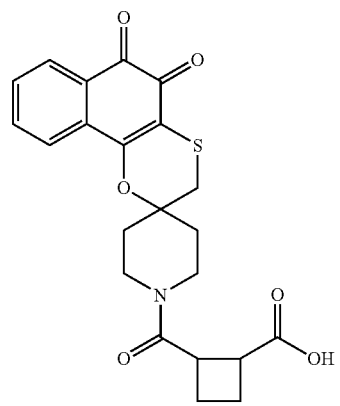
236
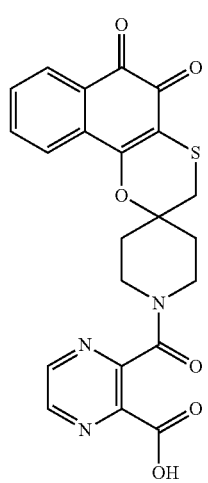
237
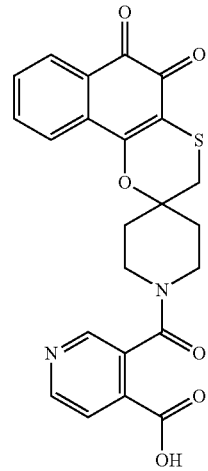
238
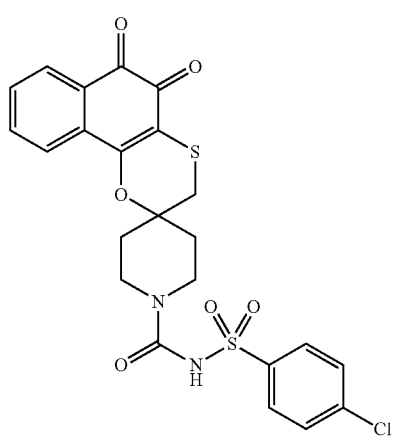
239
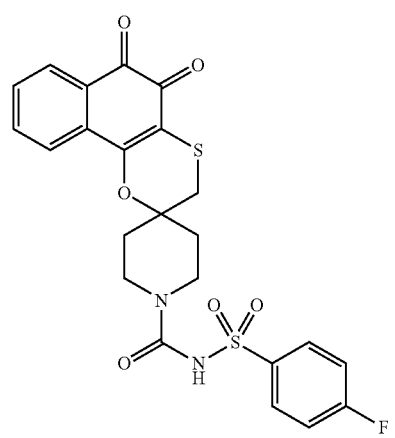

279
-continued
240
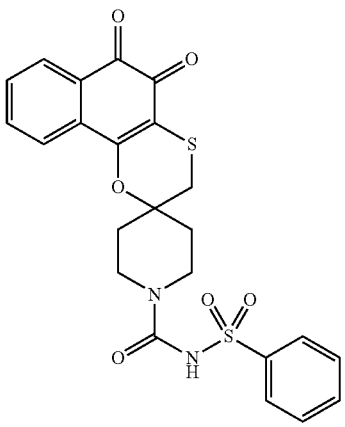
241
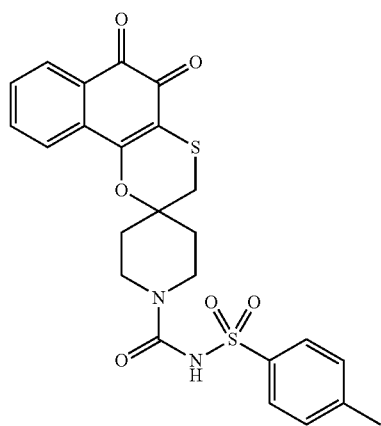
242
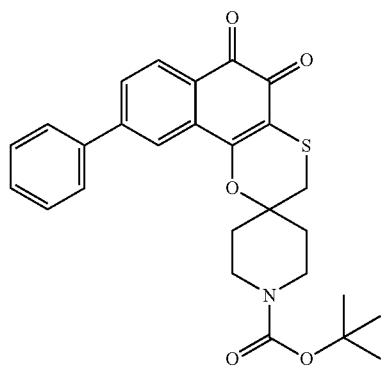
243
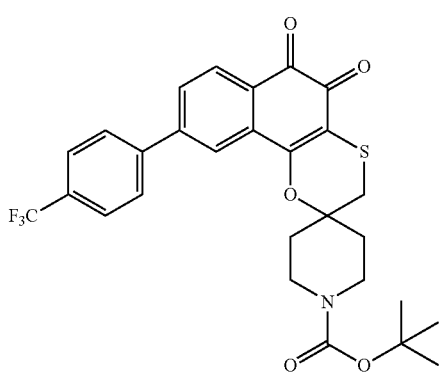
280
-continued
244
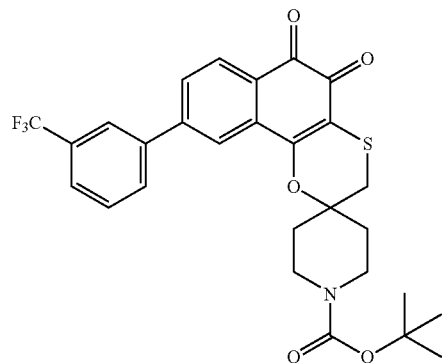
245
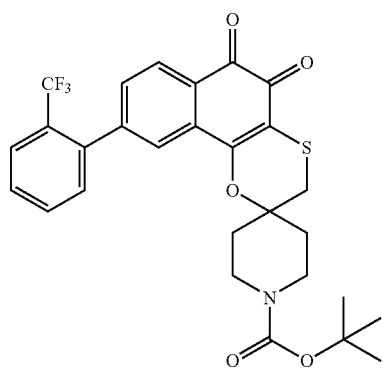
246
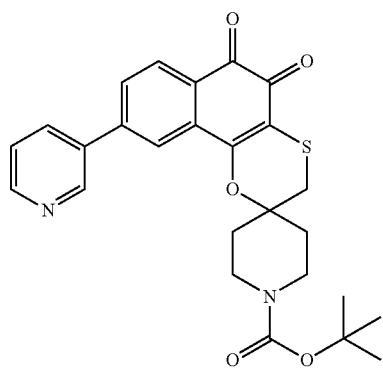
247
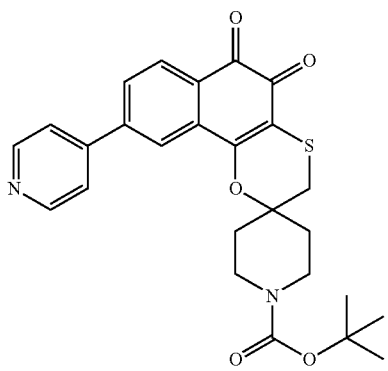

248
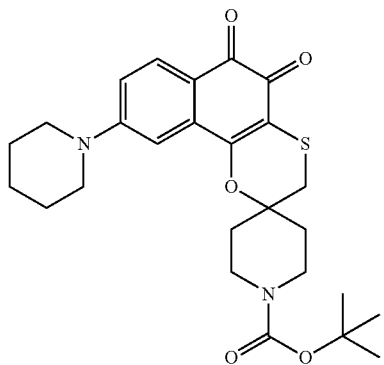
249
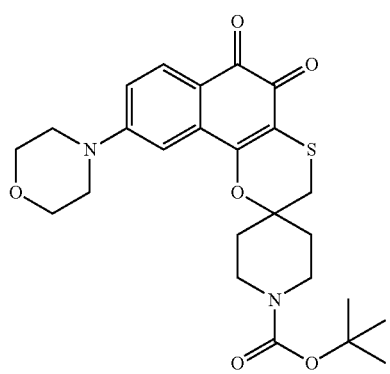
250
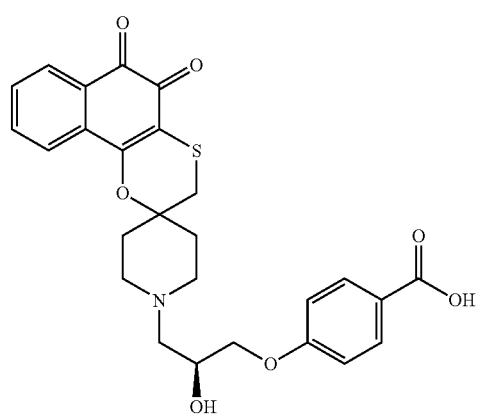
251
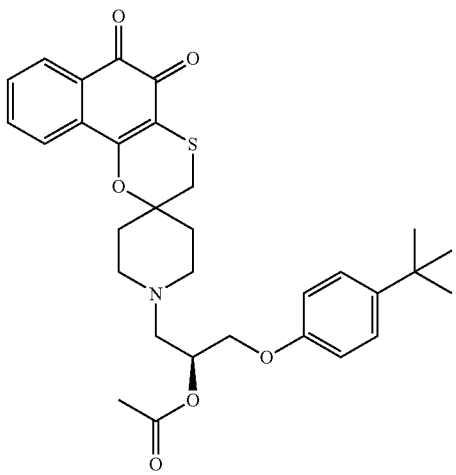
252
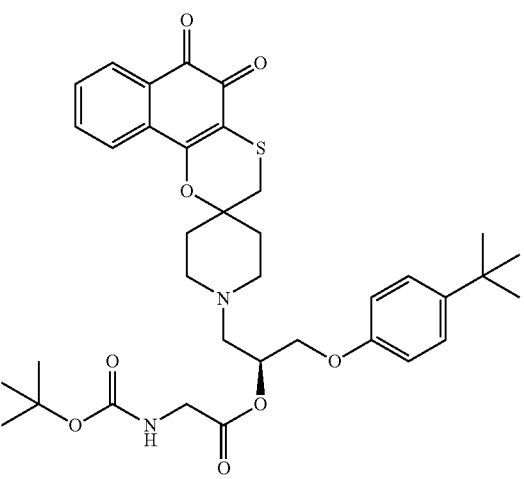
253
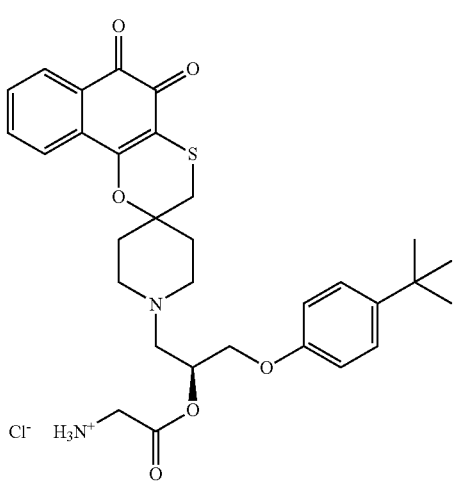
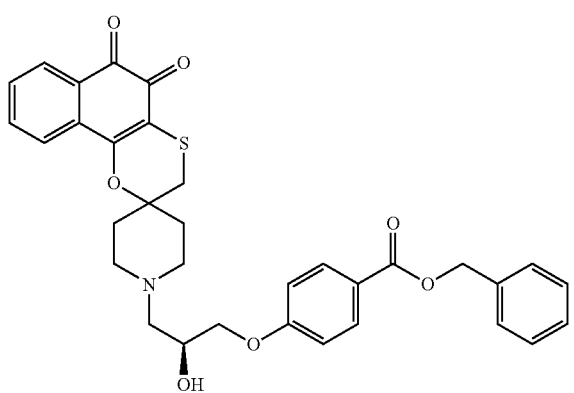

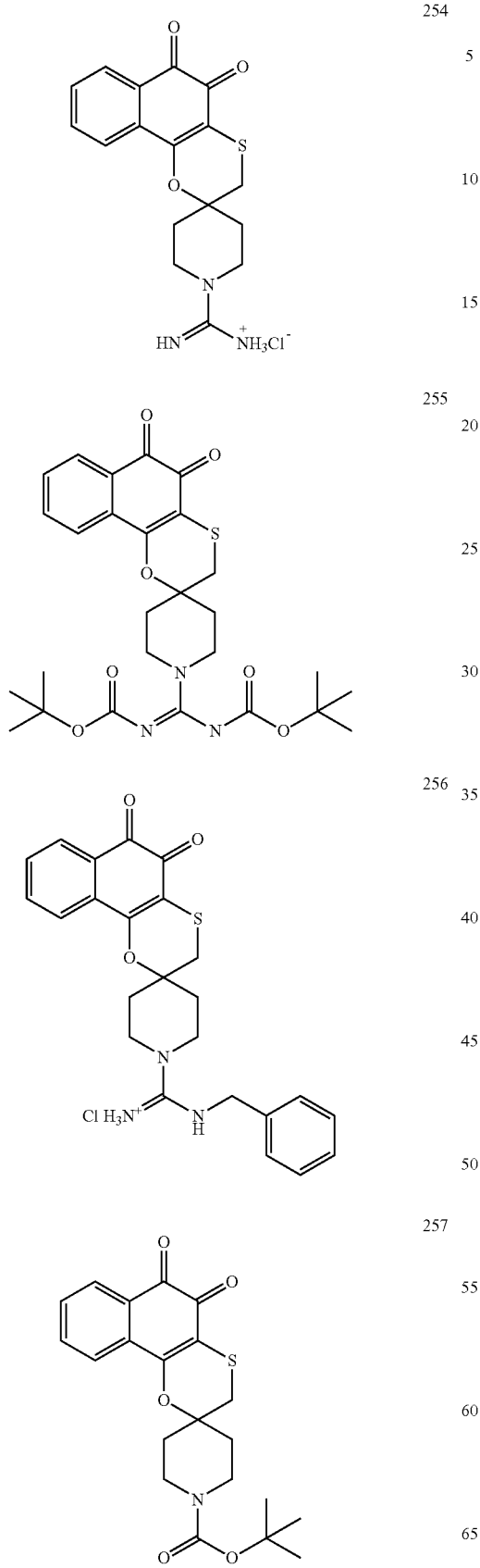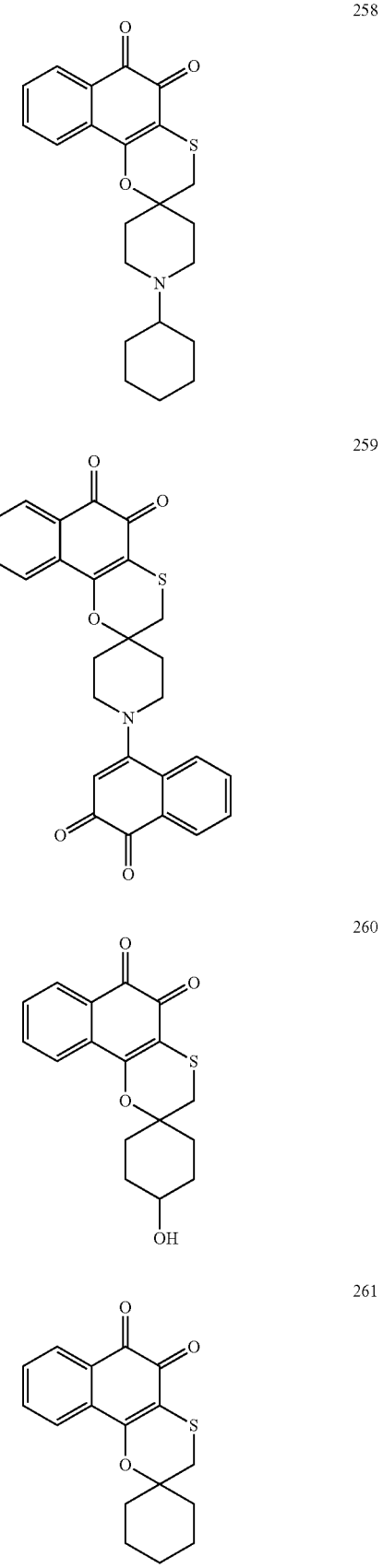

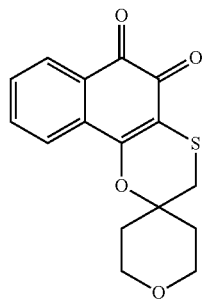
262
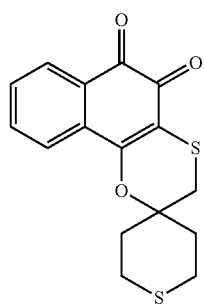
263
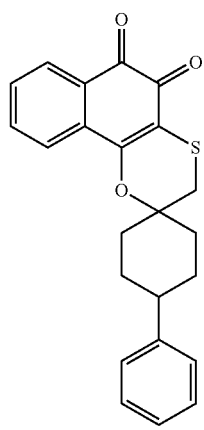
264
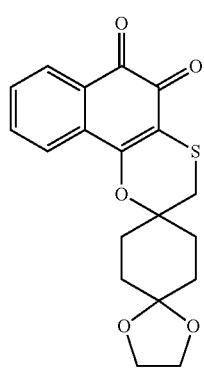
265
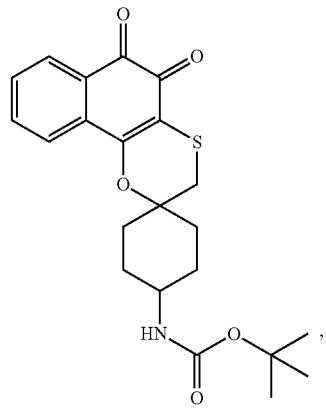
267
or a pharmaceutically acceptable salt and/or an individual diastereomer thereof.
50. A compound selected from the group consisting of:
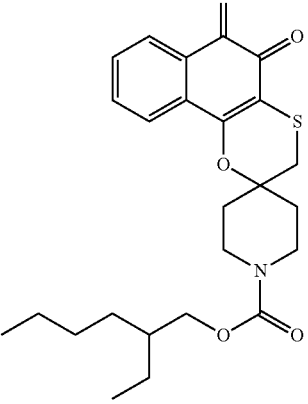
95
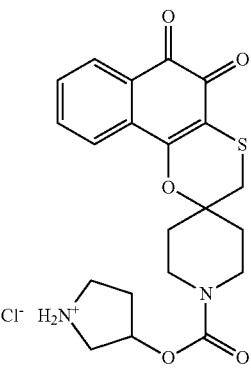
113
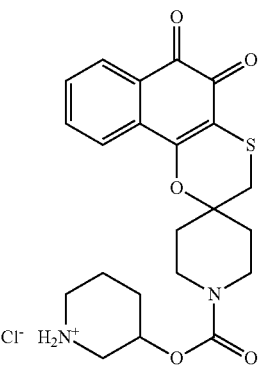
115

287
-continued
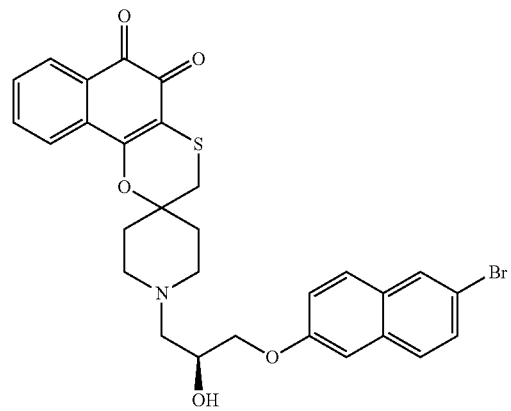
216
217
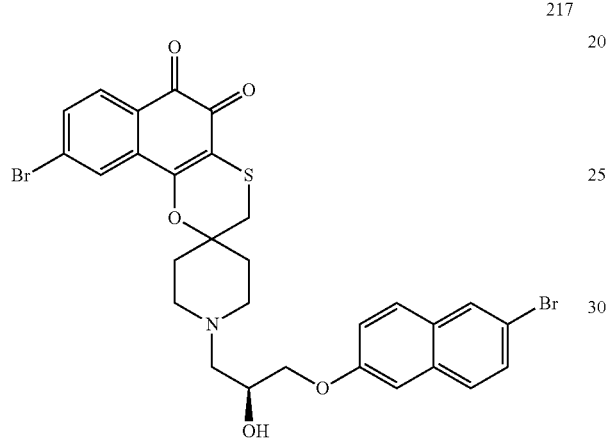
288
-continued
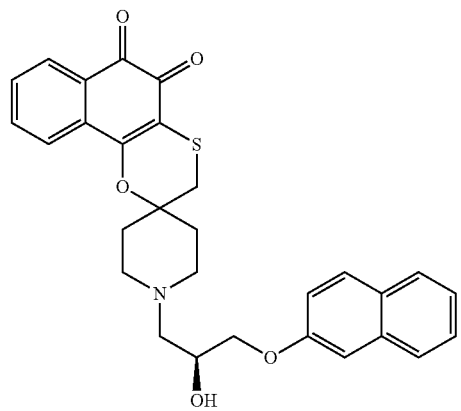
221
266
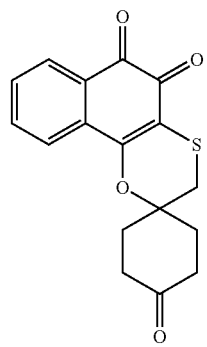
or a pharmaceutically acceptable salt and/or an individual diastereomer thereof.
* * * * *

UNITED STATES PATENT AND TRADEMARK OFFICE
CERTIFICATE OF CORRECTION

| | | |
|---|---|---|
| PATENT NO. | : 7,902,354 B2 | Page 1 of 2 |
| APPLICATION NO. | : 11/894900 | |
| DATED | : March 8, 2011 | |
| INVENTOR(S) | : Mark A. Ashwell et al. | |

It is certified that error appears in the above-identified patent and that said Letters Patent is hereby corrected as shown below:

At col. 217, lines 4-5, the term "4-fluorophenyl-5,6-dioxo-5,6-dihydro-1'H-spiro[naphtho[1,2-b][2,4]oxathiine-2,4'-piperidine]-1'-carboxylate" should read "4-fluorophenyl-5,6-dioxo-5,6-dihydro-1'H-spiro[naphtho[1,2-b][1,4]oxathiine-2,4'-piperidine]-1'-carboxylate".

At col. 225, lines 50-65, the compound with the following structure:

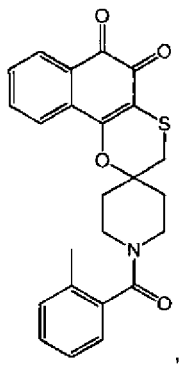

should be the compound with the following structure:

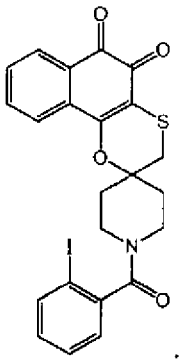

Signed and Sealed this
Nineteenth Day of April, 2011

David J. Kappos
*Director of the United States Patent and Trademark Office*

CERTIFICATE OF CORRECTION (continued)
U.S. Pat. No. 7,902,354 B2

At col. 283, lines 55-65, the compound with the following structure:

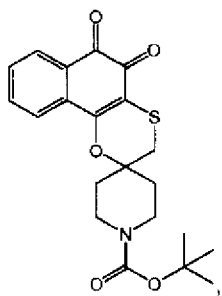

should be the compound with the following structure: